(12) United States Patent
Ajamian et al.

(10) Patent No.: US 9,636,298 B2
(45) Date of Patent: May 2, 2017

(54) PRODRUGS OF COMPOUNDS THAT ENHANCE ANTIFUNGAL ACTIVITY AND COMPOSITIONS OF SAID PRODRUGS

(71) Applicant: MethylGene Inc., Montreal (CA)

(72) Inventors: Alain Ajamian, Montreal (CA); Yves Andre Chantigny, Pincourt (CA); Arkadii Vaisburg, Kirkland (CA); Franck Raeppel, Montreal (CA); Stephane Raeppel, St-Lazare (CA); Robert Deziel, Mount-Royal (CA)

(*) Notice: Subject to any disclaimer, the term of this patent is extended or adjusted under 35 U.S.C. 154(b) by 0 days.

(21) Appl. No.: 14/597,911

(22) Filed: Jan. 15, 2015

(65) Prior Publication Data

US 2015/0203517 A1    Jul. 23, 2015

Related U.S. Application Data

(60) Provisional application No. 61/928,978, filed on Jan. 17, 2014.

(51) Int. Cl.

| | |
|---|---|
| *C07D 207/16* | (2006.01) |
| *C07D 211/60* | (2006.01) |
| *C07C 259/06* | (2006.01) |
| *C07C 271/60* | (2006.01) |
| *C07C 275/16* | (2006.01) |
| *C07C 309/15* | (2006.01) |
| *C07D 239/557* | (2006.01) |
| *C07D 241/08* | (2006.01) |
| *C07D 263/22* | (2006.01) |
| *C07D 205/04* | (2006.01) |
| *C07D 273/08* | (2006.01) |
| *C07D 211/34* | (2006.01) |
| *C07D 211/44* | (2006.01) |
| *C07D 211/58* | (2006.01) |
| *C07D 211/62* | (2006.01) |
| *A61K 31/223* | (2006.01) |
| *A61K 31/40* | (2006.01) |
| *A61K 31/661* | (2006.01) |
| *A61K 31/495* | (2006.01) |
| *A61K 31/5377* | (2006.01) |
| *A61K 31/397* | (2006.01) |
| *A61K 45/06* | (2006.01) |
| *A61K 9/00* | (2006.01) |
| *A61K 31/5375* | (2006.01) |
| *C07D 309/12* | (2006.01) |
| *C07D 295/185* | (2006.01) |
| *C07D 295/192* | (2006.01) |

(Continued)

(52) U.S. Cl.
CPC .......... *A61K 9/0019* (2013.01); *A61K 31/223* (2013.01); *A61K 31/397* (2013.01); *A61K 31/40* (2013.01); *A61K 31/495* (2013.01); *A61K 31/5375* (2013.01); *A61K 31/5377* (2013.01); *A61K 31/661* (2013.01); *A61K 45/06* (2013.01); *C07C 259/06* (2013.01); *C07C 271/60* (2013.01); *C07C 275/16* (2013.01); *C07C 309/15* (2013.01); *C07D 205/04* (2013.01); *C07D 207/16* (2013.01); *C07D 211/34* (2013.01); *C07D 211/44* (2013.01); *C07D 211/58* (2013.01); *C07D 211/60* (2013.01); *C07D 211/62* (2013.01); *C07D 239/557* (2013.01); *C07D 241/08* (2013.01); *C07D 263/22* (2013.01); *C07D 273/08* (2013.01); *C07D 295/185* (2013.01); *C07D 295/192* (2013.01); *C07D 295/205* (2013.01); *C07D 309/12* (2013.01); *C07F 9/091* (2013.01); *C07C 2101/02* (2013.01); *C07C 2101/08* (2013.01); *C07C 2101/14* (2013.01)

(58) Field of Classification Search
CPC ....... C07F 9/06; C07C 237/52; A61K 31/223; A61K 31/40; A61K 31/661; A61K 31/495; A61K 31/5377; A61K 31/5375; A61K 31/397; A61K 45/06; A61K 9/0019; C07D 207/16; C07D 211/60
See application file for complete search history.

(56) References Cited

U.S. PATENT DOCUMENTS

| | | |
|---|---|---|
| 2,279,560 A | 4/1942 | Dietrich |
| 2,279,973 A | 4/1942 | Dietrich |
| 2,480,356 A | 8/1949 | Christiana |

(Continued)

FOREIGN PATENT DOCUMENTS

| | | | |
|---|---|---|---|
| CN | 102078356 A | | 6/2011 |
| GB | WO 2007/054725 | * | 5/2007 |

(Continued)

OTHER PUBLICATIONS

Hynes, John B. Hydroxylamine Derivatives as Potential Antimalarial Agents. 2. Hydroxamates and Amidoximes. J. Med. Chem. 1972, 15(11), 1194-1196.*
Database Registry Chemical Abstracts Service, Columbus, Ohio, Accession No. RN 1048355-23-2, Entered STN: Sep. 10, 2008.*
Database Registry Chemical Abstracts Service, Columbus, Ohio, Accession No. RN 1349517-30-1, Entered STN: Dec. 6, 2011.*
Ito, Nobuyuki. Cancer Science 94(1), (2003) 3-8.*

(Continued)

*Primary Examiner* — Samantha Shterengarts
(74) *Attorney, Agent, or Firm* — McDonnell Boehnen Hulbert & Berghoff LLP

(57) ABSTRACT

The invention relates to prodrugs for use in the inhibition of histone deacetylase. The prodrugs of the present invention have good aqueous solubility and good aqueous stability. The prodrugs of the invention advantageously are metabolized to the active ingredient in plasma or in the blood stream of a warm-blooded animal. The invention also provides compositions and, and methods for making the prodrugs, and methods for using the prodrugs to treat fungal infections.

7 Claims, No Drawings

(51) Int. Cl.
  *C07D 295/205*   (2006.01)
  *C07F 9/09*   (2006.01)

(56) References Cited

U.S. PATENT DOCUMENTS

| | | | |
|---|---|---|---|
| 2,484,065 A | 10/1949 | Ashton et al. | |
| 2,490,579 A | 12/1949 | Clewell | |
| 2,754,286 A | 7/1956 | Martin | |
| 2,909,525 A * | 10/1959 | Fand | C07D 213/20 546/347 |
| 3,208,990 A | 9/1965 | Benz et al. | |
| 3,263,924 A | 8/1966 | Kolze | |
| 3,576,869 A | 4/1971 | Schellenbaum et al. | |
| 4,013,768 A | 3/1977 | Fauran et al. | |
| 4,035,376 A | 7/1977 | Janssen et al. | |
| 4,173,577 A | 11/1979 | Sallman et al. | |
| 4,792,560 A | 12/1988 | Huang et al. | |
| 4,977,188 A | 12/1990 | Kneen et al. | |
| 4,994,479 A | 2/1991 | Mase et al. | |
| 5,028,629 A | 7/1991 | Hite et al. | |
| 5,137,918 A | 8/1992 | Weiershausen et al. | |
| 5,218,124 A | 6/1993 | Failli et al. | |
| 5,276,515 A | 1/1994 | Katsumata et al. | |
| 5,332,750 A | 7/1994 | Mederski et al. | |
| 5,364,944 A | 11/1994 | Failli et al. | |
| 5,366,878 A | 11/1994 | Pederson et al. | |
| 5,635,377 A | 6/1997 | Pederson et al. | |
| 5,652,355 A | 7/1997 | Metelev et al. | |
| 5,700,811 A | 12/1997 | Breslow et al. | |
| 5,773,647 A | 6/1998 | Leone-Bay et al. | |
| 5,776,888 A | 7/1998 | Leone-Bay et al. | |
| 5,929,097 A | 7/1999 | Levin et al. | |
| 5,945,450 A | 8/1999 | Takenouchi et al. | |
| 6,034,251 A | 3/2000 | Aslanian et al. | |
| 6,090,958 A | 7/2000 | Leone-Bay et al. | |
| 6,174,905 B1 | 1/2001 | Suzuki et al. | |
| 6,180,844 B1 | 1/2001 | Fujita et al. | |
| 6,376,515 B2 | 4/2002 | Zhu et al. | |
| 6,541,661 B1 | 4/2003 | Delorme et al. | |
| 6,632,815 B2 | 10/2003 | Zhu et al. | |
| 6,653,309 B1 | 11/2003 | Saunders et al. | |
| 6,777,217 B1 | 8/2004 | Schreiber et al. | |
| 6,897,220 B2 | 5/2005 | Delorme et al. | |
| 7,253,204 B2 | 8/2007 | Delorme et al. | |
| RE39,850 E | 9/2007 | Delorme et al. | |
| 7,282,608 B2 | 10/2007 | Raeppel et al. | |
| 7,595,343 B2 | 9/2009 | Delorme et al. | |
| 7,799,782 B2 | 9/2010 | Munson et al. | |
| 8,030,344 B2 | 10/2011 | Frechette et al. | |
| 2002/0061860 A1 | 5/2002 | Li et al. | |
| 2003/0096844 A1 | 5/2003 | Kozlowski et al. | |
| 2003/0232859 A1 | 12/2003 | Kozlowski et al. | |
| 2004/0010013 A1 | 1/2004 | Friary et al. | |
| 2004/0044051 A1 | 3/2004 | Kozlowski et al. | |
| 2004/0072770 A1 | 4/2004 | Besterman | |
| 2004/0087798 A1 | 5/2004 | Yamada | |
| 2004/0106599 A1 | 6/2004 | Delorme et al. | |
| 2004/0132804 A1 | 7/2004 | Tong et al. | |
| 2004/0147569 A1 | 7/2004 | Suzuki et al. | |
| 2004/0186148 A1 | 9/2004 | Shankar et al. | |
| 2005/0096222 A1 | 5/2005 | Hidaka et al. | |
| 2005/0222410 A1 | 10/2005 | Stokes | |
| 2005/0245518 A1 | 11/2005 | Delorme et al. | |
| 2005/0288282 A1 | 12/2005 | Delorme et al. | |
| 2006/0058298 A1 | 3/2006 | Delorme et al. | |
| 2006/0063210 A1 | 3/2006 | Li et al. | |
| 2007/0117824 A1 | 5/2007 | Berk et al. | |
| 2007/0173527 A1 | 7/2007 | Bressi et al. | |
| 2007/0197550 A1 | 8/2007 | Georgopapadakou et al. | |
| 2007/0213330 A1 | 9/2007 | Delorme et al. | |
| 2008/0132503 A1 | 6/2008 | Moradei et al. | |
| 2010/0143507 A1* | 6/2010 | Gant | A61K 31/19 424/722 |
| 2011/0150825 A1 | 6/2011 | Buggy et al. | |
| 2012/0046331 A1* | 2/2012 | Besterman | 514/415 |
| 2014/0024608 A1* | 1/2014 | Deziel | C07D 213/56 514/25 |
| 2014/0081017 A1* | 3/2014 | Raeppel | C07C 259/06 540/467 |

FOREIGN PATENT DOCUMENTS

| | | | |
|---|---|---|---|
| JP | 2001-191350 | * | 7/2001 |
| WO | 00/71703 | A1 | 11/2000 |
| WO | 01/38322 | A1 | 5/2001 |
| WO | 01/70675 | A1 | 9/2001 |
| WO | 02/069947 | A1 | 9/2002 |
| WO | 02/092899 | A1 | 11/2002 |
| WO | 03/024448 | A2 | 3/2003 |
| WO | 2004/005513 | A1 | 1/2004 |
| WO | 2004/035525 | A1 | 4/2004 |
| WO | 2004/069823 | A1 | 8/2004 |
| WO | 2005/030704 | A1 | 4/2005 |
| WO | 2005/030705 | A1 | 4/2005 |
| WO | 2005/097747 | A1 | 10/2005 |
| WO | 2007/072179 | A2 | 6/2007 |
| WO | 2007/118137 | A1 | 10/2007 |
| WO | 2008/021944 | A2 | 2/2008 |
| WO | 2008/074132 | A1 | 6/2008 |
| WO | 2008/109994 | A1 | 9/2008 |
| WO | 2012/021982 | A1 | 2/2012 |

OTHER PUBLICATIONS

Augenbraun et al., "Fluconazole and MGCD290 in vulvo vaginal candidiasis (VVC): Results from a randomized phase II study", 2013, 2 pages.

1330 Poster, Augenbraun et al., "Fluconazole and MGCD290 in vulvo vaginal candidiasis (VVC): Results from a randomized phase II study", 2013, 1 page.

Schlimme et al., "Carbamate Prodrug Concept for Hydroxamate HDAC Inhibitors", ChemMedChem, 2011, vol. 6, 1193-1198.

Rerat et al., "αvβ3 Integrin-Targeting Arg-Gly-Asp (RGD) Peptidomimetics Containing Oligoethylene Glycol (OEG) Spacers", Journal of Medicinal Chemistry, 2009, vol. 52, 7029-7043.

Zhang et al., "Structural Requirements for a Lipoamino Acid in Modulating the Anticonvulsant Activities of Systemically Active Galanin Analogues", Journal of Medicinal Chemistry, 2009, vol. 52, 1310-1316.

Usachova et al., "Synthesis of Hydroxamic Acids by Activation of Carboxylic Acids with N,N'-Carbonyldiimidazole: Exploring the Efficiency of the Method", Synthetic Communications, 2010, 40(6), 927-935.

* cited by examiner

PRODRUGS OF COMPOUNDS THAT ENHANCE ANTIFUNGAL ACTIVITY AND COMPOSITIONS OF SAID PRODRUGS

RELATED APPLICATION

This application claims priority to U.S. Provisional Application No. 61/928,978, filed on Jan. 17, 2014, the disclosure of which is incorporated herein by reference in its entirety.

BACKGROUND OF THE INVENTION

Field of the Invention

This invention relates to prodrugs of compounds having antifungal activity, and compostions thereof. More particularly, this invention relates to such prodrugs having improved solubility in aqueous compostions.

Summary of the Related Art

It is known in the art that certain compounds that inhibit the enzyme activity of histone deacetylases (HDACs) also have antifungal activities. Such compounds are disclosed, for example, in U.S. RE 39,850. HDAC inhibitors that are known to enhance the activity of antifungal agents are disclosed in US2007/0197550. U.S. Patent Application No. US-2008-0146623-A1 discloses compounds that inhibit HDAC activity, and prodrugs thereof, and the use thereof in the treatment of fungal infections. The disclosures of all of these references are incorporated herein by reference in their entireties.

While some HDAC inhibitors have been shown to be efficacious in the treatment of fungal infections, and good bioavaialblitly, some HDAC inhibotors as disclosed in the aforementioned references have limited solubility in aqueous solutions.

SUMMARY OF THE INVENTION

It would be desirable to provide prodrugs of histone deacetylase inhibitors, which prodrugs have good aqueous solubility and good aqueous stability. It further would be desirable to provide such prodrugs which can be metabolized in plasma to yield the active ingredient as a cleavage product. It further would be desirable to provide such prodrugs that can be used in combination with other antifungal agents, and particularly azole antifungal agents, to enhance the antifungal activity of such agents.

The invention provides prodrugs, compositions of such prodrugs, and methods for treating fungal infection by administering such prodrugs and compositions. These prodrugs are stable in aqueous solutions, and preferably are cleavable in plasma or in a bloodstream of warmblooded animals. For the purpose of clarity, a "prodrug compound" or "prodrug" of the present invention is intended to mean a non-cleaved compound as defined by Formula (2) below. A "cleavage product" of the prodrug is intended to mean a prodrug compound from which the pro-moiety has been removed. The invention further provides such prodrugs and prodrug compositions for use in combination with other antifungal agents, and in particular azole antifungal agents, and antifungal agents that are inhibitors of ergosterol biosynthesis.

In one embodiment, the invention provides prodrugs of inhibitors of histone deacetylase, the prodrugs having the formula (2):

$$Cy—L^2—Ar—Y^2—C(O)N(R^x)—Z \quad (2)$$

and pharmaceutically acceptable salts thereof, wherein

Cy is H or is cycloalkyl, aryl, heteroaryl, or heterocyclyl, any of which may be optionally substituted, provided that Cy is not a (spirocycloalkyl)heterocyclyl;

$L^2$ is $C_1$-$C_6$ saturated alkylene, $C_2$-$C_6$ alkenylene or $C_2$-$C_6$ alkynylene, wherein the alkylene or alkenylene optionally may be substituted, and wherein one or two of the carbon atoms of the alkylene is optionally replaced by a heteroatomic moiety independently selected from the group consisting of O; NR', R' being alkyl, acyl, or hydrogen; S; S(O); or $S(O)_2$;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted;

$Y^2$ is a chemical bond or a straight- or branched-chain saturated alkylene, which may be optionally substituted, provided that the alkylene is not substituted with a substituent of the formula —C(O)R wherein R comprises an α-amino acyl moiety;

$R^x$ is H, —OH, or —$R^{20}$;

Z is —O—$R^{20}$ or —$R^{21}$ wherein each —$R^{20}$ is selected from the group consisting of
—C(O)—$R^{10}$,
—C(O)-[C($R^{40}$)($R^{41}$)]$_n$OP(O)(OH)(OH),
—C(O)N($R^{31}$)[C($R^{40}$)($R^{41}$)]$_n$SO$_2$OH, and
—C(O)NH[C($R^{40}$)($R^{41}$)]$_n$C(O)O[C($R^{40}$)($R^{41}$)]$_n$$R^{42}$;

each $R^{10}$ is independently selected from the group consisting of
—[C($R^{40}$)($R^{41}$)]$_n$$R^{42}$,
—N($R^{30}$)[C($R^{40}$)($R^{41}$)]$_n$
—O[C($R^{40}$)($R^{41}$)]$_n$,
—[C($R^{40}$)($R^{41}$)]$_n$NHC(O)[C($R^{40}$)($R^{41}$)]$_n$$R^{42}$,
—[C($R^{40}$)($R^{41}$)]$_n$NHC(O)O[C($R^{40}$)($R^{41}$)]$_n$$R^{42}$,
—[C($R^{40}$)($R^{41}$)]$_n$NHC(O)[C(H)(NH$_2$.HX)][C($R^{40}$)($R^{41}$)]$_n$ $R^{42}$,
—[C($R^{40}$)($R^{41}$)]$_n$NHC(O)[C($R^{40}$)($R^{41}$)]$_n$NH[C($R^{40}$)($R^{41}$)]$_n$NH$_2$.HX,
—[C($R^{40}$)($R^{41}$)]$_n$N($R^{30}$)C(O)C[(H)(N(H)C(O))][C($R^{40}$)($R^{41}$)]$_n$$R^{42}$][C($R^{40}$)($R^{41}$)]$_n$N(H)C(O)—[C($R^{40}$)($R^{41}$)]$_n$$R^{42}$,
—[C($R^{40}$)($R^{41}$)]$_n$NHR$^{60}$,
—[C($R^{40}$)($R^{41}$)]$_n$C(O)N[[C($R^{40}$)($R^{41}$)]$_n$C(O)N(H)CH$_2$R$^{56}$]$_2$,
—[C($R^{40}$)($R^{41}$)]$_n$NHC(O)[C($R^{40}$)($R^{41}$)]$_n$N(R$^{60}$)[[C($R^{40}$)($R^{41}$)]$_n$N(H)(R$^{60}$)],
—[C($R^{40}$)($R^{41}$)]$_n$N($R^{30}$)C(O)[C(H)(N(H)R$^{60}$)][C($R^{40}$)($R^{41}$)]$_n$N(H)R$^{60}$,
—[C($R^{40}$)($R^{41}$)]$_n$N($R^{30}$)C(O)[C($R^{40}$)($R^{41}$)]$_n$N(H)C(O)[C($R^{40}$)($R^{41}$)]$_n$N(H)R$^{56}$,
—C[(H)(N(H)R$^{60}$)][C($R^{40}$)($R^{41}$)]$_n$N(H)R$^{60}$,
—[C($R^{40}$)($R^{41}$)]$_n$NHC(O)[C(H)(NH$_2$)](CR$^{40}$R$^{41}$)$_n$NHR$^{60}$,
—$R^{50}$,
—$R^{50}$C(O)C[(H)(NH$_2$.HX)][C($R^{40}$)($R^{41}$)]$_n$NH$_2$.HX,
—$R^{50}$C(O)C[(H)(N(H)R$^{60}$)][C($R^{40}$)($R^{41}$)]$_n$N(H)R$^{60}$,
—$R^{50}$C(O)[C($R^{40}$)($R^{41}$)]$_n$NHC(O)NH[C($R^{40}$)($R^{41}$)]$_n$R$^{56}$,
—$R^{50}$R$^{60}$,
—[C($R^{40}$)($R^{41}$)]$_n$OR$^{51}$,
—$R^{45}$ amino.HX,
—$R^{45}$N(H)C(O)[C($R^{40}$)($R^{41}$)]$_n$N(R$^{30}$)(R$^{31}$), and
—$R^{45}$[C($R^{40}$)($R^{41}$)]$_n$NHC(O)[C(H)(NH$_2$.HX)][C($R^{40}$)($R^{41}$)]$_n$N(R$^{30}$)(R$^{31}$);

$R^{21}$ is selected from [C($R^{40}$)($R^{41}$)]$_n$R$^{52}$[C($R^{40}$)($R^{41}$)]$_n$ and [C($R^{40}$)($R^{41}$)]$_n$OH;

$R^{30}$ and $R^{31}$ are each independently selected from hydrogen and hydrocarbyl;

$R^{40}$ and $R^{41}$ are each independently selected from hydrogen, $NH_2$, $NH_2.HX$, optionally substituted alkyl, optionally substituted arylalkyl, and oxo, or $R^{40}$ and $R^{41}$ together with the carbon atom to which they are attached form an optionally substituted cycloalkyl;

$R^{42}$ is selected from hydrogen, optionally substituted alkyl, optionally substituted aryl, —$NH_2.HX$, optionally substituted cycloalkyl, optionally substituted alkoxy, acyl, —$NHC(O)CH_3$, and —$OC(O)CH_3$;

$R^{45}$ is optionally substituted arylene;

$R^{50}$ is selected from the group consisting of —$[C(R^{40})(R^{41})]_tR^{51}$, —$[C(R^{40})(R^{41})]_tO$—$R^{51}$, and —$[C(R^{40})(R^{41})]_tC(O)R^{51}$, where t is an integer from 0-4;

$R^{51}$ is a 4-8 membered optionally substituted heterocycloalkyl or heterocycloalkenyl comprising at least one nitrogen ring atom;

$R^{56}$ is —$[C(R^{40})(R^{41})OC(R^{40})(R^{41})]_mH$;

$R^{60}$ is —$C(O)R^{56}$;

X is a salt-forming radical, preferably halide, most preferably chloride;

each m is independently an integer from 1 to 20, or from 1 to 10, or from 1 to 5; and each n is independently an integer from 0 to 6.

In some embodiments of the invention the prodrugs exist in the form of salts. In some embodiments of the invention the salts are halide salts. In some embodiments of the invention the salts are chloride salts.

In some embodiments of the invention, the moiety Z comprises one or more ethylene glycol or polyethylene glycol chains. In some embodiments of the invention, the ethylene glycol or polyethylene glycol chains are connected to the moiety Z via an amide linkage. In some embodiments the polyethylene glycol chain is linear. In some embodiments the polyethylene glycol chain is branched. In some embodiments two polyethylene glycol chains and their linkages are linked together to form a polyethylene glycol ring structure. In some embodiments, the moiety $R^{56}$ represents a polyethylene glycol chain.

DETAILED DESCRIPTION OF THE PREFERRED EMBODIMENTS

The invention provides prodrugs and methods for inhibiting histone deacetylase enzymatic activity. The invention also provides compositions and methods for treating diseases or conditions ameliorated by modulating HDAC activity, such as cell proliferative diseases and conditions, and fungal infection. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used:

Unless otherwise indicated by context, the terms "histone deacetylase" and "HDAC" are intended to refer to any one of a family of enzymes that remove acetyl groups from the ε-amino groups of lysine residues at the N-terminus of a histone. Unless otherwise indicated by context, the term "histone" is meant to refer to any histone protein, including H1, H2A, H2B, H3, H4, and H5, from any species. Preferred histone deacetylases include class I and class II enzymes. Preferably the histone deacetylase is a human HDAC, including, but not limited to, HDAC-1, HDAC-2, HDAC-3, HDAC-4, HDAC-5, HDAC-6, HDAC-7, HDAC-8, HDAC-9, HDAC-10, and HDAC-11. In some other preferred embodiments, the histone deacetylase is derived from a protozoal or fungal source. Preferred fungi include, but are not limited to *Saccharomyces cerevisiae*, *Candida* spp. (such as *C. albicans*, *C. glabrata*, *C. tropicalis*, *C. parapsilosis*, *C. krusei*, *C. lusitaniae*, *C. dubliniensis*), *Aspergillus* spp. (such as *A. fumigatus*, *A. flavus*, *A. niger*, *A. terreus*), *Fusarium* spp., *Paecilomyces lilacinus*, *Rhizopus arrhizus* and *Coccidioides immitis*. In certain preferred embodiments, the histone deacetylase is a fungal HDAC including, but not limited to Rpd3, Hos1, Hos2, Hda1, Hos3, Sir2, Hst, and homologs thereof. In preferred embodiments, a cleavage product of a prodrug compound of the present invention shows synergistic activity with an antifungal agent against a fungal species, preferably at concentrations of inhibitor not toxic to mammalian cells. Preferably such antifungal agents are azole antifungal agents (a large number of active antifungal agents have an azole functionality as part of their structure; such an antifungal agent is generally referred to as an "antifungal azole", an "azole antifungal agent" or an "azole"). Such combinations, and compositions thereof, can be used to selectively treat fungal infection.

The term "antifungal agent" is intended to mean a substance capable of inhibiting or preventing the growth, viability and/or reproduction of a fungal cell. Preferable antifungal agents are those capable of preventing or treating a fungal infection in an animal or plant. A preferable antifungal agent is a broad spectrum antifungal agent. However, an antifungal agent can also be specific to one or more particular species of fungus.

Preferred antifungal agents are ergosterol synthesis inhibitors, and include, but are not limited to azoles and fenpropimorph. Other antifungal agents include, but are not limited to terbinafine. Preferred azoles include imidazoles and triazoles. Further preferred antifungal agents include, but are not limited to, ketoconazole, itraconazole, fluconazole, voriconazole, posaconazole, ravuconazole and miconazole. Like azoles, fenpropimorph is an ergosterol synthesis inhibitor, but acts on the ergosterol reductase (ERG24) step of the synthesis pathway. Terbinafine, is also an ergosterol inhibitor, but acts on the squalene eposidase (ERG1) step.

The term "histone deacetylase inhibitor" or "inhibitor of histone deacetylase" is used to identify a compound having a structure as defined herein, which is capable of interacting with a histone deacetylase and inhibiting its enzymatic activity. Inhibiting histone deacetylase enzymatic activity means reducing the ability of a histone deacetylase to remove an acetyl group from a histone. In some preferred embodiments, such reduction of histone deacetylase activity is at least about 50%, more preferably at least about 75%, and still more preferably at least about 90%. In other preferred embodiments, histone deacetylase activity is reduced by at least 95% and more preferably by at least 99%.

Preferably, such inhibition is specific, i.e., the histone deacetylase inhibitor reduces the ability of a histone deacetylase to remove an acetyl group from a histone at a concentration that is lower than the concentration of the inhibitor that is required to produce another, unrelated biological effect. Preferably, the concentration of the inhibitor required for histone deacetylase inhibitory activity is at least 2-fold lower, more preferably at least 5-fold lower, even more preferably at least 10-fold lower, and most preferably at least 20-fold lower than the concentration required to produce an unrelated biological effect. In certain preferred embodiments of the present invention, cleavage (e.g., hydrolysis) of the prodrug releases a compound (a cleavage (e.g., hydrolyzation) product) which is an inhibitor of histone deacetylase that is more active against a fungal histone decetylase than against a mammalian histone deacetylase. In certain preferred embodiments of the present invention, the inhibitor of histone deacetylase is specific for a fungal histone deacetylase.

The terms "treating," "treatment," or the like, as used herein covers the treatment of a disease-state in an animal and includes at least one of: (i) preventing the disease-state from occurring, in particular, when such animal is predisposed to the disease-state but has not yet developed symptoms of having it; (ii) inhibiting the disease-state, i.e., partially or completely arresting its development; (iii) relieving the disease-state, i.e., causing regression of symptoms of the disease-state, or ameliorating a symptom of the disease; and (iv) reversal or regression of the disease-state, preferably eliminating or curing of the disease. In a preferred embodiment the terms "treating," "treatment," or the like, covers the treatment of a disease-state in an animal and includes at least one of (ii), (iii) and (iv) above. In a preferred embodiment of the present invention the animal is a mammal, preferably a primate, more preferably a human. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B-, wherein a is 0 or 1. In such instances, when a is 0 the moiety is B- and when a is 1 the moiety is A-B-.

For simplicity, reference to a "$C_n$-$C_m$" heterocyclyl or "$C_n$-$C_m$" heteroaryl means a heterocyclyl or heteroaryl having from "n" to "m" annular atoms, where "n" and "m" are integers. Thus, for example, a $C_5$-$C_6$-heterocyclyl is a 5- or 6-membered ring having at least one heteroatom, and includes pyrrolidinyl ($C_5$) and piperidinyl ($C_6$); $C_6$-heteroaryl includes, for example, pyridyl and pyrimidyl.

The term "ethylene glycol" refers to the molecule HO—$(CH_2)_2$—OH, or to the unit —O—$(CH_2)_2$—OH when attached as a ligand to a compound of the present invention.

The term "polyethylene glycol" refers to compounds of the formula H[O—$(CH_2)_2$]$_m$—OH or to the units —[O—$(CH_2)_2$]$_m$—OH when attached as a ligand to a compound of the present invention, where m is independently an integer from 1 to 20, or from 1 to 10, or from 1 to 5.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$-$C_3$-hydrocarbyl" includes a covalent bond, methyl, ethyl, ethenyl, ethynyl, propyl, propenyl, propynyl, and cyclopropyl.

The term "alkyl" is intended to mean a straight or branched chain aliphatic group having from 1 to 12 carbon atoms, preferably 1-8 carbon atoms, and more preferably 1-6 carbon atoms. Other preferred alkyl groups have from 2 to 12 carbon atoms, preferably 2-8 carbon atoms and more preferably 2-6 carbon atoms. Preferred alkyl groups include, without limitation, methyl, ethyl, propyl, isopropyl, butyl, isobutyl, sec-butyl, tert-butyl, pentyl, and hexyl. A "$C_0$" alkyl (as in "$C_0$-$C_3$-alkyl") is a covalent bond.

The term "alkenyl" is intended to mean an unsaturated straight or branched chain aliphatic group with one or more carbon-carbon double bonds, having from 2 to 12 carbon atoms, preferably 2-8 carbon atoms, and more preferably 2-6 carbon atoms. Preferred alkenyl groups include, without limitation, ethenyl, propenyl, butenyl, pentenyl, and hexenyl.

The term "alkynyl" is intended to mean an unsaturated straight or branched chain aliphatic group with one or more carbon-carbon triple bonds, having from 2 to 12 carbon atoms, preferably 2-8 carbon atoms, and more preferably 2-6 carbon atoms. Preferred alkynyl groups include, without limitation, ethynyl, propynyl, butynyl, pentynyl, and hexynyl.

The terms "alkylene," "alkenylene," or "alkynylene" as used herein are intended to mean an alkyl, alkenyl, or alkynyl group, respectively, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propynylene, and butynylene.

The term "cycloalkyl" is intended to mean a saturated or unsaturated mono-, bi, tri- or poly-cyclic hydrocarbon group having about 3 to 15 carbons, preferably having 3 to 12 carbons, preferably 3 to 8 carbons, and more preferably 3 to 6 carbons. In certain preferred embodiments, the cycloalkyl group is fused to an aryl, heteroaryl or heterocyclic group. Preferred cycloalkyl groups include, without limitation, cyclopenten-2-enone, cyclopenten-2-enol, cyclohex-2-enone, cyclohex-2-enol, cyclopropyl, cyclobutyl, cyclopentyl, cyclopentenyl, cyclohexyl, cyclohexenyl, cycloheptyl, and cyclooctyl.

The term "heteroalkyl" is intended to mean a saturated or unsaturated, straight or branched chain aliphatic group, wherein one or more carbon atoms in the chain are independently replaced by a heteroatom selected from the group consisting of O, $S(O)_{0-2}$, N and $N(R^{33})$.

The term "aryl" is intended to mean a mono-, bi-, tri- or polycyclic $C_6$-$C_{14}$ aromatic moiety, preferably comprising one to three aromatic rings. Preferably, the aryl group is a $C_6$-$C_{10}$ aryl group, more preferably a $C_6$ aryl group. Preferred aryl groups include, without limitation, phenyl, naphthyl, anthracenyl, and fluorenyl.

The terms "aralkyl" or "arylalkyl" is intended to mean a group comprising an aryl group covalently linked to an alkyl group. If an aralkyl group is described as "optionally substituted", it is intended that either or both of the aryl and alkyl moieties may independently be optionally substituted or unsubstituted. Preferably, the aralkyl group is ($C_1$-$C_6$)alk ($C_6$-$C_{10}$)aryl, including, without limitation, benzyl, phenethyl, and naphthylmethyl. For simplicity, when written as "arylalkyl" this term, and terms related thereto, is intended to indicate the order of groups in a compound as "aryl-alkyl". Similarly, "alkyl-aryl" is intended to indicate the order of the groups in a compound as "alkyl-aryl".

The terms "heterocyclyl", "heterocyclic" or "heterocycle" are intended to mean a group which is a mono-, bi-, or polycyclic structure having from about 3 to about 14 atoms, wherein one or more atoms are independently selected from the group consisting of N, O, and S. The ring structure may be saturated, unsaturated or partially unsaturated. In certain preferred embodiments, the heterocyclic group is non-aromatic. In a bicyclic or polycyclic structure, one or more rings may be aromatic; for example one ring of a bicyclic heterocycle or one or two rings of a tricyclic heterocycle may be aromatic, as in indan and 9,10-dihydro anthracene. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

In certain preferred embodiments, the heterocyclic group is a heteroaryl group. As used herein, the term "heteroaryl" is intended to mean a mono-, bi-, tri- or polycyclic group having 5 to 14 ring atoms, preferably 5, 6, 9, or 10 ring atoms; having 6, 10, or 14 pi electrons shared in a cyclic array; and having, in addition to carbon atoms, between one or more heteroatoms independently selected from the group consisting of N, O, and S. For example, a heteroaryl group may be pyrimidinyl, pyridinyl, benzimidazolyl, thienyl, benzothiazolyl, benzofuranyl and indolinyl. Preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

The terms "arylene," "heteroarylene," or "heterocyclylene" are intended to mean an aryl, heteroaryl, or heterocyclyl group, respectively, as defined hereinabove, that is positioned between and serves to connect two other chemical groups.

Preferred heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, thiadiazolyl (e.g., 1,2,3-thiadiazolyl, 1,2,4-thiadiazolyl, 1,2,5-thiadiazolyl, 1,3,4-thiadiazolyl), thianthrenyl, thiazolyl, thienyl, thienothiazolyl, thienooxazolyl, thienoimidazolyl, thiophenyl, triazinyl, triazolyl (e.g., 1,2,3-triazolyl, 1,2,4-triazolyl, 1,2,5-triazolyl, 1,3,4-triazolyl), and xanthenyl.

Aromatic polycycles include, but are not limited to, bicyclic and tricyclic fused ring systems, including for example naphthyl.

Non-aromatic polycycles include, but are not limited to, bicyclic and tricyclic fused ring systems where each ring can be 4-9 membered and each ring can containing zero, 1 or more double and/or triple bonds. Suitable examples of non-aromatic polycycles include, but are not limited to, decalin, octahydroindene, perhydrobenzocycloheptene and perhydrobenzo-[f]-azulene.

Polyheteroaryl groups include bicyclic and tricyclic fused rings systems where each ring can independently be 5 or 6 membered and contain one or more heteroatom, for example, 1, 2, 3 or 4 heteroatoms, independently chosen from from O, N and S such that the fused ring system is aromatic. Suitable examples of polyheteroaryl ring systems include quinoline, isoquinoline, pyridopyrazine, pyrrolopyridine, furopyridine, indole, benzofuran, benzothiofuran, benzindole, benzoxazole, pyrroloquinoline, and the like.

Non-aromatic polyheterocyclic groups include but are not limited to bicyclic and tricyclic ring systems where each ring can be 4-9 membered, contain one or more heteratom, for example 1, 2, 3 or 4 heteratoms, independently chosen from O, N and S, and contain zero, or one or more C—C double or triple bonds. Suitable examples of non-aromatic polyheterocycles include but are not limited to, hexitol, cis-perhydro-cyclohepta[b]pyridinyl, decahydro-benzo[f][1,4]oxazepinyl, 2,8-dioxabicyclo[3.3.0]octane, hexahydro-thieno[3,2-b]thiophene, perhydropyrrolo[3,2-b]pyrrole, perhydronaphthyridine, perhydro-1H-dicyclopenta[b,e]pyran.

Mixed aryl and non-aryl polyheterocycle groups include but are not limited to bicyclic and tricyclic fused ring systems where each ring can be 4-9 membered, contain one or more heteroatom independently chosen from O, N and S and at least one of the rings must be aromatic. Suitable examples of mixed aryl and non-aryl polyheteorcycles include 2,3-dihydroindole, 1,2,3,4-tetrahydroquinoline, 5,11-dihydro-10H-dibenz[b,e][1,4]diazepine, 5H-dibenzo[b,e][1,4]diazepine, 1,2-dihydropyrrolo[3,4-b][1,5]benzodiazepine, 1,5-dihydropyrido[2,3-b][1,4]diazepin-4-one, 1,2,3,4,6,11-hexhydro-benzo[b]pyrido[2,3-e][1,4]diazepine-5-one, methylenedioxyphenyl, bis-methylenedioxyphenyl, 1,2,3,4-tetrahydronaphthalene, dibenzosuberane dihydroanthracene and 9H-fluorene.

As employed herein, and unless stated otherwise, when a moiety (e.g., alkyl, heteroalkyl, cycloalkyl, aryl, heteroaryl, heterocyclyl, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—) nitro, halohydrocarbyl, hydrocarbyl, alkyl, cycloalkyl, heterocyclyl, aryl, heteroaryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, aryloxy, cyano, and ureido groups. Preferred substituents, which are themselves not further substituted (unless expressly stated otherwise) are:

(a) halo, cyano, oxo, carboxy, formyl, nitro, amino, amidino, guanidino, (b) $C_1$-$C_5$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, $C_5$-$C_{15}$ heteroaryl or any of these rings fused or spiro-fused to a cycloalkyl, heterocyclyl, or aryl, wherein each of the foregoing is further optionally substituted with one more moieties listed in (a), above; and (c) —$(CR^{32}R^{33a})_s$—$NR^{30}R^{31}$, wherein s is from 0 (in which case the nitrogen is directly bonded to the moiety that is substituted) to 6, $R^{32}$ and $R^{33a}$ are each independently hydrogen, halo, hydroxyl or $C_1$-$C_4$alkyl, and $R^{30}$ and $R^{31}$ are each independently hydrogen, cyano, oxo, hydroxyl, -$C_1$-$C_8$ alkyl, $C_1$-$C_8$ heteroalkyl, $C_1$-$C_8$ alkenyl, carboxamido, $C_1$-$C_3$ alkyl-carboxamido, carboxamido-$C_1$-$C_3$ alkyl, amidino, $C_2$-$C_8$hydroxyalkyl, $C_1$-$C_3$ alkylaryl, aryl-$C_1$-$C_3$ alkyl, $C_1$-$C_3$ alkylheteroaryl, heteroaryl-$C_1$-$C_3$ alkyl, $C_1$-$C_3$ alkylheterocyclyl, heterocyclyl-$C_1$-$C_3$ alkyl $C_1$-$C_3$ alkylcycloalkyl, cycloalkyl-$C_1$-$C_3$ alkyl, $C_2$-$C_8$ alkoxy, $C_2$-$C_8$ alkoxy-$C_1$-$C_4$alkyl, $C_1$-$C_8$ alkoxycarbonyl, aryloxycarbonyl, aryl-$C_1$-$C_3$ alkoxycarbonyl, heteroaryloxycarbonyl, heteroaryl-$C_1$-$C_3$ alkoxycarbonyl, $C_1$-$C_8$ acyl, $C_0$-$C_8$ alkyl-carbonyl, aryl-$C_0$-$C_8$ alkyl-carbonyl, heteroaryl-$C_0$-$C_8$ alkyl-carbonyl, cycloalkyl-$C_0$-$C_8$ alkyl-carbonyl, $C_0$-$C_8$ alkyl-NH-carbonyl, aryl-$C_0$-$C_8$ alkyl-NH-carbonyl, heteroaryl-$C_0$-$C_8$ alkyl-NH-carbonyl, cycloalkyl-$C_0$-$C_8$ alkyl-NH-carbonyl, $C_0C_8$ alkyl-O-carbonyl, aryl-$C_0$-$C_8$ alkyl-O-carbonyl, heteroaryl-$C_0$-$C_8$ alkyl-O-carbonyl, cycloalkyl-$C_0$-$C_8$ alkyl-O-carbonyl, $C_1$-$C_8$ alkylsulfonyl, arylalkylsulfonyl, arylsulfonyl, heteroarylalkylsulfonyl, heteroarylsulfonyl, $C_1$-$C_8$ alkyl-NH-sulfonyl, arylalkyl-NH-sulfonyl, aryl-NH-sulfonyl, heteroarylalkyl-NH-sulfonyl, heteroaryl-NH-sulfonyl aroyl, aryl, cycloalkyl, heterocyclyl, heteroaryl, aryl-$C_1$-$C_3$ alkyl-, cycloalkyl-$C_1$-$C_3$ alkyl-, heterocyclyl-$C_1$-$C_3$ alkyl-, heteroaryl-$C_1$-$C_3$ alkyl-, or protecting group, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents selected from the group consisting of (a) above, a protecting group, and ($X^{30}$-$Y^{31}$-), wherein said heterocyclyl may also be bridged (forming a bicyclic moiety with a methylene, ethylene or propylene bridge); wherein $X^{30}$ is selected from the group consisting of $C_1$-$C_8$alkyl, $C_2$-$C_8$alkenyl-, $C_2$-$C_8$alkynyl-, -$C_0$-$C_3$alkyl-$C_2$-$C_8$alkenyl-$C_0$-$C_3$alkyl, $C_0$-$C_3$alkyl-$C_2$-$C_8$alkynyl-$C_0$-$C_3$alkyl, $C_0$-$C_3$alkyl-O-$C_0$-$C_3$alkyl-, HO-$C_0$-$C_3$alkyl-, $C_0$-$C_4$alkyl-N($R^{30}$)-$C_0$-$C_3$alkyl-, N($R^{30}$)($R^{31}$)-$C_0$-$C_3$alkyl-, N($R^{30}$)($R^{31}$)-$C_0$-$C_3$alkenyl-, N($R^{30}$)($R^{31}$)-$C_0$-$C_3$alkynyl-, (N($R^{30}$)($R^{31}$))$_2$—C=N—, $C_0$-$C_3$alkyl-S(O)$_{0-2}$-$C_0$-$C_3$alkyl-, $CF_3$-$C_0$-$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, N($R^{30}$)($R^{31}$)-heterocyclyl-$C_1$-$C_3$alkyl-, wherein the aryl, cycloalkyl, heteroaryl and heterocycyl are optionally substituted with from 1 to 3 substituents from (a); and $Y^{31}$ is selected from the group consisting of a direct bond, —O—, —N($R^{30}$)—, —C(O)—, —O—C(O)—, —C(O)—O, —N($R^{30}$)—C(O)—, —C(O)—N($R^{30}$)—, —N($R^{30}$)—C(S)—, —C(S)—N($R^{30}$)—, —N($R^{30}$)—C(O)—N($R^{31}$)—, —N($R^{30}$)—C(N$R^{30}$)—N($R^{31}$)—, —N($R^{30}$)—C(N$R^{31}$)—, —C(N$R^{31}$)—N($R^{30}$), —N($R^{30}$)—C(S)—N($R^{31}$)—, —N($R^{30}$)—C(O)—O—, —O—C(O)—N($R^{31}$)—, —N($R^{30}$)—C(S)—O—, —O—C(S)—N($R^{31}$)—, —S(O)$_{0-2}$—, —SO$_2$N($R^{31}$)—, —N($R^{31}$)—SO$_2$— and —N($R^{30}$)—SO$_2$N($R^{31}$)—.

As a non-limiting example, substituted phenyls include 2-fluorophenyl, 3,4-dichlorophenyl, 3-chloro-4-fluoro-phenyl, 2-fluoro-3-propylphenyl. As another non-limiting example, substituted n-octyls include 2,4-dimethyl-5-ethyl-octyl and 3-cyclopentyl-octyl. Included within this definition are methylenes (—CH$_2$—) substituted with oxygen to form carbonyl —CO—.

When there are two optional substituents bonded to adjacent atoms of a ring structure, such as for example phenyl, thiophenyl, or pyridinyl, the substituents, together with the atoms to which they are bonded, optionally form a 5- or 6-membered cycloalkyl or heterocycle having 1, 2, or 3 annular heteroatoms.

In a preferred embodiment, hydrocarbyl, alkyl, alkenyl, alkynyl, heteroalkyl, cycloalkyl, heterocyclic, aryl, heteroaryl, aromatic polycycle, non-aromatic polycycle, polyheteroaryl, non-aromatic polyheterocyclic and mixed aryl and non-aryl polyheterocycle groups are unsubstituted.

In other preferred embodiments, hydrocarbyl, alkyl, alkenyl, alkynyl, heteroalkyl, cycloalkyl, heterocyclic, aryl, heteroaryl, aromatic polycycle, non-aromatic polycycle, polyheteroaryl, non-aromatic polyheterocyclic and mixed aryl and non-aryl polyheterocycle groups are substituted with from 1 to 3 independently selected substituents.

Preferred substituents on alkyl groups include, but are not limited to, hydroxyl, halogen (e.g., a single halogen substituent or multiple halo substituents; in the latter case, groups such as $CF_3$ or an alkyl group bearing more than one Cl), cyano, nitro, alkyl, cycloalkyl, alkenyl, cycloalkenyl, alkynyl, heterocycle, aryl, —OR$^u$, —SR$^u$, —S(=O)R$^y$, —S(=O)$_2$R$^y$, —P(=O)$_2$R$^y$, —S(=O)$_2$OR$^y$, —P(=O)$_2$OR$^y$, —NR'R$^w$, —NR'S(=O)$_2$R$^y$, —NR'P(=O)$_2$R$^y$, —S(=O)$_2$NR'R$^w$, —P(=O)$_2$NR'R$^w$, —C(=O)OR$^y$, —C(=O)R$^u$, —C(=O)NR'R$^w$, —OC(=O)R$^u$, —OC(=O)NR'R$^w$, —NR'C(=O)OR$^y$, —NR$^{xx}$C(=O)NR'R$^w$, —NR$^{xx}$S(=O)$_2$NR'R$^w$, —NR$^{xx}$P(=O)$_2$NR'R$^w$, —NR'C(=O)R$^u$ or —NR'P(=O)$_2$R$^y$, wherein R$^u$ is hydrogen, alkyl, cycloalkyl, alkenyl, cycloalkenyl, alkynyl, heterocycle or aryl; R$^v$, R$^w$ and R$^{xx}$ are independently hydrogen, alkyl, cycloalkyl, heterocycle or aryl, or said R$^v$ and R$^w$ together with the N to which they are bonded optionally form a heterocycle; and R$^y$ is alkyl, cycloalkyl, alkenyl, cycloalkenyl, alkynyl, heterocycle or aryl. In the aforementioned exemplary substituents, groups such as alkyl, cycloalkyl, alkenyl, alkynyl, cycloalkenyl, heterocycle and aryl can themselves be optionally substituted.

Preferred substituents on alkenyl and alkynyl groups include, but are not limited to, alkyl or substituted alkyl, as well as those groups recited as preferred alkyl substituents.

Preferred substituents on cycloalkyl groups include, but are not limited to, nitro, cyano, alkyl or substituted alkyl, as well as those groups recited about as preferred alkyl substituents. Other preferred substituents include, but are not limited to, spiro-attached or fused cyclic substituents, preferably spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Preferred substituents on cycloalkenyl groups include, but are not limited to, nitro, cyano, alkyl or substituted alkyl, as well as those groups recited as preferred alkyl substituents. Other preferred substituents include, but are not limited to, spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Preferred substituents on aryl groups include, but are not limited to, nitro, cycloalkyl or substituted cycloalkyl, cycloalkenyl or substituted cycloalkenyl, cyano, alkyl or substituted alkyl, as well as those groups recited above as preferred alkyl substituents. Other preferred substituents include, but are not limited to, fused cyclic groups, especially fused cycloalkyl, fused cycloalkenyl, fused heterocycle, or fused aryl, where the aforementioned cycloalky, cylcoalkenyl, heterocycle and aryl substituents can themselves be optionally substituted. Still other preferred substituents on aryl groups (phenyl, as a non-limiting example) include, but are not limited to, haloalkyl and those groups recited as preferred alkyl substituents.

Preferred substituents on heterocylic groups include, but are not limited to, cycloalkyl, substituted cycloalkyl, cycloalkenyl, substituted cycloalkenyl, nitro, oxo (i.e., =O), cyano, alkyl, substituted alkyl, as well as those groups recited as preferred alkyl substituents. Other preferred substituents on heterocyclic groups include, but are not limited to, spiro-attached or fused cylic substituents at any available point or points of attachement, more preferably spiro-attached cycloalkyl, spiro-attached cycloalkenyl, spiro-attached heterocycle (excluding heteroaryl), fused cycloalkyl, fused cycloakenyl, fused heterocycle and fused aryl, where the aforementioned cycloalkyl, cycloalkenyl, heterocycle and aryl substituents can themselves be optionally substituted.

In a preferred embodiment, a heterocyclic group is substituted on carbon, nitrogen and/or sulfur at one or more positions. Preferred substituents on nitrogen include, but are not limited to N-oxide, alkyl, aryl, aralkyl, alkylcarbonyl, alkylsulfonyl, arylcarbonyl, arylsulfonyl, alkoxycarbonyl, or aralkoxycarbonyl. Preferred substituents on sulfur include, but are not limited to, oxo and $C_{1-6}$alkyl. In certain preferred embodiments, nitrogen and sulfur heteroatoms may independently be optionally oxidized and nitrogen heteroatoms may independently be optionally quatemized.

Especially preferred substituents on alkyl groups include halogen and hydroxy.

Especially preferred substituents on ring groups, such as aryl, heteroaryl, cycloalkyl and heterocyclyl, include halogen, alkoxy, alkyl, and haloalkyl.

Preferred substituents on aromatic polycycles include, but are not limited to, oxo, $C_1$-$C_6$alkyl, cycloalkylalkyl (e.g. cyclopropylmethyl), oxyalkyl, halo, nitro, amino, alkylamino, aminoalkyl, alkyl ketones, nitrile, carboxyalkyl, alkylsulfonyl, arylsulfonyl, aninosulfonyl and $OR^{aa}$, such as alkoxy, wherein $R^{aa}$ is selected from the group consisting of H, $C_1$-$C_6$alkyl, $C_4$-$C_9$cycloalkyl, $C_4$-$C_9$heterocycloalkyl, aryl, heteroaryl, arylalkyl, heteroarylalkyl and $(CH_2)_{0-6}Z^aR^{bb}$, wherein $Z^a$ is selected from the group consisting of O, $NR^{cc}$, S and S(O), and $R^{bb}$ is selected from the group consisting of H, $C_1$-$C_6$alkyl, $C_4$-$C_9$cycloalkyl, $C_4$-$C_9$heterocycloalkyl, $C_4$-$C_9$heterocycloalkylalkyl, aryl, mixed aryl and non-aryl polycycle, heteroaryl, arylalkyl, (e.g. benzyl), and heteroarylalkyl (e.g. pyridylmethyl); and $R^{cc}$ is selected from the group consisting of H, $C_1$-$C_6$alkyl, $C_4$-$C_9$cycloalkyl, $C_4$-$C_9$heterocycloalkyl, aryl, heteroaryl, arylalkyl (e.g. benzyl), heteroarylalkyl (e.g. pyridylmethyl) and amino acyl.

Preferred substituents on non-aromatic polycycles include, but are not limited to, oxo, $C_3$-$C_9$cycloalkyl, such as cyclopropyl, cyclobutyl, cyclopentyl, cyclohexyl and the like. Unless otherwise noted, non-aromatic polycycle substituents include both unsubstituted cycloalkyl groups and cycloalkyl groups that are substituted by one or more suitable substituents, including but not limited to, $C_1$-$C_6$alkyl, oxo, halo, hydroxy, aminoalkyl, oxyalkyl, alkylamino and $OR^{aa}$, such as alkoxy. Preferred substituents for such cycloalkyl groups include halo, hydroxy, alkoxy, oxyalkyl, alkylamino and aminoalkyl. Preferred substituents on carbon atoms of polyheteroaryl groups include but are not limited to, straight and branched optionally substituted $C_1$-$C_6$alkyl, unsaturation (i.e., there are one or more double or triple C—C bonds), acyl, oxo, cycloalky, halo, oxyalkyl, alkylamino, aminoalkyl, acylamino, $OR^{aa}$ (for example alkoxy), and a substituent of the formula —O—$(CH_2CH=CH(CH_3)(CH_2))_{1-3}H$. Examples of suitable straight and branched $C_1$-$C_6$alkyl substituents include but are not limited to methyl, ethyl, n-propyl, 2-propyl, n-butyl, sec-butyl, t-butyl and the like. Preferred substituents include halo, hydroxy, alkoxy, oxyalkyl, alkylamino and aminoalkyl. Preferably substitutions on nitrogen atoms include, for example by N-oxide or $R^{cc}$. Preferred substituents on nitrogen atoms include H, $C_1$-$C_4$alkyl, acyl, aminoacyl and sulfonyl. Preferably sulfur atoms are unsubstituted. Preferred substituents on sulfur atoms include but are not limited to oxo and lower alkyl.

Preferred substituents on carbon atoms of non-aromatic polyheterocyclic groups include but are not limited to straight and branched optionally substituted $C_1$-$C_6$alkyl, unsaturation (i.e., there are one or more double or triple C—C bonds), acyl, oxo, cycloalky, halo, oxyalkyl, alkylamino, aminoalkyl, acylamino and $OR^{aa}$, for example alkoxy. Examples of suitable straight and branched $C_1$-$C_6$alkyl substituents include but are not limited to methyl, ethyl, n-propyl, 2-propyl, n-butyl, sec-butyl, t-butyl and the like. Preferred substituents include halo, hydroxy, alkoxy, oxyalkyl, alkylamino and aminoalkyl. Preferably substitutions on nitrogen atoms include, for example, N-oxide or $R^{cc}$. Preferred N substituents include H, $C_1$-$C_4$ alkyl, acyl, aminoacyl and sulfonyl. Preferably, sulfur atoms are unsubstituted. Preferred S substituents include oxo and lower alkyl.

Preferred substituents on mixed aryl and non-aryl polyheterocycle groups include, but are not limited to, nitro or as described above for non-aromatic polycycle groups. Preferred subsituents on carbon atoms include, but are not limited to, —N—OH, =N—OH, optionally substituted alkyl, unsaturation (i.e., there are one or more double or triple C—C bonds), oxo, acyl, cycloalky, halo, oxyalkyl, alkylamino, aminoalkyl, acylamino and $OR^{aa}$, for example alkoxy. Preferably substitutions on nitrogen atoms include, for example, N-oxide or $R^{cc}$. Preferred N substituents include H, $C_{1-4}$alkyl, acyl aminoacyl and sulfonyl. Preferably sulfur atoms are unsubstituted. Preferred S substituents include oxo and lower alkyl.

A "halohydrocarbyl" is a hydrocarbyl moiety in which from one to all hydrogens have been replaced with one or more halo.

The term "halogen" or "halo" is intended to mean chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally optionally substituted. The term "sulfonamido" refers to a sulfonamide substituent attached by either the sulfur or the nitrogen atom. The term "amino" is meant to include $NH_2$, alkylamino, arylamino, and cyclic amino groups. The term "ureido" as employed herein refers to a substituted or unsubstituted urea moiety.

The term "radical" is intended to mean a chemical moiety comprising one or more unpaired electrons.

Where optional substituents are chosen from "one or more" groups it is to be understood that this definition includes all substituents being chosen from one of the specified groups or the substituents being chosen from two or more of the specified groups.

In addition, substituents on cyclic moieties (i.e., cycloalkyl, heterocyclyl, aryl, heteroaryl) include 5-6 membered mono- and 9-14 membered bi-cyclic moieties fused to the parent cyclic moiety to form a bi- or tri-cyclic fused ring system. Substituents on cyclic moieties also include 5-6 membered mono- and 9-14 membered bi-cyclic moieties attached to the parent cyclic moiety by a covalent bond to form a bi- or tri-cyclic bi-ring system. For example, an optionally substituted phenyl includes, but is not limited to, the following:

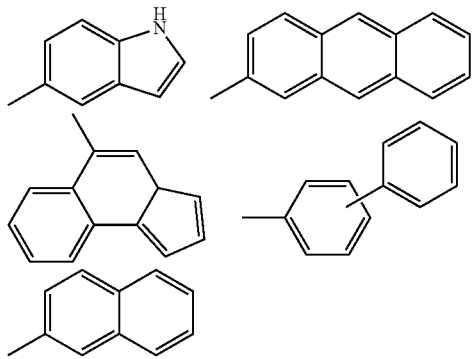

An "unsubstituted" moiety (e.g., unsubstituted cycloalkyl, unsubstituted heteroaryl, etc.) means that moiety as defined above that does not have an optional substituent. Thus, for example, "unsubstituted aryl" does not include phenyl substituted with a halo.

As used herein, "an amino protecting group" refers to any functional group commonly used to protect an a-amino group. Suitable amino protecting groups include, but are not limited to, t-butyloxycarbonyl, isoamyloxycarbonyl, o-nitrophenylsulfenyl, fluoroenylmethyloxycarbonyl, o-nitropyridinylsulfenyl and biphenylproploxycarbonyl.

An "amino acid residue" refers to any residue of a natural or unnatural amino acid, non-limiting examples of which are residues of alanine, arginine, asparagine, aspartic acid, cysteine, homocysteine, glutamine, glutamic acid, isoleucine, norleucine, glycine, phenylglycine, leucine, histidine, methionine, lysine, phenylalanine, homophenylalanine, ornithine, praline, serine, homoserine, valine, norvaline, threonine, tryptophane, tyrosine and the like. With the exception of glycine, all amino acids may be in the D-, L- or D,L-form.

The term "radical" is intended to mean a chemical moiety comprising one or more unpaired electrons.

Some compounds of the invention may have one or more chiral centers and/or geometric isomeric centers (E- and Z-isomers), and it is to be understood that the invention encompasses all such optical, diastereoisomers and geometric isomers. The invention also comprises all tautomeric forms of the compounds disclosed herein.

All of the compounds in this application were named using Chemdraw Ultra version 9 or 10, which are available through Cambridgesoft.co, 100 Cambridge Park Drive, Cambridge, Mass. 02140.

Compounds

In one embodiment, the invention provides prodrugs of inhibitors of histone deacetylase, the prodrugs represented by formula (2):

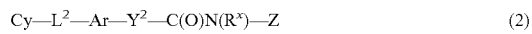

$$Cy\!-\!L^2\!-\!Ar\!-\!Y^2\!-\!C(O)N(R^x)\!-\!Z \qquad (2)$$

and pharmaceutically acceptable salts thereof, wherein

Cy is H or is cycloalkyl, aryl, heteroaryl, or heterocyclyl, any of which may be optionally substituted, provided that Cy is not a (spirocycloalkyl)heterocyclyl;

$L^2$ is $C_1$-$C_6$ saturated alkylene or $C_2$-$C_6$ alkenylene, wherein the alkylene or alkenylene optionally may be substituted, and wherein one or two of the carbon atoms of the alkylene is optionally replaced by a heteroatomic moiety independently selected from the group consisting of O; NR', R' being alkyl, acyl, or hydrogen; S; S(O); or $S(O)_2$;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^2$ is a chemical bond or a straight- or branched-chain saturated alkylene, which may be optionally substituted, provided that the alkylene is not substituted with a substituent of the formula —C(O)R wherein R comprises an a-amino acyl moiety;

$R^x$ is H, —OH, or —$R^{20}$;

Z is —O—$R^{20}$ or —$R^{21}$ wherein each —$R^{20}$ is selected from the group consisting of
—C(O)—$R^{10}$, —C(O)—$[C(R^{40})(R^{41})]_n$OP(O)(OH)(OH),
—C(O)N($R^{31}$)$[C(R^{40})(R^{41})]_n$SO$_2$OH, and
—C(O)NH$[C(R^{40})(R^{41})]_n$C(O)O$[C(R^{40})(R^{41})]''R^{42}$;

each $R^{10}$ is independently selected from the group consisting of
—$[C(R^{40})(R^{41})]_n R^{42}$,
—N($R^{30}$)$[C(R^{40})(R^{41})]_n$
—O $[C(R^{40})(R^{41})]_n$,
—$[C(R^{40})(R^{41})]_n$NHC(O)$[C(R^{40})(R^{41})]_n R^{42}$,
—$[C(R^{40})(R^{41})]_n$NHC(O)O$[C(R^{40})(R^{41})]_n R^{42}$,
—$[C(R^{40})(R^{41})]_n$NHC(O)$[C(H)(NH_2.HX)][C(R^{40})(R^{41})]_n R^{42}$,
—$[C(R^{40})(R^{41})]_n$NHC(O)$[C(R^{40})(R^{41})]_n$NH$[C(R^{40})(R^{41})]_n$NH$_2$.HX
—$[C(R^{40})(R^{41})]_n$N($R^{30}$)C(O)C$[(H)(N(H)C(O))][C(R^{40})(R^{41})]_n R^{42}][C(R^{40})(R^{41})]_n$N(H)C(O)—$[C(R^{40})(R^{41})]_n R^{42}$, —[C(R$^{40}$)(R$^{41}$)]$_n$NHR$^{60}$,
—[C(R$^{40}$)(R$^{41}$)]$_n$C(O)N[[C(R$^{40}$)(R$^{41}$)]$_n$C(O)N(H)CH$_2$R$^{56}$]$_2$,
—[C(R$^{40}$)(R$^{41}$)]$_n$NHC(O)[C(R$^{40}$)(R$^{41}$)]$_n$N(R$^{60}$)[[C(R$^{40}$)(R$^{41}$)]$_n$N(H)(R$^{60}$)],
—[C(R$^{40}$)(R$^{41}$)]$_n$N(R$^{30}$)C(O)[C(H)(N(H)R$^{60}$)][C(R$^{40}$)(R$^{41}$)]$_n$N(H)R$^{60}$,
—[C(R$^{40}$)(R$^{41}$)]$_n$N(R$^{30}$)C(O)[C(R$^{40}$)(R$^{41}$)]$_n$N(H)C(O)[C(R$^{40}$)(R$^{41}$)]$_n$N(H)R$^{56}$,
—C[(H)(N(H)R$^{60}$)][C(R$^{40}$)(R$^{41}$)]$_n$N(H)R$^{60}$,
—[C(R$^{40}$)(R$^{41}$)]$_n$NHC(O)[C(H)(NH$_2$)](CR$^{40}$R$^{41}$)$_n$NHR$^{60}$,
—R$^{50}$,
—R$^{50}$C(O)C[(H)(NH$_2$.HX)][C(R$^{40}$)(R$^{41}$)]$_n$NH$_2$.HX
—R$^{50}$C(O)C[(H)(N(H)R$^{60}$)][C(R$^{40}$)(R$^{41}$)]$_n$N(H)R$^{60}$,
—R$^{50}$C(O)[C(R$^{40}$)(R$^{41}$)]$_n$NHC(O)NH)[C(R$^{40}$)(R$^{41}$)]$_n$R$^{56}$,
—R$^{50}$R$^{60}$,
—[C(R$^{40}$)(R$^{41}$)]$_n$OR$^{51}$,
—R$^{45}$ amino.HX,
—R$^{45}$N(H)C(O)[C(R$^{40}$)(R$^{41}$)]$_n$N(R$^{30}$)(R$^{31}$), and
—R$^{45}$[C(R$^{40}$)(R$^{41}$)]$_n$NHC(O)[C(H)(NH$_2$.HX)][C(R$^{40}$)(R$^{41}$)]$_n$N(R$^{30}$)(R$^{31}$);

R$^{21}$ is selected from [C(R$^{40}$)(R$^{41}$)]$_n$R$^{52}$[C(R$^{40}$)(R$^{41}$)]$_n$ and [C(R$^{40}$)(R$^{41}$)]$_n$OH;

R$^{30}$ and R$^{31}$ are each independently selected from hydrogen and hydrocarbyl;

R$^{40}$ and R$^{41}$ are each independently selected from hydrogen, NH$_2$, optionally substituted alkyl, optionally substituted arylalkyl, and oxo, or R$^{40}$ and R$^{41}$ together with the carbon atom to which they are attached form an optionally substituted cycloalkyl;

R$^{42}$ is selected from hydrogen, optionally substituted alkyl, optionally substituted aryl, —NH$_2$.HX, optionally substituted cycloalkyl, optionally substituted alkoxy, acyl, —NHC(O)CH$_3$, and —OC(O)CH$_3$;

R$^{45}$ is optionally substituted arylene;

R$^{50}$ is selected from the group consisting of —[C(R$^{40}$)(R$^{41}$)]$_t$R$^{51}$, —[C(R$^{40}$)(R$^{41}$)]$_t$O—R$^{51}$, and —[C(R$^{40}$)(R$^{41}$)]$_t$C(O)R$^{51}$, where t is an integer from 0-4;

R$^{51}$ is a 4-8 membered optionally substituted heterocycloalkyl or heterocycloalkenyl comprising at least one nitrogen ring atom;

R$^{56}$ is —[C(R$^{40}$)(R$^{41}$)OC(R$^{40}$)(R$^{41}$)]$_m$H;

R$^{60}$ is —C(O)R$^{56}$;

X is a salt-forming radical, preferably halide, most preferably chloride;

each m is independently an integer from 1 to 20, or from 1 to 10, or from 1 to 5; and each n is independently an integer from 0 to 6.

In certain embodiments of the invention the compounds are present as salts. In certain embodiments of the invention the salts are halide salts. In certain embodiments of the invention the salts are chloride salts.

In certain preferred embodiments, Cy is C$_6$-C$_{14}$ aryl, more preferably C$_6$-C$_{10}$ aryl, and most preferably phenyl or naphthyl, any of which may be optionally substituted. In certain other preferred embodiments, Cy is heteroaryl. In some preferred embodiments, the heteroaryl group is selected from the group consisting of thienyl, benzothienyl, furyl, benzofuryl, quinolyl, isoquinolyl, and thiazolyl, any of which may be optionally substituted. In certain particularly preferred embodiments, Cy is selected from the group consisting of phenyl, naphthyl, thienyl, benzothienyl, and quinolyl, any of which may be optionally substituted. In certain other preferred embodiments, Cy is phenyl, pyridine or indole, more preferably phenyl or indole. In certain preferred embodiments, Cy is substituted with one or more substituents selected from the group consisting of trihaloalkyl (preferably trifluoroalkyl), halogen, CN, amidine, sulfone, alkylsulfone, imidate and alkylimidate. In certain preferred embodiments, Cy is phenyl substituted with one or more substituents selected from the group consisting of trihaloalkyl (preferably trifluoroalkyl), halogen, CN, amidine, sulfone, alkylsulfone, imidate and alkylimidate, preferably selected from the group consisting of trihaloalkyl (preferably trifluoroalkyl) and halogen. In certain preferred embodiment, Cy is unsubstituted phenyl Preferably, Ar is C$_6$-C$_{14}$ arylene, more preferably C$_6$-C$_{10}$ arylene, any of which may be additionally substituted. In certain preferred embodiments, Ar is phenylene, preferably 4-phenylene. In some preferred embodiments, the phenylene is fused to an aryl or heteroaryl ring, or to a saturated or partially unsaturated cycloalkyl or heterocyclic ring, any of which groups also may be optionally substituted.

Y$^1$ is a chemical bond or is a straight- or branched-chain alkylene, which may be optionally substituted. In some preferred embodiments, Y$^1$ is a chemical bond, and the group —C(O)NH—Z is directly attached to Ar. In some other preferred embodiments, Y$^1$ is alkylene, preferably saturated alkylene. Preferably, the saturated alkylene is C$_1$-C$_8$ alkylene, more preferably C$_1$-C$_6$ alkylene, still more preferably C$_1$-C$_3$ alkylene, and yet still more preferably C$_1$-C$_2$ alkylene, any of which may be optionally substituted. In some particularly preferred embodiments, Y$^1$ is methylene.

In some preferred embodiments, L$^2$ is saturated C$_1$-C$_8$ alkylene, more preferably C$_1$-C$_6$ alkylene, still more preferably C$_1$-C$_4$ alkylene, any of which groups may be optionally substituted. In some other preferred embodiments, L$^2$ is C$_2$-C$_8$ alkenylene, more preferably C$_2$-C$_6$ alkenylene, and still more preferably C$_2$-C$_4$ alkenylene, any of which groups may be optionally substituted. The alkylene or alkenylene group may be substituted at one or more carbon positions with a substituent preferably selected from the list of preferred substituents recited above. More preferably, L$^2$ is substituted at one or two positions with a substituent independently selected from the group consisting of C$_1$-C$_6$ alkyl, C$_6$-C$_{10}$ aryl, amino, oxo, hydroxy, C$_1$-C$_4$ alkoxy, and C$_6$-C$_{10}$ aryloxy. In some particularly preferred embodiments, the alkylene or alkenylene group is substituted with one or two oxo or hydroxy groups.

In some preferred embodiments, L$^2$ is C$_1$-C$_6$ saturated alkylene, wherein one of the carbon atoms of the saturated alkylene is replaced by a heteroatom moiety selected from the group consisting of O; NR', R' being alkyl, acyl, or hydrogen; S; S(O); or S(O)$_2$. Preferably, the carbon atom adjacent to Cy is replaced by a heteroatom moiety. In some particularly preferred embodiments, L$^2$ is selected from the group consisting of —S—(CH$_2$)$_2$—, —S(O)—(CH$_2$)$_2$—, —S(O)$_2$—(CH$_2$)$_2$—, —S—(CH$_2$)$_3$—, —S(O)—(CH$_2$)$_3$—, and —S(O)$_2$—(CH$_2$)$_3$—.

In some preferred embodiments of the prodrugs of inhibitors of histone deacetylase, Z is —O—R$^{20}$ wherein R$^{20}$ is —C(O)—R$^{10}$.

Naturally-occurring or non-naturally occurring amino acids are used to prepare the prodrugs of the invention. In particular, standard amino acids suitable as a prodrug moiety include valine, leucine, isoleucine, methionine, phenylalanine, asparagine, glutamic acid, glutamine, histidine, lysine, arginine, aspartic acid, glycine, alanine, serine, threonine, tyrosine, tryptophan, cysteine and proline. Particularly preferred are L-amino acids. Optionally an included amino acid is an α-, β-, or γ-amino acid. Also, naturally-occurring, non-standard amino acids can be utilized in the compositions and methods of the invention. For example, in addition to the standard naturally occurring amino acids commonly found in proteins, naturally occurring amino acids also illustratively include 4-hydroxyproline,.gamma.-carboxyglutamic acid, selenocysteine, desmosine, 6-N-methyllysine,.epsilon.-N,N,N-trimethyllysine, 3-methylhistidine, O-phosphoserine, 5-hydroxylysine,.epsilon.-N-acetyllysine,. omega-N-methylarginine, N-acetylserine,.gamma.-aminobutyric acid, citrulline, ornithine, azaserine, homocysteine,. beta.-cyanoalanine and S-adenosylmethionine. Non-naturally occurring amino acids include phenyl glycine, meta-tyrosine, para-amino phenylalanine, 3-(3-pyridyl)-L-alanine-, 4-(trifluoromethyl)-D-phenylalanine, and the like.

In some embodiments, the prodrugs of inhibitors of histone deacetylase of the invention comprise those of formula (2) as defined above, wherein
  Cy is optionally substituted aryl, preferably optionally substituted phenyl;
  Ar is optionally substituted aryl, preferably optionally substituted phenyl;
  $R^x$ is —H, —OH or $R^{20}$; and
  Z is —O—$R^{20}$ or $R^{21}$.

In other embodiments, the prodrugs of inhibitors of histone deacetylase of the invention comprise those of formula (2) as defined above, wherein
  Cy is optionally substituted aryl, preferably optionally substituted phenyl;
  Ar is optionally substituted aryl, preferably optionally substituted phenyl;
  $R^x$ is —H, —OH, or $R^{20}$; and
  Z is —O—$R^{20}$ or $R^{21}$, wherein
  $R^{20}$ is selected from —C(O)—$R^{10}$, —C(O)—[C($R^{40}$)($R^{41}$)]$_{1-4}$—OP(O)(OH)(OH), —C(O)N($R^{31}$)(C$R^{40}R^{41}$)$_n$ SO$_2$OH, and —C(O)NH(C$R^{40}R^{41}$)$_n$C(O))—(C$R^{40}R^{41}$)$_n R^{42}$.

In other embodiments, the prodrugs of inhibitors of histone deacetylase of the invention comprise those of formula (2) as defined above, wherein
  Cy is optionally substituted aryl, preferably optionally substituted phenyl;
  Ar is optionally substituted aryl, preferably optionally substituted phenyl;
  $R^x$ is —H or —OH; and
  Z is —O—$R^{20}$ or $R^{21}$.

In other embodiments, the prodrugs of inhibitors of histone deacetylase of the invention comprise those of formula (2) as defined above, wherein
  Cy is optionally substituted aryl, preferably optionally substituted phenyl;
  Ar is optionally substituted aryl, preferably optionally substituted phenyl;
  $R^x$ is —H or —OH; and
  Z is —O—$R^{20}$ or $R^{21}$, wherein
  $R^{20}$ is —C(O)—$R^{10}$.

In other embodiments, the prodrugs of inhibitors of histone deacetylase of the invention comprise those of formula (2) as defined above, wherein
  Cy is optionally substituted aryl, preferably optionally substituted phenyl, wherein the substituents are preferably selected from the group consisting of —CF$_3$, halo, heterocyclyl and fused heterocyclyl;
  $L^2$ is saturated C$_3$alkyl or C$_4$alkyl, preferably unsubstituted;
  Ar is optionally substituted aryl, preferably optionally substituted phenyl;
  $Y^2$ is C$_1$alkyl or C$_2$alkyl, preferably C$_1$alkyl, optionally substituted;
  $R^x$ is H;
  Z is —O—$R^{20}$;
  $R^{20}$ is —C(O)—$R^{10}$;
  each $R^{10}$ is independently selected from the group consisting of
    —[C($R^{40}$)($R^{41}$)]$_n R^{42}$,
    —[C($R^{40}$)($R^{41}$)]$_n$NHC(O)[C(H)(NH$_2$.HX)][C($R^{40}$)($R^{41}$)]$_n R^{42}$,
    —[C($R^{40}$)($R^{41}$)]$_n$NHC(O)[C($R^{40}$)($R^{41}$)]$_n$NH[C($R^{40}$)($R^{41}$)]$_n$NH$_2$.HX
    —[C($R^{40}$)($R^{41}$)]$_n$N($R^{30}$)C(O)[C(H)(N(H)$R^{60}$)][C($R^{40}$)($R^{41}$)]$_n$N(H)$R^{60}$,
    —$R^{50}$, and
    —$R^{50}R^{60}$, where
  $R^{30}$ and $R^{31}$ are each independently selected from hydrogen and hydrcarbyl;
  $R^{40}$ and $R^{41}$ are each independently selected from hydrogen, NH$_2$, NH$_2$.HX, alkyl, arylalkyl, and oxo, or $R^{40}$ and $R^{41}$ together with the carbon atom to which they are attached form an optionally substituted cycloalkyl;
  $R^{42}$ is selected from hydrogen, acyl, optionally substituted alkyl, optionally substituted aryl, —NH$_2$.HX, optionally substituted cycloalkyl, optionally substituted alkoxy, —NHC(O)CH$_3$, —OC(O)CH$_3$;
  $R^{50}$ is selected from the group consisting of —[C($R^{40}$)($R^{41}$)]$_t R^{51}$—, —[C($R^{40}$)($R^{41}$)]$_t$O—$R^{51}$, and —[C($R^{40}$)($R^{41}$)]$_t$C(O)—$R^{51}$, where t is an integer from 0-4;
  $R^{51}$ is a 4-8 membered optionally substituted heterocycloalkyl comprising at least one nitrogen ring atom to which a substituent group is attached;
  $R^{56}$ is —[C($R^{40}$)($R^{41}$)—O—C($R^{40}$)($R^{41}$)]$_m$H;
  $R^{60}$ is —C(O)$R^{56}$;
  X is a salt-forming radical, preferably, halide, most preferably chloride;
  each m is independently an integer from 1 to 20, or from 1 to 10, or from 1 to 5; and
  each n is independently 0, 1, 2, 3, 4, 5, or 6.

In other embodiments, the prodrugs of inhibitors of histone deacetylase of the invention comprise those of formula (2) as defined above, wherein
  Cy is optionally substituted aryl, preferably optionally substituted phenyl, wherein the substituents are preferably selected from the group consisting of —CF$_3$, halo, heterocyclyl and fused heterocyclyl;
  $L^2$ is saturated C$_3$alkyl or C$_4$alkyl, preferably unsubstituted;
  Ar is optionally substituted aryl, preferably optionally substituted phenyl;
  $Y^2$ is C$_1$alkyl or C$_2$alkyl, preferably C$_1$alkyl, optionally substituted;
  $R^x$ is —H or —OH, preferably H;
  Z is —O—$R^{20}$;
  $R^{20}$ is —C(O)—$R^{10}$;
  each $R^{10}$ is independently selected from the group consisting of
    —[C($R^{40}$)($R^{41}$)]$_n$NHC(O)[C(H)(NH$_2$.HX)][C($R^{40}$)($R^{41}$)]$_n R^{42}$,
    —[C($R^{40}$)($R^{41}$)]$_n$NHC(O)[C($R^{40}$)($R^{41}$)]$_n$NH[C($R^{40}$)($R^{41}$)]$_n$NH$_2$.HX,
    —[C($R^{40}$)($R^{41}$)]$_n$N($R^{30}$)C(O)C [(H)(N(H)$R^{60}$)][C($R^{40}$)($R^{41}$)]$_n$N(H)$R^{60}$,
    —$R^{50}$,
    —$R^{50}R^{60}$, and
    —[C($R^{40}$)($R^{41}$)]$_n$NHC(O)(C$R^{40}R^{41}$)$_n$NH[C($R^{40}$)($R^{41}$)]$_n$NH$_2$.HX, where $R^{30}$ and $R^{31}$ are each independently selected from hydrogen and hydrcarbyl;

$R^{40}$ and $R^{41}$ are each independently selected from hydrogen, $NH_2$, $NH_2.HX$, and alkyl, or $R^{40}$ and $R^{41}$ together with the carbon atom to which they are attached form an optionally substituted cycloalkyl;

$R^{42}$ is selected from hydrogen, acyl, optionally substituted alkyl, optionally substituted aryl, —$NH_2.HX$, optionally substituted cycloalkyl, optionally substituted alkoxy, —$NHC(O)CH_3$, —$OC(O)CH_3$;

$R^{45}$ is optionally substituted aryl;

$R^{50}$ is selected from the group consisting of —$[C(R^{40})(R^{41})]_tR^{51}$—, —$[C(R^{40})(R^{41})]_tO$—$R^{51}$, and —$[C(R^{40})(R^{41})]_tC(O)$—$R^{51}$, where t is an integer from 0-4;

$R^{51}$ is a 4-8 membered optionally substituted heterocycloalkyl comprising at least one nitrogen ring atom to which a substituent group is attached;

$R^{56}$ is —$[C(R^{40})(R^{41})$—$O$—$C(R^{40})(R^{41})]_mH$;

$R^{60}$ is —$C(O)R^{56}$;

X is a salt forming radical, preferably halide, most preferably chloride;

each m is independently an integer from 1 to 20, or from 1 to 10, or from 1 to 5; and each n is independently 0, 1, 2, 3, 4, 5, or 6.

In other embodiments, the prodrugs of inhibitors of histone deacetylase of the invention comprise those of formula (2) as defined above, wherein Cy is optionally substituted phenyl, wherein the substituents are preferably selected from the group consisting of —$CF_3$, halo, heterocyclyl and fused heterocyclyl;

$L^2$ is saturated unsubstituted $C_4$alkyl;

Ar is optionally substituted phenyl;

$Y^2$ is $C_1$alkyl or $C_2$alkyl, preferably $C_1$alkyl, optionally substituted;

$R^x$ is —H or —OH, preferably H;

Z is —O—$R^{20}$;

$R^{20}$ is —$C(O)$—$R^{10}$;

each $R^{10}$ is independently selected from the group consisting of

—$[C(R^{40})(R^{41})]_nNHC(O)[C(H)(NH_2.HX)][C(R^{40})(R^{41})]_n R^{42}$,

—$[C(R^{40})(R^{41})]_nNHC(O)[C(R^{40})(R^{41})]_nNH[C(R^{40})(R^{41})]_nNH_2.HX$,

—$[C(R^{40})(R^{41})]_nN(R^{30})C(O)[C(H)(N(H)R^{60})][C(R^{40})(R^{41})]_nN(H)R^{60}$,

—$R^{50}$, and

—$R^{50}R^{60}$, here $R^{30}$ and $R^{31}$ are each independently selected from hydrogen and hydrcarbyl;

$R^{40}$ and $R^{41}$ are each independently selected from hydrogen, $NH_2$, $NH_2.HX$, and alkyl, or $R^{40}$ and $R^{41}$ together with the carbon atom to which they are attached form an optionally substituted cycloalkyl;

$R^{42}$ is selected from hydrogen, acyl, optionally substituted alkyl, optionally substituted aryl, —$NH_2.HX$, optionally substituted cycloalkyl, optionally substituted alkoxy, —$NHC(O)CH_3$, —$OC(O)CH_3$;

$R^{45}$ is optionally substituted aryl;

$R^{50}$ is selected from the group consisting of —$[C(R^{40})(R^{41})]_tR^{51}$—, —$[C(R^{40})(R^{41})]_tO$—$R^{51}$, and —$[C(R^{40})(R^{41})]_tC(O)$—$R^{51}$, where t is an integer from 0-4;

$R^{51}$ is a 4-8 membered optionally substituted heterocycloalkyl comprising at least one nitrogen ring atom to which a substituent group is attached;

$R^{56}$ is —$[C(R^{40})(R^{41})$—$O$—$C(R^{40})(R^{41})]_mH$;

$R^{60}$ is —$C(O)R^{56}$;

X is a salt-forming radical, preferably halide, most preferably chloride.

each m is independently an integer from 1 to 20, or from 1 to 10, or from 1 to 5; and each n is independently 0, 1, 2, 3, 4, 5, or 6.

In other embodiments, the prodrugs of inhibitors of histone deacetylase of the invention comprise those of formula (2) as defined above, wherein Cy is optionally substituted aryl, preferably optionally substituted phenyl, wherein the substituents are preferably selected from the group consisting of —$CF_3$, halo, heterocyclyl and fused heterocyclyl;

$L^2$ is saturated $C_3$alkyl or $C_4$alkyl, preferably unsubstituted;

Ar is optionally substituted aryl, preferably optionally substituted phenyl;

$Y^2$ is $C_1$alkyl or $C_2$alkyl, preferably $C_1$alkyl, optionally substituted;

$R^x$ is H or OH, preferably H;

Z is —O—$R^{20}$;

$R^{20}$ is —$C(O)$—$R^{10}$;

each $R^{10}$ is independently selected from the group consisting of $R^{50}R^{60}$ and —$[C(R^{40})(R^{41})]_nN(R^{30})C(O)[C(H)(N(H)R^{60})][C(R^{40})(R^{41})]_nN(H)R^{60}$, $R^{30}$ and $R^{31}$ are each independently selected from hydrogen and hydrcarbyl;

$R^{40}$ and $R^{41}$ are each independently selected from hydrogen, $NH_2$, $NH_2.HX$, and alkyl, or $R^{40}$ and $R^{41}$ together with the carbon atom to which they are attached form an optionally substituted cycloalkyl;

$R^{50}$ is selected from the group consisting of —$[C(R^{40})(R^{41})]_tR^{51}$—, —$[C(R^{40})(R^{41})]_tO$—$R^{51}$, and —$[C(R^{40})(R^{41})]_tC(O)$—$R^{51}$, where t is an integer from 0-4;

$R^{51}$ is a 4-8 membered optionally substituted heterocycloalkyl comprising at least one nitrogen ring atom to which a substituent group is attached;

$R^{56}$ is —$[C(R^{40})(R^{41})$—$O$—$C(R^{40})(R^{41})]_mH$;

$R^{60}$ is —$C(O)R^{56}$;

each m is independently an integer from 1 to 20, or from 1 to 10, or from 1 to 5; and each n is independently 0, 1, 2, 3, 4, 5, or 6.

Preferred prodrugs of the invention include those in Table A:

TABLE A

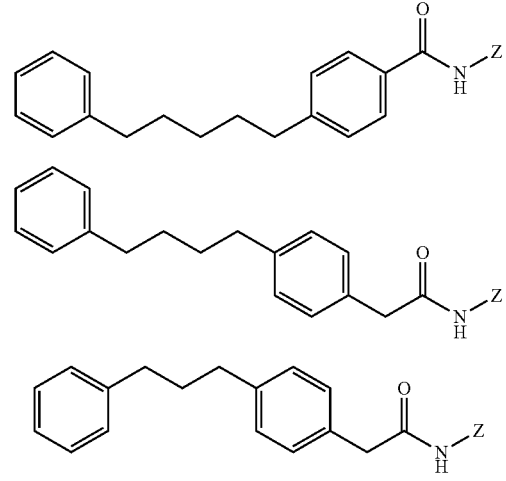

TABLE A-continued

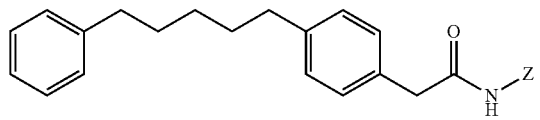

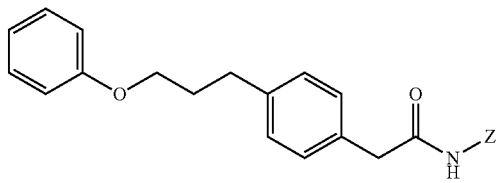

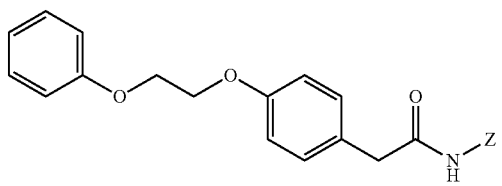

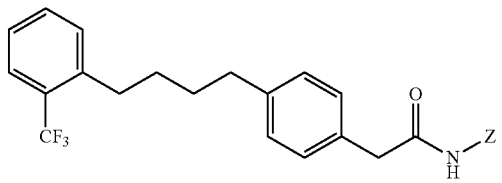

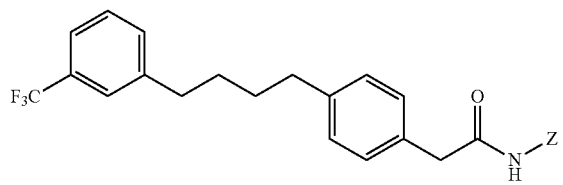

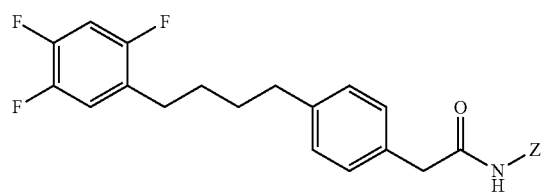

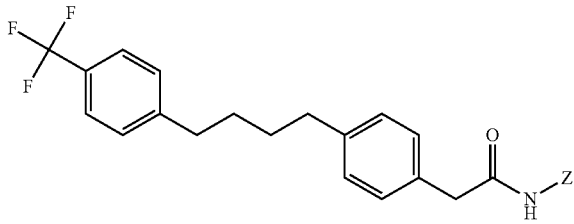

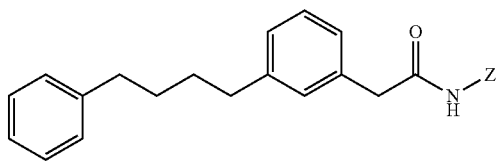

TABLE A-continued

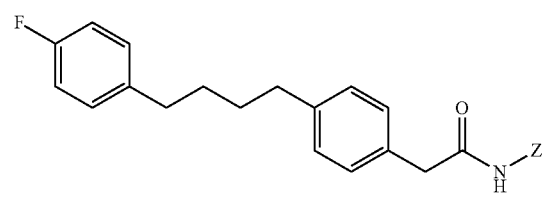

Preferred prodrug compounds of the invention are cleavable (e.g., hydrolysable) in plasma and/or in a bloodstream of warm-blooded mammals into compounds (cleavage products) in which Z in formula (2) is —OH. Such cleavage products are active histone deacetylase inhibitors.

Preferred cleavage products of the prodrug compounds of the invention include those in Table A in which Z is —OH.

In one preferred embodiment of the invention, the cleavage product is

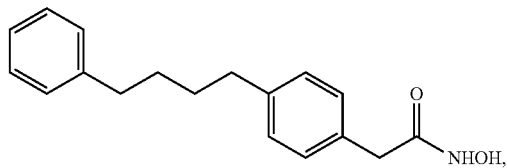

known as N-hydroxy-2-(4-(4-phenylbutyl)phenyl)acetamide, and referred to hereinafter as "compound 1" or "hydroxamate 1."

All compounds of the invention can be racemic or diastereomerically or enantiomerically enriched. In addition, compounds of the invention can be in the form of a hydrate, solvate, pharmaceutically acceptable salt, and/or complex.

In one preferred embodiment of the invention, —$R^{20}$ is —C(O)—$R^{10}$.

In one embodiment, $R^{10}$ is —[C($R^{40}$)($R^{41}$)]$_n$$R^{42}$ where $R^{42}$ is selected from hydrogen, optionally substituted alkyl, optionally substituted cycloalkyl, and optionally substituted alkoxy. Representative compounds include

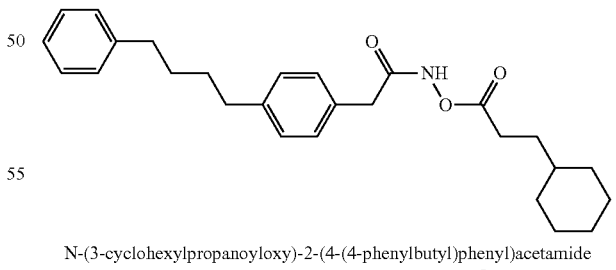

N-(3-cyclohexylpropanoyloxy)-2-(4-(4-phenylbutyl)phenyl)acetamide

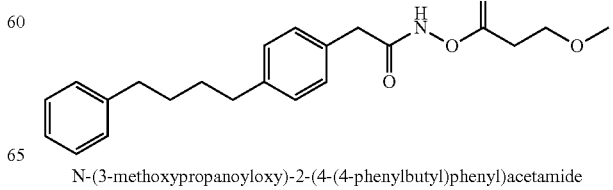

N-(3-methoxypropanoyloxy)-2-(4-(4-phenylbutyl)phenyl)acetamide

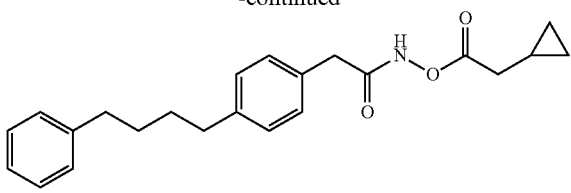

N-(2-cyclopropylacetoxy)-2-(4-(4-phenylbutyl)phenyl)acetamide

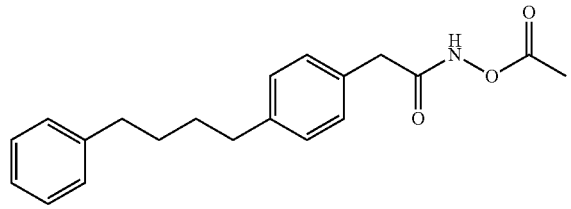

N-acetoxy-2-(4-(4-phenylbutyl)phenyl)acetamide

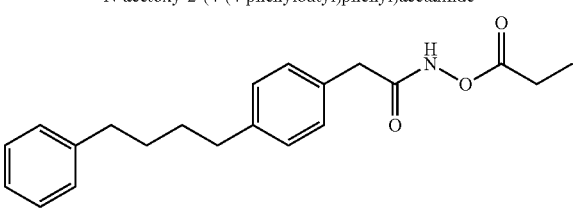

2-(4-(4-phenylbutyl)phenyl)-N-(propionyloxy)acetamide

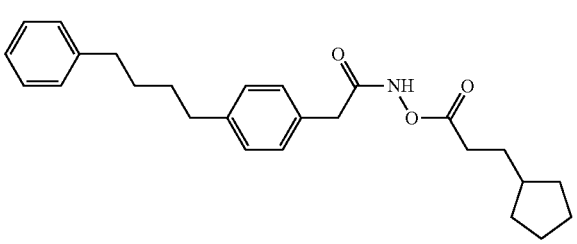

N-(3-cyclopentylpropanoyloxy)-2-(4-(4-phenylbutyl)phenyl)acetamide

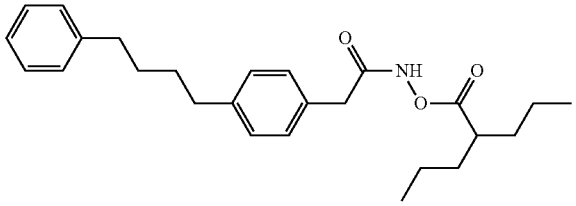

2-(4-(4-Phenylbutyl)phenyl)-N-(2-propylpentanoyloxy)acetamide

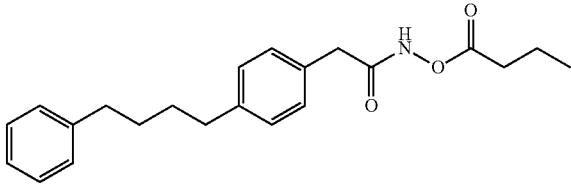

N-(butyryloxy)-2-(4-(4-phenylbutyl)phenyl)acetamide

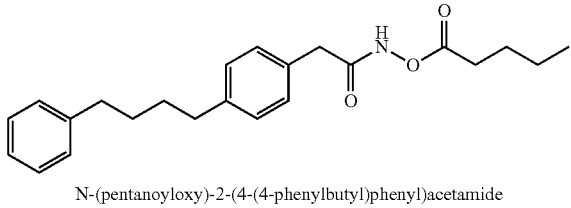

N-(pentanoyloxy)-2-(4-(4-phenylbutyl)phenyl)acetamide and their pharmaceutically acceptable salts.

In one embodiment of the invention $R^{10}$ is $-R^{50}$ where $R^{50}$ is selected from the group consisting of $-[C(R^{40})(R^{41})]_t R^{51}-$, $-[C(R^{40})(R^{41})]_t O-R^{51}-$, and $-[C(R^{40})(R^{41})]_t C(O)-R^{51}$, where t is an integer from 0-4, and $R^{51}$ is a 4-8 membered optionally substituted heterocycloalkyl or heterocycloalkenyl comprising at least one nitrogen ring atom. Representative compounds include

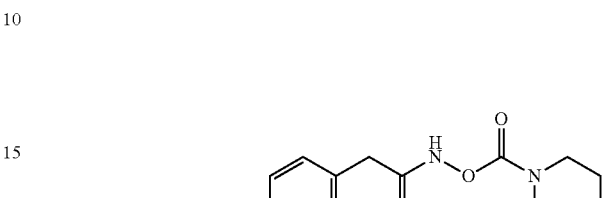

N-(morpholine-4-carbonyloxy)-2-(4-(4-phenylbutyl)phenyl)acetamide

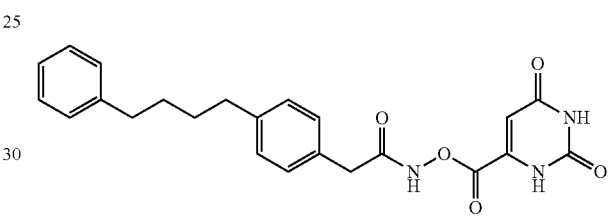

N-(2,6-Dioxo-1,2,3,6-tetrahydropyrimidine-4-carbonyloxy)-2-(4-(4-phenylbutyl)phenyl)acetamide

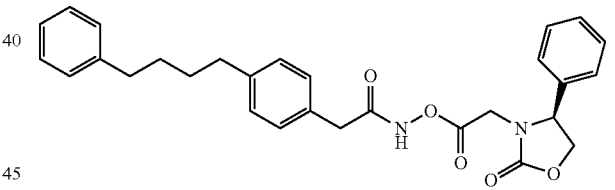

(S)-N-(2-(2-oxo-4-phenyloxazolidin-3-yl)acetoxy)-2-(4-(4-phenylbutyl)phenyl)acetamide and their pharmaceutically acceptable salts.

In one embodiment of the invention the prodrugs exist in salt form. Preferably the salts are the halide salts, most prefereably the chloride salts. In one embodiment $R^{10}$ is $-[C(R^{40})(R^{41})]_n R^{42}$ where $R^{42}$ is $-NH_2 \cdot HX$. In one embodiment $R^{10}$ is $-[C(R^{40})(R^{41})]_n NHC(O)[(C(H)(NH_2 \cdot X)][C(R^{40})(R^{41})]_n R^{42}$ where $R^{42}$ is $-NH_2 \cdot HX$. In one embodiment $R^{10}$ is $-[C(R^{40})(R^{41})]_n NHC(O)[C(R^{40})(R^{41})]_n NH[C(R^{40})(R^{41})]_n NH_2 \cdot HX$. In one embodiment of the invention $R^{10}$ is $-R^{50}$ where $R^{50}$ is selected from the group consisting of $-[C(R^{40})(R^{41})]_t R^{51}-$, $-[C(R^{40})(R^{41})]_t O-R^{51}-$, and $-[C(R^{40})(R^{41})]_t C(O)-R^{51}$, where t is an integer from 0-4, and $R^{51}$ is a 4-8 membered optionally substituted heterocycloalkyl or heterocycloalkenyl comprising at least one nitrogen ring atom, wherein a salt is formed at the at least one nitrgoen ring atom. Representative salts include

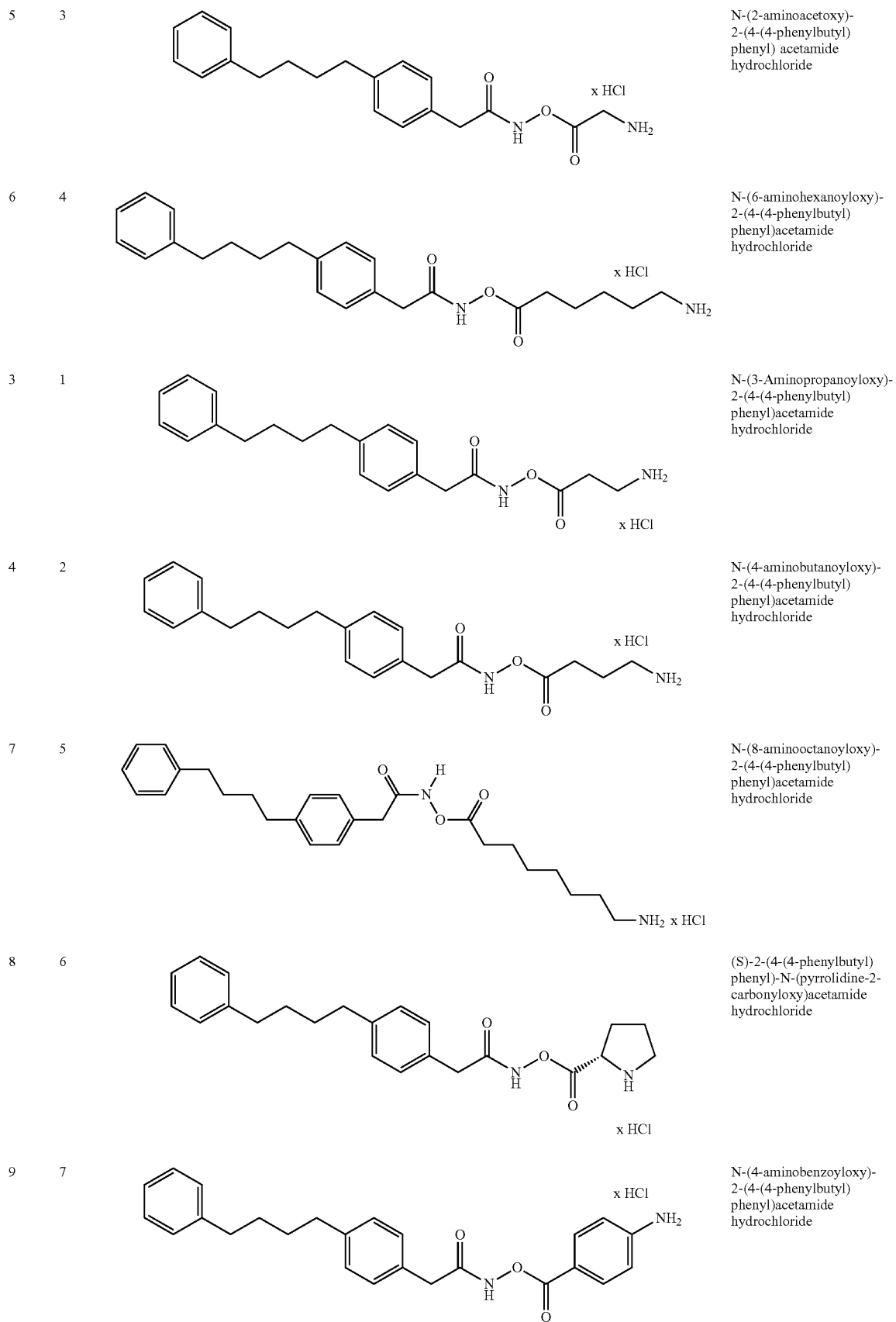

-continued

| | | Structure | Name |
|---|---|---|---|
| 14 | 9 | 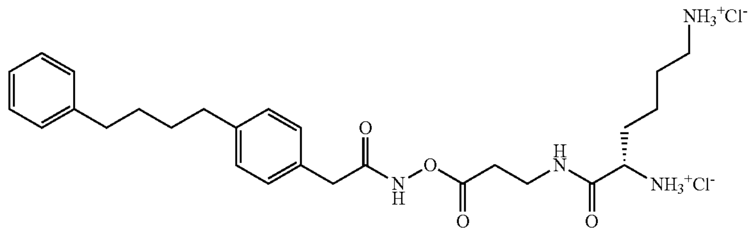 | ((S)-2,6-Diamino-N-(3-oxo-3-(2-(4-(4-phenylbutyl)phenyl)acetamidooxy)propyl)hexanamide dihydrochloride |
| 18 | 10 | 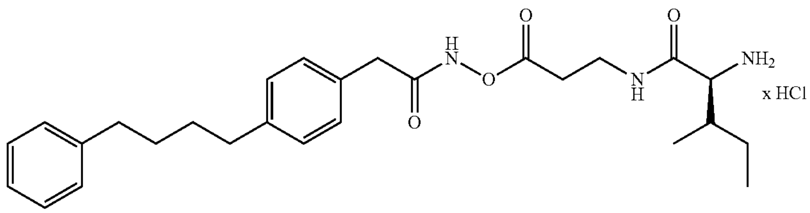 [SMILES: CCC(C)[C@H](N)C(=O)NCCC(=O)ONC(=O)Cc1ccc(CCCCc2ccccc2)cc1] | (2S,3S)-2-Amino-3-methyl-N-(3-oxo-3-(2-(4-(4-phenylbutyl)phenyl)acetamidooxy)propyl)pentanamide hydrochloride |
| 19 | 11 | 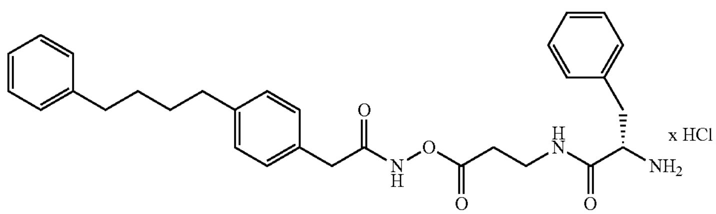 [SMILES: N[C@@H](Cc1ccccc1)C(=O)NCCC(=O)ONC(=O)Cc1ccc(CCCCc2ccccc2)cc1] | (S)-2-amino-N-(3-oxo-3-(2-(4-(4-phenylbutyl)phenyl)acetamidooxy)propyl)-3-phenylpropanamide hydrochloride |
| 20 | 12 | 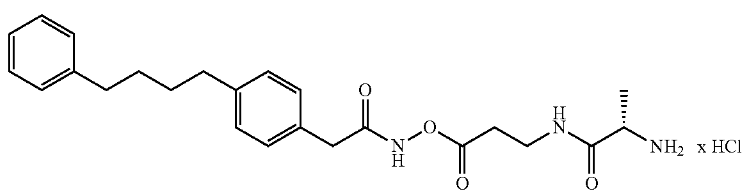 [SMILES: C[C@H](N)C(=O)NCCC(=O)ONC(=O)Cc1ccc(CCCCc2ccccc2)cc1 ; "x HCl"] | (S)-2-amino-N-(3-oxo-3-(2-(4-(4-phenylbutyl)phenyl)acetamidooxy)propyl) propanamide hydrochloride |
| 21 | 13 | 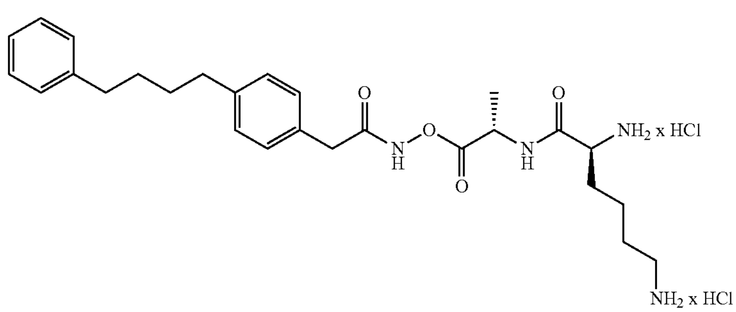 | (S)-2,6-diamino-N-((S)-1-oxo-1-(2-(4-(4-phenylbutyl)phenyl)acetamidooxy)propan-2-yl)hexanamide dihydrochloride |
| 22 | 14 | 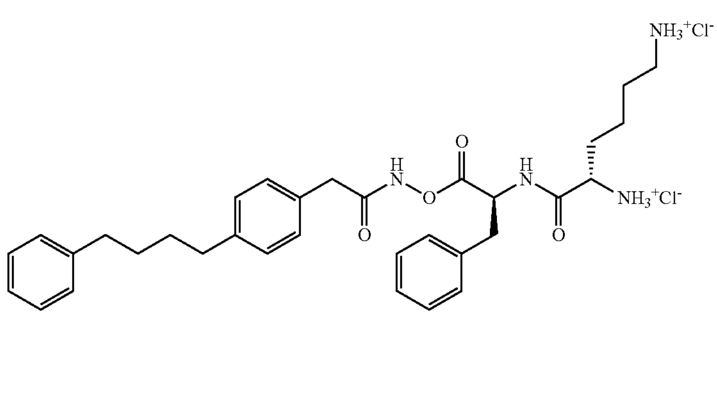 | (S)-6-oxo-6-((S)-1-oxo-3-phenyl-1-(2-(4-(4-phenylbutyl)phenyl)acetamidooxy)propan-2-ylamino)hexane-1,5-diaminiumchloride |

-continued

| | | | |
|---|---|---|---|
| 22A | 14-A | 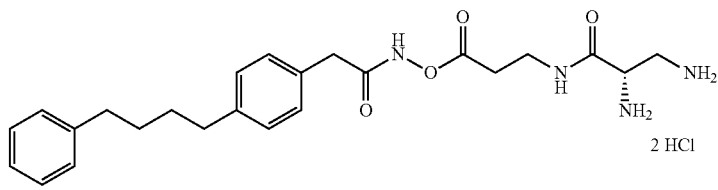 [SMILES: NC[C@H](N)C(=O)NCCC(=O)ONC(=O)Cc1ccc(CCCCc2ccccc2)cc1] 2 HCl | ((S)-2,3-diamino-N-(3-oxo-3-(2-(4-(4-phenylbutyl)phenyl)acetamidooxy)propyl)propanamide di-hydrochloride |
| 22B | 14-B | 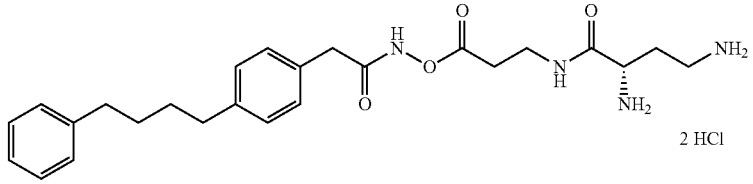 [SMILES: NCC[C@H](N)C(=O)NCCC(=O)ONC(=O)Cc1ccc(CCCCc2ccccc2)cc1] 2 HCl | (S)-2,4-diamino-N-(3-oxo-3-(2-(4-(4-phenylbutyl)phenyl)acetamidooxy)propyl)butanamide di-hydrochloride |
| 22C | 14-C | 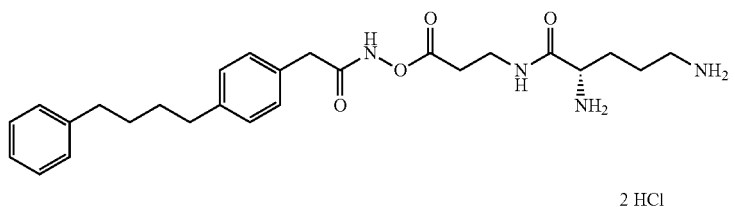 [SMILES: NCCC[C@H](N)C(=O)NCCC(=O)ONC(=O)Cc1ccc(CCCCc2ccccc2)cc1] 2 HCl | (S)-2,5-diamino-N-(3-oxo-3-(2-(4-(4-phenylbutyl)phenyl)acetamidooxy)propyl)pentanamide di-hydrochloride |
| 22D | 14-D | 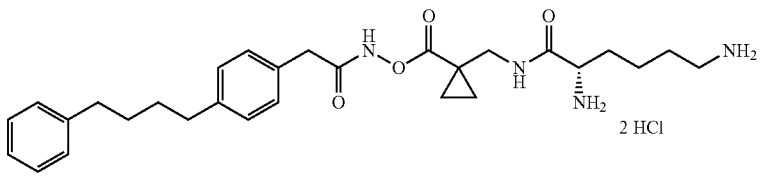 [SMILES: NCCCC[C@H](N)C(=O)NCC1(C(=O)ONC(=O)Cc2ccc(CCCCc3ccccc3)cc2)CC1] 2 HCl | (S)-2,6-diamino-N-((1-((2-(4-(4-phenylbutyl)phenyl)acetamidooxy)carbonyl)cyclopropyl)methyl)hexanamide di-hydrochloride |
| 27 | 15 | 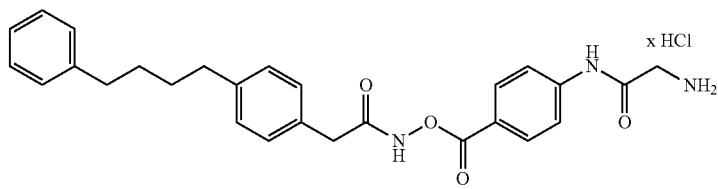 [SMILES: NCC(=O)Nc1ccc(C(=O)ONC(=O)Cc2ccc(CCCCc3ccccc3)cc2)cc1] x HCl | 2-amino-N-(4-((2-(4-(4-phenylbutyl)phenyl)acetamidooxy)carbonyl)phenyl)acetamide hydrochloride |
| 28 | 16 | 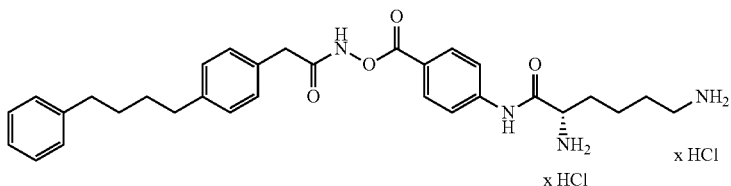 [SMILES: NCCCC[C@H](N)C(=O)Nc1ccc(C(=O)ONC(=O)Cc2ccc(CCCCc3ccccc3)cc2)cc1 ; "x HCl"] x HCl  x HCl | (S)-2,6-diamino-N-(4-((2-(4-(4-phenylbutyl)phenyl)acetamidooxy)carbonyl)phenyl)hexanamide dihydrochloride |
| 29 | 17 | 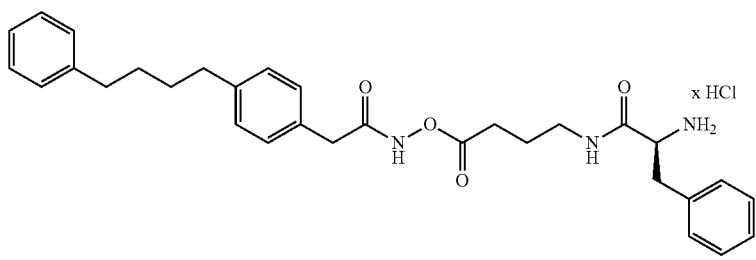 [SMILES: N[C@@H](Cc1ccccc1)C(=O)NCCCC(=O)ONC(=O)Cc1ccc(CCCCc2ccccc2)cc1] x HCl | (S)-2-amino-N-(4-oxo-4-(2-(4-(4-phenylbutyl)phenyl)acetamidooxy)butyl)-3-phenylpropanamide hydrochloride |

-continued

| | | | |
|---|---|---|---|
| 30 | 18 | 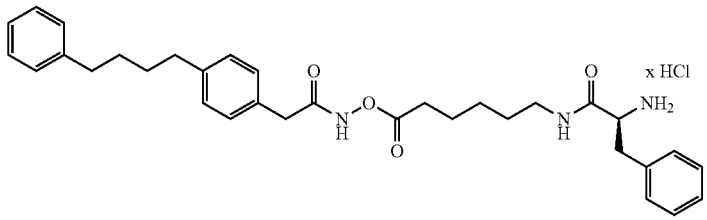 [SMILES: N[C@@H](Cc1ccccc1)C(=O)NCCCCCC(=O)ONC(=O)Cc1ccc(CCCCc2ccccc2)cc1] x HCl | (S)-2-amino-N-(6-oxo-6-(2-(4-(4-phenylbutyl)phenyl)acetamidooxy)hexyl)-3-phenylpropanamide hydrochloride |
| 31 | 19 | 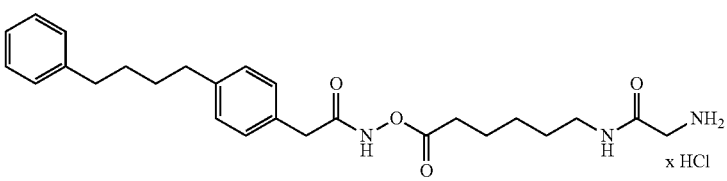 [SMILES: NCC(=O)NCCCCCC(=O)ONC(=O)Cc1ccc(CCCCc2ccccc2)cc1] x HCl | 2-amino-N-(6-oxo-6-(2-(4-(4-phenylbutyl)phenyl)acetamidooxy)hexyl)acetamide hydrochloride |
| 32 | 20 | 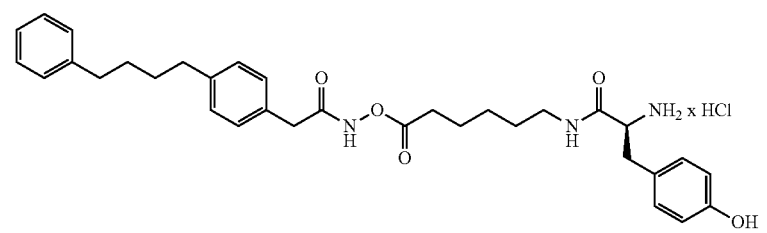 x HCl | (S)-2-amino-3-(4-hydroxyphenyl)-N-(6-oxo-6-(2-(4-(4-phenylbutyl)phenyl)acetamidooxy)hexyl)propanamide hydrochloride |
| 44 | 23 | 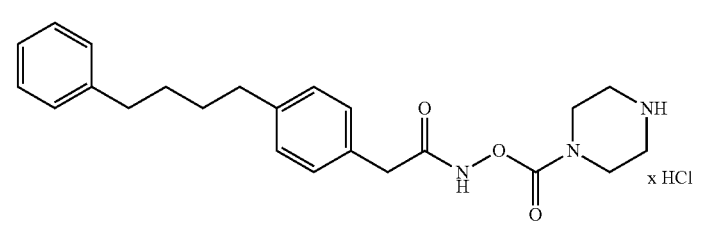 [SMILES: O=C(Cc1ccc(CCCCc2ccccc2)cc1)NOC(=O)N1CCNCC1] x HCl | 2-(4-(4-Phenylbutyl)phenyl)-N-(piperazine-1-carbonyloxy) acetamide hydrochloride |
| 45 | 24 | 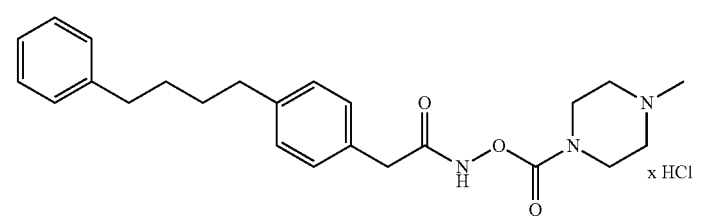 [SMILES: CN1CCN(C(=O)ONC(=O)Cc2ccc(CCCCc3ccccc3)cc2)CC1] x HCl | N-4-Methylpiperazine-1-carbonyloxy)-2-(4-(4-phenylbutyl)phenyl) acetamide hydrochloride |
| 46 | 25 | 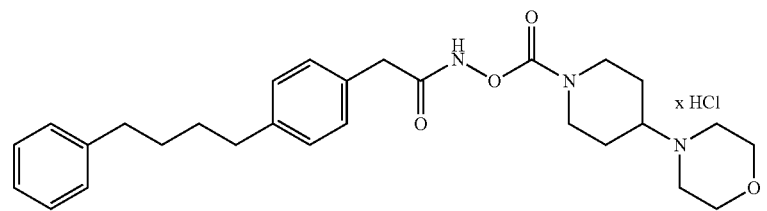 [SMILES: O=C(Cc1ccc(CCCCc2ccccc2)cc1)NOC(=O)N1CCC(N2CCOCC2)CC1 ; "x HCl"] x HCl | N-(4-morpholinopiperidine-1-carbonyloxy)-2-(4-(4-phenylbutyl)phenyl) acetamide hydrochloride |
| 65 | 40 | 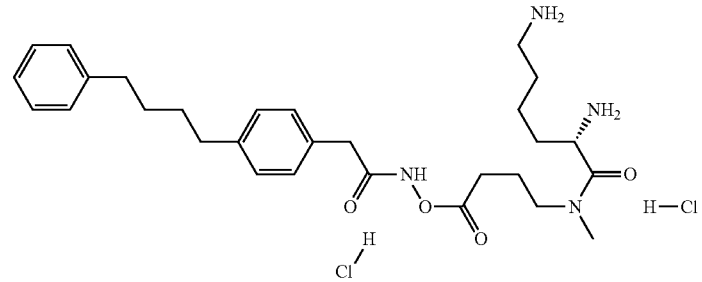 | (S)-2,6-Diamino-N-methyl-N-(4-oxo-4-(2-(4-(4-phenylbutyl)phenyl)acetamidooxy)butyl)hexanamide dihydrochloride |

| | | | |
|---|---|---|---|
| 86 | 57 | 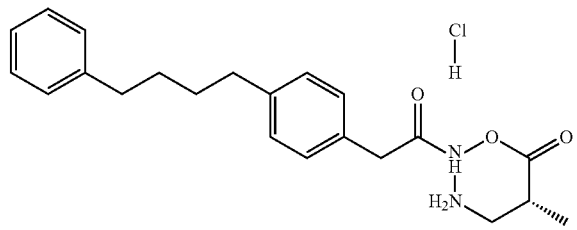 | (S)-N-(3-Amino-2-methylpropanoyloxy)-2-(4-(4-phenylbutyl)phenyl) acetamide hydrochloride |
| 90 | 59 | 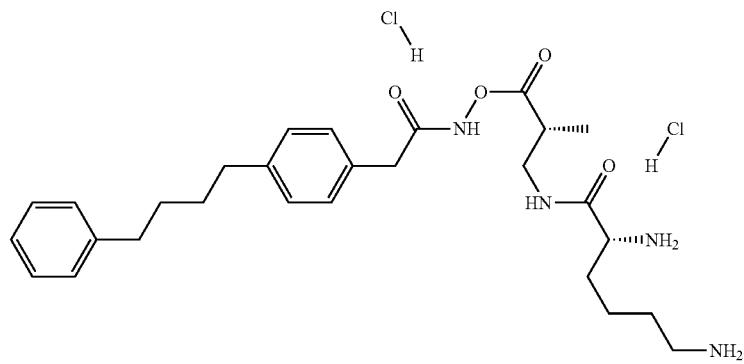 | (S)-2,6-Diamino-N-((S)-2-methyl-3-oxo-3-(2-(4-(4-phenylbutyl)phenyl)acetamidooxy)propyl)hexanamide dihydrochloride |
| 94 | 60 | 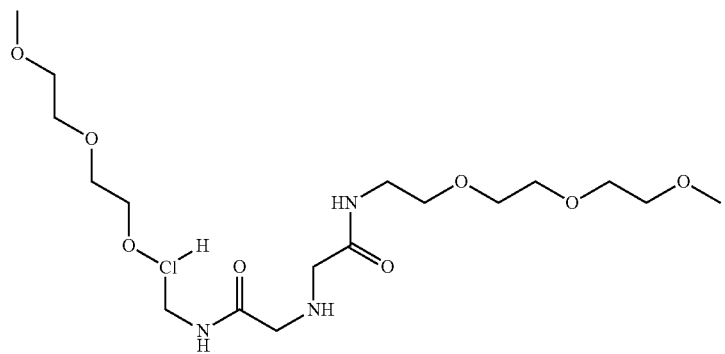 | 2,2'-Azanediylbis(N-(2-(2-(2-methoxyethoxy)ethoxy)ethyl)acetamide) hydrochloride |
| 98 | 61 | 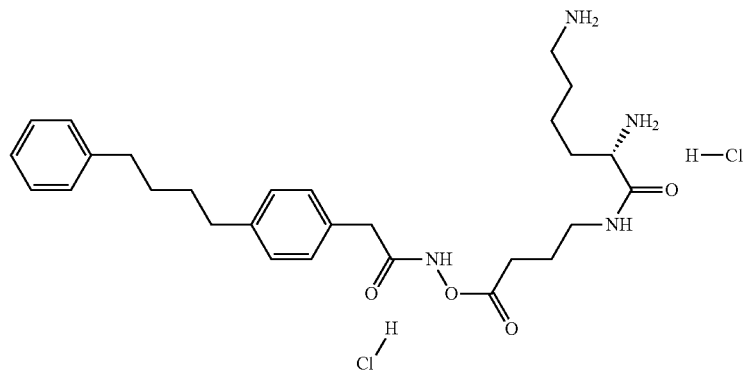 | (S)-2,6-Diamino-N-(4-oxo-4-(2-(4-(4-phenylbutyl)phenyl)acetamidooxy)butyl)hexanamide dihydrochloride |
| 106 | 66 | 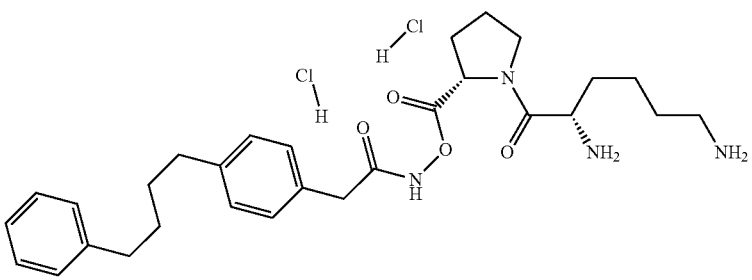 | N-((S)-1-((S)-2,6-Diaminohexanoyl)pyrrolidine-2-carbonyloxy)-2-(4-(4-phenylbutyl)phenyl) acetamide dihydrochloride |

| | | | |
|---|---|---|---|
| 110 | 69 | | 2-(4-(4-Phenylbutyl)phenyl)-N-(3-(piperidin-4-yl)propanoyloxy) acetamide hydrochloride |
| 118 | 77 | | 2-(4-(4-phenylbutyl)phenyl)-N-(piperidine-4-carbonyloxy)acetamide hydrochloride |
| 121 | 80 | | 2-(4-(4-phenylbutyl)phenyl)-N-(4-(piperidin-4-yl)butanoyloxy) acetamide hydrochloride |
| 123 | 82 | | N-(4-oxo-4-(piperazin-1-yl)butanoyloxy)-2-(4-(4-phenylbutyl)phenyl) acetamide hydrochloride |
| 125 | 84 | | 2-(4-(4-phenylbutyl)phenyl)-N-(2-(piperidin-4-yloxy)acetoxy)acetamide hydrochloride |
| 128 | 86 | | N-(3-(2-oxopiperazin-1-yl)propanoyloxy)-2-(4-(4-phenylbutyl)phenyl)acetamide hydrochloride |
| 128A | 86A | | N-(4-(azetidin-3-yl)butanoyloxy)-2-(4-(4-phenylbutyl)phenyl) acetamide hydrochloride |

| 133 | 87 | | 2-(2-Aminoethylamino)-N-(4-oxo-4-(2-(4-(4-phenylbutyl)phenyl)acetamidooxy)butyl)acetamide dihydrochloride |
| 135 | 89 | | 2-(2-aminoethylamino)-N-(3-oxo-3-(2-(4-(4-phenylbutyl)phenyl)acetamidooxy)propyl)acetamide dihydrochloride |
| 142 | 91 | | (S)-2-Amino-6-(2-(2-(2-methoxyethoxy)ethoxy)acetamido)-N-(3-oxo-3-(2-(4-(4-phenylbutyl)phenyl)acetamidooxy)propyl)hexanamide hydrochloride |

In one embodiment of the invention the salt forms of the compounds are useful as prodrugs. In one embodiment of the invention the salt forms of the compounds can be used to synthesize PEGylated compounds which are useful as prodrugs.

In one embodiment of the invention, $R^{10}$ is —$[C(R^{40})(R^{41})]_n NHR^{60}$. Representative compounds include

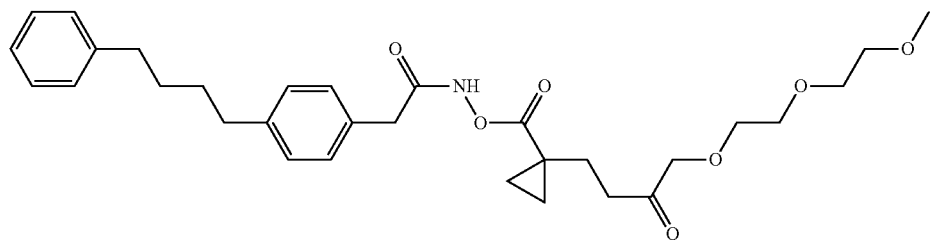

2-(2-(2-Methoxyethoxy)ethoxy)-N-((1-((2-(4-(4-phenylbutyl)phenyl)acetamidooxy)carbonyl)cyclopropyl)methyl)acetamide

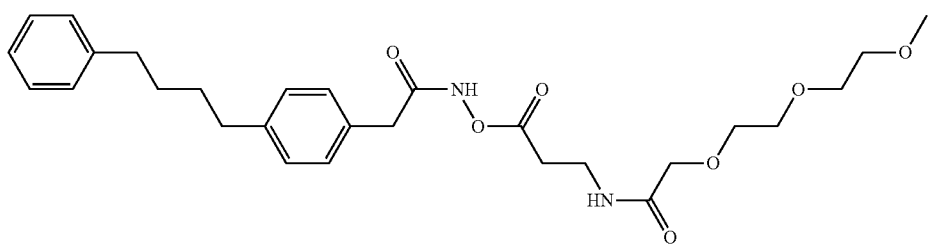

2-(2-(2-methoxyethoxy)ethoxy)-N-(3-oxo-3-(2-(4-(4-phenylbutyl)phenyl)acetamidooxy)propyl)acetamide

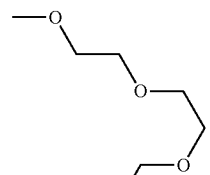

N-((1-((2-(4-(4-phenylbutyl)phenyl)acetamidooxy)carbonyl)cyclopropyl)methyl)-2,5,8,11,14-pentaoxahexadecan-16-amide

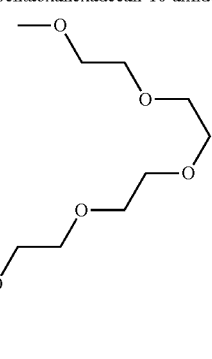

N-(3-oxo-3-(2-(4-(4-phenylbutyl)phenyl)acetamidooxy)propyl)-2,5,8,11,14-pentaoxahexadecan-16-amide

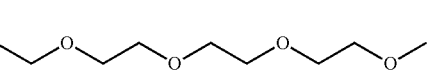

(S)-N-(2-Methyl-3-oxo-3-(2-(4-(4-phenylbutyl)phenyl)acetamidooxy)propyl)-2,5,8,11,14-pentaoxahexadecan-16-amide

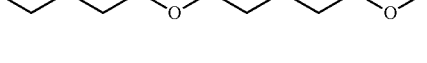

(S)-N-(4-oxo-4-(2-(4-(4-phenylbutyl)phenyl)acetamidooxy)butan-2-yl)-2,5,8,11,14-pentaoxahexadecan-16-amide

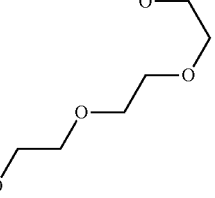

N-(3-oxo-3-(2-(4-(4-phenylbutyl)phenyl)acetamidooxy)propyl)-2,5,8,11,14,17-hexaoxanonadecan-19-amide -continued

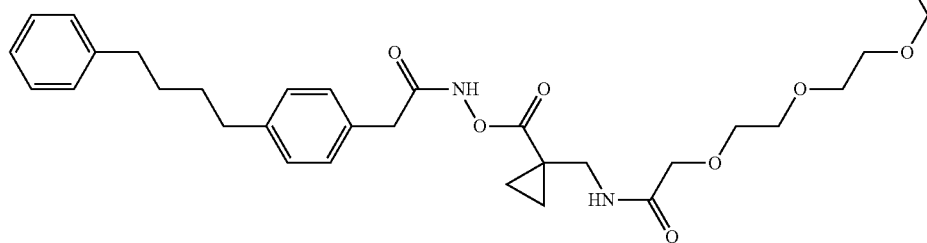

N-((1-(((2-(4-(4-phenylbutyl)phenyl)acetamidooxy)carbonyl)cyclopropyl)methyl)-2,5,8,11,14,17-hexaoxanonadecan-19-amide

20 and their pharmaceutically acceptable salts.

In one embodiment of the invention, $R^{10}$ is —[C($R^{40}$)($R^{41}$)]$_n$N($R^{30}$)C(O)C[(H)(N(H)$R^{60}$)][C($R^{40}$)($R^{41}$)]$_n$N(H)$R^{60}$. Representative compounds include

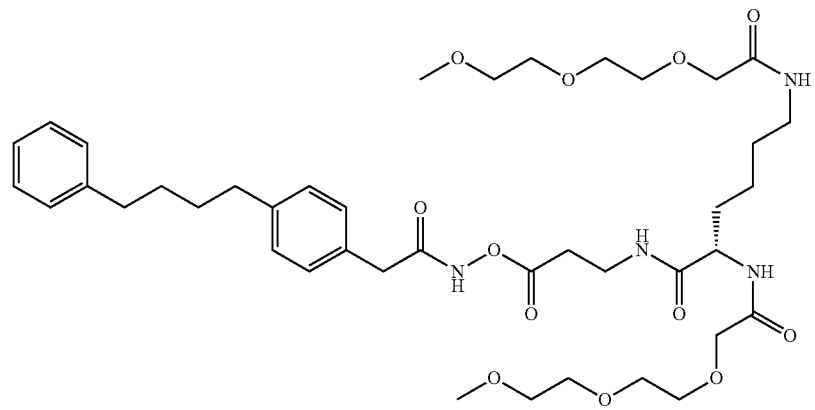

(S)-N,N'-(6-Oxo-6-(3-oxo-3-(2-(4-(4-phenylbutyl)phenyl)acetamidooxy)propylamino)hexane-1,5-diyl)bis(2-(2-(2-methoxyethoxy)ethoxy)acetamide)

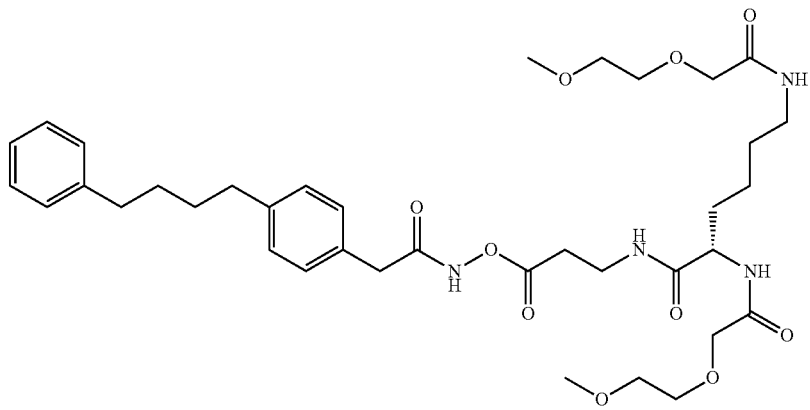

(S)-N,N'-(6-Oxo-6-(3-oxo-3-(2-(4-(4-phenylbutyl)phenyl)acetamidooxy)propylamino)hexane-1,5-diyl)bis(2-(2-methoxyethoxy)acetamide)

-continued

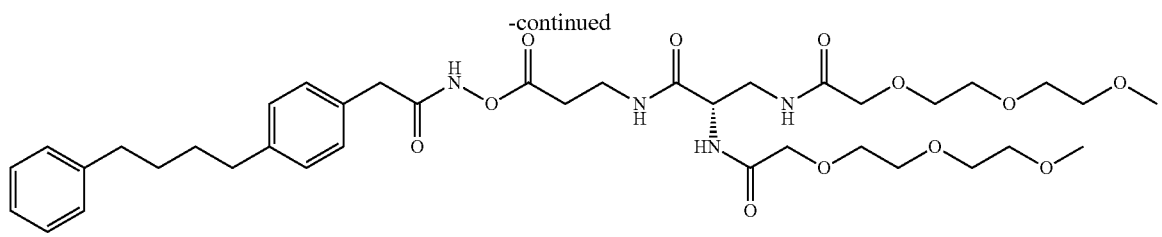

(S)-N,N'-(3-oxo-3-(3-oxo-3-(2-(4-(4-phenylbutyl)phenyl)acetamidooxy)propylamino)propane-1,2-diyl)bis(2-(2-methoxyethoxy)acetamide)

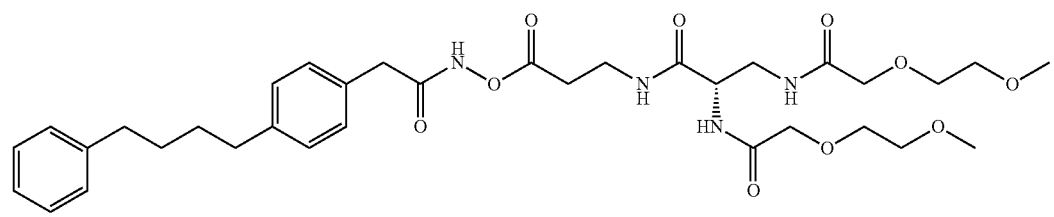

(S)-N,N'-(3-oxo-3-(3-oxo-3-(2-(4-(4-phenylbutyl)phenyl)acetamidooxy)propylamino)propane-1,2-diyl)bis(2-(2-methoxyethoxy)acetamide)

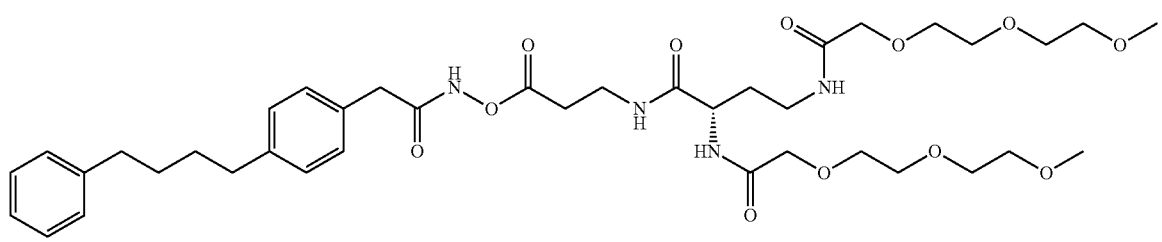

(S)-N,N'-(4-oxo-4-(3-oxo-3-(2-(4-(4-phenylbutyl)phenyl)acetamidooxy)propylamino)butane-1,3-diyl)bis(2-(2-(2-methoxyethoxy)ethoxy)acetamide)

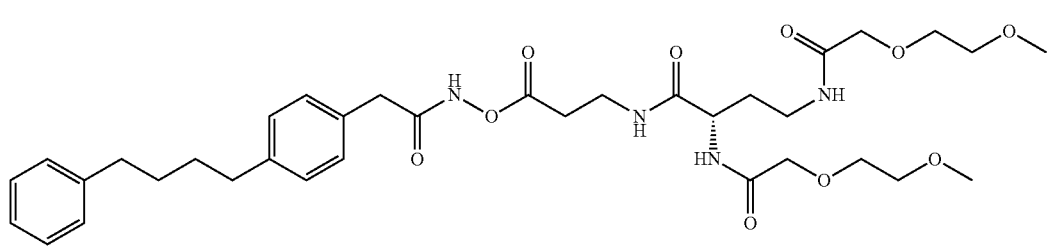

(S)-N,N'-(4-Oxo-4-(3-oxo-3-(2-(4-(4-phenylbutyl)phenyl)acetamidooxy)propylamino)butane-1,3-diyl)bis(2-(2-methoxyethoxy)acetamide)

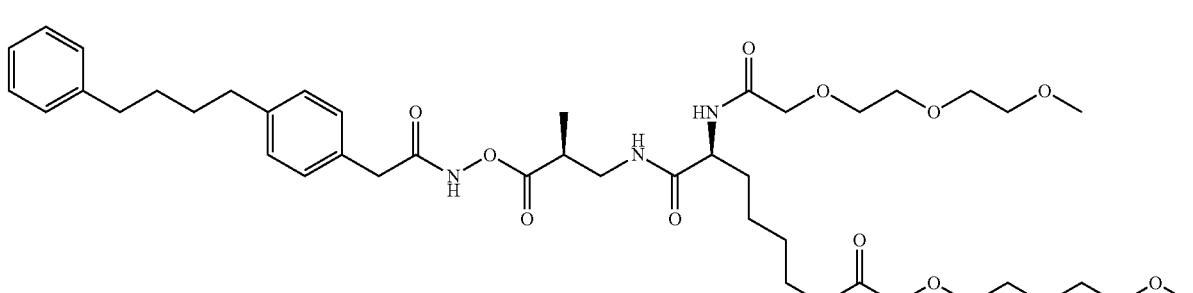

N,N'-((S)-6-((S)-2-Methyl-3-oxo-3-(2-(4-(4-phenylbutyl)phenyl)acetamidooxy)propylamino)-6-oxohexane-1,5-diyl)bis(2-(2-(2-methoxyethoxy)ethoxy)acetamide)

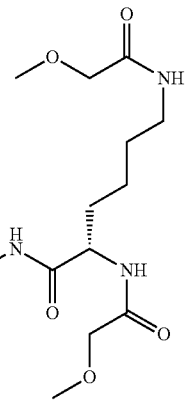

(S)-N,N'-(6-Oxo-6-(3-oxo-3-(2-(4-(4-phenylbutyl)phenyl)acetamidooxy)propylamino)hexane-1,5-diyl)bis(2-methoxyacetamide)

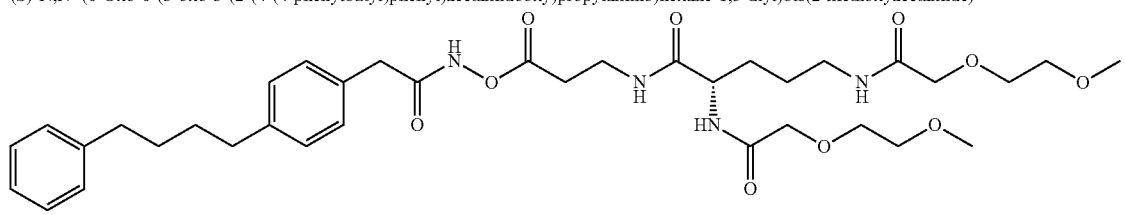

(S)-N,N'-(5-oxo-5-(3-oxo-3-(2-(4-(4-phenylbutyl)phenyl)acetamidooxy)propylamino)pentane-1,4-diyl)bis(2-(2-methoxyethoxy)acetamide)

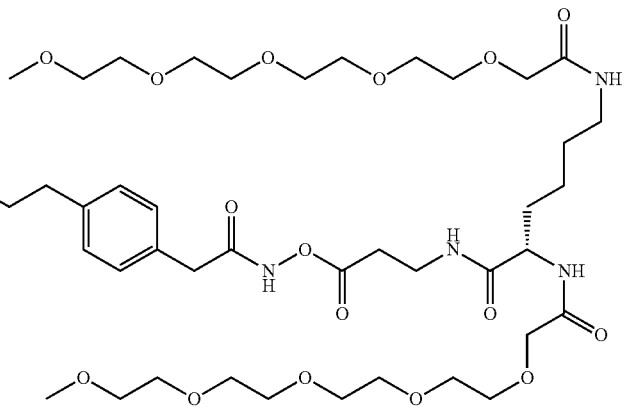

(S)-N,N'-(6-Oxo-6-(3-oxo-3-(2-(4-(4-phenylbutyl)phenyl)acetamidooxy)propylamino)hexane-1,5-diyl)bis(2,5,8,11,14-pentaoxahexadecan-16-amide)

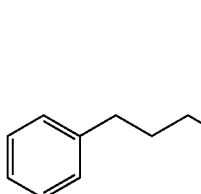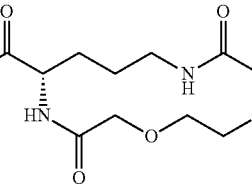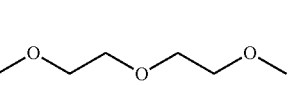

(S)-N,N'-(5-oxo-5-(3-oxo-3-(2-(4-(4-phenylbutyl)phenyl)acetamidooxy)propylamino)pentane-1,4-diyl)bis(2-(2-(2-methoxyethoxy)ethoxy)acetamide)

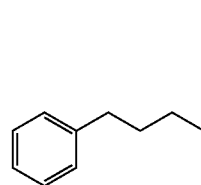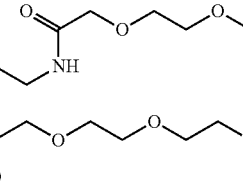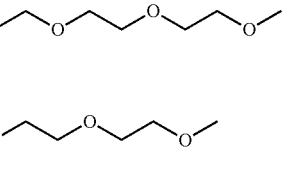

(S)-N,N'-(4-oxo-4-(3-oxo-3-(2-(4-(4-phenylbutyl)phenyl)acetamidooxy)propylamino)butane-1,3-diyl)bis(2,5,8,11,14-pentaoxahexadecan-16-amide)

-continued

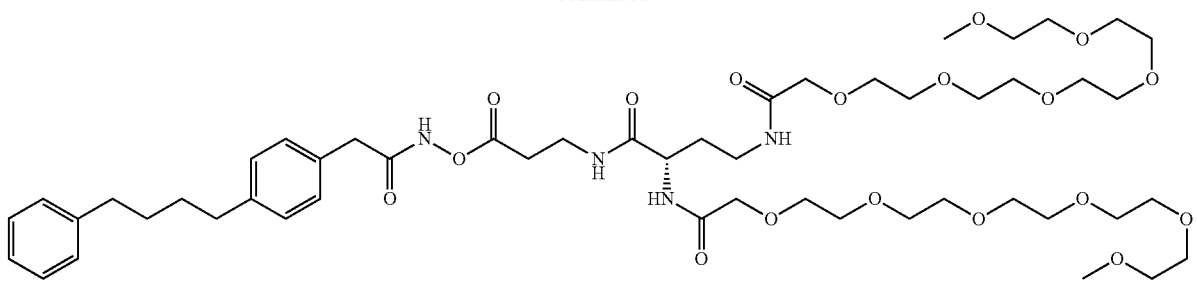

(S)-N,N'-(4-oxo-4-(3-oxo-3-(2-(4-(4-phenylbutyl)phenyl)acetamidooxy)propylamino)butane-1,3-diyl)bis(2,5,8,11,14,17-hexaoxanonadecan-19-amide)

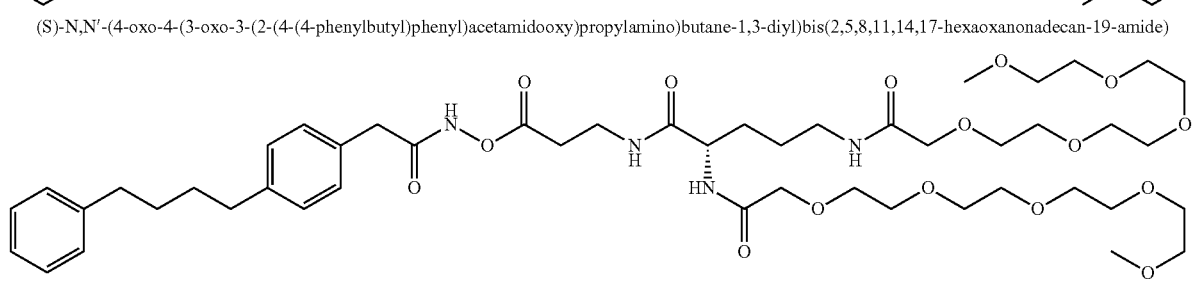

(S)-N,N'-(6-oxo-6-((1-((2-(4-(4-phenylbutyl)phenyl)acetamidooxy)carbonyl)cyclopropyl)methylamino)hexane-1,5-diyl)bis(2-(2-methoxyethoxy)acetamide)

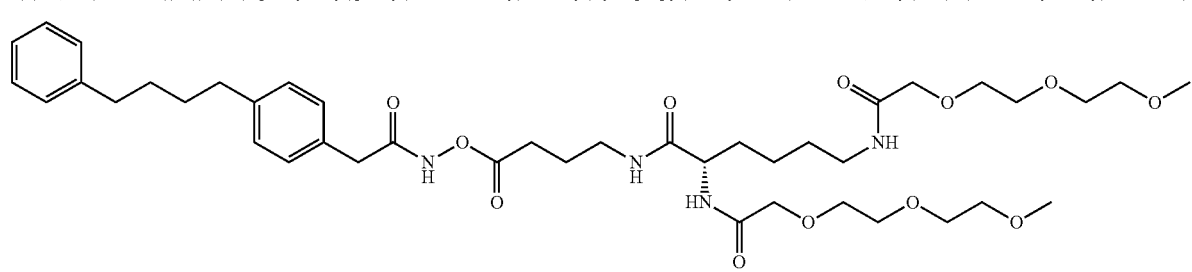

(S)-N,N'-(6-Oxo-6-(4-oxo-4-(2-(4-(4-phenylbutyl)phenyl)acetamidooxy)butylamino)hexane-1,5-diyl)bis(2-(2-(2-methoxyethoxy)acetamide)

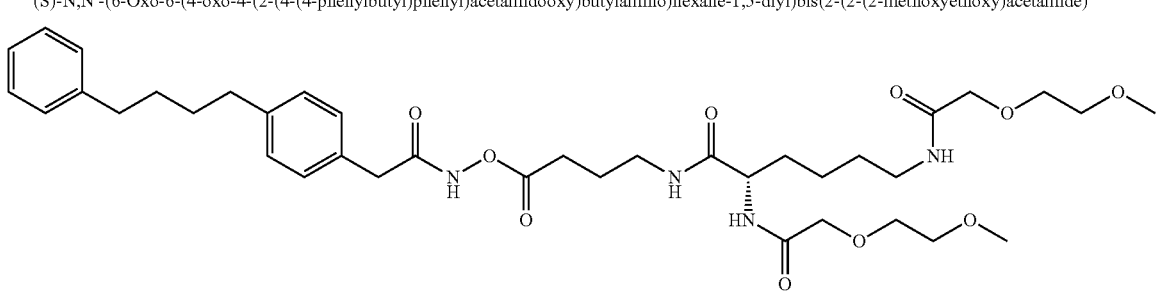

(S)-N,N'-(6-Oxo-6-(4-oxo-4-(2-(4-(4-phenylbutyl)phenyl)acetamidooxy)butylamino)hexane-1,5-diyl)bis(2-(2-(2-methoxyethoxy)acetamide)

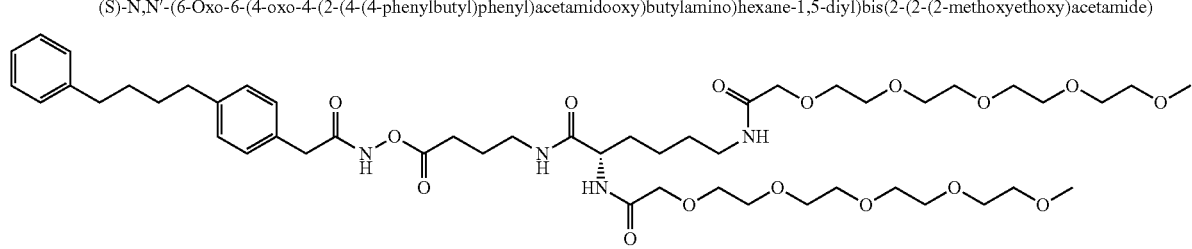

(S)-N,N'-(6-oxo-6-(4-oxo-4-(2-(4-(4-phenylbutyl)phenyl)acetamidooxy)butylamino)hexane-1,5-diyl)bis(2,5,8,11,14-pentaoxahexadecan-16-amide)

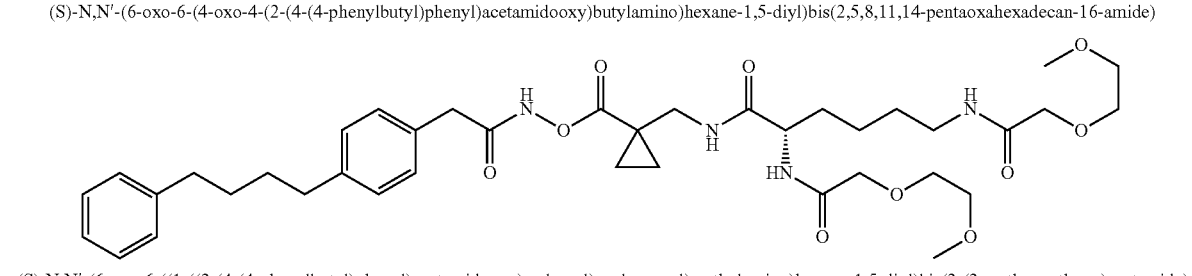

(S)-N,N'-(6-oxo-6-((1-((2-(4-(4-phenylbutyl)phenyl)acetamidooxy)carbonyl)cyclopropyl)methylamino)hexane-1,5-diyl)bis(2-(2-methoxyethoxy)acetamide)

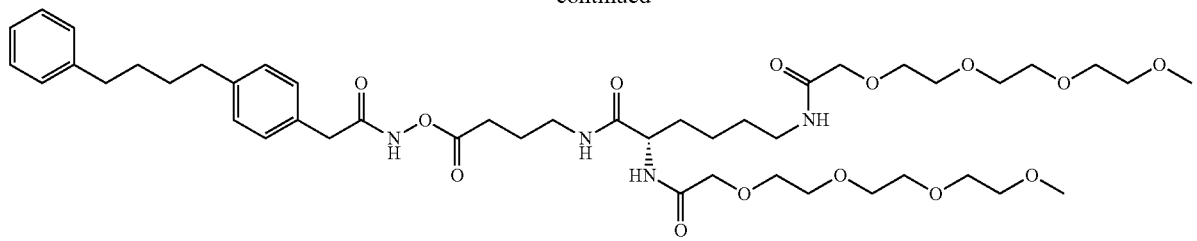

(S)-N,N'-(6-oxo-6-(4-oxo-4-(2-(4-(4-phenylbutyl)phenyl)acetamidooxy)butylamino)hexane-1,5-diyl)bis(2,5,8,11-tetraoxatridecan-13-amide)

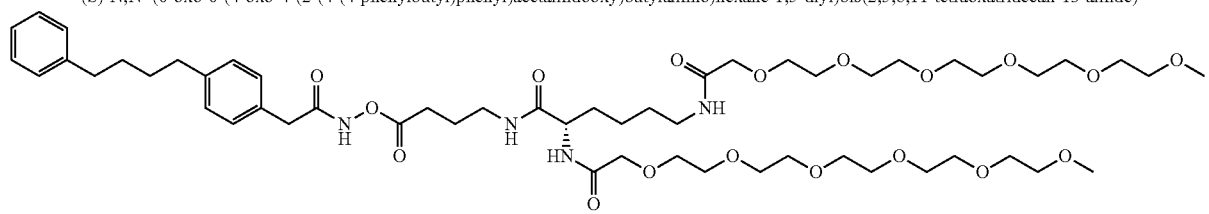

(S)-N,N'-(6-oxo-6-(4-oxo-4-(2-(4-(4-phenylbutyl)phenyl)acetamidooxy)butylamino)hexane-1,5-diyl)bis(2,5,8,11,14,17-haxaoxanonadecan-19-amide)

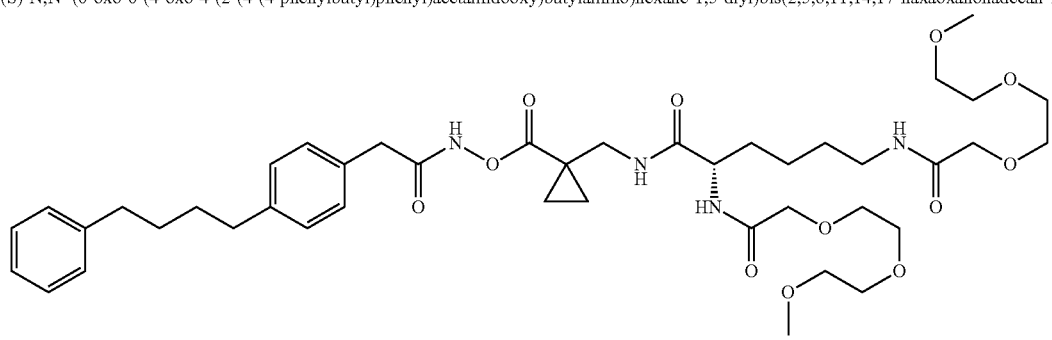

(S)-N,N'-(6-oxo-6-((1-((2-(4-(4-phenylbutyl)phenyl)acetamidooxy)carbonyl)cyclopropyl)methylamino)hexane-1,5-diyl)bis(2-(2-(2-methoxyethoxy)ethoxy)acetamide)

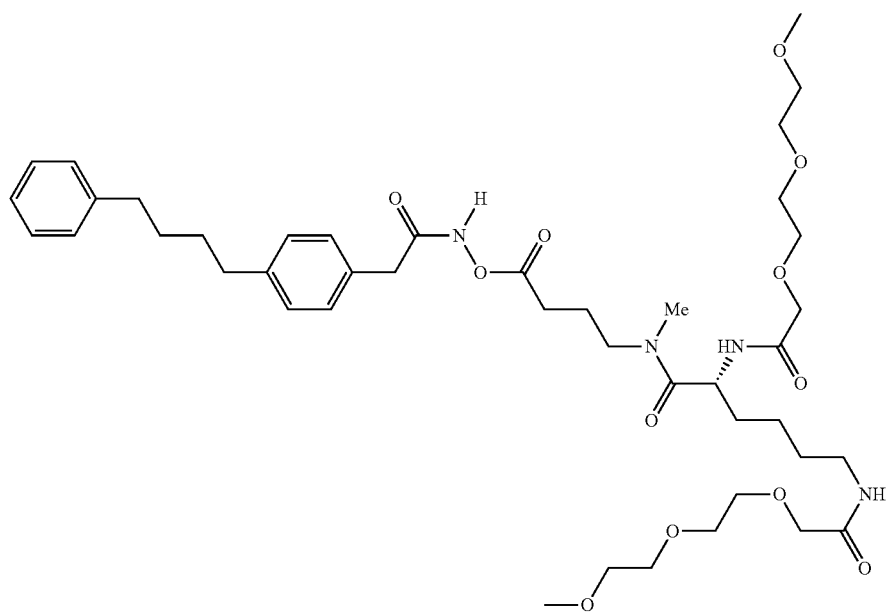

(S)-N,N'-(6-(Methyl(4-oxo-4-(2-(4-(4-phenylbutyl)phenyl)acetamidooxy)butyl)amino)-6-oxohexane-1,5-diyl)bis(2-(2-(2-methoxyethoxy)ethoxy)acetamide)

and their pharmaceutically acceptable salts.

In one embodiment of the invention, two polyethylene glycol chains and their linkages are linked together to form a polyethylene glycol ring structure. Representative compounds include

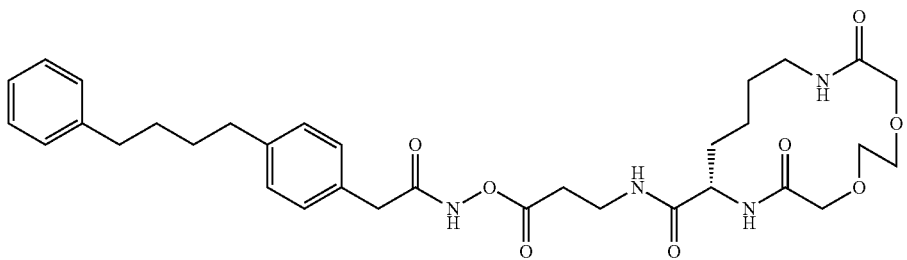

(S)-6,14-Dioxo-N-(3-oxo-3-(2-(4-(4-phenylbutyl)phenyl)acetamidooxy)propyl)-1,4-dioxa-7,13-diazacyclopentadecane-8-carboxamide

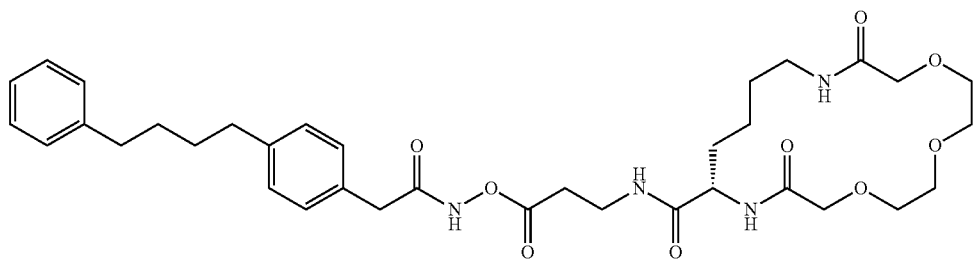

(S)-9,17-dioxo-N-(3-oxo-3-(2-(4-(4-phenylbutyl)phenyl)acetamidooxy)propyl)-1,4,7-trioxa-10,16-diazacyclo octadecane-11-carboxamide and their pharmaceutically acceptable salts.

In one embodiment of the invention $R^{10}$ is —$R^{50}R^{60}$.

Representative compounds include

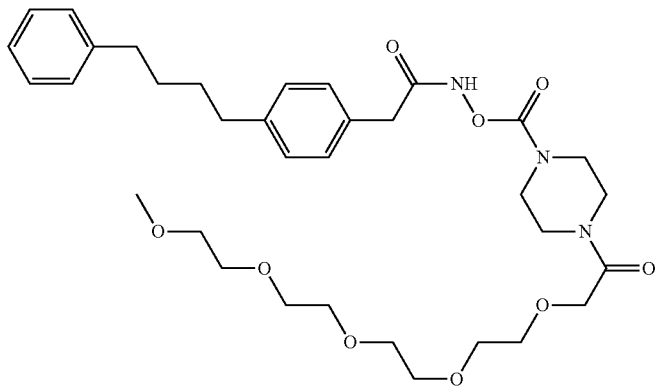

N-(4-2,5,8,11,14-pentaoxahexadecanepiperazine-1-carbonyloxy)-2-(4-(4-phenylbutyl)phenyl)acetamide

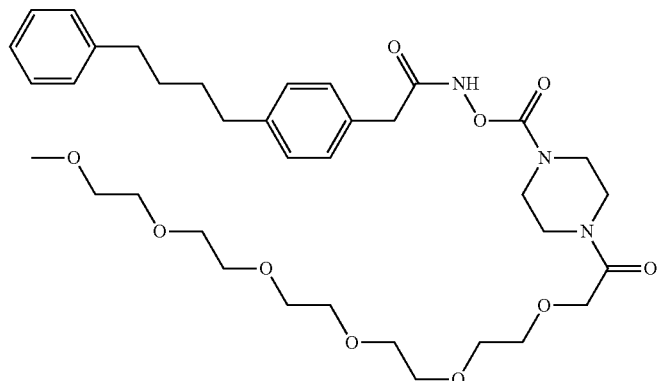

N-(4-2,5,8,11,14,17-hexaoxanonadecanepiperazine-1-carbonyloxy)-2-(4-(4-phenylbutyl)phenyl)acetamide -continued

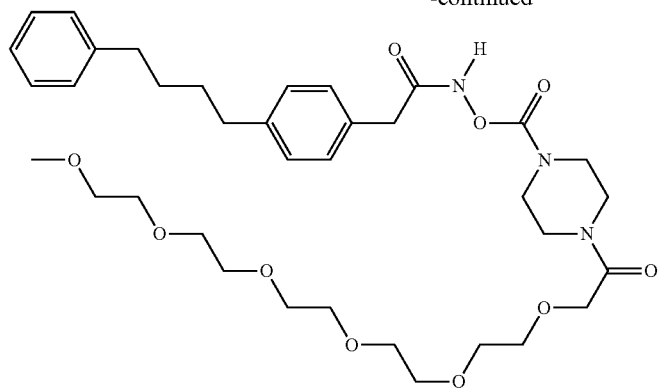

N-(1-2,5,8,11,14,17-Hexaoxanonadecanepiperazine-4-carbonyloxy)-2-(4-(4-phenylbutyl)phenyl)acetamide

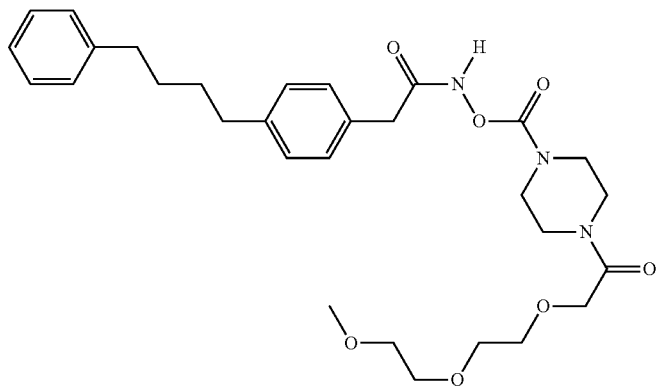

N-(1-2-(2-(2-Methoxyethoxy)ethoxy)acetyl)piperidine-4-carbonyloxy)-2-(4-(4-phenylbutyl)phenyl)acetamide

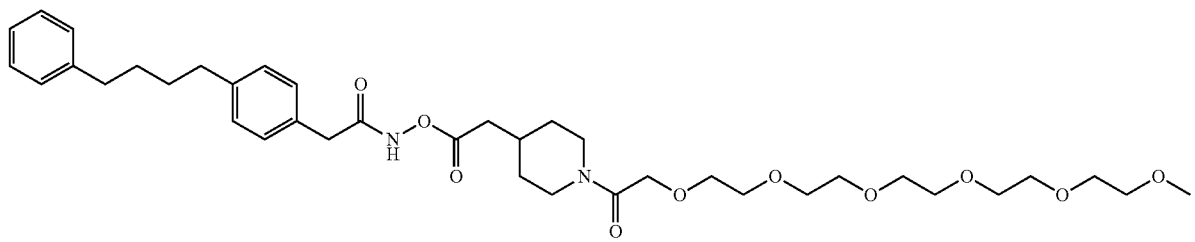

(S)-N,N'-(6-(Methyl(4-oxo-4-(2-(4-(4-phenylbutyl)phenyl)acetamidooxy)butyl)amino)-6-oxohexane-1,5-diyl)bis(2-(2-(2-methoxyethoxy)ethoxy)acetamide)

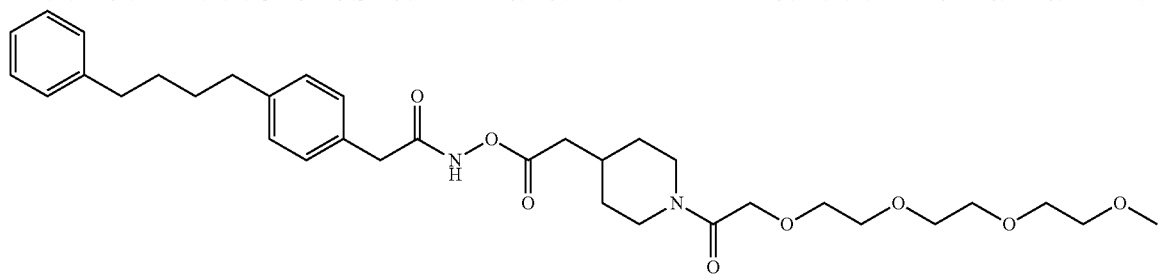

N-(2-(1-5,8,11-tetraoxatridecanepiperidin-4-yl)acetoxy)-2-(4-(4-phenylbutyl)phenyl)acetamide

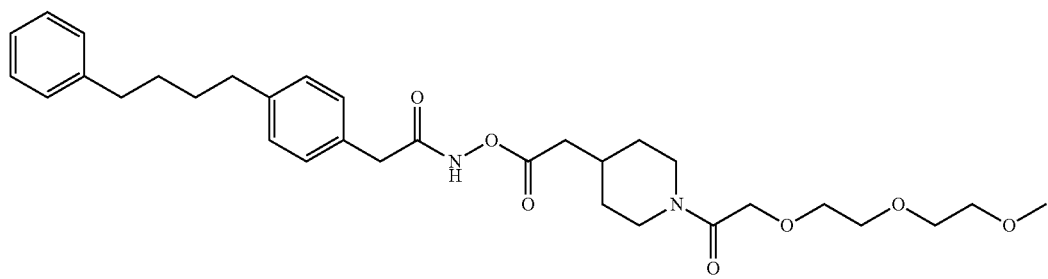

N-(2-(1-(2-(2-(2-methoxyethoxy)ethoxy)acetyl)piperidin-4-yl)acetoxy)-2-(4-(4-phenylbutyl)phenyl)acetamide

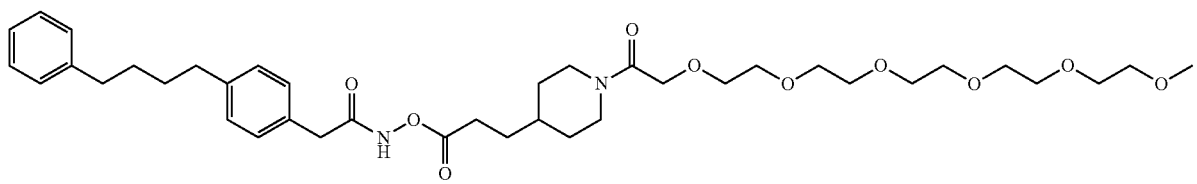

N-(3-(1-2,5,8,11,14,17-Hexaoxanonadecanepiperidin-4-yl)propanoyloxy)-2-(4-(4-phenylbutyl)phenyl)acetamide

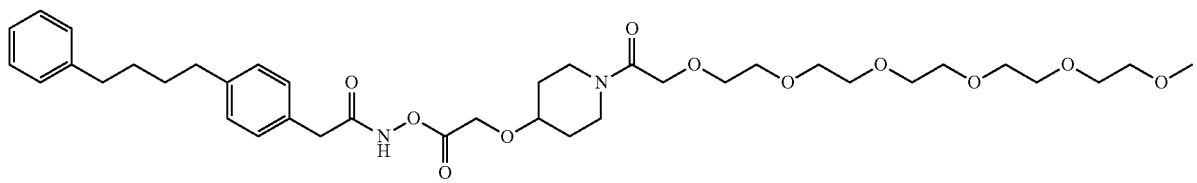

N-(2-(1-2,5,8,11,14,17-hexaoxanonadecanepiperidin-4-yloxy)acetoxy)-2-(4-(4-phenylbutyl)phenyl)acetamide

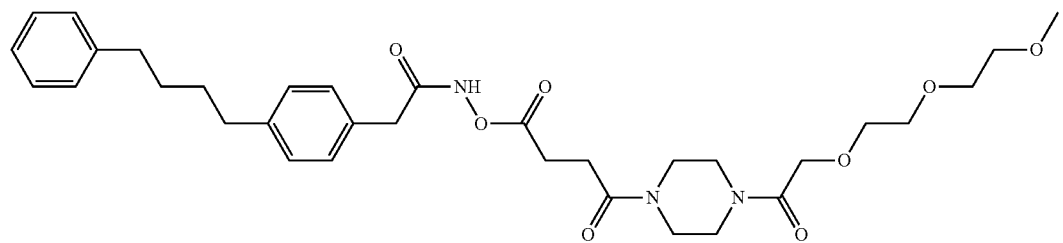

N-(4-(4-(2-(2-(2-Methoxyethoxy)ethoxy)acetyl)piperazin-1-yl)-4-oxobutanoyloxy)-2-(4-(4-phenylbutyl)phenyl)acetamide

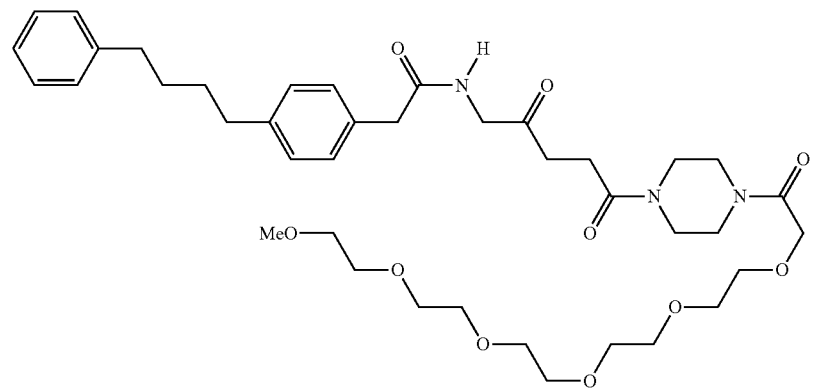

N-(4-(1-2,5,8,11,14,17-Hexaoxanonadecanepiperidin-4-yl)butanoyloxy)-2-(4-(4-phenylbutyl)phenyl)acetamide

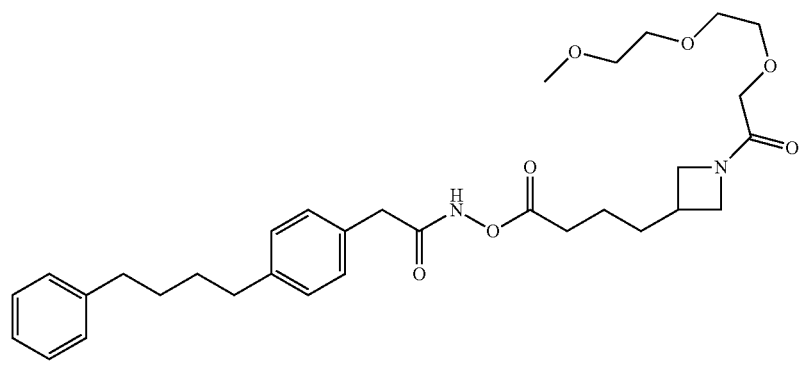

N-(4-(1-(2-(2-(2-methoxyethoxy)ethoxy)acetyl)azetidin-3-yl)butanoyloxy)-2-(4-(4-phenylbutyl)phenyl)acetamide

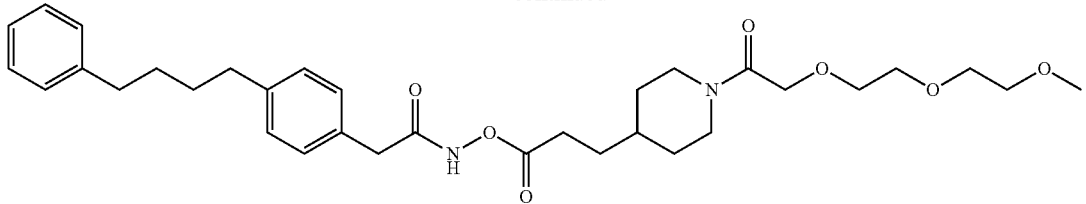

N-(3-(1-(2-(2-(2-methoxyethoxy)ethoxy)acetyl)piperidin-4-yl)propanoyloxy)-2-(4-(4-phenylbutyl)phenyl)acetamide

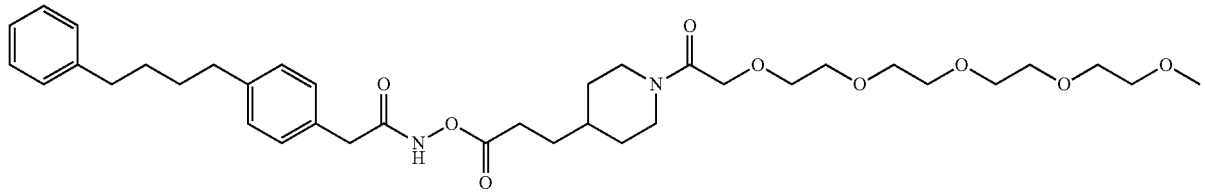

N-(3-(1-2,5,8,11,14-pentaoxahexadecanepiperidin-4-yl)propanoyloxy)-2-(4-(4-phenylbutyl)phenyl)acetamide and their pharmaceutically acceptable salts.

The invention further comprisies compounds selected from the group consisting of
- N-Hydroxy-N-(morpholinomethyl)-2-(4-(4-phenylbutyl) phenyl)acetamide,
- N-hydroxy-N-((4-methylpiperazin-1-yl)methyl)-2-(4-(4-phenylbutyl)phenyl)acetamide,
- N-hydroxy-N-(hydroxymethyl)-2-(4-(4-phenylbutyl)phenyl)acetamide,
- (S)-2,6-diamino-N-((S)-1-oxo-1-(2-(4-(4-phenylbutyl)phenyl)acetamidooxy)propan-2-yl)hexanamide,
- (S)-6-oxo-6-((S)-1-oxo-3-phenyl-1-(2-(4-(4-phenylbutyl)phenyl)acetamidooxy)propan-2-ylamino)hexane-1,5-diamine,
- N-(4-aminobenzoyloxy)-2-(4-(4-phenylbutyl)phenyl)acetamide,
- N-(6-aminohexanoyloxy)-2-(4-(4-phenylbutyl)phenyl)acetamide,
- 2-amino-N-(4-((2-(4-(4-phenylbutyl)phenylacetamidooxy)carbonyl)phenyl)acetamide hydrochloride,
- (S)-2,6-diamino-N-(4-((2-(4-(4-phenylbutyl)phenyl)acetamidooxy)carbonyl)phenyl)hexanamide di-hydrochloride,
- (S)-2,6-Diamino-N-(3-oxo-3-(2-(4-(4-phenylbutyl)phenyl)acetamidooxy)propyl)hexanamide,
- Methyl (1-((2-(4-(4-phenylbutyl)phenyl)acetamidooxy)carbonyl)cyclopropyl)methylcarbamate,
- (S)-N,N'-(6-Oxo-6-(2-(4-(4-phenylbutyl)phenyl)acetamidooxy)hexane-1,5-diyl)bis(2-(2-(2-methoxyethoxy)ethoxy)acetamide),
- N-(Isopropylcarbamoyloxy)-2-(4-(4-phenylbutyl)phenyl)acetamide,
- N-(Isopropylcarbamoyloxy)-2-(4-(4-phenylbutyl)phenyl)acetamide,
- N-(ethylcarbamoyloxy)-2-(4-(4-phenylbutyl)phenyl)acetamide,
- (S)-N,N'-(6-Oxo-6-(2-(4-(4-phenylbutyl)phenyl)acetamidooxy)hexane-1,5-diyl)bis(2-(2-methoxyethoxy)acetamide),
- N-([ethoxycarbonylmethyl]carbamoyl)-N-([ethoxycarbonylmethyl]carbamoyloxy)-2-(4-(4-phenylbutyl)phenyl)acetamide,
- (S)-N,N'-(6-Oxo-6-(3-oxo-3-(2-(4-(4-phenylbutyl)phenyl)acetamidooxy)propylamino)hexane-1,5-diyl)diacetamide,
- (S)-N,N'-(3-oxo-3-(3-oxo-3 -(2-(4-(4-phenylbutyl)phenyl)acetamidooxy)propylamino)propane-1,2-diyl)bis(3-methoxypropanamide,
- (S)-10-(2-acetoxyacetamido)-2,5,9,13-tetraoxo-1-(4-(4-phenylbutyl)phenyl)-4-oxa-3,8,12-triazatetradecan-14-yl acetate,
- N-1-(2-(2-(2-Methoxyethoxy)ethoxy)ethyl)-N-3-(2-(1-((2-(4-(4-phenylbutyl)phenyl)acetamidooxy)carbonylcyclopropyl)methyl)carbamoylethyl)urea,
- N-1-(2-(2-(2-methoxyethoxy)ethoxy)ethyl)-N-3-(2-(1-(4-(2-(4-(4-phenylbutyl)phenyl)acetamidooxy)carbonylpiperazine)carbamoyl)ethyl)urea,
- (S)-N,N'-(6-oxo-6-(3-oxo-3 -(2-(4-(4-phenylbutyl)phenyl)acetamiooxy)propylamino)hexane-1,5-diyl)bis(3-methoxypropanamide),
- (S)-10-(2-acetoxyacetamido)-2,5,9,16-tetraoxo-1-(4-(4-phenylbutyl)phenyl)-4-oxa-3,8,15-tri azaheptadecan-17-yl acetate),
- (S)-N,N'-(5-oxo-5-(3-oxo-3-(2-(4-(4-phenylbutyl)phenyl)acetamidooxy)propylamino)pentane-1,4-diyl)bis(3-methoxypropanamide)),
- (S)-dimethyl 6-oxo-6-(3-oxo-3-(2-(4-(4-phenylbutyl)phenyl)acetamidooxy)propylamino)hexane-1,5-diyldicarbamate),
- 4-oxo-N,N-bis(12-oxo-2,5,8-trioxa-11-azatridecan-13-yl)-4-(2-(4-(4-phenylbutyl)phenyl)acetamidooxy)butanamide,
- (S)-10-(2-acetoxyacetamido)-2,5,9,15-tetraoxo-1-(4-(4-phenylbutyl)phenyl)-4-oxa-3,8,14-triazahexadecan-16-yl acetate),
- (S)-10-(2-acetoxyacetamido)-2,5,9,14-tetraoxo-1-(4-(4-phenylbutyl)phenyl)-4-oxa-3,8,13-triazapentadecan-15-yl acetate,
- (S)-N,N'-(4-oxo-4-(3-oxo-3-(2-(4-(4-phenylbutyl)phenyl)acetamidooxy)propylamino)butane-1,3-diyl)bis(3-methoxypropanamide),
- N,N'-((S)-6-Oxo-6-((S)-2-((2-(4-(4-phenylbutyl)phenyl)acetamidooxy)carbonyl)pyrrolidin-1-yl)hexane-1,5-diyl)bis(2-(2-(2- methoxyethoxy)ethoxy)acetamide),
- N-((S)-1-((S)-2,6-Diaminohexanoyl)pyrrolidine-2-carbonyloxy)-2-(4-(4-phenylbutyl)phenyl)acetamide,
- N,N'-((S)-6-oxo-6-((S)-2-((2-(4-(4-phenylbutyl)phenyl)acetamidooxy)carbonyl)pyrrolidin-1-yl)hexane-1,5-diyl)bis(2-(2- methoxyethoxy)acetamide),
- (S)-2-Amino-6-(2-(2-(2-methoxyethoxy)ethoxy)acetamido)-N-(3-oxo-3-(2-(4-(4-phenylbutyl)phenyl)acetamidooxy)propyl)hexanamide hydrochloride, 2-(2-(2-Methoxyethoxy)ethoxy)-N-(2-oxo-2-(4-oxo-4-(2-(4-(4-phenylbutyl)phenyl)acetamidooxy)butylamino)ethyl)-N-(10-oxo-2,5,8-trioxa-11-azatridecan-13-yl)acetamide,
2-(2-(2-methoxyethoxy)ethoxy)-N-(2-oxo-2-(3-oxo-3-(2-(4-(4-phenylbutyl)phenyl)acetamidooxy)propylamino)ethyl)-N-(10-oxo-2,5,8- trioxa-11-azatridecan-13-yl) acetamide,2-(4-(4-phenylbutyl)phenyl)-N-(2-(piperidin-4-yl)acetoxy)acetamide hydrochloride, and pharmaceutically acceptable salts thereof.

Syntheses

The compounds of the invention can be prepared according to the reaction schemes or the examples illustrated below utilizing methods known to one of ordinary skill in the art. These schemes serve to exemplify some procedures that can be used to make the compounds of the invention. One skilled in the art will recognize that other general synthetic procedures may be used. The compounds of the invention can be prepared from starting components that are commercially available. Any kind of substitutions can be made to the starting components to obtain the compounds of the invention according to procedures that are well known to those skilled in the art.

All reagents and solvents were obtained from commercial sources and used as received. $^{1}$H-NMR spectra were recorded on a Mercury Plus Varian 400 MHz instrument in the solvents indicated. Low resolution mass-spectra (LRMS) were acquired on an Agilent MSD instrument. Analytical HPLC was performed on an Agilent 1100 instrument. Conditions/methods are provided below as GRADI40, GRADI50, ACEPOLAR30, ACEPOLAR40 and ACEPOLAR50.

GRADI40:
Mobile phase: A: water+0.1% formic acid, B: MeOH+0.1% formic acid; Gradient: 40% B to 95% B over 12 min, Isocratic: 95% B for 3 min; Post-time of 3 min; Flow: 1 ml/min; Temperature: 22° C. Column: Agilent, Zorbax C8, 4.6×50 mm, 3.5 μm.

GRADI50:
Mobile phase: A: water+0.1% formic acid, B: MeOH+0.1% formic acid; Gradient: 50% B to 95% B over 12 min, Isocratic: 95% B for 3 min; Post-time of 3 min; Flow: 1 ml/min; Temperature: 22° C. Column: Agilent, Zorbax C8, 4.6×50 mm, 3.5 μm.

ACEPOLAR30:
Mobile phase: A: water+0.1% formic acid, B: MeOH+0.1% formic acid; Gradient: 30% B to 95% B over 12 min, Isocratic: 95% B for 3 min; Post-time of 3 min; Flow: 1 ml/min; Temperature: 22° C. Column: Ace, Aquasil C18, 4.6×100 mm, 5 μm.

ACEPOLAR40:
Mobile phase: A: water+0.1% formic acid, B: MeOH+0.1% formic acid; Gradient: 40% B to 95% B over 12 min, Isocratic: 95% B for 3 min; Post-time of 3 min; Flow: 1 ml/min; Temperature: 22° C. Column: Ace, Aquasil C18, 4.6×100 mm, 5 μm.

ACEPOLAR50:
Mobile phase: A: water+0.1% formic acid, B: MeOH+0.1% formic acid; Gradient: 50% B to 95% B over 12 min, Isocratic: 95% B for 3 min; Post-time of 3 min; Flow: 1 ml/min; Temperature: 22° C. Column: Ace, Aquasil C18, 4.6×100 mm, 5 μm.

Automated column chromatography was performed on a Biotage SP1 or Biotage SP4 instruments using Biotage® SNAP, SiliaSep™ or SiliaFlash® cartridges. Flash column chromatography was performed using silica gel (40-63 μM, pore size 60 Å, SiliCycle®).

For purposes of the present invention, the following abbreviations will be used (unless expressly stated otherwise)

Ac acetyl
AcOEt ethyl acetate
AcOH acetic acid
aq aqueous
bd broad doublet (NMR)
br s broad singlet (NMR)
CV column volume
d doublet (NMR)
dd doublet of doublets (NMR)
DCC dicyclohexyl carbodiimide
DCM dichloromethane
DIPEA diisopropyl ethylamine
DMAP dimethylamino pyridine
DMF N,N-dimethylformamide
DMSO dimethylsulfoxide
DMSO-$d_6$ dimethylsulfoxide-$d_6$
EDC 1-(3-dimethylaminopropyl)-3-ethyl-carbodiimide
Et ethyl
EDC 1-(3-dimethylaminopropyl)-3-ethyl-carbodiimide
Et$_3$N triethylamine
EtOH ethanol
EtOAc ethyl acetate
Et$_2$O diethyl ether
equiv equivalent
g gram (grams)
h hour (hours)
HOBT 1-hydroxybenzotriazole
m multiplet (NMR)
mL milliliter
μL microliter
Me methyl
MeOH methanol
MeOH-$d_4$ methanol-$d_4$
mg milligram (milligrams)
min minute (minutes)
MS mass-spectroscopy
m/z mass-to-charge ratio
NMP N-methyl-2-pyrrolidone
NMR nuclear magnetic resonance spectroscopy
rt room temperature
s singlet (NMR)
t triplet (NMR)
TFA trifluoroacetic acid
THF tetrahydrofuran The following schemes and examples are intended to further illustrate certain preferred embodiments of the invention, and are not intended to limit the scope of the invention.

Scheme 1

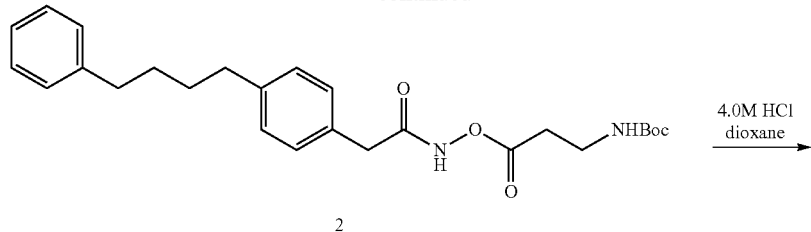

2

4.0M HCl dioxane →

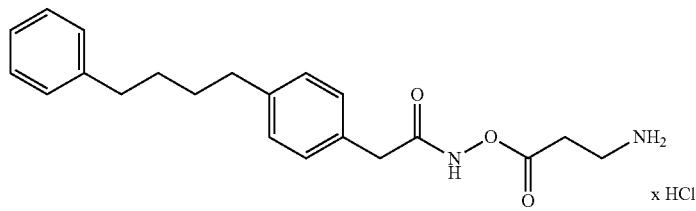

3: Example 1

EXAMPLE 1

N-(3-Aminopropanoyloxy)-2-(4-(4-phenylbutyl)phenyl)acetamide hydrochloride (3)

Step 1. tert-Butyl 3-oxo-3-(2-(4-(4-phenylbutyl)phenyl)acetamidooxy)propylcarbamate (2)

To a solution of N-hydroxy-2-(4-(4-phenylbutyl)phenyl)acetamide (1, WO 2008/074132) (1 g, 3.53 mmol) and N-tert-butoxycarbonyl-beta-alanine (0.868 g, 4.59 mmol) in DMF (5 mL) were added HOBt×H$_2$O (0.477 g, 3.53 mmol) then EDC×HCl (0.880 g, 4.59 mmol). The mixture was stirred overnight, diluted with EtOAc then washed with ice-water (×2), saturated NaHCO$_3$ solution and brine, dried over Na$_2$SO$_4$, filtered and concentrated. The residue was purified by column chromatography eluting with 0% to 50% EtOAc in hexanes to afford the title compound 2 (1 g, 2.200 mmol, 62.3% yield) as a white solid. LRMS(ESI): (calc.) 454.6 (found) 455.6(MH)$^+$.

Step 2. N-(3-Aminopropanoyloxy)-2-(4-(4-phenylbutyl)phenyl)acetamide hydrochloride (3)

Compound 2 (1 g, 2.20 mmol) was treated with 4M HCl in dioxane (16 mL, 64.0 mmol) and stirred for 1.5 h. The mixture was concentrated to form a white solid which was triturated with Et$_2$O (10 ml) for 2 h to afford the title compound 3 (0.8 g, 2.047 mmol, 93% yield) as a white solid, presumably as a hydrochloride salt. $^1$H NMR (400 MHz, DMSO-d$_6$) δ (ppm): 12.21 (s, 1H), 8.08 (br s, 3H), 7.26-7.72 (m, 2H), 7.18-7.12 (m, 5H), 7.12-7.06 (m, 2H), 3.43 (s, 2H), 3.08-2.98 (m, 2H), 2.84 (t, J=7.1 Hz, 2H), 2.60-2.50 (m, 4H), 1.60-1.48 (m, 4H). LRMS (ESI): (calc.) 354.2 (found) 355.4 (MH)$^+$.

Compounds 4-10 (examples 2-8) were obtained starting from hydroxamate 1 by following the procedures described above for the synthesis of compound 3 (scheme 1) by replacing N-tert-butoxycarbonyl-beta-alanine in the step 1 with 4-(tert-butoxycarbonylamino)butanoic acid, 2-(tert-butoxycarbonylamino)acetic acid, 6-(tert-butoxycarbonylamino)hexanoic acid, 8-(tert-butoxycarbonylamino)octanoic acid, (S)-1-(tert-butoxycarbonyl)pyrrolidine-2-carboxylic acid, 4-(tert-butoxycarbonylamino)benzoic acid or 4-(di-tert-butoxyphosphoryloxy)butanoic acid, respectively. Characterization of compounds 4-10 (examples 2-8) is provided in Table 1.

TABLE 1

Characterization of compounds 4-10 (examples 2-8).

| Cpd | Ex. | Structure | Characterization |
|---|---|---|---|
| 4 | 2 | ![structure] N-(4-aminobutanoyloxy)-2-(4-(4-phenylbutyl)phenyl)acetamide hydrochloride × HCl | $^1$H NMR (400 MHz, DMSO-d$_6$) δ (ppm): 11.99 (s, 1H), 7.83 (br s, 3H), 7.27-7.20 (m, 2H), 7.18-7.06 (m, 7H), 3.41 (s, 2H), 2.88-2.74 (m, 2H), 2.60-2.50 (m, 4H), 2.34-2.28 (m, 1H), 1.87-1.68 (m, 3H), 1.60-1.50 (m, 4H). LRMS (ESI): (calc.) 368.2 (found) 369.5 (MH)+ |

TABLE 1-continued

Characterization of compounds 4-10 (examples 2-8).

| Cpd | Ex. | Structure | Characterization |
|---|---|---|---|
| 5 | 3 | 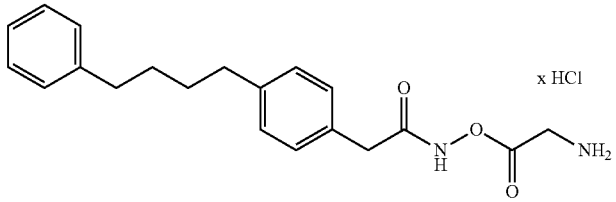<br>N-(2-aminoacetoxy)-2-(4-(4-phenylbutyl)phenyl)acetamide hydrochloride | $^1$H NMR (400 MHz, DMSO-$d_6$) δ (ppm): 12.4 (br s, 1H), 8.48 (br s, 3H), 7.28 (m, 2H), 7.20-7.06 (m, 7H), 4.03 (s, 2H), 3.46 (s, 2H), 2.62-2.50 (m, 4H), 1.62-1.48 (m, 4H).<br>LRMS (ESI): (calc.) 340.2 (found) 341.5 (MH)+ |
| 6 | 4 | 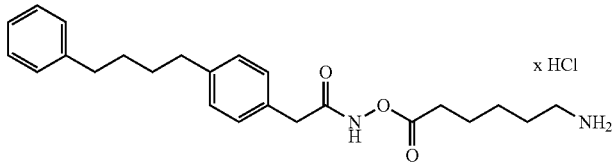<br>N-(6-aminohexanoyl)-2-(4-(4-phenylbutyl)phenyl)acetamide hydrochloride | $^1$H NMR (400 MHz, DMSO-$d_6$) δ (ppm): 11.92 (s, 1H), 7.68 (br s, 3H), 7.28-7.20 (m, 2H); 7.18-7.06 (m, 7H); 3.42 (s, 2), 3.30-3.20 (m, 2H), 2.80-2.68 (m, 2H); 2.60-2.50 (m, 4H); 2.47-2.38 (m, 2H); 1.60-1.46 (m, 6H); 1.40-1.28 (m, 2H).<br>LRMS (ESI): (calc.) 396.2 (found) 397.5 (MH)+ |
| 7 | 5 | 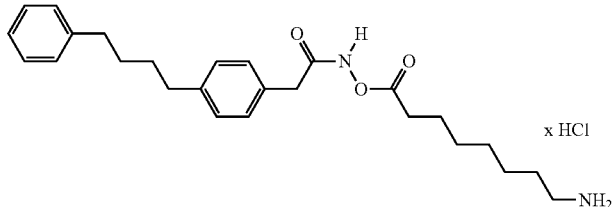<br>N-(8-aminooctanoyloxy)-2-(4-(4-phenylbutyl)phenyl)acetamide hydrochloride | $^1$H NMR (DMSO-d6) δ (ppm): 8.78 (br. s, 3H), 7.28-7.24 (m, 2H), 7.18-7.10 (m, 7H), 3.41 (s, 2H), 2.74 (t, J = 7.4 Hz, 2H), 2.61-2.56 (m, 4H), 2.43 (t, J = 7.2 Hz, 2H), 1.59-1.50 (m, 8H), 1.28 (br. s, 6H). LRMS (ESI): (calc.) 424.6 (found) 425.3 (MH)+ |
| 8 | 6 | 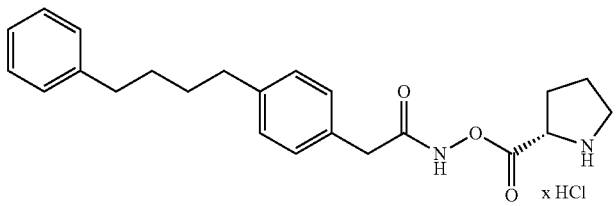<br>(S)-2-(4-(4-phenylbutyl)phenyl)-N-(pyrrolidine-2-carbonyloxy)actamide hydrochloride | $^1$H NMR (400 MHz, DMSO-$d_6$) δ (ppm): 12.51 (s, 1H), 11.00-8.50 (br s, 2H), 7.27-7.21 (m, 2H), 7.19-7.06 (m, 7H), 4.59 (t, J = 7.8 Hz, 1H), 3.46 (s, 2H), 3.28-3.10 (m, 2H), 2.60-2.50 (m, 4H), 2.40-2.25 (m, 1H), 2.15-2.00 (m, 1H), 2.00-1.80 (m, 2H), 1.10-0.98 (m, 4H).<br>LRMS (ESI): (calc.) 380.2 (found) 381.4 (MH)+ |
| 9 | 7 | 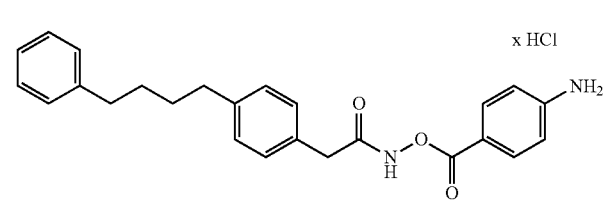<br>N-(4-aminobenzoyloxy)-2-(4-(4-phenylbutyl)phenyl)acetamide hydrochloride | $^1$H NMR (400 MHz, DMSO-$d_6$) δ (ppm): 11.95 (br s, 1H), 7.67 (d, J = 8.8 Hz, 2H), 7.26-7.08 (m, 12H), 6.63 (d, J = 8.8 Hz, 2H), 3.44 (s, 2H), 2.60-2.52 (m, 4H), 1.58-1.50 (m, 4H).<br>LRMS (ESI): (calc.) 402.2 (found) 403.4 (MH)+ |
| 10 | 8 | 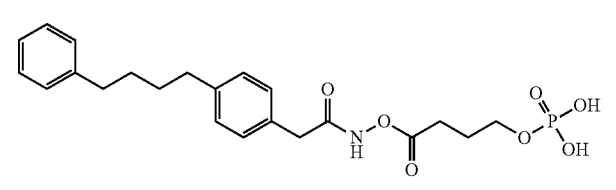<br>4-oxo-4-(2-(4-(4-phenylbutyl)phenyl)acetamidooxy)butyl dihydrogen phosphate | $^1$H NMR (400 MHz, DMSO-$d_6$) δ (ppm): 11.90 (s, 1H), 7.27-7.20 (m, 2H), 7.18-7.12 (m, 5H), 7.12-7.07 (m, 2H), 3.82 (q, J = 13.7 and 6.5 Hz, 2H), 3.40 (s, 2H), 2.60-2.5 (m, 6H), 1.89-1.79 (m, 2H), 1.60-1.50 (m, 4H).<br>LRMS (ESI): (calc.) 449.2 (found) 450.4 (MH)+ |

Scheme 2

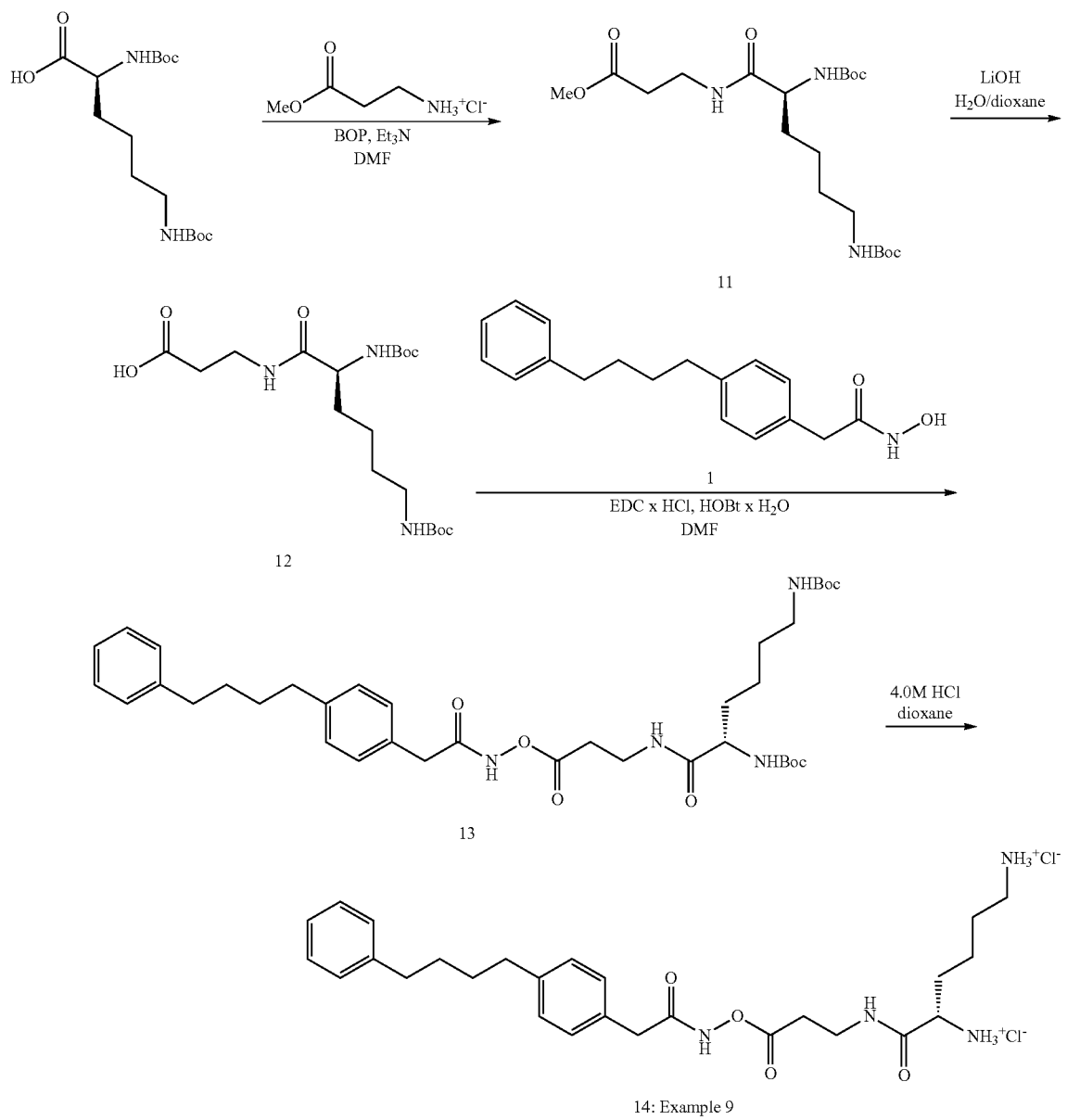

EXAMPLE 9

(S)-2,6-Diamino-N-(3-oxo-3-(2-(4-(4-phenylbutyl)phenyl)acetamidooxy)propyl)hexanamide di-hydrochloride (14)

Step 1. (S)-Methyl3-(2,6-bis(tert-butoxycarbonylamino)hexanamido)propanoate (11).

Title compound 11 was obtained using a modified procedure, published in *Bioorg. Med. Chem. Lett.*, 1998, 8, pp.1873-1986.

To a solution of beta-alanine hydrochloride (0.4 g, 2.87 mmol), N,N'-bis-Boc-Lysine (0.993 g, 2.87 mmol) and BOP (1.647 g, 3.73 mmol) in DMF (3 mL) at RT was added Et$_3$N (2.395 mL, 17.19 mmol). The reaction mixture was stirred overnight, partitioned between EtOAc and 0.1M aq HCl solution. The organic phase was separated, dried over Na$_2$SO$_4$, filtered and concentrated under reduced pressure. The residue was purified by silica gel column chromatography eluting with 5-80% EtOAc in hexanes, to afford title compound 11 (1.200 g, 97% yield). The material was taken to the next step without characterization.

Step 2. (S)-3-(2,6-bis(tert-Butoxycarbonylamino)hexanamido)propanoic acid (12).

Title compound 12 was obtained using a modified procedure, published in *Bioorg. Med. Chem. Lett.*, 1998, 8, pp.1873-1986.

LiOH (0.200 g, 8.34 mmol) was added to a solution of the ester 11 (1.2 g, 2.78 mmol) in a solvent mixture of dioxane (1 mL) and water (1 mL) at RT. The reaction mixture was then stirred overnight, quenched with 1M HCl, partitioned between H$_2$O and EtOAc. The organic phase was separated, dried over Na$_2$SO$_4$, filtered and concentrated under reduced pressure. The residue was purified by silica gel column chromatography eluting with 60-100% EtOAc, to afford the title compound 12 (0.978 g, 87% yield). The material was taken to the next step without characterization.

Step 3. (S)-tert-Butyl 6-oxo-6-(3-oxo-3-(2-(4-(4-phenylbutyl)phenyl)acetamidooxy)propylamino)hexane-1,5-diyldicarbamate (13).

EDC×HCl (0.449 g, 2.343 mmol) was added to a solution of HOBt×H$_2$O (0.239 g, 1.562 mmol), hydroxamate 1 (0.443 g, 1.562 mmol) and the acid 12 (0.978 g, 2.343 mmol) in DMF (7 mL) at RT. The reaction mixture was then stirred overnight, partitioned between H$_2$O and EtOAc. The organic phase was separated, dried over Na$_2$SO$_4$, filtered and concentrated under reduced pressure. The residue was purified by silica gel column chromatography eluting with 10-100% EtOAc in hexanes, to afford the title compound 11 (0.223 g, 20.9% yield). LRMS (ESI): (calc.) 682.9 (found) 683.8 (MH)+.

Step 4. ((S)-2,6-Diamino-N-(3-oxo-3-(2-(4-(4-phenylbutyl)phenyl)acetamidooxy)propyl)hexanamide (14)

A 4M HCl solution in dioxane (6 mL, 24.0 mmol) was added to compound 13 (0.233 g, 0.327 mmol) at RT. The reaction mixture was then stirred for 40 min. The solvent was evaporated and the residue triturated with diethyl ether, collected by filtration and dried in vacuum to afford the title compound 14 presumably as a di-hydrochloride salt (0.138 g, 75.8% yield). $^1$H NMR (400 MHz, DMSO-d$_6$) δ (ppm): 12.08 (s, 1H), 8.71 (bs, 1H), 8.18 (bs, 3H), 7.84 (bs, 3H), 7.25-7.08 (m, 9H), 3.67 (m, 1H), 3.42 (s, 2H), 3.38 (m, 2H), 2.68 (m, 4H), 2.55 (m, 4H), 1.66 (m, 2H), 1.54 (m, 6H), 1.28 (m, 2H). LRMS (ESI): (calc.) 482.6 (found) 483.7 (MH)$^+$.

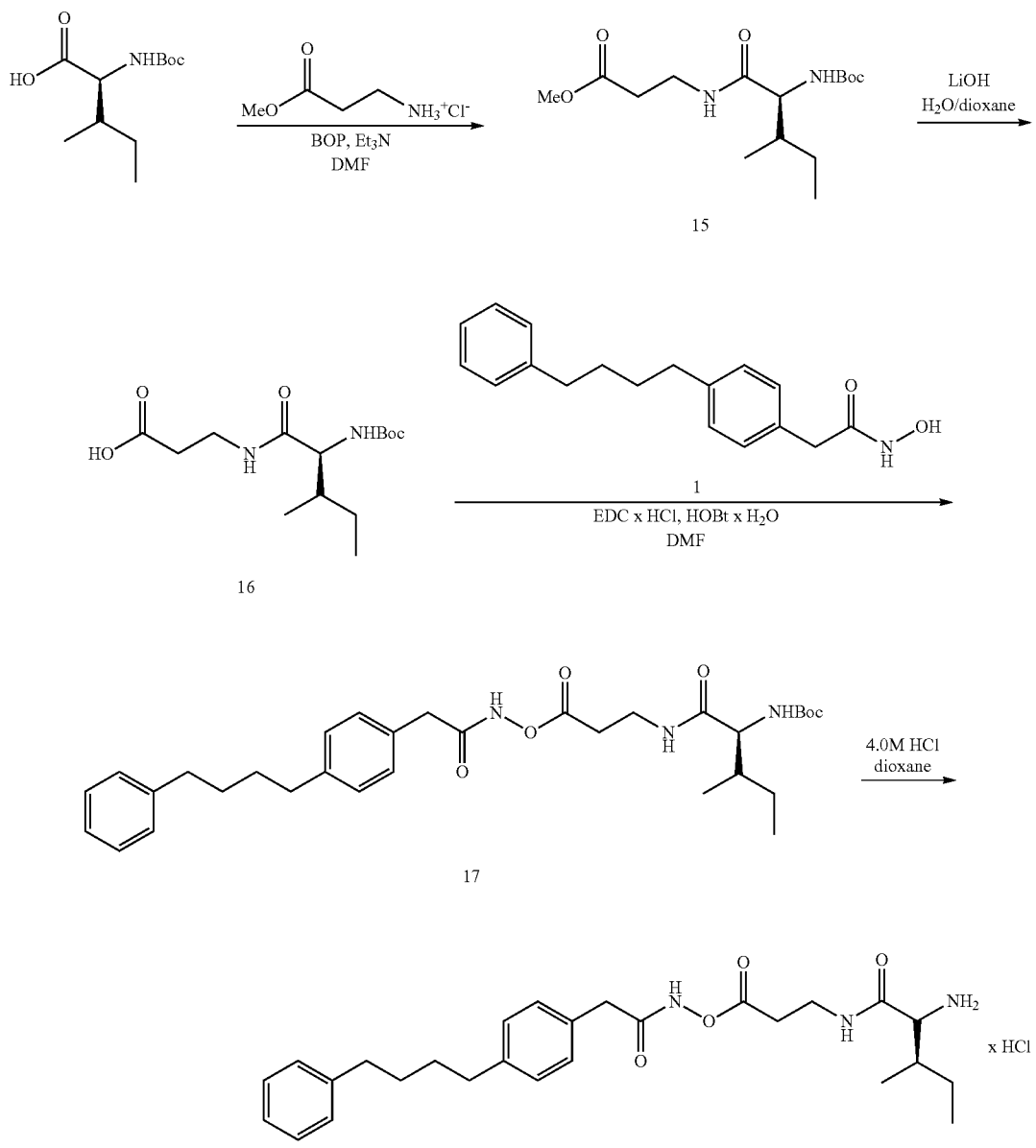

Scheme 3

18: Example 10

EXAMPLE 10

(2S,3S)-2-Amino-3-methyl-N-(3-oxo-3-(2-(4-(4-phenylbutyl)phenyl)acetamidooxy)propyl)pentanamide hydrochloride (18)

Step 1. Methyl 3-((2S,3S)-2-(tert-butoxycarbonylamino)-3-methylpentanamido)propanoate (15).

Et₃N (1.796 mL, 12.90 mmol) was added to a solution of beta-alanine hydrochloride (0.3 g, 2.149 mmol), isoleucine (0.497 g, 2.149 mmol) and BOP (1.235 g, 2.79 mmol) in DMF (3 mL) at RT. The reaction mixture was then stirred for 1 h partitioned between water and EtOAc. The organic phase was separated, dried over Na₂SO₄, filtered and concentrated under reduced pressure. The residue was purified by silica gel column chromatography eluting with 10-100% EtOAc in hexanes to afford title compound 15 (0.675 g, 99% yield). LRMS (ESI): (calc.) 316.9 (found) 317.4 (MH)⁺.

Step 2. 3-((2S,3S)-2-(tert-Butoxycarbonylamino)-3-methylpentanamido)pronanoic acid (16).

LiOH (0.154 g, 6.40 mmol) was added to a solution of the acid 17 (0.675 g, 2.133 mmol) in a solvent mixture of dioxane (1 mL) and water (1 mL) at RT. The reaction mixture was then stirred overnight, quenched with 1M HCl, partitioned between water and EtOAc. The organic phase was separated, dried over Na₂SO₄, filtered and concentrated under reduced pressure. The residue was purified by silica gel column chromatography eluting with 60-100% EtOAc in hexanes to afford title compound 16 (0.598 g, 92.7% yield). LRMS (ESI): (calc.) 302.4 (found) 303.4 (MH)⁺.

Step 3. tert-Butyl (2S,3S)-3-methyl-1-oxo-1-(3-oxo-3-(2-(4-(4-phenylbutyl)phenyl)acetamidooxy)propylamino)pentan-2-ylcarbamate (17).

EDC×HCl (0.379 g, 1.978 mmol) was added to a solution of HOBt×H₂O (0.178 g, 1.318 mmol), hydroxamate 1 (0.374 g, 1.318 mmol), and acid 16 (0.598 g, 1.978 mmol) in DMF (7 mL) at RT. The reaction mixture was then stirred overnight, partitioned between water and EtOAc. The organic phase was separated, dried over Na₂SO₄, filtered and concentrated under reduced pressure. The residue was purified by silica gel column chromatography eluting with 10-100% EtOAc in hexanes, to afford title compound 17 (0.135 g, 18.0% yield). The material was taken to the next step without characterization.

Step 4. (2S,3S)-2-Amino-3-methyl-N-(3-oxo-3-(2-(4-(4-phenylbutyl)phenyl)acetamidooxy)propyl)pentanamide hydrochloride (18).

A solution of HCl (4M in dioxane) (6 mL, 24.00 mmol) was added to, compound 17 (0.135 g, 0.238 mmol) at RT. The reaction mixture was then stirred for 40 min. The solvent was evaporated, the residue was triturated with diethyl ether, collected by filtration and dried in vaccum to afford title compound 18, presumably as a hysrochloride salt (64 mg, 53.4% yield). ¹H NMR (400 MHz, DMSO-d₆) δ (ppm): 12.02 (bs, 1H), 8.55 (bs, 1H), 8.05 (bs, 3H), 7.25-7.07 (m, 9H), 3.50 (m, 1H), 3.46 (m, 2H), 3.41 (s, 2H), 2.65 (t, J=6.4 Hz, 2H), 2.54 (m, 4H), 1.74 (m, 1H), 1.54 (m, 4H), 1.41 (m, 1H), 1.06 (m, 1H), 0.83 (m, 6H). LRMS (ESI): (calc.) 467.2 (found) 468.8 (MH)⁺.

Compounds 19-22 (examples 11-14) were obtained starting from hydroxamate 1 by following the procedures described above for the synthesis of compound 14 (scheme 2), by replacing (S)-3-(2,6-bis(tert-butoxycarbonylamino)hexanamido)propanoic acid (12) as the di-peptide intermediate with the acids 23-26, respectively. Characterization of compounds 19-22 (examples 11-14) is provided in Table 2.

(S)-3-(2-(tert-Butoxycarbonylamino)-3-phenylpropanamido)propanoic acid (23) (*Organic Letters*, 2007, 9(7), pp. 1347-1350) that was used in the synthesis of compound 19 (example 11), was obtained by following procedures similar to the ones employed in the synthesis of compound 12 (scheme 2). LRMS (ESI): (calc.) 336.4 (found) 337.4 (MH)⁺.

(S)-3-(2-(tert-butoxycarbonylamino)propanamido)propanoic acid (24) (*Bioorg. & Med Chem*, 2003, 11(14), pp. 3083-3099) that was used in the synthesis of compound 20 (example 12) was obtained by following procedures similar to the ones employed in the synthesis of compound 12 (scheme 2). LRMS (ESI): (calc.) 260.3 (found) 261.3 (MH)⁺.

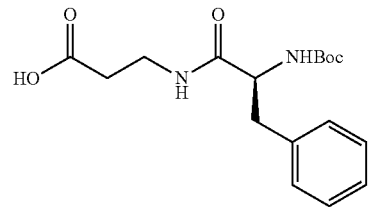

23

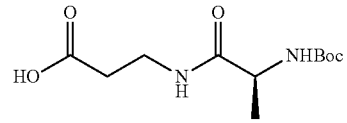

24

(S)-2-((S)-2,6-bis(tert-butoxycarbonylamino)hexanamido)propanoic acid (25) (*Bioorg. Med. Chem. Lett.*, 1998, 8, pp.1873-1986; WO 1995/000846) that was used in the synthesis of compound 21 (example 13) was obtained by following procedures similar to the ones employed in the synthesis of compound 12 (scheme 2). LRMS (ESI): (calc.) 417.5 (found) 418.6 (MH)⁺.

(S)-2-((S)-2,6-bis(tert-butoxycarbonylamino)hexanamido)-3-phenylpropanoic acid (26) (Ger. Offen., 1975, DE 2518256 A1 19751106) that was used in the synthesis of compound 22 (example 14) was obtained by following procedures similar to the ones employed in the synthesis of compound 12 (scheme 2). LRMS (ESI): (calc.) 493.6 (found) 494.6 (MH)⁺.

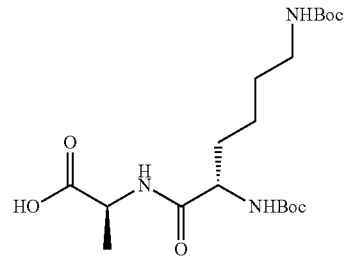

25

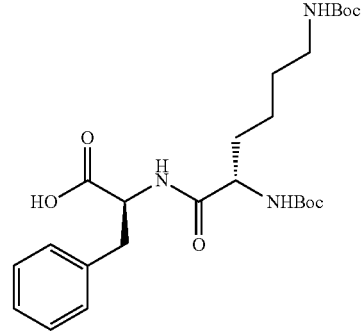

26

Compounds 22-A-22-D (examples 14-A-14-D) were obtained starting from hydroxamate 1 by following the procedures described above for the synthesis of compound 14 (scheme 2), and using instead of (S)-3-(2,6-bis(tert-butoxycarbonylamino)hexanamido)propanoic acid (12) corresponding acids of the di-peptide nature prepared similarly to the acid 12. Characterization of compounds 22-A-22-D (examples 14-A-14-D) is provided in Table 2.

TABLE 2

Characterization of compounds 19-22 (examples 11-14) and 22-A-22-D (examples 14-A-14-D).

| Cpd | Ex. | Structure | Characterization |
|---|---|---|---|
| 19 | 11 | 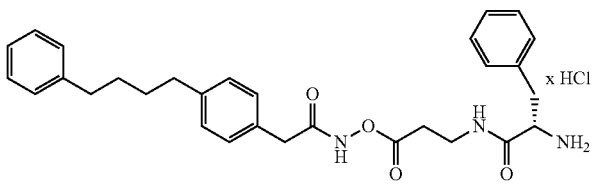<br>(S)-2-amino-N-(3-oxo-3-(2-(4-(4-phenylbutyl)phenyl)acetamidooxy)propyl)-3-phenylpropanamide hydrochloride | $^1$H NMR (400 MHz, DMSO-$d_6$) δ (ppm): 12.02 (bs, 1H), 8.60 (bs, 1H), 8.18 (bs, 3H), 7.30-7.06 (m, 14H), 3.90m (m, 1H), 3.41 (s, 2H), 3.24 (m, 1H), 2.98 (m, 3H), 2.54 (m, 6H), 1.54 (m, 4H)<br>LRMS (ESI): (calc.) 501.2 (found) 502.6 (MH)+ |
| 20 | 12 | 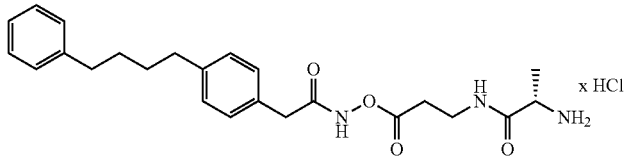<br>(S)-2-amino-N-(3-oxo-3-(2-(4-(4-phenylbutyl)phenyl)acetamidooxy)propyl) propanamide hydrochloride | $^1$H NMR (400 MHz, DMSO-$d_6$) δ (ppm): 12.00 (s, 1H), 8.52 (bs, 1H), 8.04 (bs, 3H), 7.25-7.08 (m, 9H), 3.73 (m, 1H), 3.41 (s, 2H), 3.39 (m, 2H), 2.64 (t, J = 6.8 Hz, 2H), 2.55 (m, 4H), 1.54 (m, 4H), 1.28 (d, J = 7.2 Hz, 3H)<br>LRMS (ESI): (calc.) 425.2 (found) 426.5 (MH)+ |
| 21 | 13 | 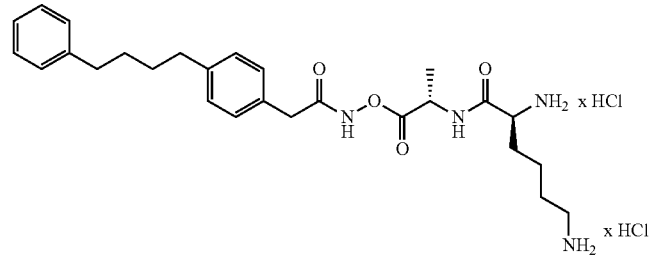<br>(S)-2,6-diamino-N-((S)-1-oxo-1-(2-(4-(4-phenylbutyl)phenyl)acetamidooxy)propan-2-yl)hexanamide dihydrochloride | $^1$H NMR (400 MHz, DMSO-$d_6$) δ (ppm): 12.17 (bs, 1H), 9.11 (bs, 1H), 8.25 (m, 3H), 7.87 (m, 3H), 7.26-7.08 (m, 9H), 4.51 (m, 1H), 3.76 (m, 1H), 3.41 (s, 2H), 2.71 (m, 2H), 2.56 (m, 4H), 1.71 (m, 2H), 1.54 (m, 6H), 1.38 (m, 5H)<br>LRMS (ESI): (calc.) 482.3 (found) 483.6 (MH)+ |
| 22 | 14 | 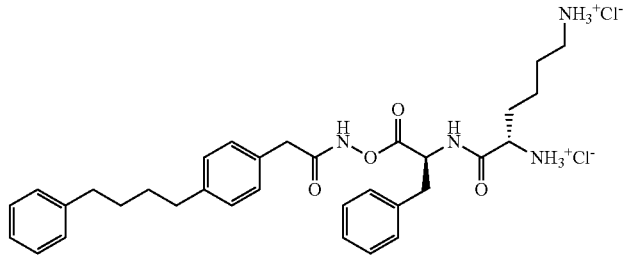<br>(S)-6-oxo-6-((S)-1-oxo-3-phenyl-1-(2-(4-(4-phenylbutyl)phenyl)acetamidooxy)propan-2-ylamino)hexane-1,5-diaminium chloride | $^1$H NMR (400 MHz, DMSO-$d_6$) δ (ppm): 12.26 (bs, 1H), 9.19 (bs, 1H), 8.21 (m, 3H), 7.91 (m, 3H), 7.32-7.22 (m, 7H), 7.16-7.08 (m, 7H), 4.72 (m, 1H), 3.69 (m, 1H), 3.43 (m, 2H), 3.19 (m, 1H), 3.00 (m, 1H), 2.71 (m, 2H), 2.55 (m, 4H), 1.72 (m, 2H), 1.55 (m, 6H), 1.33 (m, 2H),<br>LRMS (ESI): (calc.) 558.3 (found) 559.6 (MH)+ |
| 22-A | 14-A | 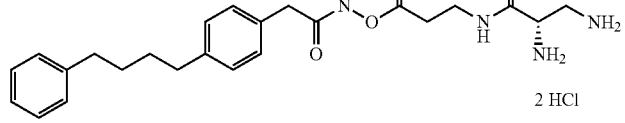<br>((S)-2,3-diamino-N-(3-oxo-3-(4-(4-phenylbutyl)phenyl)acetamidooxy)propyl) propanamide hydrochloride | LRMS (ESI): (calc.) 440.4 (found) 441.3 (MH)+ |

TABLE 2-continued

Characterization of compounds 19-22 (examples 11-14) and 22-A-22-D (examples 14-A-14-D).

| Cpd | Ex. | Structure | Characterization |
|---|---|---|---|
| 22-B | 14-B | (S)-2,4-diamino-N-(3-oxo-3-(2-(4-(4-phenylbutyl)phenyl)acetamidooxy)propyl)butanamide di-hydrochloride | LRMS (ESI): (calc.) 454.2 (found) 455.2 (MH)+ |
| 22-C | 14-C | (S)-2,5-diamino-N-(3-oxo-3-(2-(4-(4-phenylbutyl)phenyl)acetamidooxy)propyl)pentanamide di-hydrochloride | LRMS (ESI): (calc.) 468.3 (found) 469.4 (MH)+ |
| 22-D | 14-D | (S)-2,6-diamino-N-((1-((2-(4-(4-phenylbutyl)phenyl)acetamidooxy)carbonyl)cyclopropyl)methyl)hexanamide di-hydrochloride | LRMS (ESI): (calc.) 508.7 (found) 509.5 (MH)+ |

Compounds 27-32 (examples 15-20) were obtained starting from hydroxamate 1 by following the procedures described above for the synthesis of compound 14 (scheme 2), by replacing (S)-3-(2,6-bis(tert-butoxycarbonylamino)hexanamido)propanoic acid (12) as the di-peptide intermediate with the acids 33-38, respectively. Characterization of compounds 27-32 (examples 15-20) is provided in Table 3.

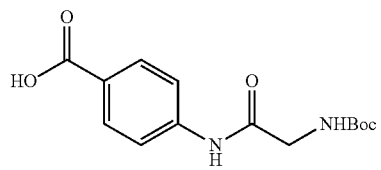

33

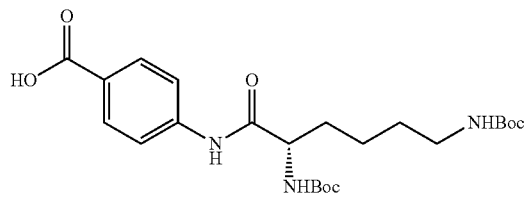

34

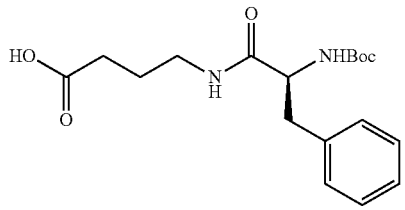

35

4-(2-(tert-Butoxycarbonylamino)acetamido)benzoic acid (33) (WO 2004/082687; *J. Org. Chem.* 1970, 35(9), pp. 2877-2881) that was used in the synthesis of compound 27 (example 15) was obtained by following procedures similar to the ones employed in the synthesis of compound 12 (scheme 2). LRMS (ESI): (calc.) 294.3 (found) 293.2 (M−H)−.

(S)-4-(2,6-bis(tert-butoxycarbonylamino)hexanamido)benzoic acid (34) (*Macro-molecules,* 2002, 35(16), pp. 6101-6111) that was used in the synthesis of compound 28 (example 16) was obtained by following procedures similar to the ones employed in the synthesis of compound 12 (scheme 2). LRMS (ESI): (calc.) 465.5 (found) 464.6 (M−H)−.

(S)-4-(2-(tert-Butoxycarbonylamino)-3-phenylpropanamido)butanoic acid (35) (Eur. Pat. Appl. 1992, EP 481311 A2 19920422) that was used in the synthesis of compound 29 (example 17) was obtained by following procedures similar to the ones employed in the synthesis of compound 12 (scheme 2). LRMS (ESI): (calc.) 350.41 (found) 357.3 (MLi)+.

(S)-6-(2-(tert-Butoxycarbonylamino)-3-phenylpropanamido)hexanoic acid (36) (*J. Chem. Soc. Chem. Commun.*, 1990, (15), pp. 1045-1047.) that was used in the synthesis of compound 30 (example 18) was obtained by following procedures similar to the ones employed in the synthesis of compound 12 (scheme 2). LRMS (ESI): (calc.) 378.5 (found) 379.4 (MH)+.

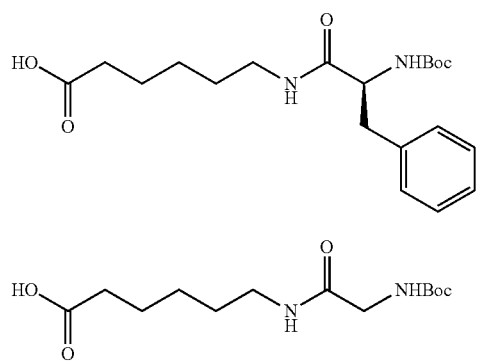

6-(2-(tert-Butoxycarbonylamino)acetamido)hexanoic acid (37) (*J. Org. Chem.* (1974), 39(5), pp. 660-668) that was used in the synthesis of compound 31 (example 19) was obtained by following procedures similar to the ones employed in the synthesis of compound 12 (scheme 2). LRMS (ESI): (calc.) 302.4 (found) 303.3 (MH)+.

(S)-6-(2-(tert-Butoxycarbonylamino)-3-(4-hydroxyphenyl)propanamido)hexanoic acid (38) that was used in the synthesis of compound 32 (example 19) was obtained via a two-step reaction sequence according to the scheme 4.

Scheme 4

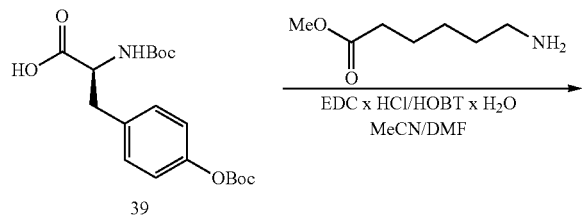

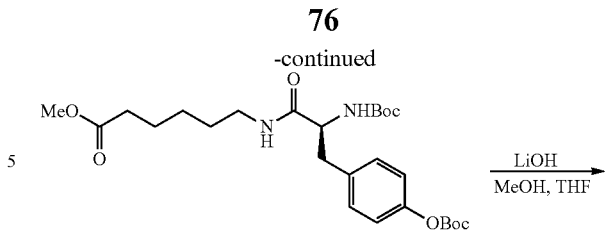

Step 1. (S)-Methyl 6-(2-(tert-butoxycarbonylamino)-3-(4-(tert-butoxycarbonyloxy)phenyl)propanamido)hexanoate (40).

HOBt×H$_2$O (1.070 g, 7.92 mmol) was added to a solution of (S)-2-(tert-butoxycarbonylamino)-3-(4-(tert-butoxycarbonyloxy)phenyl)propanoic acid (39, 3.02 g, 7.92 mmol) and methyl 6-aminohexanoate (1.15 g, 7.92 mmol) in a solvent mixture of DCM (30 mL) and acetonitrile (15 mL) followed by the EDC×HCl (2.278 g, 11.88 mmol). The reaction mixture was stirred overnight, diluted in EtOAc (80 mL) and washed with water (3×20 mL), brine (20 mL) and a saturated NaHCO$_3$ solution (20 mL). The solution was then dried over Na$_2$SO$_4$, filtreted and concentrated to dryness. The remained solid was triturated with Et$_2$O to afford title compound 40 as a white solid (1.55 g, 3.05 mmol, 38.5% yield). LRMS (ESI): (caic.) 508.6 (found) 509.6 (MH)+.

Step 2. (S)-6-(2-(tert-Butoxycarbonylamino)-3-(4-hydroxyphenyl)propanamido)hexanoic acid (38)

To a solution of 40 (1.5 g, 2.95 mmol) in 4 mL of THF/MeOH was added a 2M aqueous solution of LiOH (5.90 mL, 11.80 mmol). The reaction mixture was then stirred at RT for 4 hours. The organic solvents were evaporated and 3N aqueous HCl solution (3.5 mL) was added to the remaining aqueous solution (pH=4), to form a precipitate that was collected by filtration, washed with water and dried to afford title compound as a yellow solid (1.12 g, 2.84 mmol, 96% yield). LRMS (ESI): (calc.) 394.5 (found) 395.5 (MH)+. The product was used with no additional purification.

TABLE 3

Characterization of compounds 27-32 (examples 15-20).

| Cpd | Ex. | Structure | Characterization |
|---|---|---|---|
| 27 | 15 | 2-amino-N-(4-((2-(4-(4-phenylbutyl)phenyl)acetamidooxy)carbonyl)phenyl)acetamide hydrochloride × HCl | $^1$H NMR (400 MHz, DMSO-d$_6$) δ (ppm): 12.16 (s, 1H), 10.97 (s, 1H), 8.15 (br s, 1H), 8.00 (dd, J = 8.8 Hz, 2H), 7.77 (d, J = 8.6 Hz, 2H), 7.28-7.08 (m, 9H), 3.82 (br s, 2H), 3.47 (s, 2H), 2.62-2.52 (m, 4H), 1.60-1.50 (m, 4H). LRMS (ESI): (calc.) 459.2 (found) 460.4 (MH)+ |

TABLE 3-continued

Characterization of compounds 27-32 (examples 15-20).

| Cpd | Ex. | Structure | Characterization |
|---|---|---|---|
| 28 | 16 | 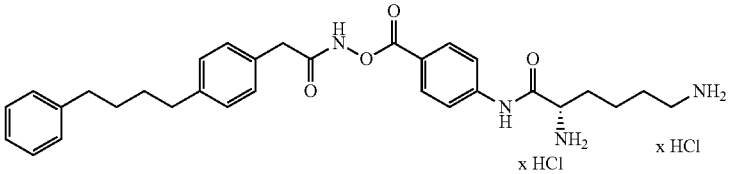<br>(S)-2,6-diamino-N-(4-((2-(4-(4-phenylbutyl)phenyl)acetamidooxy)carbonyl)phenyl) hexanamide dihydrochloride | $^1$H NMR (400 MHz, DMSO-d$_6$) δ (ppm): 12.22 (s, 1H), 11.53 (s, 1H), 8.46 (s, 3H), 7.99 (d, J = 8.6 Hz, 2H), 7.93 (s, 3H), 7.87 (d, J = 8.8 Hz, 2H), 4.12 (s, J = 1H), 3.48 (s, 2H), 2.80-2.70 (m, 2H), 2.61-2.52 (m, 4H), 1.94-1.78 (m, 2H), 1.66-1.50 (m, 6H), 1.48-1.36 (m, 2H).<br>LRMS (ESI): (calc.) 530.3 (found) 531.6 (MH)+ |
| 29 | 17 | 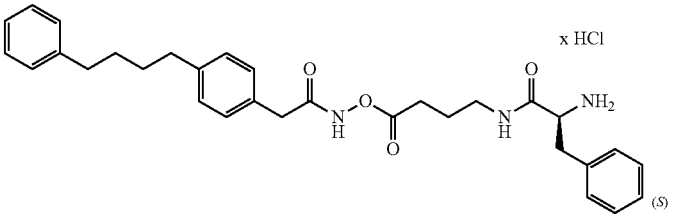<br>(S)-2-amino-N-(4-oxo-4-(2-(4-(4-phenylbutyl)phenyl)acetamidooxy)butyl)-3-phenylpropanamide hydrochloride | $^1$H NMR (400 MHz, DMSO-d$_6$) δ (ppm): 11.97 (s, 1H), 8.44 (s, 1H), 8.27 (s, 3H), 7.34-7.10 (m, 14H), 3.91 (s, 1H), 3.43 (s, 2H), 3.13-3.11 (m, 1H), 3.05-2.99 (m, 3H), 2.57 (m, 4H), 2.32 (t, J = 7.3 Hz, 2H), 1.56 (m, 6H).<br>LRMS (ESI): (calc.) 515.6 (found) 516.7 (MH)+ |
| 30 | 18 | 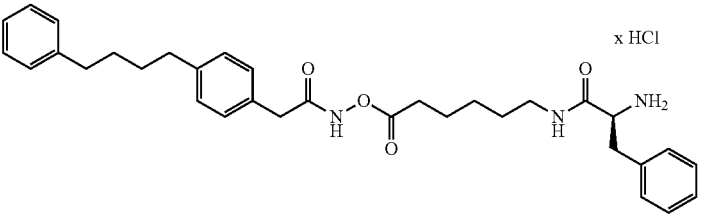<br>(S)-2-amino-N-(6-oxo-6-(2-(4-(4-phenylbutyl)phenyl)acetamidooxy)hexyl)-3-phenylpropanamide hydrochloride | $^1$H NMR (400 MHz, DMSO-d$_6$) δ (ppm): 11.98 (s, 1H), 8.39 (t, J = 5.1 Hz, 1H), 8.29 (bs, 1H), 7.33-7.09 (m, 14H), 3.93 (s, 1H), 3.42 (s, 2H), 3.11 (m, 1H), 3.01 (m, 2H), 2.93 (m, 1H), 2.57 (m, 4H), 2.38 (t, J = 7.2 Hz, 2H), 1.56 (m, 4 Hz), 1.48 (m, 2H), 1.29-1.23 (m, 2H), 1.19-1.13 (m, 2H).<br>LRMS (ESI): (calc.) 543.3 (found) 544.6 (MH)+ |
| 31 | 19 | 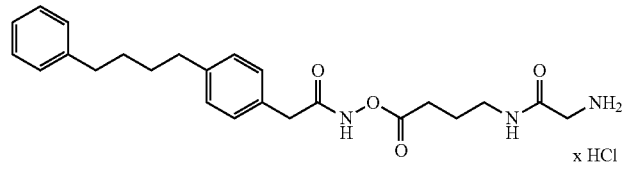<br>2-amino-N-(6-oxo-6-(2-(4-(4-phenylbutyl)phenyl)acetamidooxy)hexyl) acetamide hydrochloride | $^1$H NMR (400 MHz, DMSO-d$_6$) δ (ppm): 11.92 (s, 1H), 8.30 (t, J = 5.5 Hz, 1H), 7.98 (s, 3H), 7.28-7.10 (m, 9H), 3.50 (s, 2H), 3.42 (s, 2H), 3.10 (q, J = 6.5 Hz, 2H), 2.61-2.54 (m, 4H), 2.43 (t, J = 7.2 Hz, 2H), 1.61-1.55 (m, 6H), 1.42 (q, J = 7.0 Hz, 2H), 1.33 (q, J = 7.9 Hz, 2H).<br>LRMS (ESI): (calc.) 453.3 (found) 454.6 (MH)+ |
| 32 | 20 | 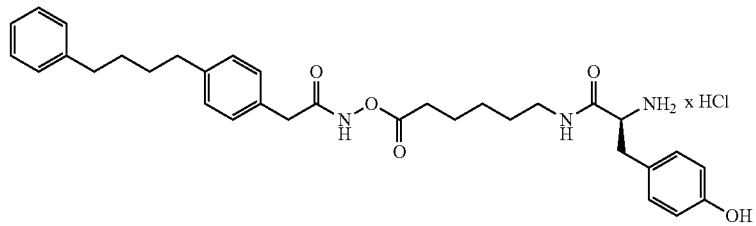<br>(S)-2-amino-3-(4-hydroxyphenyl)-N-(6-oxo-6-(2-(4-(4-phenylbutyl)phenyl) acetamidooxy)hexyl)propanamide hydrochloride | $^1$H NMR (400 MHz, DMSO-d$_6$) δ (ppm): 11.90 (s, 1H), 9.36 (s, 1H), 8.25 (s, 1H), 8.09 (s, 3H), 7.28-7.11 (m, 9H), 7.00 (d, J = 8.2 Hz, 2H), 6.69 (d, J = 8.2 Hz, 2H), 3.79 (s, 1H), 3.41 (s, 2H), 3.16-2.84 (m, 4H), 2.57 (m, 4H), 2.33-2.27 (m, 2H), 1.56 (s, 6H), 1.31 (m, 2H), 1.19 (m, 2H).<br>LRMS (ESI): (calc.) 559.7 (found) 560.65 (MH)+ |

Scheme 5

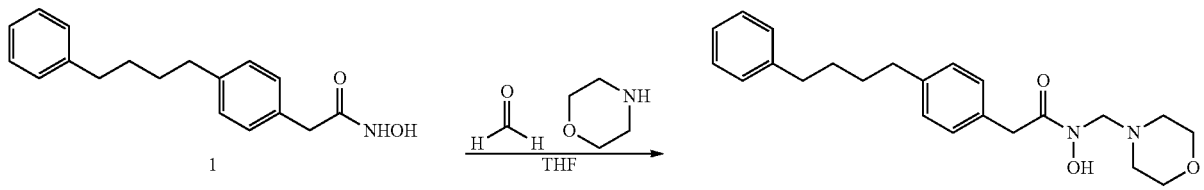

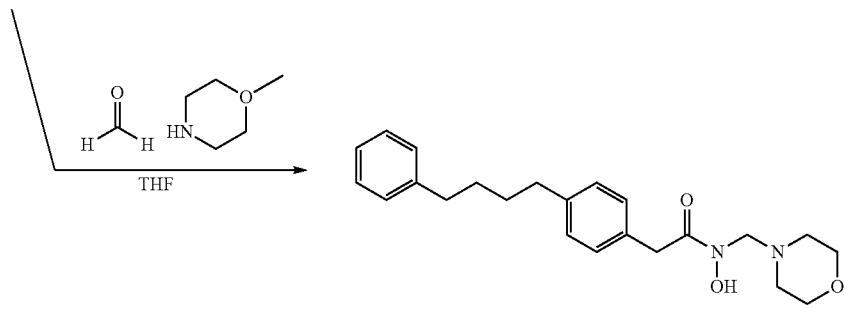

EXAMPLE 21

N-Hydroxy-N-(morpholinomethyl)-2-(4-(4-phenyl-butyl)phenyl)acetamide (41)

To a solution of morpholine (0.154 ml, 1.765 mmol) and formaldehyde (37% aqueous solution, 0.164 ml, 2.206 mmol) in THF (17.65 ml) was added hydroxamate 1 (0.5 g, 1.765 mmol). The mixture was heated to 60° C. for 30 min and allowed to cool to r.t. overnight. Methylcyclohexane (60 mL) was added and the mixture was allowed to crystallize over 2 hrs. The mixture was then filtered to afford title compound as a white solid (0.433 g, 64.2% yield). $^1$H NMR (400 MHz, DMSO-$d_6$) δ (ppm): 9.85 (s, 1H), 7.26-7.21 (m, 2H), 7.17-7.05 (m, 7H), 4.27 (s, 2H), 3.68 (s, 2H), 3.54-3.47 (m, 4H), 2.60-2.46 (m, 8H), 1.61-1.49 (m, 4H). LRMS (ESI): (calc.) 382.5 (found) 405.3 (M+Na)$^+$.

EXAMPLE 22

N-hydroxy-N-((4-methylpiperazin-1-yl)methyl)-2-(4-(4-phenylbutyl)phenyl)acetamide (42)

To a solution of 1-methylpiperazine (0.196 ml, 1.765 mmol) and formaldehyde (37% aqueous solution, 0.164 ml, 2.206 mmol) in THF (17.65 ml) was added hydroxamate 1 (0.5 g, 1.765 mmol). The mixture was heated to 60° C. for 30 min and allowed to cool to r.t. overnight. Cyclohexane (60 mL) was added and the mixture was allowed to crystallize over 2 hrs. The mixture was filtered to afford the title compound 42 as a white solid (0.25 g, 50.1% yield). $^1$H NMR (400 MHz, DMSO-$d_6$) δ (ppm): 9.80 (s, 1H), 7.27-7.20 (m, 2H), 7.18-7.03 (m, 7H), 4.27 (s, 2H), 3.66 (s, 2H), 2.62-2.46 (m, 8H), 2.32-2.14 (m, 4H), 2.10 (s, 3H), 1.61-1.47 (m, 4H). LRMS (ESI): (calc.) 395.3 (found) 396.6 (MH)$^+$.

Scheme 6

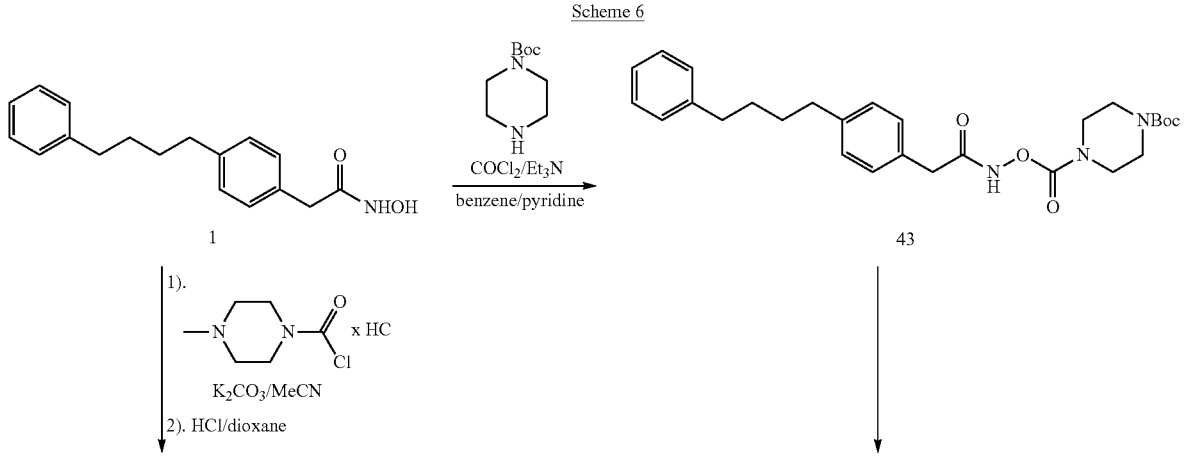

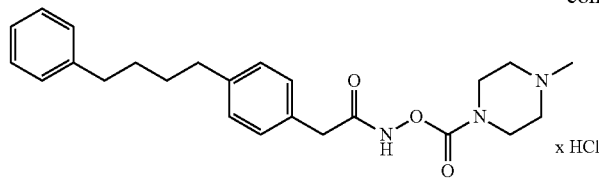

45: Example 24

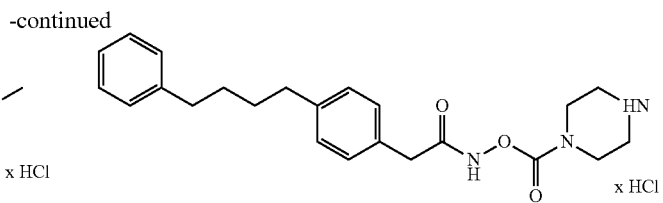

44: Example 23

EXAMPLE 23

2-(4-(4-Phenylbutyl)phenyl)-N-(piperazine-1-carbonyloxy)acetamide hydrochloride (44)

Step 1. tert-Butyl 4-((2-(4-(4-phenylbutyl)phenyl)acetamidooxy)carbonyl)piperazine-1-carboxylate (43).

To a stirred solution of phosgene (20% solution in toluene, 5.65 mL, 10.74 mmol) in benzene (22.37 mL) at 0° C. was added dropwise over 30 min a solution of tert-butyl 1-piperazine-carboxylate (1 g, 5.37 mmol) and $Et_3N$ (0.624 ml, 4.47 mmol) in benzene (22.37 ml). The reaction mixture was stirred for 2 h at RT, concentrated, re-dissolved in pyridine and hydroxamate 1 (1 g, 3.53 mmol) was added. The combined mixture was stirred over the weekend then concentrated. The residue was partitioned between water and EA. The organic phase was collected and the aqueous phase was further extracted with EA. The combined organics were washed with brine and dried over $Na_2SO_4$, filtered and concentrated. The residue was dissolved in DCM with a small amount of THF and the solvent was purified by flash column chromatography on silica gel, eluent 0% to 70% of EtOAc in hexanes, to afford title compound 43 as a white solid (0.52 g, 1.049 mmol, 23.45% yield). LRMS (ESI): (calc.) 495.6 (found) 496.6 (MH)$^+$.

Step 2. 2-(4-(4-Phenylbutyl)phenyl)-N-(piperazine-1-carbonyloxy)acetamide hydrochloride (44)

A solution of 4M HCl in dioxane (6 ml, 197 mmol) was added to compound 43 (0.52 g, 1.049 mmol) and the reaction mixture was stirred for 1 h. The milky solution was then concentrated to a white solid, which was triturated with $Et_2O$ (10 mL) and collected by filtration and dried, to afford title compound 44 (0.334 g, 0.773 mmol, 73.7% yield) as a white fluffy solid presumably as a hydrochloride salt. $^1$H NMR (400 MHz, DMSO-$d_6$) δ (ppm): 11.95 (s, 1H), 9.27 (bs, 4H), 7.24-7.05 (m, 9H), 3.59 (s, 3H), 3.36 (s, 2H), 3.07 (t, J=5.1Hz, 4H), 3.01 (m, 1H), 2.53 (d, J=8.8 Hz, 4H), 1.52 (s, 4H). LRMS (ESI): (calc.) 395.2 (found) 396.4 (MH)$^+$.

EXAMPLE 24

N-(4-Methylpiperazine-1-carbonyloxy)-2-(4-(4-phenylbutyl)phenyl)acetamide hydrochloride (45)

To a stirred suspension of hydroxamate 1 (1 g, 3.53 mmol) and $K_2CO_3$ (2.439 g, 17.65 mmol) in MeCN (5 mL) was added 4-methyl-l-piperazinecarbonyl chloride hydrochloride (0.773 g, 3.88 mmol). The mixture was stirred for 5 h at 22 RT and stored in the freezer overnight. The mixture was then filtered and concentrated. The filtrate was taken up in EtOAc, filtered and concentrated again. The residue was purifed by flash column chromatography on silica gel, eluent 0% to 10% MeOH/DCM, to provide a white solid that was dissolved in DCM (15 mL) and treated with 4M HCl in dioxane (15 mL). The mixture was concentrated and the remained white solid was triturated with $Et_2O$ (10 mL) to afford title compound 45 (0.646 g, 1.577 mmol, 44.7% yield) as a white solid. $^1$H NMR (400 MHz, DMSO-$d_6$) δ (ppm): 11.99 (s, 1H), 10.93 (br s, 1H), 7.27-7.20 (m, 2H), 7.18-7.05 (m, 7H), 4.04 (br s, 2H), 3.39 (s, 2H), 2.99 (s, 2H), 2.75 (s, 3H), 2.60-2.51 (m, 4H), 1.60-1.46 (m, 4H). LRMS (ESI): (calc.) 409.2 (found) 410.5 (MH)+.

Compounds 46-47 (examples 25-26) were obtained starting from hydroxamate 1 by following the procedures described above for the synthesis of compound 43 (scheme 6), by replacing tert-butyl piperazine-1-carboxylate with 4-(piperidin-4-yl)morpholine or 2-(methylamino)ethanesulfonic acid, respectively. Compound 48 (example 27) was obtained by following the procedures described above for the synthesis of compound 45 (scheme 6) by replacing 4-methylpiperazine-1-carbonyl chloride with morpholine-4-carbonyl chloride. Characterization of compounds 46-48 (examples 25-27) is provided in Table 4.

TABLE 4

Characterization of compounds 46-48 (examples 25-27).

| Cpd | Ex. | Structure | Characterization |
|---|---|---|---|
| 46 | 25 | N-(4-morpholinopiperidine-1-carbonyloxy)-2-(4-(4-phenylbutyl)phenyl)acetamide hydrochloride | $^1$H NMR (400 MHz, DMSO-$d_6$) δ (ppm): 11.86 (s, 1H), 10.38 (s, 1H), 7.28-7.09 (m, 9H), 4.08 (m, 2H), 3.98 (d, J = 11.9 Hz, 2H), 3.74 (t, J = 12.1 Hz, 2H), 3.43 (s, 2H), 3.07 (m, 2H), 2.89 (bs, 2H), 2.57 (d, J = 9.0 Hz, 4H), 2.13 (d, J = 11.5 Hz, 2H), 1.56 (s, 6H). LRMS (ESI): (calc.) 479.6 (found) 480.6 (MH)+ |

TABLE 4-continued

Characterization of compounds 46-48 (examples 25-27).

| Cpd | Ex. | Structure | Characterization |
|---|---|---|---|
| 47 | 26 | ![structure] 2-(methyl((2-(4-(4-phenylbutyl)phenyl)acetamidooxy)carbonyl)amino)ethanesulfonic acid | $^1$H NMR (400 MHz, DMSO-$d_6$) δ (ppm): 11.68 (s, 1H), 7.24-7.18 (m, 2H), 7.15-7.02 (m, 7H), 3.45-3.38 (m, 2H), 3.33 (s, 2H), 2.85 and 2.81 (2s, 3H), 2.70-2.48 (m, 6H), 1.58-1.45 (m, 4H). |
| 48 | 27 | ![structure] N-(morpholine-4-carbonyloxy)-2-(4-(4-phenylbutyl)phenyl)acetamide | $^1$H NMR (400 MHz, DMSO-$d_6$) δ (ppm): 11.76 (s, 1H), 7.25-7.18 (m, 2H), 7.16-7.02 (m, 7H), 3.58-3.46 (m, 2H), 3.44-3.20 (m, 6H), 2.58-2.48 (m, 4H), 1.58-1.44 (m, 4H). LRMS (ESI): (calc.) 396.2 (found) 397.5 (MH)+ |

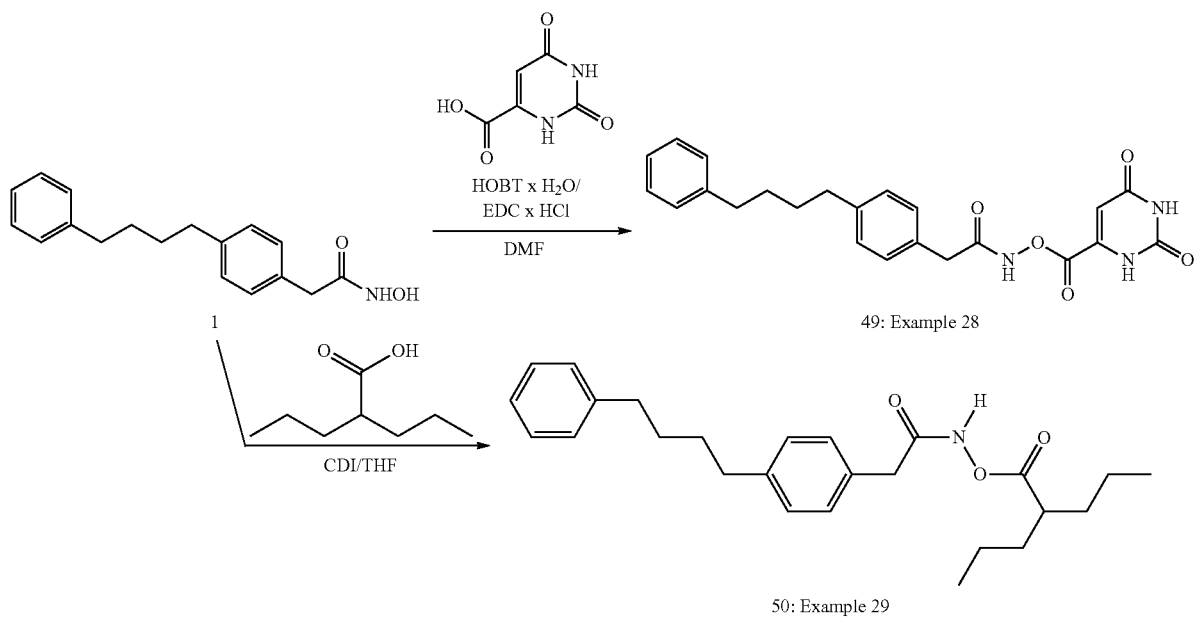

Scheme 7

EXAMPLE 28

N-(2,6-Dioxo-1,2,3,6-tetrahydropyrimidine-4-carbonyloxy)-2-(4-(4-phenylbutyl)phenyl)acetamide (49)

EDC×HCl (0.304 g, 1.588 mmol) was added to a solution of HOBt×H$_2$O (0.162 g, 1.059 mmol), hydroxamate 1 (0.3 g, 1.059 mmol), and orotic acid (0.248 g, 1.588 mmol) in DMF (7 mL) at RT. The reaction was then stirred overnight, partitioned between H$_2$O and EtOAc. The organic phase was separated, dried over Na$_2$SO$_4$, filtered and concentrated under reduced pressure. The residue was purified by silica gel column chromatography eluting with 10-100% EtOAc in hexanes, to afford title compound 49 (0.40 g, 90% yield). $^1$H NMR (400 MHz, DMSO-$d_6$) δ (ppm): 12.60 (s, 1H), 11.46 (s, 1H), 11.37 (s, 1H), 7.13 (m, 9H), 6.12 (s, 1H), 3.45 (s, 2H), 2.53 (m, 4H), 1.51 (m, 4H). LRMS (ESI): (calc.) 421.1 (found) 444.4 (MNa)+.

EXAMPLE 29

2-(4-(4-Phenylbutyl)phenyl)-N-(2-propylpentanoyloxy)acetamide (50)

Title compound was prepared by following the protocol described in *Synth. Commun.*, 2010, 40, pp. 927-935.

To a solution of valproic acid (0.136 g, 0.946 mmol) in dry THF (10 mL) was added CDI (0.230 g, 1.419 mmol). The reaction mixture was stirred for 3 hours at RT. The hydroxamate 1 (0.268 g, 0.946 mmol) was then added and the combined mixture was stirred overnight. The solvent was partially evaporated; the remaining solution was diluted with EtOAc and washed twice with a 5% $KHSO_4$ aqueous solution, then brine. The organic phase was finally dried over anhydrous $MgSO_4$, filtered and evaporated. The residue was purified 3 times by flash chromatography, eluting with 20% AcOEt in hexanes, then eluting with DCM (second purification), and finally with MeOH (2.5%) in DCM (third purification), to afford title compound 50 (0.230 g, 59.4%) as a white solid. $^1$H NMR (DMSO-d6) δ(ppm): 11.86 (s, 1H), 7.28-7.24 (m, 2H), 7.18-7.10 (m, 7H), 3.40 (s, 2H), 2.61-2.55 (m, 4H), 2.49-2.46 (m, 1H, partially overlaps with the residual signal of DMSO), 1.58-1.25 (m, 12H), 0.85 (t, J=7.2 Hz, 6H). LRMS (ESI): (calc.) 409.7 (found) 410.3 $(MH)^+$.

Compounds 51-52 (examples 30-31) as well as compounds 52A-52G (examples 31A-31G) were obtained starting from hydroxamate 1 by following the procedures described above for the synthesis of compound 50 (scheme 7), and replacing the valproic acid with the corresponding acids, respectively. Characterization of compounds 51-52 (examples 30-31) as well as compounds 52A-52G (examples 31A-31G) is provided in Table 5.

TABLE 5

Characterization of compounds 51-52 (examples 30-31) and 52A-52G (examples 31A-31G)

| Cpd | Ex. | Structure | Characterization |
|---|---|---|---|
| 51 | 30 | 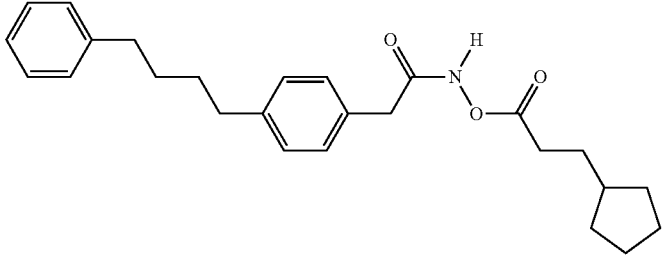<br>N-(3-cyclopentylpropanoyloxy)-2-(4-(4-phenylbutyl)phenyl)acetamide | $^1$H NMR (DMSO-d6) δ (ppm): 11.87 (s, 1H), 7.28-7.24 (m, 2H), 7.18-7.10 (m, 7H), 3.41 (s, 2H), 2.61-2.57 (m, 4H), 2.43 (t, J = 7.4 Hz, 2H), 1.80-1.67 (m, 3H), 1.60-1.45 (m, 10H), 1.10-1.03 (m, 2H).<br>LRMS (ESI): (calc.) 407.6 (found) 408.2 (MH)+ |
| 52 | 31 | 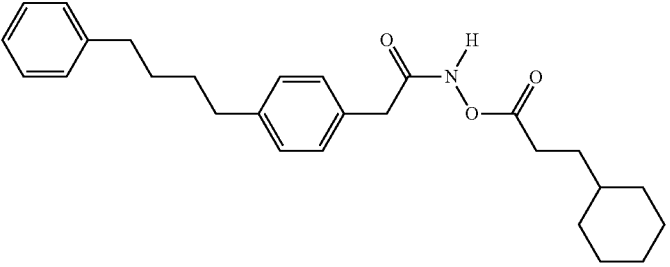<br>N-(3-cyclohexylpropanoyloxy)-2-(4-(4-phenylbutyl)phenyl)acetamide | $^1$H NMR (DMSO-d6) δ (ppm): 11.86 (s, 1H), 7.28-7.24 (m, 2H), 7.18-7.10 (m, 7H), 3.41 (s, 2H), 2.61-2.55 (m, 4H), 2.43 (t, J = 7.6 Hz, 2H), 1.68-1.49 (m, 9H), 1.46 (q, J = 7.2 Hz, 2H), 1.27-1.08 (m, 4H), 0.90-0.83 (m, 2H).<br>LRMS (ESI): (calc.) 421.6 (found) 422.2 (MH)+ |
| 52A | 31A | 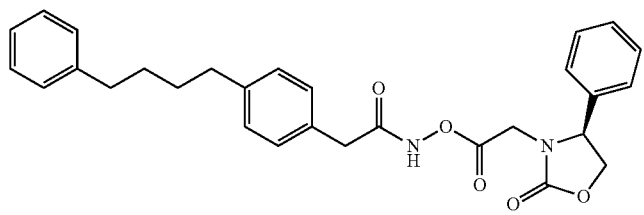<br>(S)-N-(2-(2-oxo-4-phenyloxazolidin-3-yl)acetoxy)-2-(4-(4-phenylbutyl)phenyl)acetamide | $^1$H NMR (400 MHz, DMSO-d$_6$) δ (ppm): 12.16 (s, 1H), 7.47-7.34 (m, 5H), 7.29-7.22 (m, 2H), 7.21-7.08 (m, 7H), 4.99 (t, J = 8.4 Hz, 1H), 4.75 (t, J = 8.7 Hz, 1H), 4.34 (d, J = 18.0 Hz, 1H), 4.10 (t, J = 8.5 Hz, 1H), 3.53 (d, J = 18.0 Hz, 1H), 3.42 (s, 2H), 2.64-2.51 (m, 4H), 1.63-1.49 (m, 4H).<br>MS (m/z): 487.15 [M + H]$^+$. |

TABLE 5-continued

Characterization of compounds 51-52 (examples 30-31) and 52A-52G (examples 31A-31G)

| Cpd | Ex. | Structure | Characterization |
|---|---|---|---|
| 52B | 31B | N-(3-methoxypropanoyloxy)-2-(4-(4-phenylbutyl)phenyl)acetamide | $^1$H NMR (DMSO-d6) δ (ppm): 11.95 (bs, 1H), 7.29-7.23 (m, 2H), 7.19-7.09 (m, 7H), 3.57 (t, J = 6.4 Hz, 2H), 3.41 (s, 2H), 3.22 (s, 3H), 2.68 (t, J = 6.4 Hz, 2H), 2.62-2.53 (m, 4H), 1.62-1.42 (m, 4H). LRMS (ESI): (calc.) 369.2 (found) 370.1 (MH)+ |
| 52C | 31C | N-(2-cyclopropylacetoxy)-2-(4-(4-phenylbutyl)phenyl)acetamide | $^1$H NMR (DMSO-d6) δ (ppm): 11.88 (bs, 1H), 7.28-7.23 (m, 2H), 7.19-7.09 (m, 7H), 3.41 (s, 2H), 2.62-2.52 (m, 4H), 2.37 (d, J = 7.2 Hz, 2H), 1.61-1.52 (m, 4H), 1.02-0.93 (m, 1H), 0.52-0.45 (m, 2H), 0.21-0.15 (m, 2H). LRMS (ESI): (calc.) 325.2 (found) 326.1 (MH)+ |
| 52D | 31D | N-acetoxy-2-(4-(4-phenylbutyl)phenyl)acetamide | $^1$H NMR (DMSO-d6) δ (ppm): 11.87 (s, 1H), 7.29-7.23 (m, 2H), 7.19-7.09 (m, 7H), 3.41 (s, 2H), 2.62-2.53 (m, 4H), 2.14 (s, 3H), 1.62-1.52 (m, 4H). LRMS (ESI): (calc.) 369.2 (found) 370.1 (MH)+ |
| 52E | 31E | 2-(4-(4-phenylbutyl)phenyl)-N-(propionyloxy)acetamide | $^1$H NMR (DMSO-d6) δ (ppm): 11.86 (bs, 1H), 7.27-7.22 (m, 2H), 7.18-7.07 (m, 7H), 3.39 (s, 2H), 2.62-2.53 (m, 4H), 2.44 (q, J = 7.6 Hz, 2H), 1.61-1.50 (m, 4H), 1.05 (t, J = 7.6 Hz, 3H). LRMS (ESI): (calc.) 339.2 (found) 340.1 (MH)+ |
| 52F | 31F | N-(butyryloxy)-2-(4-(4-phenylbutyl)phenyl)acetamide | $^1$H NMR (DMSO-d6) δ (ppm): 11.86 (s, 1H), 7.27-7.23 (m, 2H), 7.19-7.09 (m, 7H), 3.41 (s, 2H), 2.63-2.54 (m, 4H), 2.41 (t, J = 7.2 Hz, 2H), 1.63-1.52 (m, 6H), 0.91 (t, J = 7.2 Hz, 3H). LRMS (ESI): (calc.) 353.3 (found) 354.2 (MH)+ |
| 52G | 31G | N-(pentanoyloxy)-2-(4-(4-phenylbutyl)phenyl)acetamide | $^1$H NMR (DMSO-d6) δ (ppm): 11.86 (s, 1H), 7.28-7.23 (m, 2H), 7.19-7.09 (m, 7H), 3.41 (s, 2H), 2.62-2.54 (m, 4H), 2.42 (t, J = 7.2 Hz, 2H), 1.62-1.50 (m, 6H), 1.39-1.27 (m, 2H), 0.86 (t, J = 7.2 Hz, 3H). LRMS (ESI): (calc.) 367.2 (found) 368.1 (MH)+ |

Scheme 8

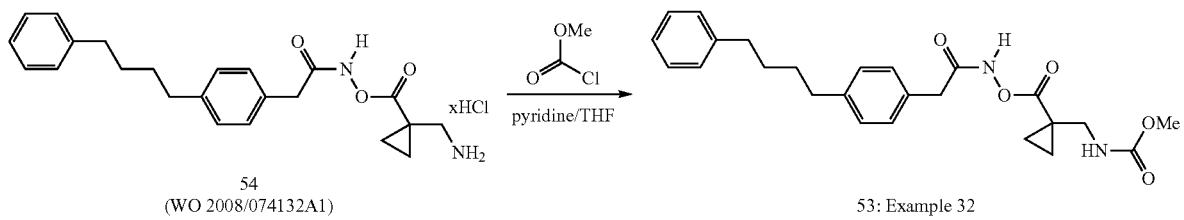

54
(WO 2008/074132A1)

53: Example 32

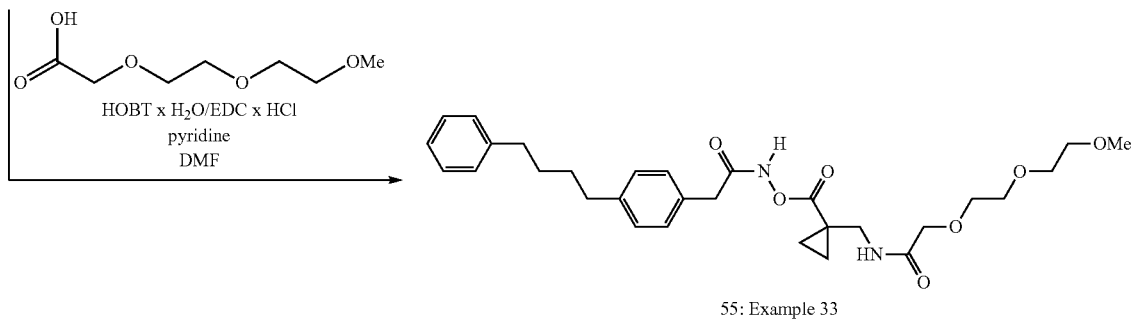

55: Example 33

EXAMPLE 32

Methyl (1-((2-(4-(4-phenylbutyl)phenyl)acetamidooxy)carbonyl)cyclopropyl)methylcarbamate (53)

To a suspension of N-(1-(aminomethyl)cyclopropanecarbonyloxy)-2-(4-(4-phenylbutyl)phenyl)acetamide (54, WO 2008/074132 A1) (0.200 g, 0.48 mmol,) in THF (20 mL) at 0° C. was added methyl chloroformate (0.2 mL, 2.59 mmol) followed by pyridine (0.2 mL, 2.48 mmol). The reaction mixture was stirred for 30 min at 0° C. then for 3 days at RT. The solvent was evaporated under reduced pressure and the residue was partitioned between a 5% $KHSO_4$ aqueous solution and EtOAc. The organic layer was collected, washed with brine, dried over anhydrous $MgSO_4$, filtered and evaporated. The residue was purified by flash column chromatography, eluent 5% MeOH in DCM to afford title compound 53 (0.03 g, 14.3% yield) as a white solid. $^1$H NMR (DMSO-$d_6$) δ(ppm): 11.94 (s, 1H), 7.28-7.24 (m, 2H), 7.18-7.10 (m, 8H, including carbamate N$\underline{H}$), 3.51 (s, 3H), 3.40 (s, 2H), 3.33 (s, 2H, C$\underline{H}_2$—NH), 2.60-2.55 (m, 4H), 1.57-1.54 (m, 4H), 1.17-1.14 (m, 2H), 1.05-1.02 (m, 2H). MS (calc.) 438.5 (found) 439.3 (MH)+ LRMS (ESI): (calc.) 438.5 (found) 439.3 (MH)+.

EXAMPLE 33

2-(2-(2-Methoxyethoxy)ethoxy)-N-((1-((2-(4-(4-phenylbutyl)phenyl)acetamidooxy)carbonyl)cyclopropyl)methyl)acetamide (55)

To a solution of the 54 (0.240 g, 0.576 mmol) in DMF (5 mL) was added 2-(2-(2-methoxyethoxy)ethoxy)acetic acid (0.205 g, 1.151 mmol) followed by HOBTxH$_2$O (0.176 g, 1.151 mmol), EDCxHCl (0.331 g, 1.727 mmol) and pyridine (0.230 ml, 2.88 mmol). The reaction mixture was stirred for 24 hours at 50° C., cooled to RT and partitioned between the brine and EtOAc. The organic layer was collected, dried over anhydrous MgSO$_4$, filtered and evaporated. The residue was purified by flash column chromatography; eluent MeOH (5%) in DCM to form an oily material which was futher purified using the same eluent. A third column purification (eluent 10% MeOH in EtOAc) afforded the title compound 55 (0.102 g, 32.8% yield) as honey-like colorless material which eventually has solidified. $^1$H NMR (DMSO-$d_6$) δ(ppm): 12.02 (br. s, 1H), 7.74 (br. t, 1H), 7.28-7.24 (m, 2H), 7.18-7.10 (m, 7H), 3.88 (s, 2H), 3.56-3.40 (m, 12H), 3.33-3.20 (m, 4H), 3.23 (s, 3H), 2.60-2.54 (m, 4H), 1.57-1.55 (m, 4H), 1.18-1.15 (m, 2H), 1.08-1.04 (m, 2H). LRMS (ESI): (calc.) 540.7 (found) 541.3 (MH)+.

Compounds 56-57 (examples 34-35) were obtained starting from compound 54 by following the procedures described above for the synthesis of compound 55 (scheme 8), and replacing 2-(2-(2-methoxyethoxy)ethoxy)acetic acid with 2,5,8,11,14-pentaoxahexadecan-16-oic acid (58, *J. Med. Chem.*, 2009, 52 (5), pp. 1310-1316) or 2,5,8,11,14,17-hexaoxanonadecan-19-oic acid (59, *Langmuir*, 2009, 25(9), pp. 5026-5030), respectively. Characterization of compounds 56-57 (examples 34-35) is provided in Table 6.

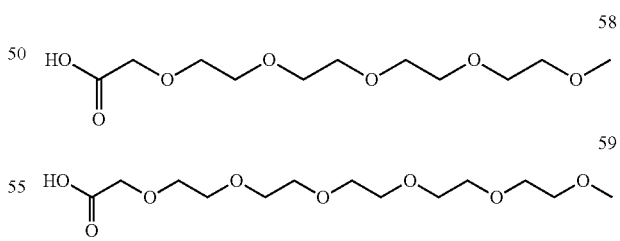

Compound 60 (example 36) was obtained starting from compound 3 (scheme 1) and following the procedures described above for the synthesis of compound 55 (scheme 8). Compounds 61-62 (examples 36-37), were obtained starting from compound 3 (scheme 1) and following the procedures described above for the synthesis of compound 60 but replacing 2-(2-(2-methoxyethoxy)ethoxy)acetic acid with the acids 58 and 59, respectively. Characterization of compounds 60-62 (examples 36-38) is provided in Table 6.

TABLE 6

Characterization of compounds 56, 57, 60-62 (examples 34-38).

| Cpd | Ex. | Structure | Characterization |
|---|---|---|---|
| 56 | 34 | N-((1-((2-(4-(4-phenylbutyl)phenyl)acetamidooxy)carbonyl)cyclopropyl)methyl)-2,5,8,11,14-pentaoxahexadecan-16-amide | $^1$H NMR (DMSO-d6) δ (ppm): 11.96 (br. s, 1H), 7.67 (br. t, 1H), 7.28-7.24 (m, 2H), 7.18-7.10 (m, 7H), 3.89 (s, 2H), 3.55-3.40 (m, 24H), 3.33 (s, 3H), 2.59-2.56 (m, 4H), 1.57-1.55 (m, 4H), 1.18-1.16 (m, 2H), 1.08-1.07 (m, 2H). LRMS (ESI): (calc.) 628.8 (found) 629.5 (MH)+ |
| 57 | 35 | N-((1-((2-(4-(4-phenylbutyl)phenyl)acetamidooxy)carbonyl)cyclopropyl)methyl)-2,5,8,11,14,17-hexaoxanonadecan-19-amide | $^1$H NMR (DMSO-d6) δ (ppm): signal of the —NH—O— is not seen, 7.81 (br. s, 1H), 7.28-7.24 (m, 2H), 7.20-7.09 (m, 7H), 3.89 (s, 2H), 3.57-3.37 (m, 18H), 3.44-3.41 (m, 4H), 3.37 (s, 2H), 3.29 (s, 3H), 2.61-2.55 (m, 4H), 1.58-1.56 (m, 4H), 1.16-1.14 (m, 2H), 1.05-1.03 (m, 2H). LRMS (ESI): (calc.) 672.8 (found) 673.8 (MH)+ |
| 60 | 36 | 2-(2-(2-methoxyethoxy)ethoxy)-N-(3-oxo-3-(2-(4-(4-phenylbutyl)phenyl)acetamidooxy)propyl)acetamide | $^1$H NMR (DMSO-d6) δ (ppm): 12.00 (br. s, 1H), 7.86 (t, J = 5.7 Hz, 1H), 7.26-7.22 (m, 2H), 7.18-7.09 (m, 7H), 3.86 (s, 2H), 3.59-3.50 (m, 6H), 3.44-3.35 (m, 6H), 3.23 (s, 3H), 2.65-2.56 (m, 6H), 1.58-1.54 (m, 4H). LRMS (ESI): (calc.) 514.6 (found) 515.4 (MH)+ |
| 61 | 37 | N-(3-oxo-3-(2-(4-(4-phenylbutyl)phenyl)acetamidooxy)propyl)-2,5,8,11,14-pentaoxahexadecan-16-amide | $^1$H NMR (DMSO-d6) δ (ppm): 11.94 (br. s, 1H), 7.81 (t, J = 5.7 Hz, 1H), 7.28-7.24 (m, 2H), 7.18-7.10 (m, 7H), 3.86 (s, 2H), 3.57-3.49 (m, 14H), 3.43-3.36 (m, 6H), 3.31 (s, 3H), 2.65 (t, J = 7.0 Hz, 2H), 2.61-2.55 (m, 4H), 1.59-1.55 (m, 4H) LRMS (ESI): (calc.) 602.7 (found) 603.4 (MH)+ |

TABLE 6-continued

Characterization of compounds 56, 57, 60-62 (examples 34-38).

| Cpd | Ex. | Structure | Characterization |
|---|---|---|---|
| 62 | 38 | 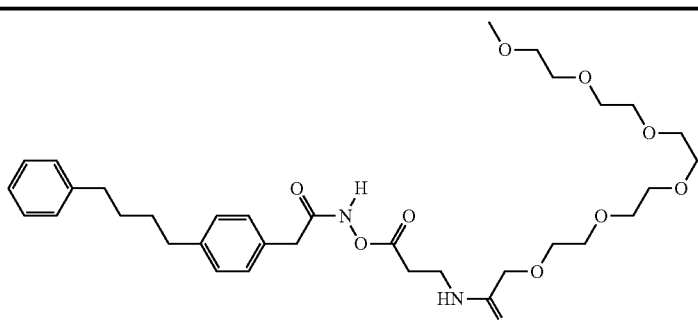<br>N-(3-oxo-3-(2-(4-(4-phenylbutyl)phenyl)acetamidooxy)propyl)-2,5,8,11,14,17-hexaoxanonadecan-19-amide | $^1$H NMR (DMSO-d6) δ (ppm): 11.93 (br. s, 1H), 7.83 (t, J = 5.9 Hz, 1H), 7.28-7.24 (m, 2H), 7.18-7.09 (m, 7H), 3.86 (s, 2H), 3.59-3.50 (m, 18H), 3.43-3.36 (m, 6H), 3.24 (s, 3H), 2.65-2.57 (m, 6H), 1.58-1.55 (m, 4H). LRMS (ESI): (calc.) 646.8 (found) 647.7 (MH)+ |

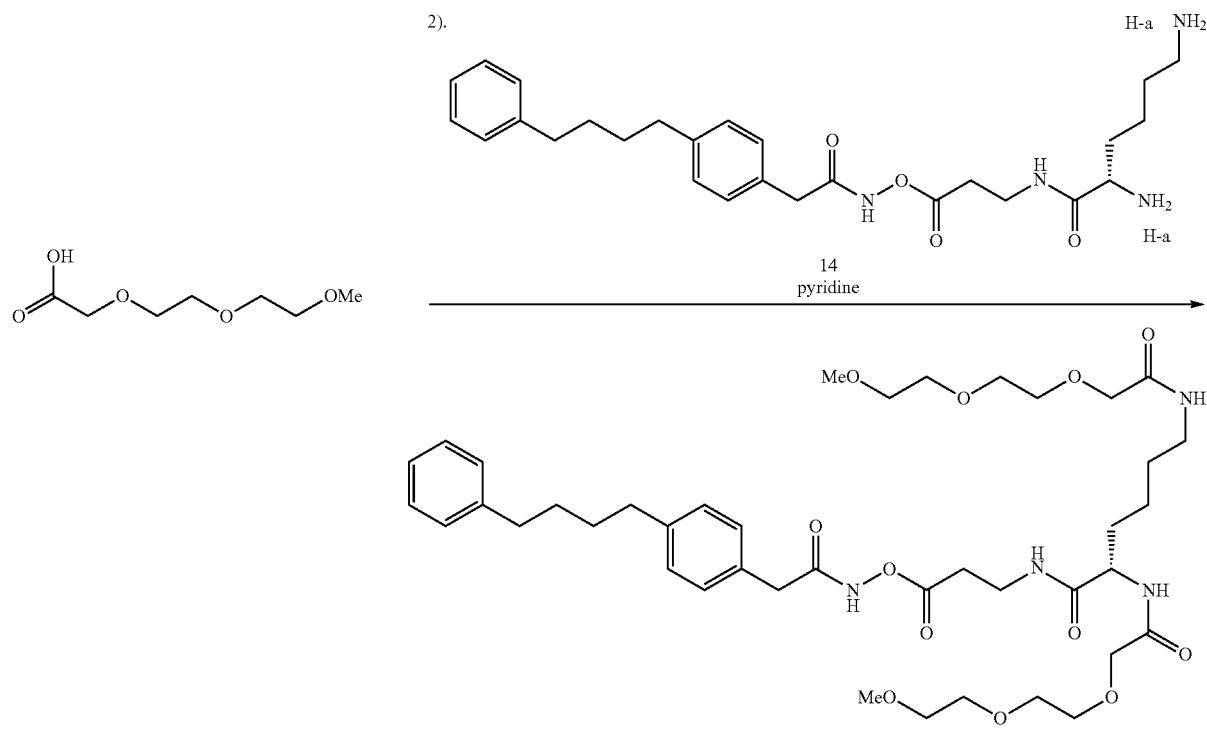

63: Example 39

EXAMPLE 39

(S)-N,N'-(6-Oxo-6-(3-oxo-3-(2-(4-(4-phenylbutyl)phenyl)acetamidooxy)propylamino)hexane-1,5-diyl) bis(2-(2-(2-methoxyethoxy)ethoxy)acetamide) (63)

To a solution of 2-(2-(2-methoxyethoxy)ethoxy)acetic acid (0.160 g, 0.900 mmol) in dry THF (10 mL) was added CDI (0.219 g, 1.350 mmol). The reaction mixture was stirred for 3 hours. The compound 14 (0.250 g mg, 0.450 mmol) was then added followed by the pyridine (0.218 mL, 2.70 mmol) and the combined mixture was stirred overnight (16 hrs). The solvent was partially evaporated, the remaining solution was diluted with EtOAc and washed twice with a 5% KHSO$_4$ solution, then brine. The organic phase was finally dried over anhydrous MgSO$_4$, filtered and evaporated. The residue was purified by flash column chromatography, eluent 6.4% MeOH in DCM followed by a second column purification using MeOH (10%) in EtOAc, and finally by a third purification eluting with MeOH (20%) in EtOAc. Title compound 63 (0.137 g, 37.9% yield) was obtained as a colorless honey-like material. $^1$H NMR (400 MHz, DMSO-d$_6$) δ (ppm): 12.02 (s, 1H), 8.29 (br. s, 1H), 7.65 (t, J=5.7 Hz, 1H), 7.59 (d, J=8.6 Hz, 1H), 7.27-7.24 (m, 2H), 7.18-7.09 (m, 7H), 4.27-4.21 (m, 1H), 3.90 (s, 2H), 3.84 (s, 2H), 3.61-3.39 (m, 20H), 3.234 (s, 3H), 3.231 (s, 3H), 3.05 (q, J=6.8 Hz, 2H), 2.65-2.56 (m, 6H), 1.73-1.55 (m, 6H), 1.50-1.36 (m, 2H), 1.23-1.16(m, 2H). LRMS (ESI): (calc.) 803.0 (found) 803.4 (MH)+ and was stirred for 4 hours at RT, partitioned between EtOAc and acidified brine. The organic phase was separated, washed with brine and finally dried over anhydrous MgSO$_4$, filtered and evaporated. The residue was purified by flash column chromatography three times eluting with 10% MeOH in DCM (first time), 5% MeOH in DCM (second time) and finally, 4% MeOH in DCM (third time). The purified material was purified yet again by Biotage® by a reverse phase chromatography (Snap 120 g cartridge KP-C18-HS, eluent 5 to 95% MeOH in water), to afford title compound 64 (0.383 g, 41.2% yield) as a colorless honey-

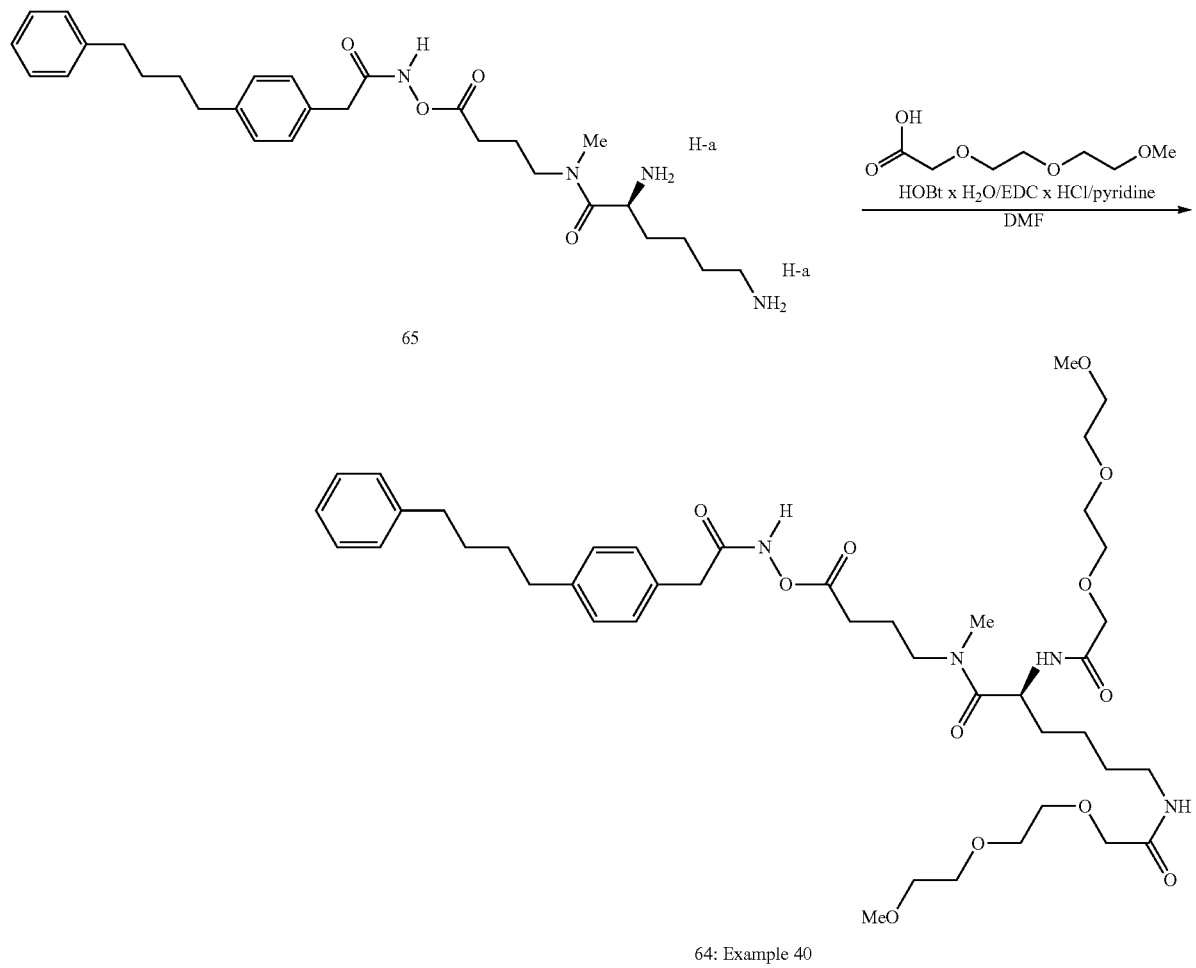

64: Example 40

EXAMPLE 40

(S)-N,N'-(6-(Methyl(4-oxo-4-(2-(4-(4-phenylbutyl)phenyl)acetamidooxy)butyl)amino)-6-oxohexane-1,5-diyl)bis(2-(2-(2- methoxyethoxy)ethoxy)acetamide) (64)

To a suspension of (S)-2,6-diamino-N-methyl-N-(4-oxo-4-(2-(4-(4-phenylbutyl)phenyl)acetamidooxy)butyl)hexanamide dihydrochloride (65, 0.653 g, 1.119 mmol) in dry DMF (15 mL) were added 2-(2-(2-methoxyethoxy)ethoxy)acetic acid (0.439 g, 2.462 mmol), HOBT×H$_2$O (0.377 g, 2.462 mmol), EDC×HCl (0.858 g, 4.48 mmol) and pyridine (0.900 mL, 11.2 mmol). The reaction mixture turned into a solution like material. $^1$H NMR (400 MHz, DMSO-d$_6$) δ (ppm): 11.87 (s, 1H), 7.37 (br. d, 2H), 7.28-7.24 (m, 2H), 7.18-7.10 (m, 7H), 4.73-4.67 (m, 1H), 3.90 (d, 2H, rotamers), 3.84 (s, 2H), 3.61-3.52 (m, 12H), 3.46-3.42 (m, 6H), 3.40-3.26 (m, 4H), 3.24 (s, 3H), 3.23 (s, 3H), 3.10-3.04 (m, 2H), 2.81 (s, 2H), 2.61-2.53 (m, 4H), 2.40 (t, J=7.4 Hz, 2H), 1.88-1.23(m, 13H). LRMS (ESI): (calc.) 831.0 (found) 831.6 (MH)$^+$ and 853.5 (MNa)$^{+\cdot}$.

(S)-2,6-Diamino-N-methyl-N-(4-oxo-4-(2-(4-(4-phenylbutyl)phenyl)acetamidooxy)butyl)hexanamide dihydrochloride (65) that was used as a starting material in the synthesis of compound 64 (example 40, scheme 10) was obtained via a four-step reaction sequence starting from N,N'-bis-Boc-Lysine and methyl 4-(methylamino)butanoate hydrochloride (WO 2008/101665 A1) and following the procedures described above for the synthesis of (S)-2,6-diamino-N-(3-oxo-3-(2-(4-(4-phenylbutyl)phenyl)acetamidooxy)propyl) hexanamide (14, scheme 2). LRMS (ESI): (calc.) 510.7 (found) 511.4 (MH)⁺.

Compounds 66-69 (examples 41-44), were obtained starting from compound 14 (scheme 2), following the procedures described above for the synthesis of compound 64 (scheme 10) and replacing 2-(2-(2-methoxyethoxy)ethoxy)acetic acid with acetic acid, 2-methoxyacetic acid, 2-(2-methoxyethoxy)acetic acid and 2,5,8,11,14-pentaoxahexadecan-16-oic acid (58), respectively.

Compounds 70-71 (examples 45-46) were obtained starting from (S)-N-(2,6-diaminohexanoyloxy)-2-(4-(4-phenylbutyl)phenyl)acetamide dihydrochloride (72, WO 2008/074132 A1)) and 2-(2-methoxyethoxy)acetic or 2-(2-(2-methoxyethoxy)ethoxy)acetic acid, respectively; and following the procedures described above for the synthesis of compound 64 (scheme 10).

Characterization of compounds 66-71 (examples 41-46) is provided in Table 7.

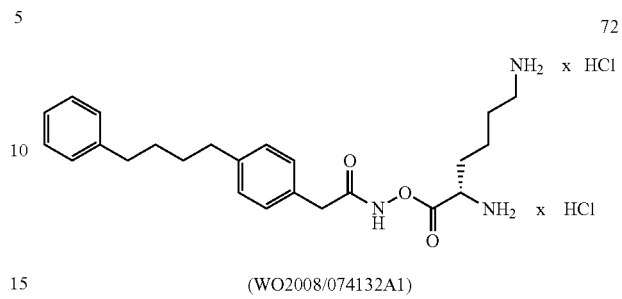

(WO2008/074132A1)

TABLE 7

Characterization of compounds 66-71 (examples 41-46).

| Cpd | Ex. | Structure | Characterization |
|---|---|---|---|
| 66 | 41 | 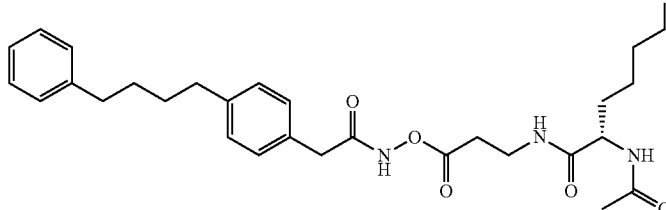<br>(S)-N,N'-(6-oxo-6-(3-oxo-3-(2-(4-(4-phenylbutyl)phenyl)acetamidooxy) propylamino)hexane-1,5-diyl)diacetamide | ¹H NMR (400 MHz, DMSO-d₆) δ (ppm): 12.00 (s, 1H), 8.11 (br. s, 1H), 7.94 (d, J = 8.2 Hz, 1H), 7.77 (t, J = 6.0 Hz, 1H), 7.28-7.24 (m, 2H), 7.18-7.09 (m, 7H), 4.15-4.09 (m, 1H), 3.41 (s, 2H), 2.97 (q, J = 7.04 and 13.1 Hz, 2H), 2.61-2.55 (m, 6H), 1.81 (s, 3H), 1.77 (s, 3H), 1.57-1.49 (m, 6H), 1.49-1.39 (m, 2H), 1.35-1.30 (m, 2H), 1.26-1.15 (m, 2H).<br>LRMS (ESI): (calc.) 566.7 (found) 567.5 (MH)+ |
| 67 | 42 | 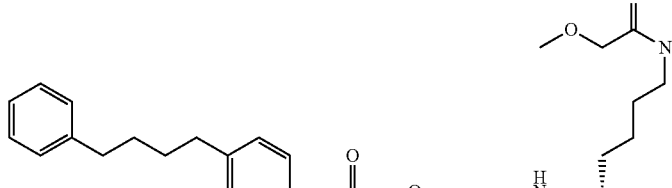<br>(S)-N,N'-(6-oxo-6-(3-oxo-3-(2-(4-(4-phenylbutyl)phenyl)acetamidooxy) propylamino)hexane-1,5-diyl)bis(2-methoxyacetamide) | ¹H NMR (400 MHz, DMSO-d₆) δ (ppm): 12.00 (s, 1H), 8.29 (br. s, 1H), 7.71 (bt, 1H), 7.62 (d, J = 8.6 Hz, 1H), 7.28-7.24 (m, 2H), 7.18-7.09 (m, 7H), 4.26-4.20 (m, 1H), 3.80 (s, 2H), 3.76 (s, 2H), 3.39 (s, 2H), 3.33-3.28 (m, 3H, 3H and 2H), overlapped with residual signal of water), 3.04 (q, J = 6.3 and 12.7 Hz, 2H), 2.61-2.55 (m, 6H), 1.58-1.52 (m, 6H), 1.44-1.34 (m, 2H), 1.23-1.15 (m, 2H).<br>LRMS (ESI): (calc.) 626.7 (found) 627.5 (MH)+ |

TABLE 7-continued

Characterization of compounds 66-71 (examples 41-46).

| Cpd | Ex. | Structure | Characterization |
|---|---|---|---|
| 68 | 43 | 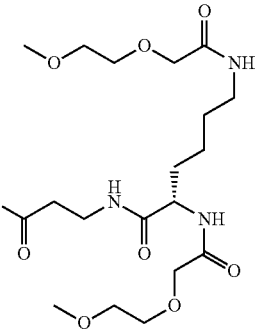<br>(S)-N,N'-(6-oxo-6-(3-oxo-3-(2-(4-(4-phenylbutyl)phenyl)acetamidooxy)propylamino)hexane-1,5-diyl)bis(2-(2-methoxyethoxy)acetamide) | $^1$H NMR (400 MHz, DMSO-$d_6$) δ (ppm): 11.98 (bs, 1H), 8.20 and 8.12 (two broad triplets, 1H, rotamers), 7.64-7.56 (m, 2H), 7.28-7.08 (m, 9H), 4.24-4.17 (m, 1H), 3.87 (s, 2H), 3.82 (s, 2H), 3.58-3.52 (m, 4H), 3.46-3.40 (m, 4H), 3.32-3.23 (m, 10H), 3.03 (q, J = 13.2 and 6.8 Hz, 2H), 2.60-2.54 (m, 4H), 2.45 (t, J = 6.8 Hz, 2H), 1.65-1.40 (m, 6H), 1.39-1.32 (m, 2H), 1.22-1.12 (m, 2H<br>LRMS (ESI): (calc.) 714.9 (found) 715.5 (MH)+ |
| 69 | 44 | 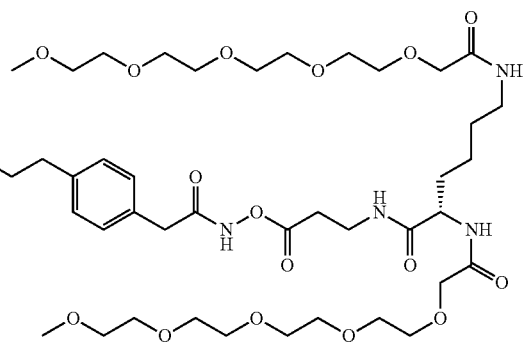<br>(S)-N,N'-(6-oxo-6-(3-oxo-3-(2-(4-(4-phenylbutyl)phenyl)acetamidooxy)propylamino)hexane-1,5-diyl)bis(2,5,8,11,14-pentaoxahexadecan-16-amide) | $^1$H NMR (400 MHz, DMSO-$d_6$) δ (ppm): signal of C(O)NHO-proton is not seen), 7.62 (br. s, 1H), 7.28-7.24 (m, 2H), 7.18-7.08 (m, 9H), 4.28-4.23 (m, 1H), 3.88 (s, 2H), 3.84 (s, 2H), 3.59-3.50 (m, 32H), 3.43-3.41 (m, 4H), 3.24 (s, 3H), 3.23 (s, 3H), 3.09-3.03 (m, 2H), 2.59-2.54 (m, 6H), 1.57 (bs, 6H), 1.42-1.36 (m, 2H), 1.26-1.15 (m, 2H).<br>LRMS (ESI): (calc.) 979.2 (found) 979.7 (MH)+ |
| 70 | 45 | 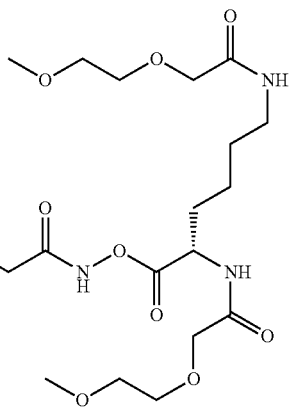<br>(S)-N,N'-(6-oxo-6-(2-(4-(4-phenylbutyl)phenyl)acetamidooxy)hexane-1,5-diyl)bis(2-(2-methoxyethoxy)acetamide) | $^1$H NMR (400 MHz, DMSO-$d_6$) δ (ppm): 12.07 (s, 1H), 8.16 and 7.96 (two dublets, J = 7.4 and 7.4 Hz, 1H, rotamers), 7.68 (t, J = 5.9 Hz, 1H), 7.27-7.24 (m, 2H), 7.18-7.10 (m, 7H), 4.42-4.38 and 4.32-4.27 (two multiplets, 1H, rotamers), 3.94 and 3.92 (two singlets, 2H, rotamers), 3.84 and 3.83 (two singlets, 2H, rotamers), 3.63 and 2.70 (two singlets, 2H, rotamers), 3.61-3.54 (m, 4H), 3.50-3.45 (m, 4H), 3.26 (s, 3H), 3.25 (s, 3H), 3.07 (bq, J = 6.0 Hz, 2H), 2.57 (bd, J = 9.2 Hz, 4H), 1.91-1.67 (m, 2H), 1.56 (bs, 4H), 1.55-1.23 (m, 4H).<br>LRMS (ESI): (calc.) 643.8 (found) 644.5 (MH)+ |

TABLE 7-continued

Characterization of compounds 66-71 (examples 41-46).

| Cpd | Ex. | Structure | Characterization |
|---|---|---|---|
| 71 | 46 | (S)-N,N'-(6-oxo-6-(2-(4-(4-phenylbutyl)phenyl)acetamidooxy)hexane-1,5-diyl)bis(2-(2-(2-methoxyethoxy)ethoxy)acetamide) | $^1$H NMR (400 MHz, DMSO-d$_6$) δ (ppm): 12.04 (bs, 1H), 8.14 (d, J = 7.4 Hz, 1H), 7.68 (t, J = 6.3 Hz, 1H), 7.28-7.24 (m, 2H), 7.18-7.10 (m, 7H), 4.41-4.37 (m, 1H), 3.95 (s, 2H), 3.84 (s, 2H), 3.60-3.51 (m, 12H), 3.44-3.40 (m, 6H), 3.230 (s, 3H), 3.226 (s, 3H), 3.07 (q, J = 12.9 and 6.7 Hz, 2H), 2.57 (bd, J = 9.6 Hz, 4H), 1.83-1.68 (m, 2H), 1.56 (bs, 4H), 1.45-1.29 (m, 4H). LRMS (ESI): (calc.) 731.9 (found) 732.4 (MH)+ |

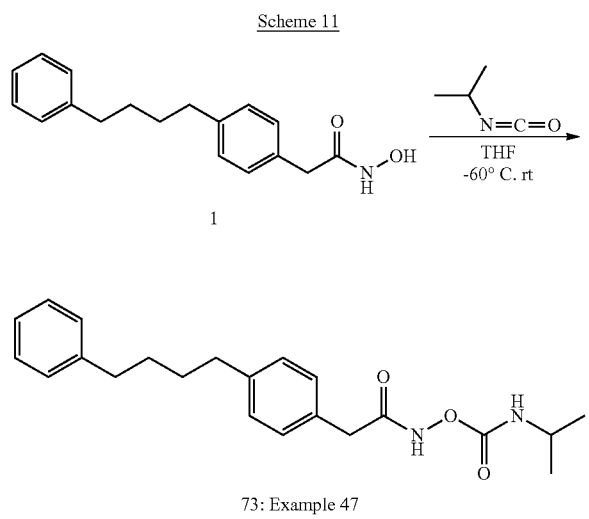

Scheme 11

73: Example 47

EXAMPLE 47

N-(Isopropylcarbamoyloxy)-2-(4-(4-phenylbutyl)phenyl)acetamide (73)

To a stirred solution of hydroxamate 1 (200 mg, 0.71 mmol) in anhydrous THF (15 ml) under nitrogen at −60° C. was added isopropyl isocyanate (71 µl, 0.71 mmol). The reaction mixture was allowed to warm-up to rt over 3 h, then the reaction mixture was stirred at rt overnight, and concentrated. The residue was purified twice by Biotage® (Snap KP-Sil 25 g cartridge; AcOEt/hexanes: 5/95 to 20/80 over 30 CV, 220 nm detection wavelength), to afford title compound 73 (125 mg, 0.34 mmol, 48% yield) as a white wax. $^1$H NMR (400 MHz, DMSO-d$_6$) δ (ppm): 10.41 (s, 1H), 8.03 (bd, J=7.6 Hz, 1H), 7.26 (t, J=7.3 Hz, 2H), 7.20-7.13 (m, 3H), AB system (δ$_A$=7.12, δ$_B$=7.10, J$_{AB}$=8.5 Hz, 4H), 3.95 (s, 2H), 3.88-3.74 (m, 1H), 2.66-2.52 (m, 4H), 1.64-1.48 (m, 4H), 1.11 (d, J=6.4 Hz, 6H). MS (m/z): 369.28 [M+H]$^+$ and 391.29 [M+Na]$^+$.

Compounds 74-75 (examples 48-49) were prepared in one step by reacting hydroxamate 1 with the corresponding alkyl isocyanates similarly to compound 73 (scheme 11).

TABLE 8

Characterization of compounds 74-75 (examples- 48-49)

| Cpd | Ex. | Structure | Characterization |
|---|---|---|---|
| 74 | 48 | N-(ethylcarbamoyloxy)-2-(4-(4-phenylbutyl)phenyl)acetamide | $^1$H NMR (400 MHz, DMSO-d$_6$) δ (ppm): 10.39 (s, 1H), 8.13 (bt, J = 5.6 Hz, 1H), 7.26 (t, J = 7.3 Hz, 2H), 7.20-7.13 (m, 3H), AB System (δ$_A$ = 7.12, δ$_B$ = 7.09, J$_{AB}$ = 8.2 Hz, 4H), 3.98 (s, 2H), 3.20-3.10 (m, 2H), 2.64-2.52 (m, 4H), 1.64-1.48 (m, 4H), 1.05 (t, J = 7.1 Hz, 3H). MS (m/z): 355.12 [M + H]$^+$. |

TABLE 8-continued

Characterization of compounds 74-75 (examples- 48-49)

| Cpd | Ex. | Structure | Characterization |
|---|---|---|---|
| 75 | 49 | 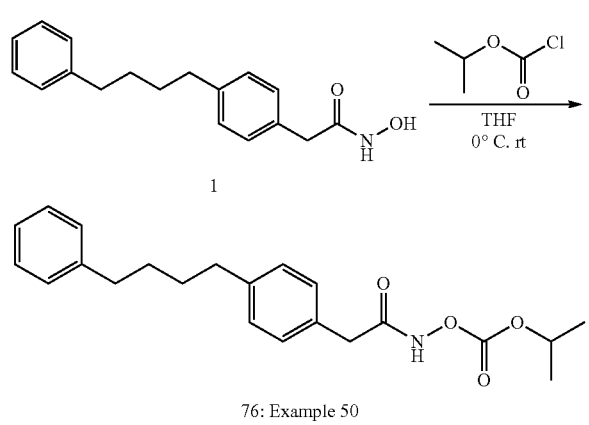<br>ethyl 2-((2-(4-(4-phenylbutyl)phenyl)acetamidooxy)carbonylamino)acetate | $^1$H NMR (400 MHz, DMSO-$d_6$) δ (ppm): 10.56 (s, 1H), 8.45 (t, J = 5.9 Hz, 1H), 7.30-7.22 (m, 2H), 7.20-7.07 (m, 7H), 4.10 (q, J = 7.1 Hz, 2H), 3.99 (s, 2H), 3.89 (d, J = 5.9 Hz, 2H), 2.64-2.53 (m, 4H), 1.63-1.50 (m, 4H), 1.19 (t, J = 7.1 Hz, 3H). MS (m/z): 413.21 [M + H]$^+$. |

EXAMPLE 50

N-(isopropoxycarbonyloxy)-2-(4-(4-phenylbutyl)phenyl)acetamide (76)

To a stirred solution of hydroxamate 1 (200 mg, 0.71 mmol) in anhydrous THF (15 mL) at 0° C. under nitrogen was added isopropyl chloroformate (741 μl, 0.74 mmol). The reaction mixture was stirred at RT overnight. More isopropyl chloroformate (10 mL, 10 mmol) was added; the reaction mixture was stirred at RT for one more day then concentrated. The residue was purified twice by Biotage® (Snap KP-Sil 25 g cartridge; AcOEt/hexanes: 5/95 to 30/70 over 35 CV, 220 nm detection wavelength) to afford the desired product 76 (25 mg, 0.07 mmol, 9% yield) as an off-white sticky solid. $^1$H NMR (400 MHz, DMSO-$d_6$) δ (ppm): 12.17 (bs, 1H), 7.29-7.22 (m, 2H), 7.20-7.08 (m, 7H), 4.82 (hept, J=6.2 Hz, 1H), 3.40 (s, 2H), 2.65-2.52 (m, 4H), 1.65-1.48 (m, 4H), 1.25 (d, J=6.1 Hz, 6H). MS (m/z): 370.30 [M+H]$^+$.

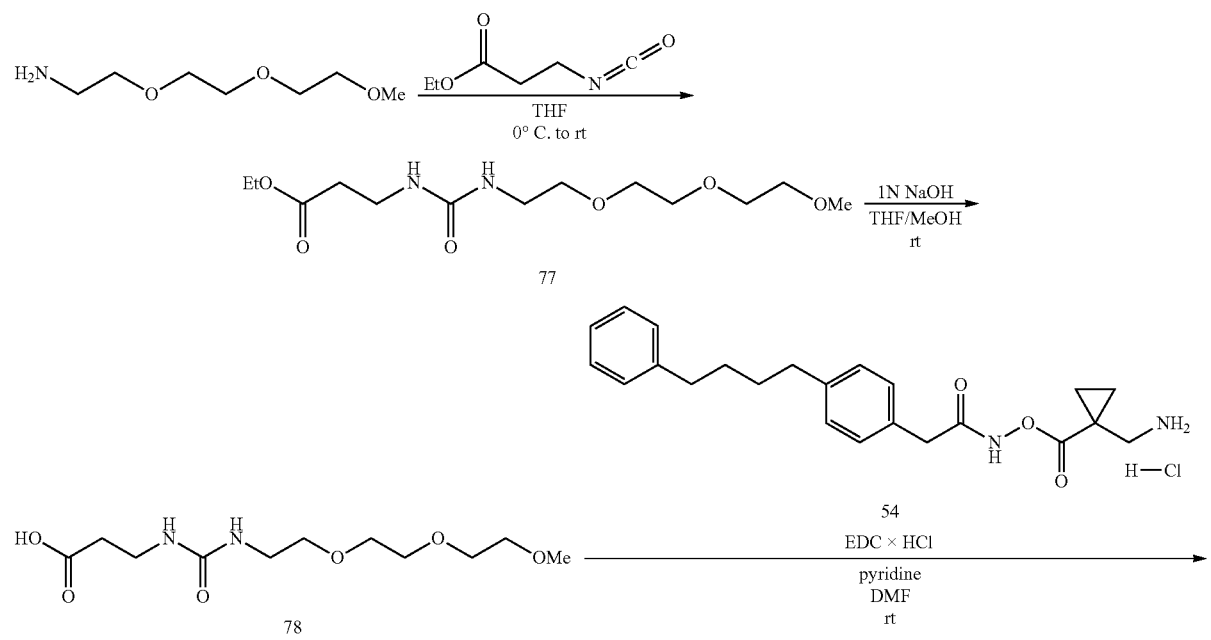

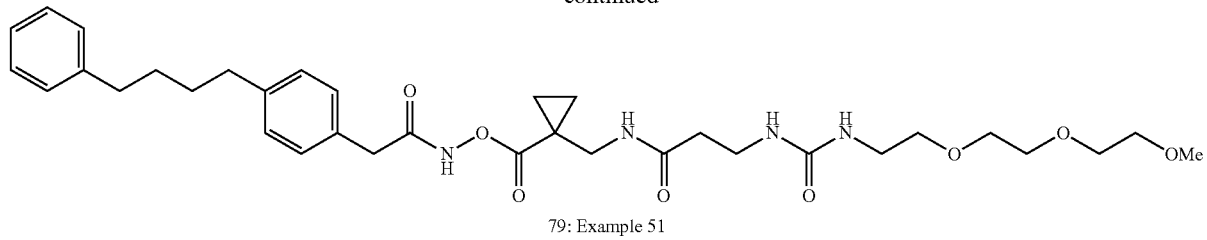

79: Example 51

EXAMPLE 51

N-1-(2-(2-(2-Methoxyethoxy)ethoxy)ethyl)-N-3-(2-(1-((2-(4-(4-phenylbutyl)phenyl)acetamidooxy)carbonylcyclopropyl)methyl)carbamoylethyl)urea (79)

Step 1. 1-(2-(Ethyloxycarbonyl)ethyl)-3-(2-(2-(2-methoxyethoxy)ethoxy)ethyl)urea (77)

To a stirred solution of 2-(2-(2-methoxyethoxy)ethoxy)ethanamine (WO 2009/109035 A1, 400 mg, 2.45 mmol) in anhydrous THF (20 mL) at 0° C. under nitrogen was added ethyl 3-isocyanatopropionate (346 µl, 0.78 mmol). The reaction mixture was then stirred at RT overnight. Title compound 77 was used in the next step without isolation and purification. MS (m/z): 307.2 [M+H]+.

Step 2. 1-(2-(Hydroxycarbonyl)ethyl)-3-(2-(2-(2-methoxyethoxy)ethoxy)ethyl) urea (78)

To a stirred solution of intermediate 77 from the previous step [2.45 mmol, in THF (20 mL)] was added MeOH (5 mL) and a solution of 1N NaOH (4.90 ml, 4.90 mmol). The reaction mixture was stirred at RT for 4 h, concentrated, diluted with water, and the pH was adjusted to 1-2 with 1N HCl. The acidic solution was then extracted nine times with DCM with traces of methanol. The combined organic layer was dried over anhydrous magnesium sulfate, filtered and concentrated to afford the desired product 78 (651 mg, 2.34 mmol, 95% yield over 2 steps) as pale yellow sticky oil. MS (m/z): 301.1 [M+Na]+.

Step 3. N-1-(2-(2-(2-Methoxyethoxy)ethoxy)ethyl)-N-3-(2-(1-((2-(4-(4-phenylbutyl)phenyl)acetamidooxy)carbonylcyclopropyl)methyl)carbamoylethyl)urea (79)

To a stirred solution of compound 54 (200 mg, 0.48 mmol) and the acid intermediate 78 (160 mg, 0.58 mmol) in DMF (5 ml) under nitrogen at RT were added EDC×HCl (184 mg, 0.96 mmol) and pyridine (194 µl, 2.40 mmol). The reaction mixture was stirred at RT overnight, diluted with AcOEt, washed with 1N HCl, and concentrated. The residue was purified by Biotage® (Snap KP-Sil 25 g cartridge; MeOH/DCM: 0/100 to 10/90 over 50 CV, 220 nm detection wavelength), to afford the desired product 79 (148 mg, 0.23 mmol, 48% yield) as a white/colorless wax. $^1$H NMR (400 MHz, DMSO-d$_6$) δ (ppm): 11.95 (bs, 1H), 8.04-7.90 (m, 1H), 7.32-7.04 (m, 9H), 5.96 (t, J=5.8 Hz, 1H), 5.91 (t, J=5.8 Hz, 1H), 3.53-3.46 (m, 6H), 3.45-3.32 (m, 8H), 3.23 (s, 3H), 3.16 (q, J=6.3 Hz, 2H), 3.11 (q, J=5.8 Hz, 2H), 2.64-2.52 (m, 4H), 2.21 (t, J=6.7 Hz, 2H), 1.64-1.49 (m, 4H), 1.22-0.96 (m, 2×2H). MS (m/z): 641.62 [M+H]+.

Compound 80 (example 52) was prepared in one step by coupling compound 44 (example 23, scheme 6) with the intermediate 78 and employing the procedure similar to the one used in the synthesis of compound 79 (scheme 13). Compounds 81 and 82 (examples 53 and 54) were obtained in a similar fashion in one step by coupling compound 44 with the acid intermediates 58 and 59, respectively. Characterization of compounds 80-82 (examples 52-54) is provided in Table 9.

TABLE 9

Characterization of compounds 80-82 (examples 52-54)

| Cpd | Ex. | Structure | Characterization |
|---|---|---|---|
| 80 | 52 | *N-1-(2-(2-(2-methoxyethoxy)ethoxy)ethyl)-N-3-(2-(1-(4-(2-(4-(4-phenylbutyl)phenyl)acetamidooxy)carbonylpiperazine)carbamoyl)ethyl)urea* | $^1$H NMR (400 MHz, DMSO-d$_6$) δ (ppm): 12.00-11.60 (bs, 1H), 7.30-7.00 (m, 9H), 6.01 (t, J = 5.6 Hz, 1H), 5.95 (t, J = 5.9 Hz, 1H), 3.53-3.32 (m, 18H), 3.26-3.17 (m, 5H), 3.11 (q, J = 5.7 Hz, 2H), 2.64-2.52 (m, 4H), 2.44 (t, J = 6.4 Hz, 2H), 1.64-1.48 (m, 4H), 2H are hidden by solvent's peaks. MS (m/z): 656.51 [M + H]+ and 678.51 [M + Na]+. |

TABLE 9-continued

Characterization of compounds 80-82 (examples 52-54)

| Cpd | Ex. | Structure | Characterization |
|---|---|---|---|
| 81 | 53 | 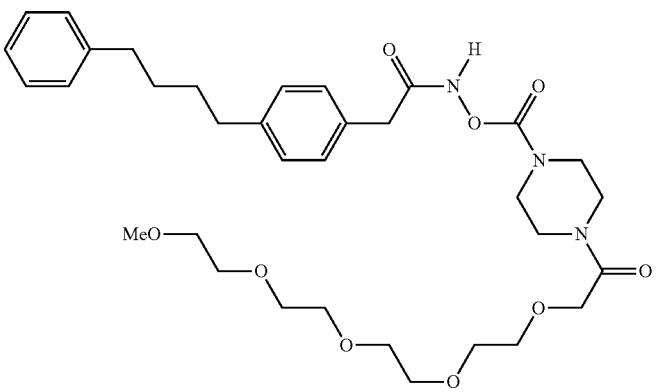<br>N-(4-2,5,8,11,14-pentaoxahexadecanepiperazine-1-carbonyloxy)-2-(4-(4-phenylbutyl)phenyl)acetamide | $^1$H NMR (DMSO-d6) δ (ppm): 11.56 (br. s, 1H), 7.28-7.24 (m, 2H), 7.18-7.09 (m, 7H), 4.14 (s, 2H), 3.57-3.39 (m, 22H), 3.23 (s, 3H), 2.61-2.55 (m, 4H), 1.60-1.56 (m, 4H), signals of the four remaining protons may be obscured by the signals of water present in the solvent.<br>LRMS (ESI): (calc.) 643.8 (found) 644.7 (MH)+ |
| 82 | 54 | 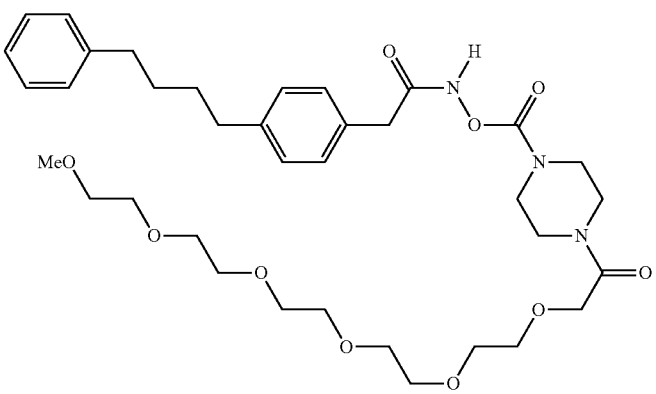<br>N-(4-2,5,8,11,14,17-hexaoxanonadecanepiperazine-1-carbonyloxy)-2-(4-(4-phenylbutyl)phenyl)acetamide | $^1$H NMR (DMSO-d6) δ (ppm): signal of NH proton is not seen; 7.28-7.23 (m, 2H), 7.18-7.05 (m, 7H), 4.16 (s, 2H), 3.57-3.23 (m, 35H, some of the signals overap with the signals of water present in the solvent), 2.59-2.55 (m, 4H), 1.58-1.55 (m, 4H).<br>LRMS (ESI): (calc.) 687.8 (found) 688.7 (MH)+ |

Scheme 14

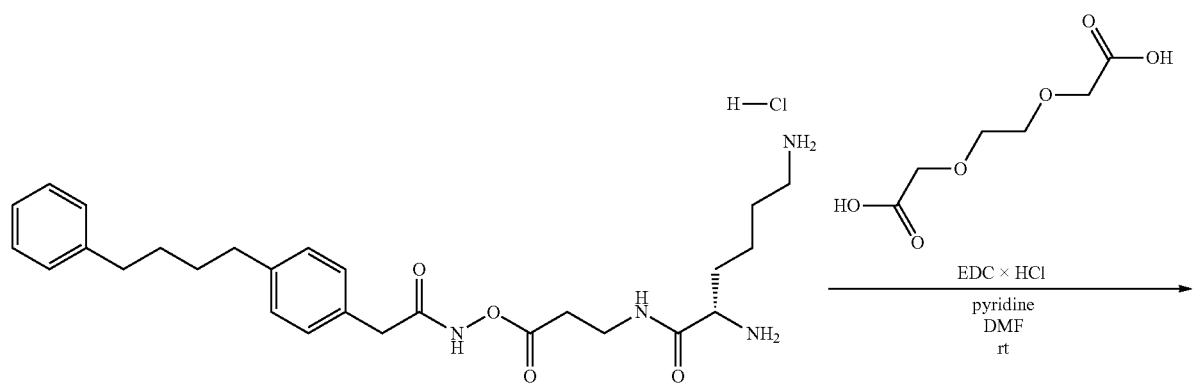

14

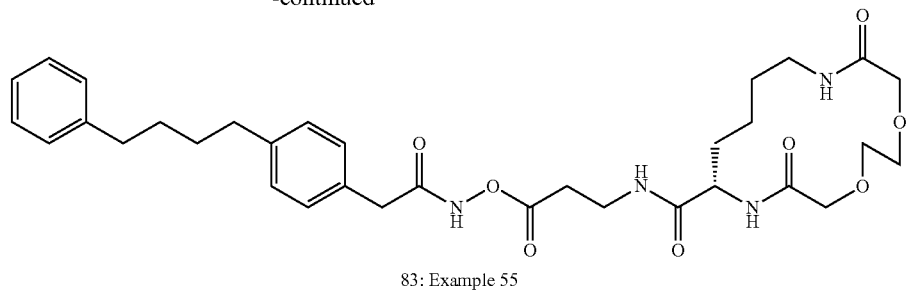

83: Example 55

EXAMPLE 55

(S)-6,14-Dioxo-N-(3-oxo-3-(2-(4-(4-phenylbutyl)phenyl)acetamidooxy)propyl)-1,4-dioxa-7,13-diaza-cyclopentadecane-8-carboxamide (83)

Compound 84 (example 56) was prepared in one step by coupling compound 14 with 2,2'-(2,2'-oxybis(ethane-2,1-diyl)bis(oxy))diacetic acid by following the procedures described above for the synthesis of compound 83 (scheme 14).

TABLE 10

Characterization of compound 84 (example 56)

| Cpd | Ex. | Structure | Characterization |
|---|---|---|---|
| 84 | 56 | (S)-9,17-dioxo-N-(3-oxo-3-(2-(4-(4-phenylbutyl)phenyl)acetamidooxy)propyl)-1,4,7-trioxa-10,16-diazacyclo octadecane-11-carboxamide | $^1$H NMR (400 MHz, DMSO-$d_6$) δ (ppm): mixture of conformers, 12.10-11.80 (m, 1H), 8.16 (bs, 1H), 7.48 (d, J = 8.2 Hz, 1H), 7.41 (t, J = 5.5 Hz, 1H), 7.32-7.06 (m, 9H), 4.26 (td, J = 8.2, 3.5 Hz, 1H), 3.96 (d, J = 14.9 Hz, 1H), 3.91-3.78 (m, 3H), 3.70-3.50 (m, 8H), 3.41 (s, 2H), 3.20-2.80 (m, 4H), 2.66-2.50 (m, 6H), 1.78-1.10 (m, 10H. MS (m/z): 669.56 [M + H]$^+$ and 691.55 [M + Na]$^+$. |

Scheme 15

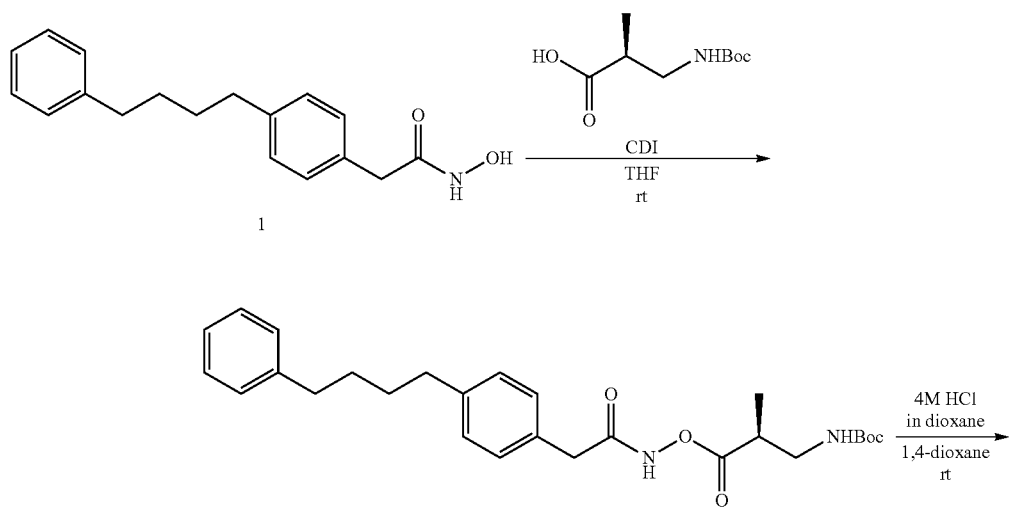

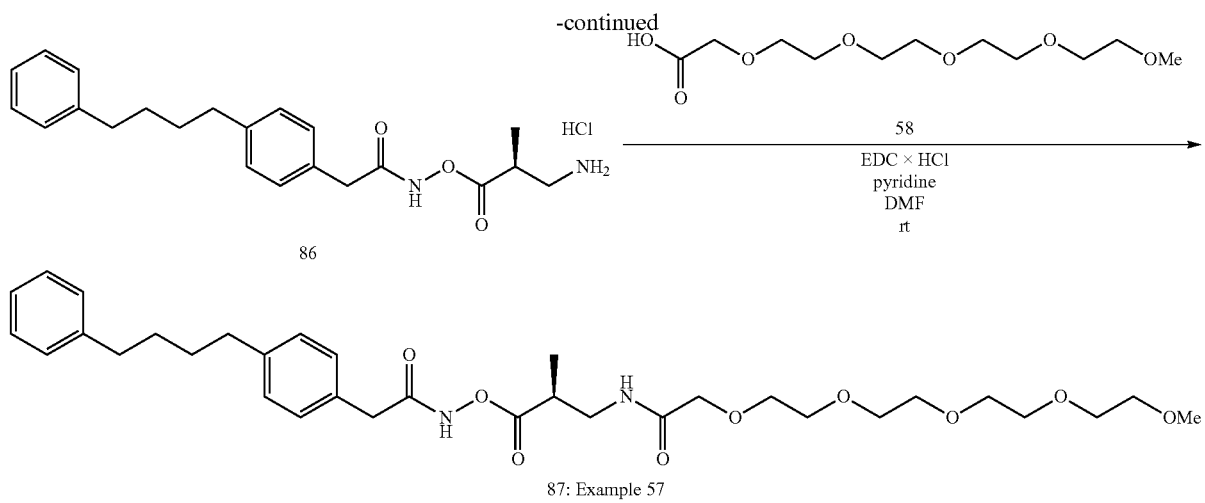

EXAMPLE 57

(S)-N-(2-Methyl-3-oxo-3-(2-(4-(4-phenylbutyl)phenyl)acetamidooxy)propyl)-2,5,8,11,14-pentaoxahexadecan-16-amide (87)

Step 1. (S)-tert-Butyl 2-methyl-3-oxo-3-(2-(4-(4-phenylbutyl)phenyl)acetamidooxy)propylcarbamate (85)

To a stirred solution of (S)-3-(tert-butoxycarbonylamino)-2-methylpropanoic acid (420 mg, 2.07 mmol) in anhydrous THF (30 ml) under nitrogen was added CDI (408 mg, 2.44 mmol). After 3 h, hydroxamate 1 (532 mg, 1.88 mmol) was added. The reaction mixture was stirred at RT overnight, diluted with AcOEt, and successively washed with an aqueous solution of 5% sodium hydrogenosulfate (×2), water and brine then concentrated. The residue was purified by Biotage® (Snap KP-Sil 25 g cartridge; MeOH/DCM: 00/100 to 03/97 over 30 CV, 220 nm detection wavelength), to afford the desired product 85 (460 mg, 0.98 mmol, 52% yield) as a white sticky solid. MS (m/z): 469.36 [M+H]$^{+\cdot}$ and 491.35 [M+Na]$^{+\cdot}$.

Step 2. (S)-N-(3-Amino-2-methylpropanoyloxy)-2-(4-(4-phenylbutyl)phenyl)acetamide hydrochloride (86)

To a stirred solution of intermediate 85 (460 mg, 0.98 mmol) in 1,4-dioxane (20 ml) was added 4M HCl in 1,4-dioxane (1.23 ml, 4.91 mmol). The reaction mixture was stirred at RT for 2.5 h, then more 4M HCl in 1,4-dioxane (1.23 ml, 4.91 mmol) was added. The reaction mixture was stirred at RT overnight then concentrated, suspended in diethyl ether, and shaken. The solid was collected by filtration, rinsed with diethyl ether, and dried to afford the desired product 86 (238 mg, 0.59 mmol, 59% yield) as a pale pinkish solid presumably as a hydrochloride salt. MS (m/z): 369.24 [M+H]$^{+\cdot}$.

Step 3. (S)-N-(2-Methyl-3-oxo-3-(2-(4-(4-phenylbutyl)phenyl)acetamidooxy)propyl)-2,5,8,11,14-pentaoxahexadecan-16-amide (87)

Compound 88 (example 58) was prepared in three steps by following the procedures described above for the synthesis of compound 87 (scheme 15) but replacing (S)-3-(tert-butoxycarbonylamino)-2-methylpropanoic acid in the step 1 with (S)-3-(boc-amino)butyric acid. Characterization of compound 88 (example 58) is provided in Table 11.

TABLE 11

Characterization of compound 88 (example 58).

| Cpd | Ex. | Structure | Characterization |
|---|---|---|---|
| 88 | 58 | (S)-N-(4-oxo-4-(2-(4-(4-phenylbutyl)phenyl)acetamido oxy)butan-2-yl)-2,5,8,11,14-pentaoxahexadecan-16-amide | $^1$H NMR (400 MHz, DMSO-d$_6$) δ (ppm): mixture of rotamers, 11.91 (bs, 1H), 7.64 (d, J = 8.4 Hz, 1H), 7.30-7.05 (m, 9H), 4.28-4.15 (m, 1H), 3.85 (s, 2H), 3.60-3.38 (m, 16H), 3.23 (s, 3H), 3.14-2.78 (m, 2H), 2.71 (dd, J = 15.3, 6.3 Hz, 1H), 2.64-2.52 (m, 4H), 1.66-1.48 (m, 4H), 1.16 (d, J = 6.7 Hz, 3H), one CH is hidden. MS (m/z): 617.55 [M + H]$^{+\cdot}$ and 639.55 [M + Na]$^{+\cdot}$. |

Scheme 16

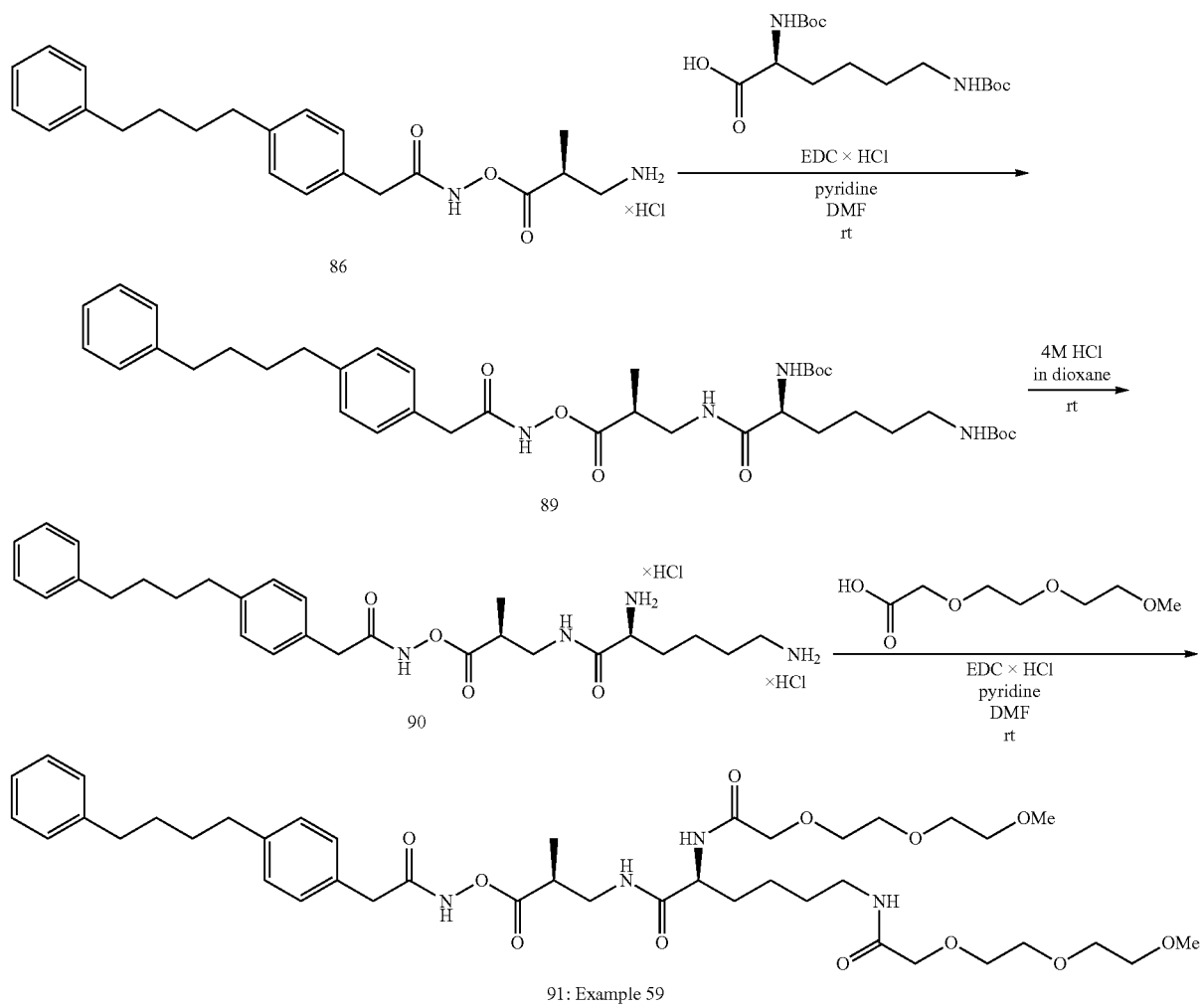

EXAMPLE 59

N,N'-((S)-6-((S)-2-Methyl-3-oxo-3-(2-(4-(4-phenyl-butyl)phenyl)acetamidooxy)propylamino)-6-oxo-hexane-1,5-diyl) bis(2-(2-(2-methoxyethoxy)ethoxy)acetamide) (91)

Step 1. tert-Butyl (S)-6-((S)-2-methyl-3-oxo-3-(2-(4-(4-phenylbutyl)phenyl)acetamidooxy)propylamino)-6-oxohexane-1,5-diyldicarbamate (89)

To a stirred solution of compound 86 (154 mg, 0.38 mmol, scheme 15) in DMF (10 mL) under nitrogen were added Boc-Lys(Boc)-OH (145 mg, 0.42 mmol), EDC×HCl (182 mg, 0.95 mmol) and pyridine (154 µl, 1.90 mmol). The reaction mixture was stirred at RT overnight. More Boc-Lys(Boc)-OH (145 mg, 0.42 mmol), EDC×HCl (182 mg, 0.95 mmol) and pyridine (154 µl, 1.90 mmol) were added. After 6 hrs, the reaction mixture was diluted with AcOEt, and successively washed with a mixture of 1N HCl/brine (×2), brine, dried over anhydrous magnesium sulfate, filtered, and concentrated. The residue was purified by Biotage® (Snap KP-Sil 10 g cartridge; MeOH/DCM: 0/100 to 5/95 over 50 CV, 220 nm detection wavelength) to afford the desired product 89 (46 mg, 0.066 mmol, 17% yield) as a colorless sticky film. MS (m/z): 697.64 [M+H]$^{+\cdot}$ and 719.64 [M+Na]$^{+}$.

Step 2. (S)-2,6-Diamino-N-((S)-2-methyl-3-oxo-3-(2-(4-(4-phenylbutyl)phenyl)acetamidooxy)propyl)hexanamide dihydrochloride (90).

A solution of compound 89 (46 mg, 0.066 mmol) in 4M HCl in 1,4-dioxane (0.825 ml, 3.3 mmol) was stirred at RT for 3 h, diluted with ethyl acetate and concentrated. The residual dioxane was removed by azeotropic distillation with EtOAc (×3), and the material was dried in high vacuum to afford the desired product 90 presumably in a form of a dihydrochloride salt as a pale pinky solid. The material was used in the next step without any further purification. MS (m/z): 497.41 [M+H]$^{+\cdot}$.

Step 3. N,N'-((S)-6-((S)-2-Methyl-3-oxo-3-(2-(4-(4-phenyl-butyl)phenyl)acetamidooxy)propylamino)-6-oxohexane-1,5-diyl) bis(2-(2-(2-methoxyethoxy)ethoxy)acetamide) (91)

To a stirred solution at RT of compound 90 (0.066 mmol) in DMF (3 ml) under nitrogen were added 2-(2-(2-methoxy-ethoxy)ethoxy)acetic acid (59 mg, 0.33 mmol), EDC×HCl (76 mg, 0.4 mmol) and pyridine (80 µl, 0.99 mmol). The reaction mixture was stirred at RT for 3.5 h, diluted with AcOEt, and successively washed with a mixture of 1N HCl/brine, brine (×2), dried over anhydrous magnesium sulfate, filtered, and concentrated. The residue was purified by Biotage® (Snap KP-Sil 10 g cartridge; MeOH/DCM: 0/100 to 5/95 over 50 CV, then 05/95 to 10/90 over 30 CV, 220 nm detection wavelength) to afford the desired product 91 (19 mg, 0.02 mmol, 35% yield) as a colorless sticky film/oil. $^1$H NMR (400 MHz, DMSO-$d_6$) δ (ppm): mixture of rotamers, 12.00 (bs, 1H), 8.50-8.05 (m, 1H), 7.68-7.55 (m, 2H), 7.30-7.06 (m, 9H), 4.29-4.19 (m, 1H), 3.89 (s, 2H), 3.84 (s, 2H), 3.63-3.36 (m, 18H), 3.23 (2s, 6H), 3.20-2.70 (m, 5H), 2.64-2.52 (m, 4H), 1.70-1.46 (m, 6H), 1.44-1.12 (m, 4H), 1.09 (d, J=7.0 Hz, 3H). MS (m/z): 817.48 [M+H]$^{+\cdot}$ and 839.46 [M+Na]$^{+\cdot}$.

EXAMPLE 60

4-oxo-N,N-bis(12-oxo-2,5,8-trioxa-11-azatridecan-13-yl)-4-(2-(4-(4-phenylbutyl)phenyl)acetamidooxy)butanamide (95)

Step 1. tert-Butyl 4-oxo-4-(2-(4-(4-phenylbutyl)phenyl)acetamidooxy)butanoate (92)

A solution of mono-tert-butyl succinate (500 mg, 2.87 mmol) and CDI (576 mg, 3.44 mmol) in anhydrous THF (30 ml) under nitrogen was stirred at RT for 4 h. To the solution then was added hydroxamate 1 (895 mg, 3.16 mmol). The reaction mixture was stirred at RT overnight, diluted with

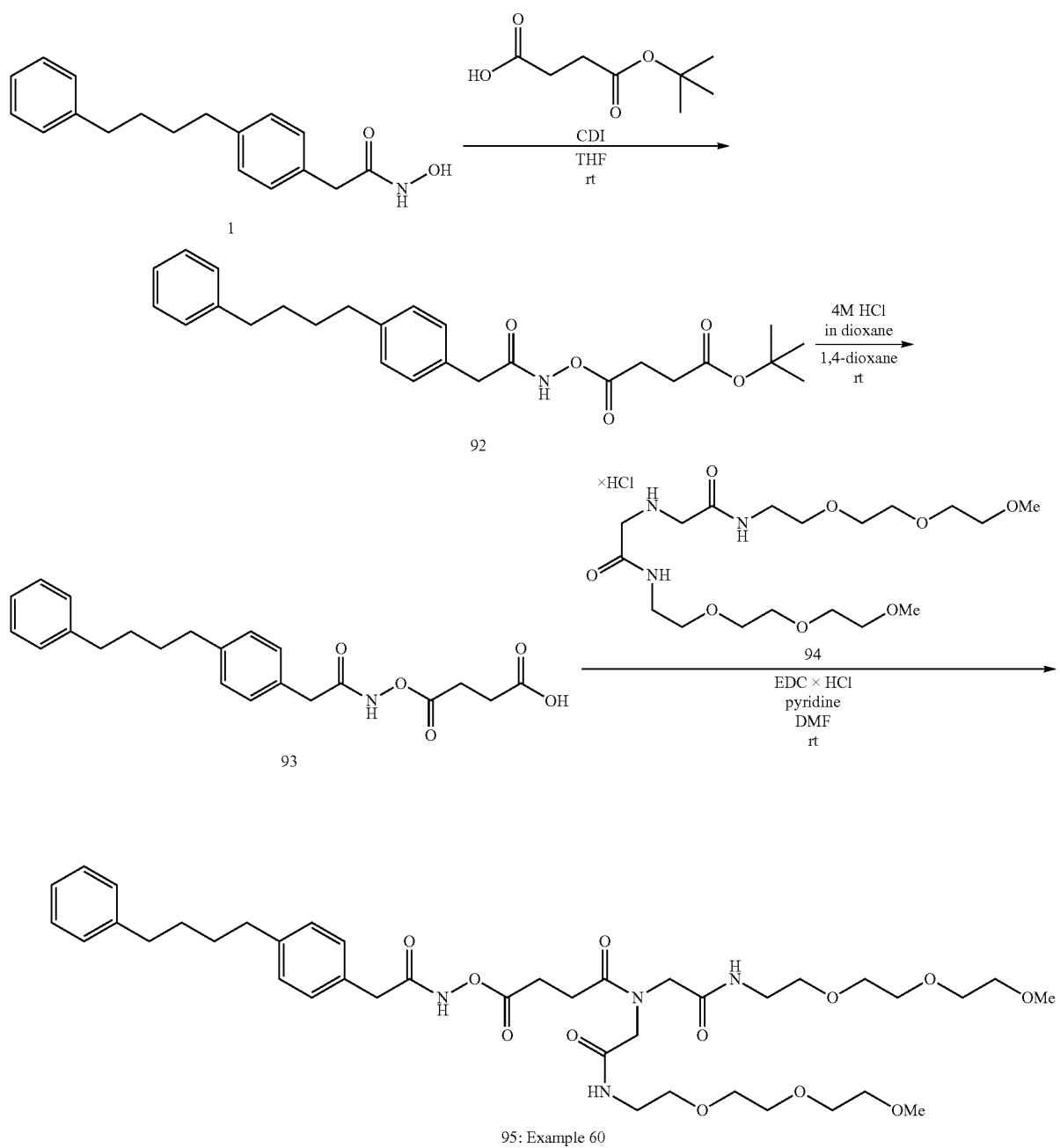

95: Example 60

AcOEt, and successively washed with an aqueous solution of 5% sodium hydrogen sulfate (×2), water and brine, and concentrated. The residue was purified by Biotage® (Snap KP-Sil 25 g cartridge; MeOH/DCM: 00/100 to 02/98 over 30 CV, 220 nm detection wavelength) to afford the desired product 92 (724 mg, 1.647 mmol, 57% yield) as a white sticky solid. MS (m/z): 440.26 [M+H]$^{+\cdot}$ and 462.26 [M+Na]$^{+\cdot}$.

Step 2. 4-Oxo-4-(2-(4-(4-phenylbutyl)phenyl)acetamidooxy)butanoic acid (93)

To a stirred solution of compound 92 (724 mg, 1.647 mmol) in 1,4-dioxane (2 ml) under nitrogen was added 4M HCl in 1,4-dioxane (6.18 ml, 24.71 mmol). The reaction mixture was stirred at RT for 3 h, then more 4M HCl in 1,4-dioxane (2 ml) was added. The reaction mixture was stirred at RT for an additional 30 min, concentrated, suspended in water and sonicated. The solid was collected by filtration, rinsed with water, and dried in vacuum to afford the desired product contaminated with the starting material. The mixture was resubmitted to deprotection with 4M HCl in 1,4-dioxane (12.35 ml, 49.4 mmol) at rt overnight, diluted with water, and sonicated. The solid was collected by filtration, rinsed with water, and dried in vacuum to afford the desired product 93 (485 mg, 1.27 mmol, 77% yield) as an off-white sticky solid (slightly contaminated). MS (m/z): 384.26 [M+H]$^{+\cdot}$ and 406.22 [M+Na]$^{+\cdot}$. The material was used in the next step with no additional purification.

Step 3. 4-Oxo-N,N-bis(12-oxo-2,5,8-trioxa-11-azatridecan-13-yl)-4-(2-(4-(4-phenylbutyl)phenyl)acetamidooxy)butanamide (95)

To a stirred solution at RT of acid 93 (86 mg, 0.23 mmol) and 2,2'-azanediylbis(N-(2-(2-(2-methoxyethoxy)ethoxy)ethyl)acetamide) hydrochloride (94) (69 mg, 0.15 mmol) in DMF (2 ml) under nitrogen were added EDC×HCl (109 mg, 0.57 mmol) and pyridine (121 µl, 1.50 mmol). The reaction mixture was stirred at RT overnight, diluted with AcOEt, and successively washed with a mixture of 1N HCl/brine and brine (×2), dried over anhydrous magnesium sulfate, filtered, and concentrated. The residue was purified twice by Biotage® (Snap KP-Sil 10 g cartridge; MeOH/DCM: 0/100 to 10/90 over 60 CV, 220 nm detection wavelength) to afford the desired product 95 (5.4 mg, 0.0068 mmol, 4% yield) as a colorless sticky film/oil. $^1$H NMR (400 MHz, MeOH-d$_4$) δ (ppm): mixture of rotamers, 3NH are not seen, 7.25-7.06 (m, 9H), 4.19 and 4.18 (2s, 2H), 4.03 (s, 2H), 3.68-3.35 (m, 32H), 2.81-2.68 (m, 4H), 2.66-2.54 (m, 4H), 1.70-1.54 (m, 4H). MS (m/z): 789.45 [M+H]$^{+\cdot}$ and 811.44 [M+Na]$^{+\cdot}$.

2,2'-Azanediylbis(N-(2-(2-(2-methoxyethoxy)ethoxy)ethyl)acetamide) hydrochloride (94) that was used in the synthesis of compound 95 (example 60) was obtained via a two-step reaction sequence according to the scheme 18.

Scheme 18

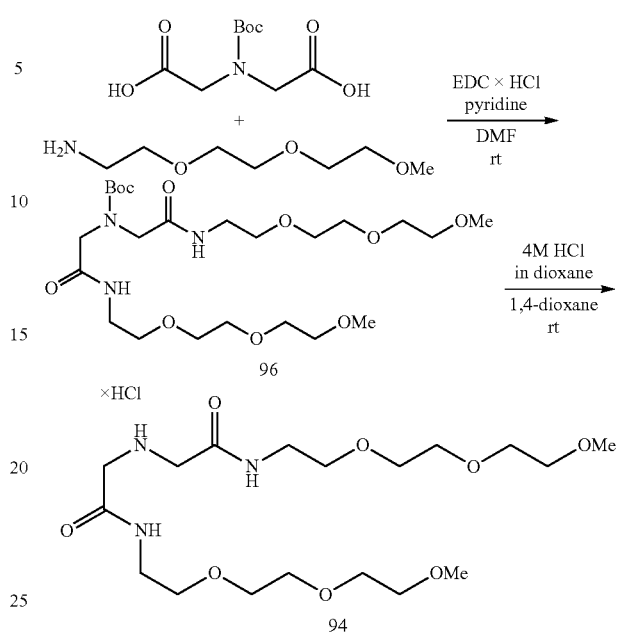

Step 1. tert-Butyl bis(12-oxo-2,5,8-trioxa-11-azatridecan-13-yl)carbamate (96)

To a stirred solution at RT of 2,2'-(tert-butoxycarbonylazanediyl)diacetic acid (300 mg, 1.29 mmol) and 2-(2-(2-methoxyethoxy)ethoxy)ethanamine (630 mg, 3.86 mmol) in DMF (5 ml) under nitrogen were added EDC×HCl (1.23 g, 6.43 mmol) and pyridine (1.04 ml, 12.86 mmol). The reaction mixture was stirred at RT over weekend, diluted with AcOEt, and successively washed with a mixture of 1N HCl/NaCl sat (×3) and brine, dried over anhydrous magnesium sulfate, filtered, and concentrated to afford the desired product 96 (81 mg, 0.16 mmol, 12% yield) as a pale yellow oily liquid. The material was used in the next step without any further purification. MS (m/z): 524.39 [M+H]$^{+\cdot}$ and 546.39 [M+Na]$^{+\cdot}$.

Step 2. 2,2'-Azanediylbis(N-(2-(2-(2-methoxyethoxy)ethoxy)ethyl)acetamide) hydrochloride (94)

To a stirred solution of compound 96 (81 mg, 0.16 mmol) in 1,4-dioxane (0.5 ml) was added 4M HCl in 1,4-dioxane (0.58 ml, 2.32 mmol). The reaction mixture was stirred at RT for 2.5 h, then more 4M HCl in 1,4-dioxane (1 ml, 4.02 mmol) was added. The reaction mixture was stirred at RT for 2 more hours and concentrated. The residual dioxane was removed by azeotropic distillation with ethyl acetate (×3), and dried in vacuum to afford title compound 94 (69 mg, 0.15 mmol). The material was used in the next step without any further purification. MS (m/z): 424.31 [M+H]$^{+\cdot}$.

Scheme 19

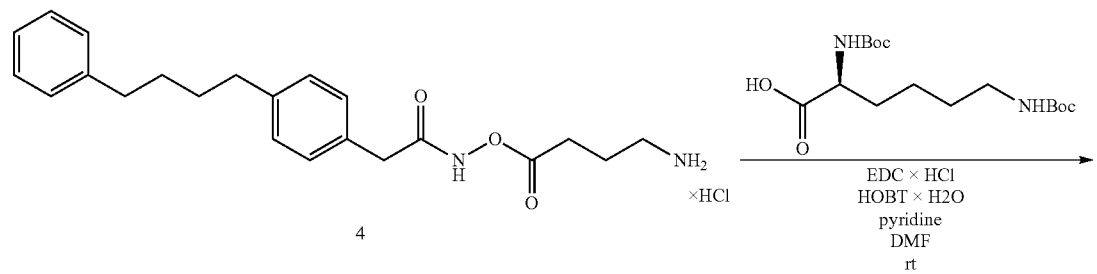

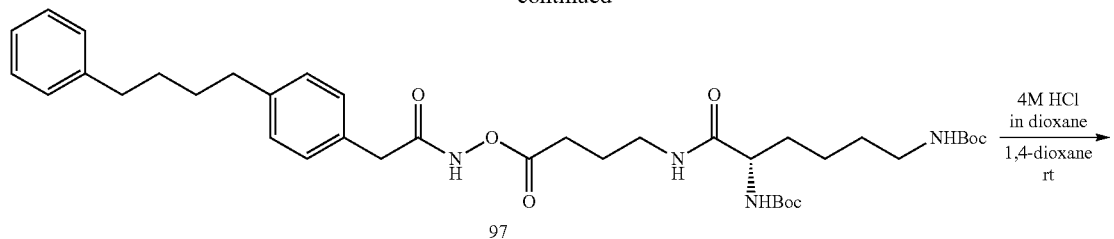

97

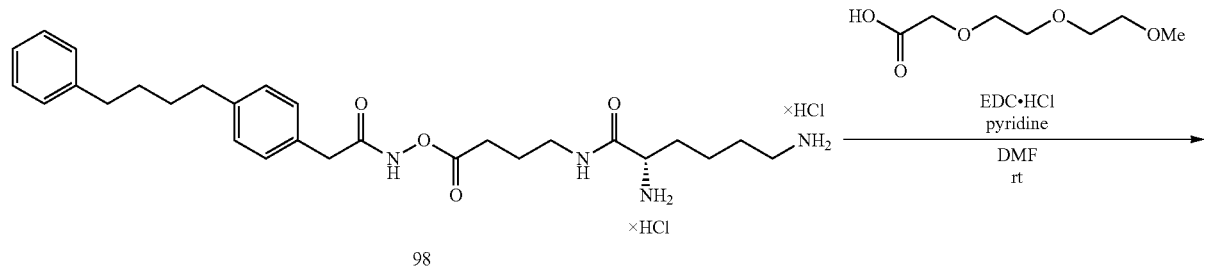

98

[Structure of compound 99]

99: Example 61

EXAMPLE 61

(S)-N,N'-(6-Oxo-6-(4-oxo-4-(2-(4-(4-phenylbutyl) phenyl)acetamido oxy)butylamino)hexane-1,5-diyl) bis(2-(2-(2- methoxyethoxy)ethoxy)acetamide) (99)

Step 1. (S)-tert-butyl 6-oxo-6-(4-oxo-4-(2-(4-(4-phenylbutyl)phenyl)acetamido oxy)butylamino)hexane-1,5-diyldicarbamate (97)

To a stirred suspension of compound 4 (2.16 g, 5.33 mmol, Table 1) and Boc-Lys(Boc)-OH (2.402 g, 6.93 mmol) in DMF (30 ml) at RT under nitrogen were added HOBT×H$_2$O (817 mg, 5.33 mmol), EDC×HCl (2.045 g, 10.67 mmol) and pyridine (2.16 ml, 26.7 mmol), respectively. The reaction mixture was stirred at rt for 3.5 h, diluted with AcOEt, and successively washed with water (×2), 1N HCl (×2), water and brine, dried over anhydrous magnesium sulfate, filtered, and concentrated. The residue was purified by Biotage® (Snap KP-Sil 100 g cartridge; MeOH/DCM: 0/100 to 5/95 over 30 CV, then 5/95 over 10 CV, 220 nm detection wavelength) to afford the desired product 97 (2.92 g, 4.19 mmol, 79% yield) as a colorless sticky film/foam (contaminated with HOBT). MS (m/z): 697.6 [M+H]$^{+\cdot}$ and 719.6 [M+Na]$^+$.

Step 2. (S)-2,6-Diamino-N-(4-oxo-4-(2-(4-(4-phenylbutyl) phenyl)acetamidooxy)butyl)hexanamide dihydrochloride (98)

To a stirred solution of compound 97 (2.92 g, 4.19 mmol) in 1,4-dioxane (10 mL) was added 4M HCl in 1,4-dioxane (15.71 mL, 62.9 mmol). The reaction mixture was stirred at rt for 2 h, diluted with diethyl ether, and sonicated. The liquid was removed by decantation; the residue was suspended in diethyl ether and shaken. The liquid was again discarded by decantation and the sticky residue was dried in high vacuum to afford the desired product 98 (2.2 g, 3.86 mmol, 92% yield) as a white paste. MS (m/z): 497.45 [M+H]$^{+\cdot}$.

Step 3. (S)-N,N'-(6-Oxo-6-(4-oxo-4-(2-(4-(4-phenylbutyl) phenyl)acetamidooxy)butylamino)hexane-1,5-diyl)bis(2-(2-(2- methoxyethoxy)ethoxy)acetamide) (99)

To a stirred solution at rt of compound 98 (2.2 g, 3.86 mmol) in DMF (15 mL) under nitrogen were added 2-(2-(2-methoxyethoxy)ethoxy)acetic acid (1.78 ml, 11.59 mmol), HOBT×H$_2$O (1.18 g, 7.73 mmol), EDC×HCl (2.96 g, 15.45 mmol) and pyridine (3.12 ml, 38.6 mmol). The reaction mixture was stirred at RT for 3 h, diluted with AcOEt, and successively washed with a mixture of 1N HCl/brine (×3), dried over anhydrous magnesium sulfate, filtered, and concentrated. The residue was purified twice by Biotage® (Snap KP-Sil 100 g cartridge KP-Sil; MeOH/

DCM: 0/100 to 10/90 over 30 CV, and by reverse phase: Snap 120 g cartridge KP-C18-HS; MeOH/water: 20/80 to 95/5 over 40 CV, 40 ml/min, 220 nm detection wavelength) to afford the desired product 99 (1.544 g, 1.89 mmol, 48.9% yield) as a colorless gel. $^1$H NMR (400 MHz, DMSO-d$_6$) δ (ppm): 11.98-11.76 (m, 1H), 8.07 (t, J=5.5 Hz, 1H), 7.62 (t, J=6.0 Hz, 1H), 7.55 (d, J=8.2 Hz, 1H), 7.30-7.06 (m, 9H), 4.24 (td, J=8.3, 5.5 Hz, 1H), 3.93 and 3.89 (2d, J=15.3 Hz, 2H), 3.84 (s, 2H), 3.65-3.37 (m, 18H), 3.24 and 3.23 (2s, 6H), 3.14-3.02 (m, 4H), 2.63-2.53 (m, 4H), 2.44 (t, J=7.4 Hz, 2H), 1.74-1.12 (m, 12H). MS (m/z): 817.6 [M+H]$^{+\cdot}$ and 839.6 [M+Na]$^{+\cdot}$.

Compounds 100-103 (examples 62-65) were prepared in one step starting from compound 98, following the procedures described above for the synthesis of compound 99 (scheme 19) but replacing 2-(2-(2-methoxyethoxy)ethoxy) acetic acid with 2-(2-methoxyethoxy)acetic acid; 2,5,8,11-tetraoxatridecan-13-oic acid (104, *Langmuir*, 2009, 25(9), pp. 5026-5030), 2,5,8,11,14-pentaoxahexadecan-16-oic acid (58) and 2,5,8,11,14,17-hexaoxanonadecan-19-oic acid (59), respectively. Characterization of compounds 100-103 (examples 62-65) is provided in Table 12.

TABLE 12

Characterization of compounds 100-103 (examples 62-65).

| Cpd | Ex. | Structure |
|---|---|---|
| 100 | 62 | 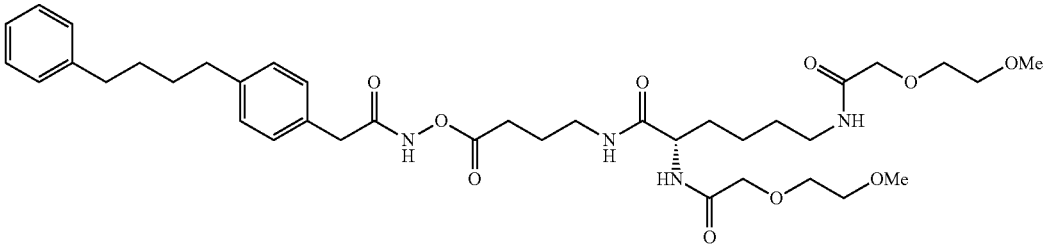<br>(S)-N,N'-(6-oxo-6-(4-oxo-4-(2-(4-(4-phenylbutyl)phenyl)acetamidooxy)butylamino)hexane-1,5-diyl)bis(2-(2-methoxyethoxy)acetamide) |
| 101 | 63 | 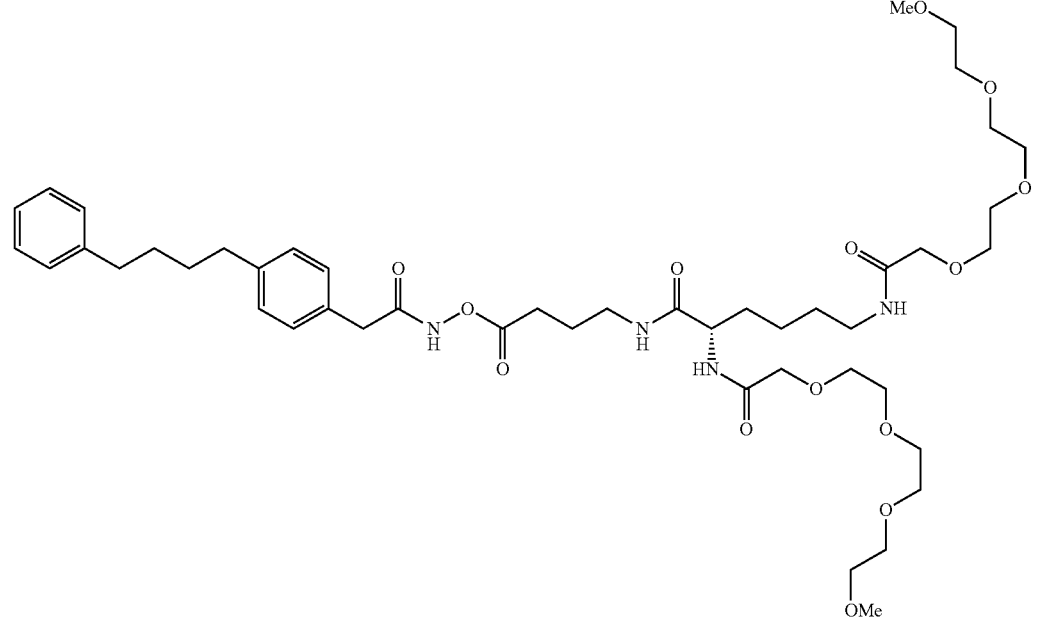<br>(S)-N,N'-(6-oxo-6-(4-oxo-4-(2-(4-(4-phenylbutyl)phenyl)acetamidooxy)butylamino)hexane-1,5-diyl)bis(2,5,8,11-tetraoxatridecan-13-amide) |

TABLE 12-continued

Characterization of compounds 100-103 (examples 62-65).

102    64

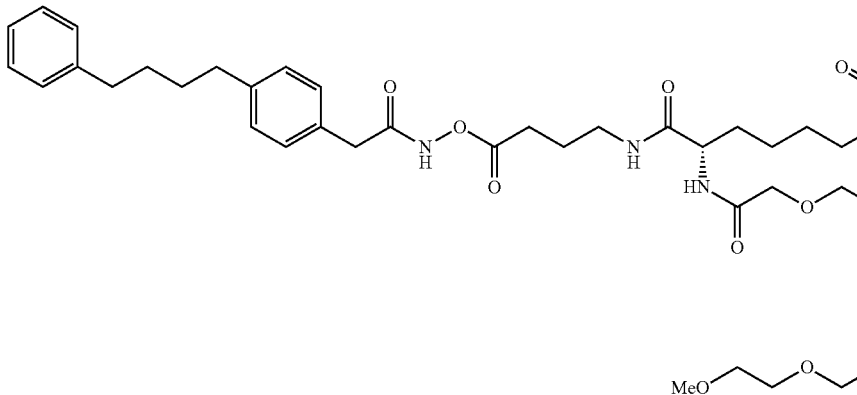

(S)-N,N'-(6-oxo-6-(4-oxo-4-(2-(4-(4-phenylbutyl)phenyl)acetamidooxy)butylamino)hexane-1,5-diyl)bis(2,5,8,11,14-pentaoxahexadecan-16-amide)

103    65

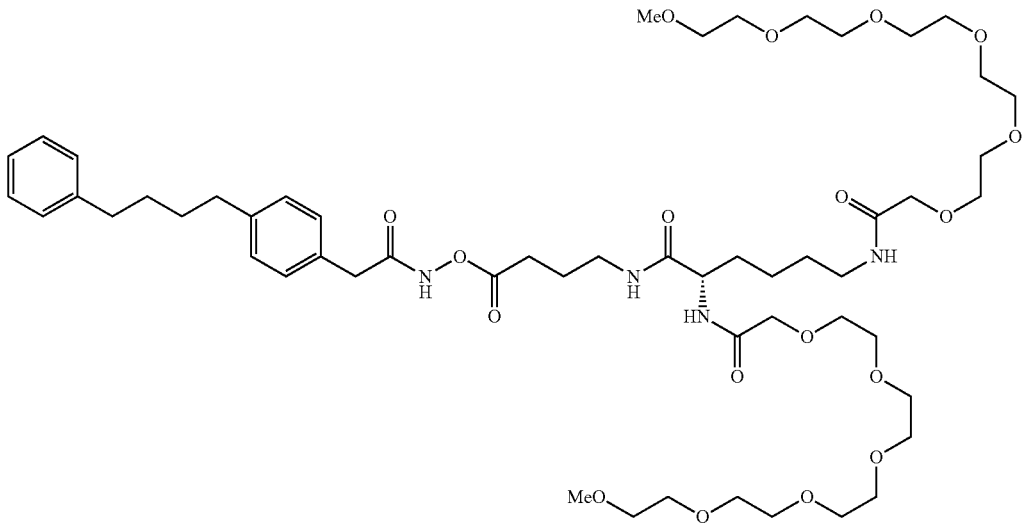

(S)-N,N'-(6-oxo-6-(4-oxo-4-(2-(4-(4-phenylbutyl)phenyl)acetamidooxy)butylamino)hexane-1,5-diyl)bis(2,5,8,11,14,17-hexaoxanonadecan-19-amide)

| Cpd | Ex. | Characterization |
|---|---|---|
| 100 | 62 | $^1$H NMR (400 MHz, DMSO-$d_6$) δ (ppm): 11.96-11.80 (m, 1H), 8.07 (t, J = 5.5 Hz, 1H), 7.66-7.55 (m, 2H), 7.30-7.07 (m, 9H), 4.24 (td, J = 8.0, 5.5 Hz, 1H), 3.90 (s, 2H), 3.84 (s, 2H), 3.65-3.44 (m, 8H), 3.41 (s, 2H), 3.27 and 3.26 (2s, 6H), 3.13-3.02 (m, 4H), 2.63-2.52 (m, 4H), 2.44 (t, J = 7.3 Hz, 2H), 1.74-1.12 (m, 12H). MS (m/z): 729.6 [M + H]$^+$ and 751.6 [M + Na]$^+$. |
| 101 | 63 | $^1$H NMR (400 MHz, DMSO-$d_6$) δ (ppm): 11.98-11.78 (m, 1H), 8.06 (t, J = 5.7 Hz, 1H), 7.61 (t, J = 5.9 Hz, 1H), 7.54 (d, J = 8.4 Hz, 1H), 7.30-7.06 (m, 9H), 4.24 (td, J = 8.2, 5.3 Hz, 1H), AB system ($δ_A$ = 3.93, $δ_B$ = 3.89, J = 15.7 Hz, 2H), 3.84 (s, 2H), 3.66-3.46 (m, 20H), 3.45-3.38 (m, 6H), 3.23 (2s, 6H), 3.14-3.01 (m, 4H), 2.65-2.53 (m, 4H), 2.44 (t, J = 7.4 Hz, 2H), 1.75-1.12 (m, 12H). MS (m/z): 905.7 [M + H]$^+$ and 927.7 [M + Na]$^+$. |
| 102 | 64 | $^1$H NMR (400 MHz, DMSO-$d_6$) δ (ppm): 12.05-11.70 (m, 1H), 8.06 (t, J = 5.5 Hz, 1H), 7.61 (t, J = 5.7 Hz, 1H), 7.55 (d, J = 8.2 Hz, 1H), 7.30-7.04 (m, 9H), 4.29-4.20 (m, 1H), 3.91 (s, 2H), 3.84 (s, 2H), 3.66-3.37 (m, 34H), 3.23 (s, 6H), 3.14-3.01 (m, 4H), 2.65-2.53 (m, 4H), 2.44 (t, J = 7.4 Hz, 2H), 1.77-1.11 (m, 12H). MS (m/z): 993.7 [M + H]$^+$ and 1015.7 [M + Na]$^+$. |

TABLE 12-continued
Characterization of compounds 100-103 (examples 62-65).
| | | |
|---|---|---|
| 103 | 65 | $^1$H NMR (400 MHz, DMSO-$d_6$) δ (ppm): 11.95-11.80 (m, 1H), 8.06 (t, J = 5.5 Hz, 1H), 7.61 (t, J = 5.9 Hz, 1H), 7.55 (d, J = 8.2 Hz, 1H), 7.30-7.06 (m, 9H), 4.24 (td, J = 8.4, 5.5 Hz, 1H), AB system (δ$_A$ = 3.93, δ$_B$ = 3.89, J = 15.6 Hz, 2H), 3.84 (s, 2H), 3.66-3.36 (m, 42H), 3.24 (s, 6H), 3.14-3.01 (m, 4H), 2.64-2.53 (m, 4H), 2.44 (t, J = 7.2 Hz, 2H), 1.76-1.10 (m, 12H).<br>MS (m/z): 1081.9 [M + H]$^+$ and 1103.9 [M + Na]$^+$. |
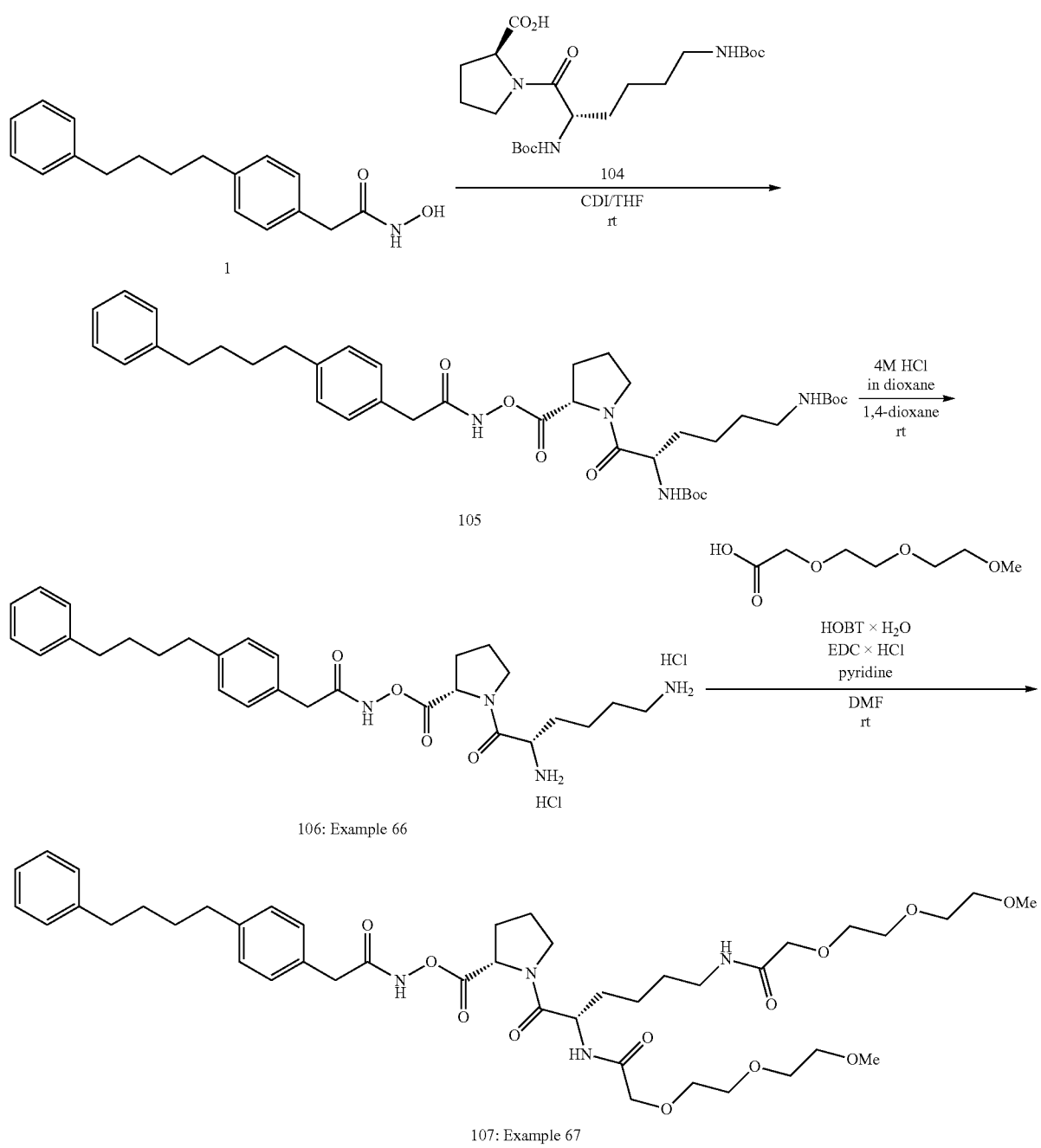

EXAMPLES 66 AND 67

N,N'-((S)-6-Oxo-6-((S)-2-((2-(4-(4-phenylbutyl) phenyl)acetamidooxy)carbonyl)pyrrolidin-1-yl) hexane-1,5-diyl)bis(2-(2-(2- methoxyethoxy)ethoxy) acetamide) (107)

Step 1. tert-Butyl (S)-6-oxo-6-((S)-2-((2-(4-(4-phenylbutyl) phenyl)acetamidooxy)carbonyl)pyrrolidin-1-yl)hexane-1,5-diyldicarbamate (105)

A solution of Boc-Lys(Boc)-Pro-OH (104) (997 mg, 2.25 mmol) and CDI (413 mg, 2.47 mmol) in anhydrous THF (20 mL) under nitrogen was stirred for 5 h. To the resultant solution was added hydroxamate 1 (413 mg, 2.25 mmol). The reaction mixture was stirred at RT for 36 hrs, diluted with AcOEt, and successively washed with 1N HCl (×2), water and brine, dried over anhydrous magnesium sulfate, filtered, suspended in DCM, filtered and the filtrate was concentrated. The residue was purified by Biotage® (Snap KP-Sil 25 g cartridge; MeOH/DCM: 00/100 to 05/95 over 40 CV, 220 nm detection wavelength) to afford the desired product 105 (594 mg, 0.83 mmol, 37% yield) as a pale-yellow sticky foam (slightly contaminated). MS (m/z): 709.6 $[M+H]^{+}$ and 731.6 $[M+Na]^{+}$.

Step 2. N-((S)-1-((S)-2,6-Diaminohexanoyl)pyrrolidine-2-carbonyloxy)-2-(4-(4-phenylbutyl)phenyl)acetamide dihydrochloride (106)

To a stirred solution of compound 106 (594 mg, 0.84 mmol) in 1,4-dioxane (3 mL) was added 4M HCl in 1,4-dioxane (6.28 mL, 25.1 mmol). The reaction mixture was stirred at RT for 2 h and concentrated. The residual dioxane was removed by azeotropic distillation with ethyl acetate, and the remained solid was suspended in diethyl ether, and sonicated for 2 h. The material was collected by filtration, rinsed with diethyl ether, and dried to afford the desired product 106 (447 mg, 0.77 mmol, 92% yield), presumably as a dihydrochloride salt as a pale-yellow sticky solid. $^1$H NMR (400 MHz, DMSO-$d_6$) δ (ppm): mixture of rotamers, 12.27 (bs, 1H), 8.50-8.25 (m, 3H), 8.17-7.95 (m, 3H), 7.30-7.04 (m, 9H), 4.58 (dd, J=8.7, 5.0 Hz, 1H), 4.21-4.11 (m, 1H), 3.83-3.70 (m, 1H), 3.61-3.50 (m, 1H), 2H are hidden by water peak, 2.80-2.67 (m, 2H), 2.64-2.52 (m, 4H), 2.35-1.34 (m, 14H). MS (m/z): 509.4 $[M+H]^{+}$.

Step 3. N,N'-((S)-6-Oxo-6-((S)-2-((2-(4-(4-phenylbutyl) phenyl)acetamidooxy)carbonyl)pyrrolidin-1-yl)hexane-1,5 -diyl)bis(2-(2-(2-methoxyethoxy)ethoxy)acetamide) (107)

To a stirred solution of compound 106 (160 mg, 0.275 mmol) in DMF (4 ml) at RT under nitrogen were added 2-(2-(2-methoxyethoxy)ethoxy)acetic acid (147 mg, 0.83 mmol), HOBT×H$_2$O (42 mg, 0.275 mmol), EDC×HCl (211 mg, 1.10 mmol) and pyridine (223 µl, 2.75 mmol). The reaction mixture was stirred at RT overnight, diluted with AcOEt, and successively washed with a mixture of 1N HCl/brine (×2), brine (×2), dried over anhydrous magnesium sulfate, filtered, and concentrated. The residue was purified twice by Biotage (Snap KP-Sil 25 g cartridge; MeOH/DCM: 0/100 to 10/90 over 40 CV, and by reverse phase: Snap 30 g cartridge KP-C18-HS; MeOH/water: 5/95 to 95/5 over 40 CV, 40 ml/min, 220 nm detection wavelength) afford the desired product 107 (57 mg, 0.07 mmol, 25% yield) as colorless gel. $^1$H NMR (400 MHz, DMSO-$d_6$) δ (ppm): mixture of rotamers, 12.26-11.96 (m, 1H), 7.74-7.58 (m, 2H), 7.32-7.04 (m, 9H), 4.68-4.20 (m, 2H), 3.97-3.80 (m, 4H), 3.76-3.66 (m, 1H), 3.64-3.36 (m, 19H), 3.24 (2s, 6H), 3.08 (q, J=6.89 Hz, 2H), 2.64-2.52 (m, 4H), 2.28-2.18 (m, 1H), 2.07-1.87 (m, 3H), 1.74-1.20 (m, 10H). MS (m/z): 829.6 $[M+H]^{+}$ and 851.6 $[M+Na]^{+}$.

Compound 108 (example 68) was prepared in one step by coupling compound 106 with 2-(2-methoxyethoxy)acetic acid similarly to compound 107 (scheme 20).
Characterization of compound 108 (example 68) is provided in Table 13.

TABLE 13

Characterization of compound 108 (example 68)

| Cpd | Ex. | Structure | Characterization |
|---|---|---|---|
| 108 | 68 | 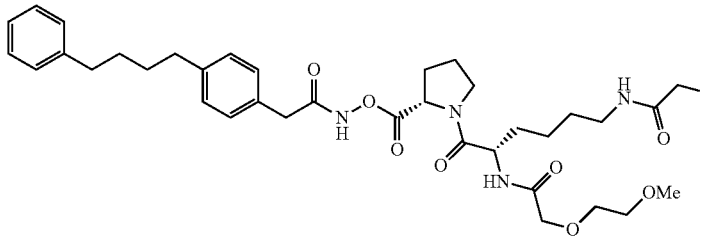<br>N,N'-((S)-6-oxo-6-((S)-2-((2-(4-(4-phenylbutyl)phenyl)acetamidooxy)carbonyl)pyrrolidin-1-yl)hexane-1,5-diyl)bis(2-(2-methoxyethoxy)acetamide) | $^1$H NMR (400 MHz, DMSO-$d_6$) δ (ppm): mixture of rotamers, 12.20-11.96 (m, 1H), 7.70 (d, J = 7.8 Hz, 1H), 7.64 (t, J = 5.8 Hz, 1H), 7.30-7.07 (m, 9H), 4.61-4.46 (m, 2H), 3.93-3.87 (m, 2H), 3.86-3.82 (m, 2H), 3.76-3.34 (m, 12H), 3.28 and 3.27 (2s, 6H), 3.07 (q, J = 6.7 Hz, 2H), 2.63-2.53 (m, 4H), 2.27-2.19 (m, 1H), 2.04-1.92 (m, 3H), 1.72-1.22 (m, 10H). MS (m/z): 741.5 $[M + H]^{+}$ and 764.5 $[M + Na]^{+}$. |

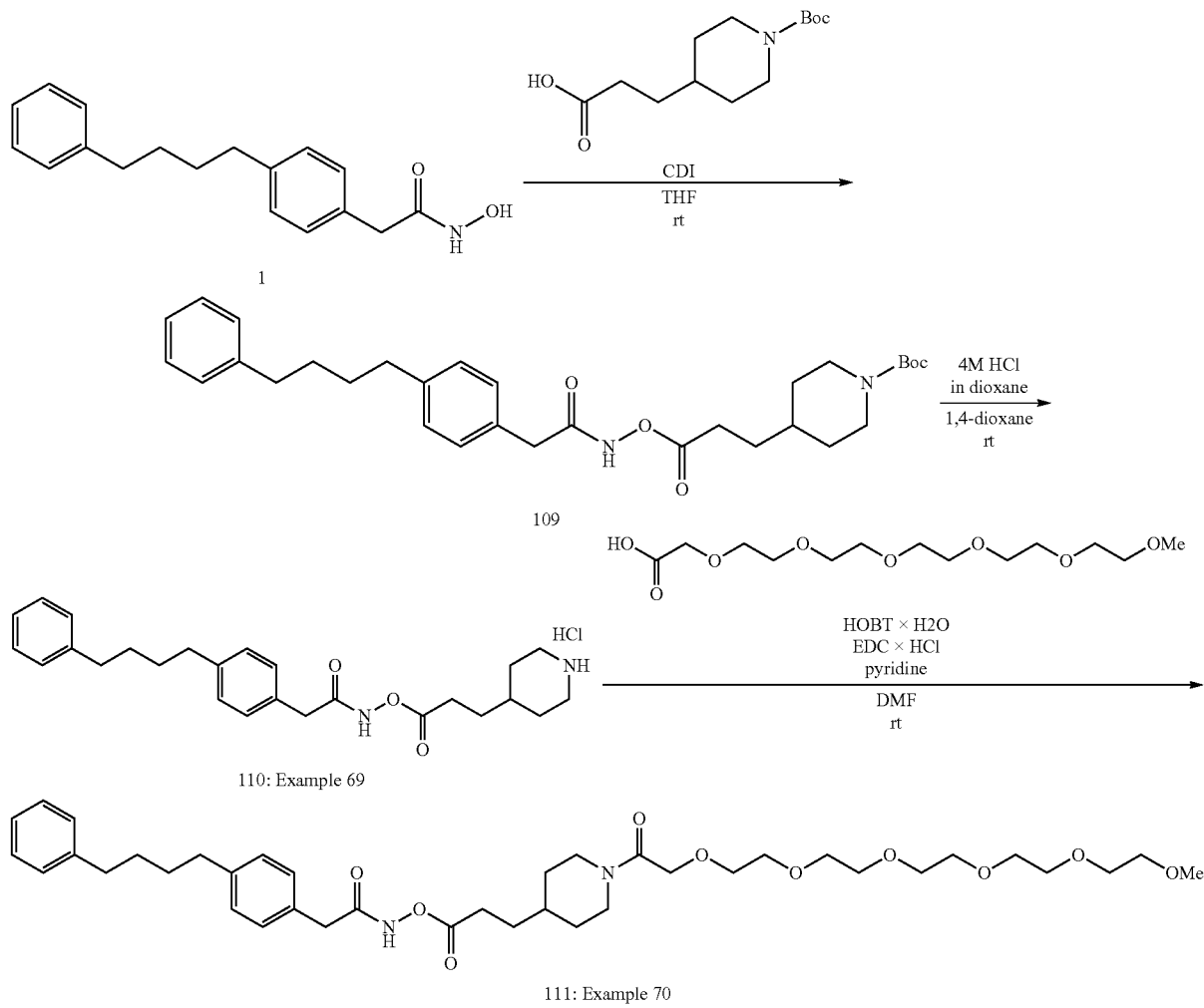

Scheme 21

EXAMPLES 69 AND 70

N-(3-(1-2,5,8,11,14,17-Hexaoxanonadecanepiperidin-4-yl)propanoyloxy)-2-(4-(4-phenylbutyl)phenyl)acetamide (111)

Step 1. tert-Butyl 4-(3-oxo-3-(2-(4-(4-phenylbutyl)phenyl)acetamidooxy)propyl)piperidine-1-carboxylate (109)

To a solution of 3-(1-(tert-butoxycarbonyl)piperidin-4-yl)propanoic acid (908 mg, 3.53 mmol) in anhydrous THF (30 ml) under nitrogen was added portionwise CDI (708 mg, 4.23 mmol) over 5 min, and the reaction mixture was stirred for 3.5 h. To the resultant solution was added hydroxamate 1 (800 mg, 2.82 mmol). The reaction mixture was stirred at RT overnight, diluted with AcOEt, and successively washed with 1N HCl (×2), water and brine, dried over anhydrous magnesium sulfate, filtered and concentrated. The residue was purified by Biotage® (Snap KP-Sil 50 g cartridge; MeOH/DCM: 00/100 to 05/95 over 45 CV, 220 nm detection wavelength) to afford the desired product 109 (1.07 g, 2.05 mmol, 72% yield) as a colorless gel. MS (m/z): 523.4 [M+H]$^{+\cdot}$ and 545.39 [M+Na]$^{+\cdot}$.

Step 2. 2-(4-(4-Phenylbutyl)phenyl)-N-(3-(piperidin-4-yl)propanoyloxy)acetamide hydrochloride (110)

To a stirred solution of compound 37 (1.07 g, 2.05 mmol) in 1,4-dioxane (20 ml) was added 4M HCl in 1,4-dioxane (7.17 ml, 28.7 mmol). The reaction mixture was stirred at rt for 5 h, concentrated not to dryness, diluted with diethyl ether, concentrated a bit, diluted with diethyl ether again and shaken for a while. The solid was collected by filtration, rinsed with diethyl ether, air-dried (few minutes) and dried under high vacuum to afford the desired product (793 mg, 1.73 mmol, 84% yield), presumably as a hydrochloride salt as an off-white fluffy solid. $^1$H NMR (400 MHz, DMSO-d$_6$) δ (ppm): one NH is missing, 9.00-8.40 (m, 2H), 7.29-7.07 (m, 9H), 3.42 (s, 2H), 3.21 (bd, J=12.5, 2H), 2.84-2.71 (m, 2H), 2.64-2.52 (m, 4H), 2.48 and 2.23 (2t, J=7.1, 2H), 1.84-1.72 (m, 2H), 1.64-1.40 (m, 7H), 1.36-1.19 (m, 2H). MS (m/z): 423.27 [M+H]$^{+\cdot}$.

Step 3. N-(3-(1-2,5,8,11,14,17-Hexaoxanonadecanepiperidin-4-yl)propanoyloxy)-2-(4-(4-phenylbutyl)phenyl)acetamide (111)

To a stirred solution at rt of compound 110 (200 mg, 0.44 mmol) in DMF (5 ml) under nitrogen were added 2,5,8,11,14,17-hexaoxanonadecan-19-oic acid (59, 176 mg, 0.57 mmol), HOBT×H$_2$O (67 mg, 0.44 mmol), EDC×HCl (167 mg, 0.87 mmol) and pyridine (176 2.18 mmol). The reaction mixture was stirred at RT overnight, diluted with AcOEt, and successively washed with a mixture of 1N HCl/brine (×3), dried over anhydrous magnesium sulfate, filtered, and concentrated. The residue was purified twice by Biotage® (Snap KP-Sil 25 g cartridge; MeOH/DCM: 0/100 to 10/90 over 30 CV, and by reverse phase: Snap 30 g cartridge KP-C18-HS; MeOH/water: 20/80 to 95/5 over 50 CV, 40 ml/min, with both 220 nm detection wavelength) to afford the desired product 111 (147 mg, 0.21 mmol, 47% yield) as a colorless gel. $^1$H NMR (400 MHz, DMSO-d$_6$) δ (ppm): 11.89 (bs, 1H), 7.29-7.06 (m, 9H), 4.30 (bd, J=12.5, 1H), AB system ($δ_A$=4.14, $δ_B$=4.07, $J_{AB}$=13.7 Hz, 2H), 3.76 (bd, J=13.3, 1H), 3.60-3.37 (m, 23H), 3.23 (s, 3H), 2.88 (bt, J=11.8 1H), 2.64-2.52 (m, 4H), 2.46 (t, J=7.1, 2H), 1.74-1.40 (m, 9H), 1.14-0.83 (m, 2H). MS (m/z): 715.6 [M+H]$^{+\cdot}$ and 737.6 [M+Na]$^{+\cdot}$.

Compounds 112-113 (examples 71-72) were prepared in one step starting from compound 110, following the procedures described above for the synthesis of compound 11 (scheme 21) but replacing 2,5,8,11,14,17-hexaoxanonadecan-19-oic acid (59) with 2-(2-(2-methoxyethoxy)ethoxy)acetic acid or 2,5,8,11,14-pentaoxahexadecan-16-oic acid (58), respectively. Characterization of compounds 112-113 (examples 71-72) is provided in Table 14.

TABLE 14

Characterization of compounds 112-113 (examples 71-72)

| Cpd | Ex. | Structure | Characterization |
|---|---|---|---|
| 112 | 71 | 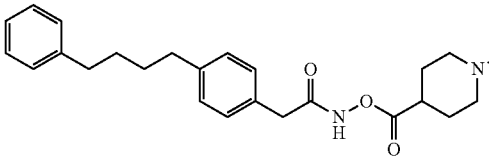<br>N-(3-(1-(2-(2-(2-methoxyethoxy)ethoxy)acetyl)piperidin-4-yl)propanoyloxy)-2-(4-(4-phenylbutyl)phenyl)acetamide | $^1$H NMR (400 MHz, DMSO-d$_6$) δ (ppm): 11.87 (bs, 1H), 7.30-7.06 (m, 9H), 4.30 (bd, J = 13.3, 1H), AB system ($δ_A$ = 4.15, $δ_B$ = 4.07, $J_{AB}$ = 13.6 Hz, 2H), 3.76 (bd, J = 13.5, 1H), 3.58-3.37 (m, 11H), 3.27-3.19 (m, 3H), 2.88 (bt, J = 12.0, 1H), 2.64-2.52 (m, 4H), 2.50-2.42 (m, 2H), 1.72-1.38 (m, 9H), 1.13-0.82 (m, 2H).<br>MS (m/z): 583.4 [M + H]$^{+\cdot}$. |
| 113 | 72 | 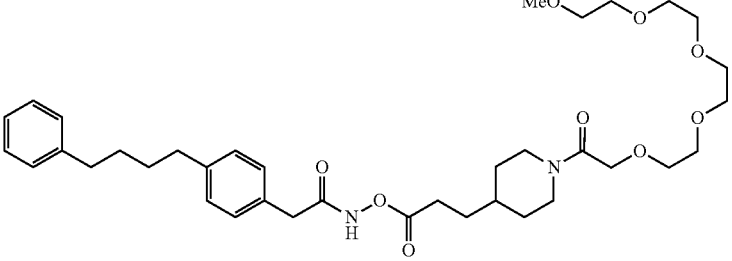<br>N-(3-(1-2,5,8,11,14-pentaoxahexadecanepiperidin-4-yl)propanoyloxy)-2-(4-(4-phenylbutyl)phenyl)acetamide | $^1$H NMR (400 MHz, DMSO-d$_6$) δ (ppm): 11.89 (bs, 1H), 7.30-7.06 (m, 9H), 4.30 (bd, J = 12.9, 1H), AB system ($δ_A$ = 4.15, $δ_B$ = 4.08, $J_{AB}$ = 13.7 Hz, 2H), 3.76 (bd, J = 12.3, 1H), 3.60-3.28 (m, 19H), 3.23 (s, 3H), 2.88 (bt, J = 11.7 1H), 2.64-2.52 (m, 4H), 2.50-2.40 (m, 2H), 1.74-1.40 (m, 9H), 1.14-0.83 (m, 2H).<br>MS (m/z): 671.7 [M + H]$^{+\cdot}$ and 693.7 [M + Na]$^{+\cdot}$. |

Compound 118 (example 77) was prepared in two steps by coupling hydroxamate 1 with 1-(tert-butoxycarbonyl)piperidine-4-carboxylic acid similarly to compound 110 (scheme 21). Compounds 119-120 (examples 78-79) were prepared in one step by coupling compound 118 with PEG-carboxylic acid derivatives similarly to compound 111 (scheme 21). Characterization of compounds—118-120 (examples 77-79) is provided in Table 16.

TABLE 16

Characterization of compounds- 118-120 (examples 77-79).

| Cpd | Ex. | Structure | Characterization |
|---|---|---|---|
| 118 | 77 | 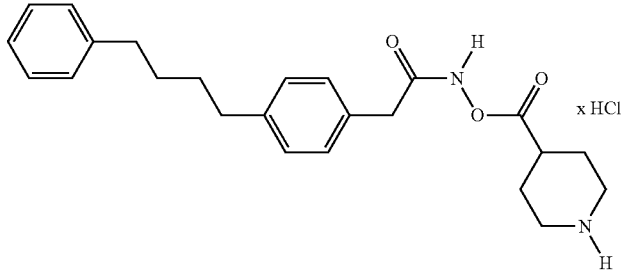<br>2-(4-(4-phenylbutyl)phenyl)-N-(piperidine-4-carbonyloxy)acetamide hydrochloride | $^1$H NMR (DMSO-d6) δ (ppm): 7.28-7.24 (m, 2H), 7.18-7.10 (m, 7H), 3.43 (s, 2H), 3.22 (br. t, 2H), 3.19 (br. t, 2H), 2.96-2.87 (m, 4H), 2.61-2.52 (m, 4H), 2.03-1.98 (m, 2H), 1.83-1.74 (m, 2H), 1.58-1.55 (m, 4H).<br>LRMS (ESI): (calc.) 394.5 (found) 395.3 (MH)+ |

TABLE 16-continued

Characterization of compounds- 118-120 (examples 77-79).

| Cpd | Ex. | Structure | Characterization |
|---|---|---|---|
| 119 | 78 | 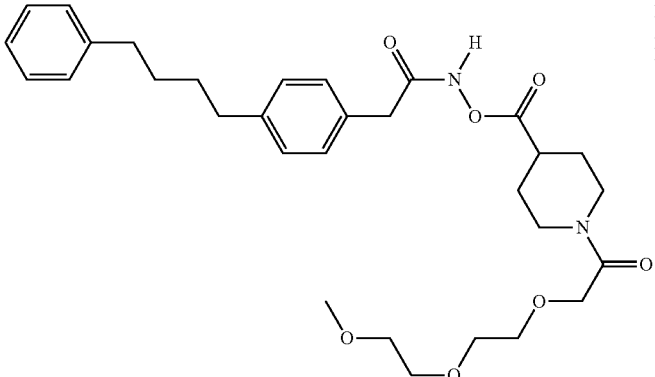<br>N-(1-(2-(2-(2-methoxyethoxy)ethoxy)acetyl)piperidine-4-carbonyloxy)-2-(4-(4-phenylbutyl)phenyl)acetamide | LRMS (ESI): (calc.) 554.7 (found) 555.5 (MH)+ and 577.5 (MNa)+ HPLC retention time is 9.4 min (GRADI40.M) and 9.6 min (ACEPOLAR50.M); |
| 120 | 79 | 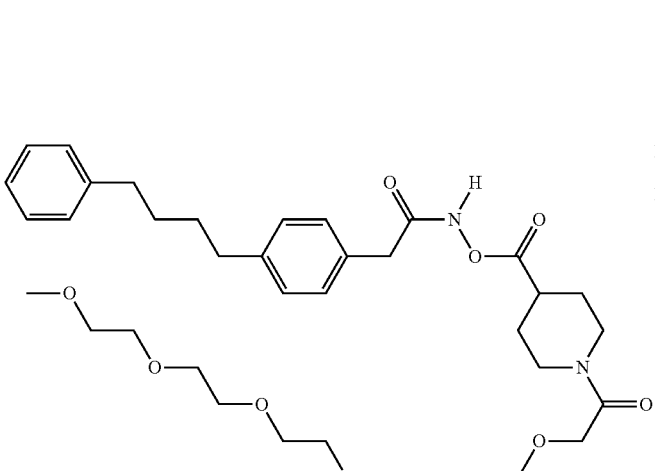<br>N-(1-2,5,8,11,14,17-hexaoxanonadecanepiperidine-4-carbonyloxy)-2-(4-(4-phenylbutyl)phenyl)acetamide | LRMS (ESI): (calc.) 686.8 (found) 687.7 (MH)+ and 709.7 (MNa)+ HPLC retention time is 8.6 min (GRADI50M) and 11.8 min (ACEPOLAR30M). |

Compound 123 (example 82) was prepared in two steps by coupling hydroxamate 1 with 4-(4-(tert-butoxycarbonyl)piperazin-1-yl)-4-oxobutanoic acid similarly to compound 110 (scheme 21). Compound 124 (examples 83) was prepared in one step by coupling compound 123 with 2-(2-(2-methoxyethoxy)ethoxy)acetic acid similarly to compound 111 (scheme 21).

Compound 128 (example 86) was prepared in two steps by coupling hydroxamate 1 with 3-(4-(tert-butoxycarbonyl)-2-oxopiperazin-1-yl)propanoic acid (129, WO 2012/116440 A1) similarly to compound 110 (scheme 21). Compound 128A (example 86A) was prepared in two steps by coupling hydroxamate 1 with 4-(1-(tert-butoxycarbonyl)azetidin-3-yl)butanoic acid (129A, scheme 25) similarly to compound 110 (scheme 21). Compound 128B (example 86B) was obtained via a coupling of compound 129A with 2-(2-(2-methoxyethoxy)ethoxy)acetic acid similarly to compound 111 (scheme 21).

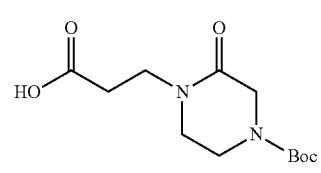

129

(WO2012/116440A1)

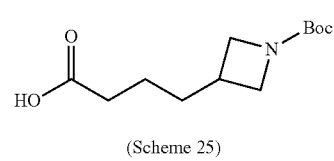

129A (Scheme 25)

Characterization of compounds 121-125, 127-128 (examples 80-86), 128A (example 86A) and 128B (example 86B).is provided in Table 17

TABLE 17

Characterization of compounds 121-125, 127-128 (examples 80-86), 128A (example 86A) and 128B (example 86B).

| Cpd | Ex. | Structure | Characterization |
|---|---|---|---|
| 121 | 80 | 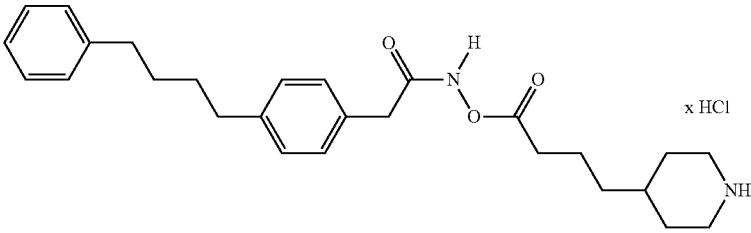<br>2-(4-(4-phenylbutyl)phenyl)-N-(4-(piperidin-4-yl)butanoyloxy)acetamide hydrochloride | $^1$H NMR (DMSO-d6) δ (ppm): signals of NH protons are not seen; 7.28-7.24 (m, 2H), 7.18-7.09 (m, 7H), 3.42 (s, 2H), 3.20 (br. d, J = 12.7 Hz, 2H), 2.79 (dt, J = 2.7; 12.5 Hz, 2H), 2.59-2.55 (m, 4H), 2.44 (t, J = 7.2 Hz, 2H), 1.75 (br. d, J = 11.7 Hz, 2H), 1.61-1.48 (m, 7H), 1.29-1.20 (m, 4H). LRMS (ESI): (calc.) 436.6 (found) 437.1 (MH)+ |
| 122 | 81 | 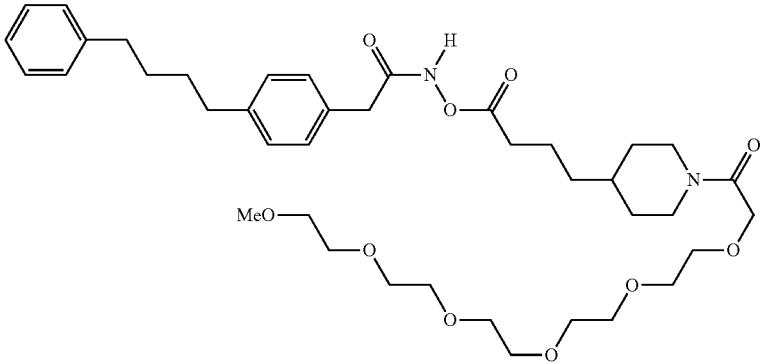<br>N-(4-(1-2,5,8,11,14,17-hexaoxanonadecanepiperidin-4-yl)butanoyloxy)-2-(4-(4-phenylbutyl)phenyl)acetamide | LRMS (ESI): (calc.) 728.9 (found) 729.5 (MH)+ HPLC retention time is 8.7 min (GRADI50M) and 10.2 min (ACEPOLAR50M). |
| 123 | 82 | 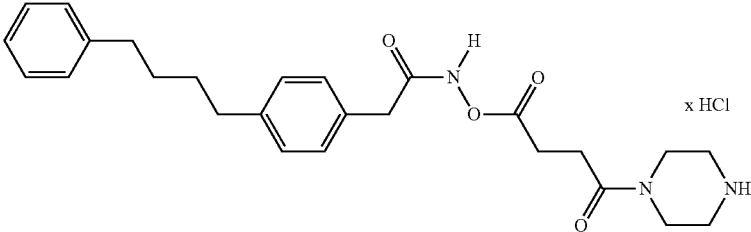<br>N-(4-oxo-4-(piperazin-1-yl)butanoyloxy)-2-(4-(4-phenylbutyl)phenyl)acetamide hydrochloride | $^1$H NMR (DMSO-d6) δ (ppm): 11.99 (br. s, 1H, NH); ): 9.03 (br. s, 2H, H$_2$N$^+$); 7.28-7.24 (m, 2H), 7.18-7.09 (m, 7H), 3.70-3.62 (m, 4H), 3.40 (s, 2H), 3.10 (br. t, 2H), 3.01 (br. t, 2H), 2.68-2.63 (m, 4H), 2.60-2.52 (m, 4H), 1.57-1.55 (m, 4H). LRMS (ESI): (calc.) 451.7 (found) 452.1 and 453.2 (MH)+ |
| 124 | 83 | 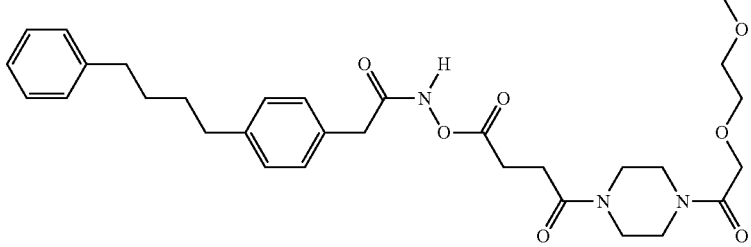<br>N-(4-(4-(2-(2-(2-methoxyethoxy)ethoxy)acetyl)piperazin-1-yl)-4-oxobutanoyloxy)-2-(4-(4-phenylbutyl)phenyl)acetamide | $^1$H NMR (DMSO-d6) δ (ppm): 11.97 (br. s, 1H), 7.28-7.24 (m, 2H), 7.18-7.09 (m, 7H), 4.17 (s, 2H), 3.57-3.35 (m, 18H, some of the signals overap with the signals of water present in the solvent), 3.23 (s, 3H), 2.66-2.56 (m, 8H), 1.57-1.55 (m, 4H). LRMS (ESI): (calc.) 611.7 (found) 612.4 (MH)+ |

TABLE 17-continued

Characterization of compounds 121-125, 127-128 (examples 80-86), 128A (example 86A) and 128B (example 86B).

| Cpd | Ex. | Structure | Characterization |
|---|---|---|---|
| 125 | 84 | 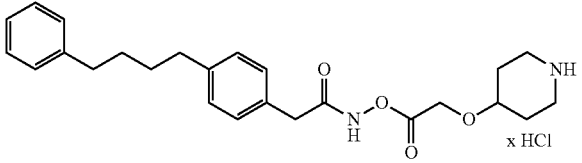<br>2-(4-(4-phenylbutyl)phenyl)-N-(2-(piperidin-4-yloxy)acetoxy) acetamide hydrochloride | $^1$H NMR (400 MHz, DMSO-$d_6$) δ (ppm): 12.40-11.90 (m, 1H), 9.10-8.60 (m, 2H), 7.30-7.07 (m, 9H), 4.39 (s, 2H), 3.72-3.63 (m, 1H), 3.45 (s, 2H), 3.19-3.06 (m, 2H), 3.00-2.86 (m, 2H), 2.64-2.52 (m, 4H), 2.03-1.90 (m, 2H), 1.79-1.65 (m, 2H), 1.63-1.43 (m, 4H). MS (m/z): 425.26 [M + H]$^+$. |
| 127 | 85 | 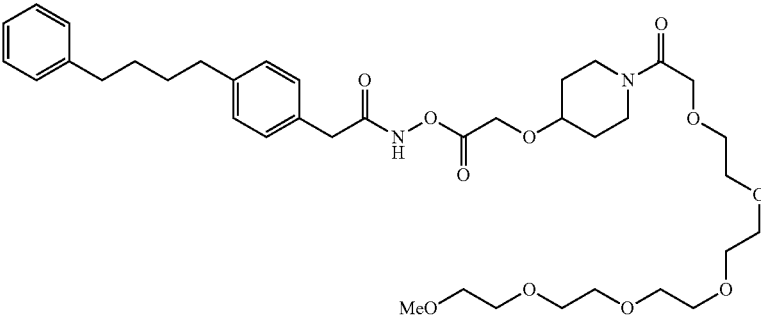<br>N-(2-(1-2,5,8,11,14,17-hexaoxanonadecanepiperidin-4-yloxy)acetoxy)-2-(4-(4-phenylbutyl)phenyl) acetamide | $^1$H NMR (400 MHz, DMSO-$d_6$) δ (ppm): 12.30-11.90 (m, 1H), 7.30-7.05 (m, 9H), 4.36 (s, 2H), AB system ($δ_A$ = 4.15, $δ_B$ = 4.10, $J_{AB}$ = 13.5 Hz, 2H), 3.85-3.73 (m, 1H), 3.66-3.36 (m, 24H), 3.23 (s, 3H), 3.18-3.00 (m, 2H), 2.64-2.52 (m, 4H), 1.90-1.73 (m, 2H), 1.63-1.27 (m, 6H). MS (m/z): 717.7 [M + H]$^+$ and 739.7 [M + Na]$^+$. |
| 128 | 86 | 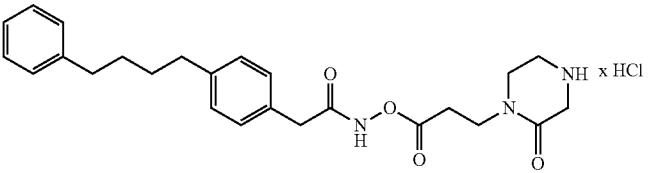<br>N-(3-(2-oxopiperazin-1-yl)propanoyloxy)-2-(4-(4-phenylbutyl)phenyl) acetamide hydrochloride | $^1$H NMR (400 MHz, DMSO-$d_6$) δ (ppm): 12.10 (s, 1H), 9.64 (bs, 2H), 7.29-7.06 (m, 9H), 3.71-3.64 (m, 2H), 3.63-3.47 (m, 6H), 3.34 (bt, J = 5.6, 2H), 2.74 (t, J = 7.0, 2H), 2.64-2.52 (m, 4H), 1.64-1.48 (m, 4H). MS (m/z): 438.6 [M + H]$^+$. |
| 128A | 86A | 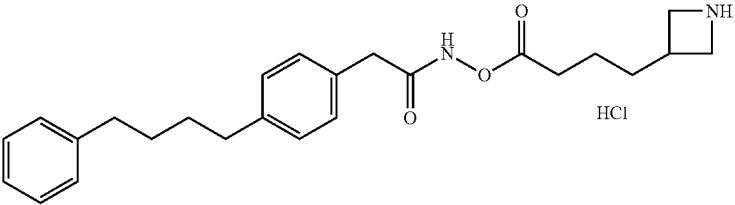 [SMILES: O=C(Cc1ccc(CCCCc2ccccc2)cc1)NOC(=O)CCCC1CNC1 ; Cl]<br>N-(4-(azetidin-3-yl)butanoyloxy)-2-(4-(4-phenylbutyl)phenyl)acetamide hydrochloride | $^1$H NMR (400 MHz, DMSO-$d_6$) δ (ppm): 12.02 (bs, 1H), 8.12 (bs, 1H), 7.30-7.22 (m, 2H), 7.20-7.08 (m, 7H), 3.98-3.84 (m, 2H), 3.79 (d, J = 4.0 Hz, 1H), 3.63-3.54 (m, 2H), 3.42 (s, 2H), 2.90-2.63 (m, 2H), 2.62-2.38 (m, 4H), 2.24-2.02 (m, 2H), 1.62-1.45 (m, 6H) LRMS (ESI): (calc.) 408.3 (found) 409.4 (MH)+ |
| 128B | 86B | 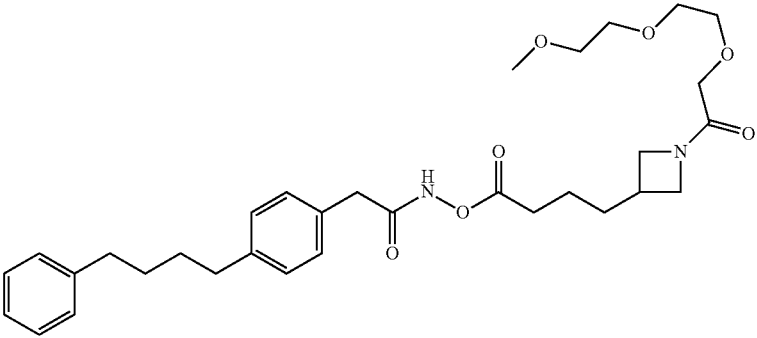<br>N-(4-(1-(2-(2-(2-methoxyethoxy)ethoxy)acetyl)azetidin-3-yl)butanoyloxy)-2-(4-(4-phenylbutyl)phenyl)acetamide | $^1$H NMR (400 MHz, DMSO-$d_6$) δ (ppm): 11.89 (bs, 1H), 7.30-7.22 (m, 2H), 7.20-7.08 (m, 7H), 4.22 (t, J = 8.8 Hz, 1H), 3.98-3.90 (m, 3H), 3.75 (dd, J = 5.6 and 8.8 Hz, 1H), 3.60-3.38 (m, 12 H), 3.23 and 3.22 (s, 3H), 2.62-2.52 (m, 4H), 2.44 (t, J = 7.2 Hz, 2H), 1.64-1.40 (m, 7H). LRMS (ESI): (calc.) 568.3 (found) 569.5 (MH)+ |

Scheme 22

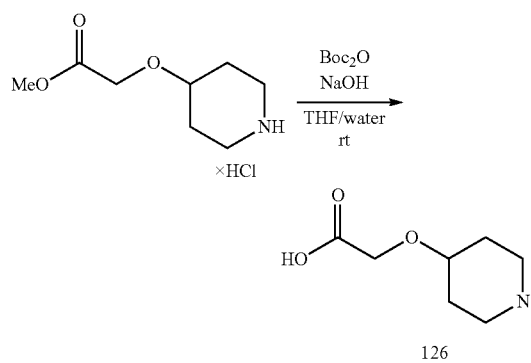

2-(1-(tert-Butoxycarbonyl)piperidin-4-yloxy)acetic acid (126)

To a stirred solution of methyl 2-(piperidin-4-yloxy)acetate hydrochloride salt (0.74 g, 3.53 mmol) in THF (15 mL) at rt was added 1N NaOH (21.18 mL) and di-tert-butyl dicarbonate (1.541 g, 7.06 mmol). The reaction mixture was stirred at RT for 3.5 days, cooled-down to 0° C., acidified with 1 N HCl to pH around 1-2, and extracted with DCM (×3). The combined organic layer was dried over anhydrous magnesium sulfate, filtered, concentrated, and dried in high vacuum to afford the desired product 126 (810 mg, 3.12 mmol, 89% yield) as a colorless gel. MS (m/z): 282.12 [M+Na]$^{+\cdot}$.

Scheme 23

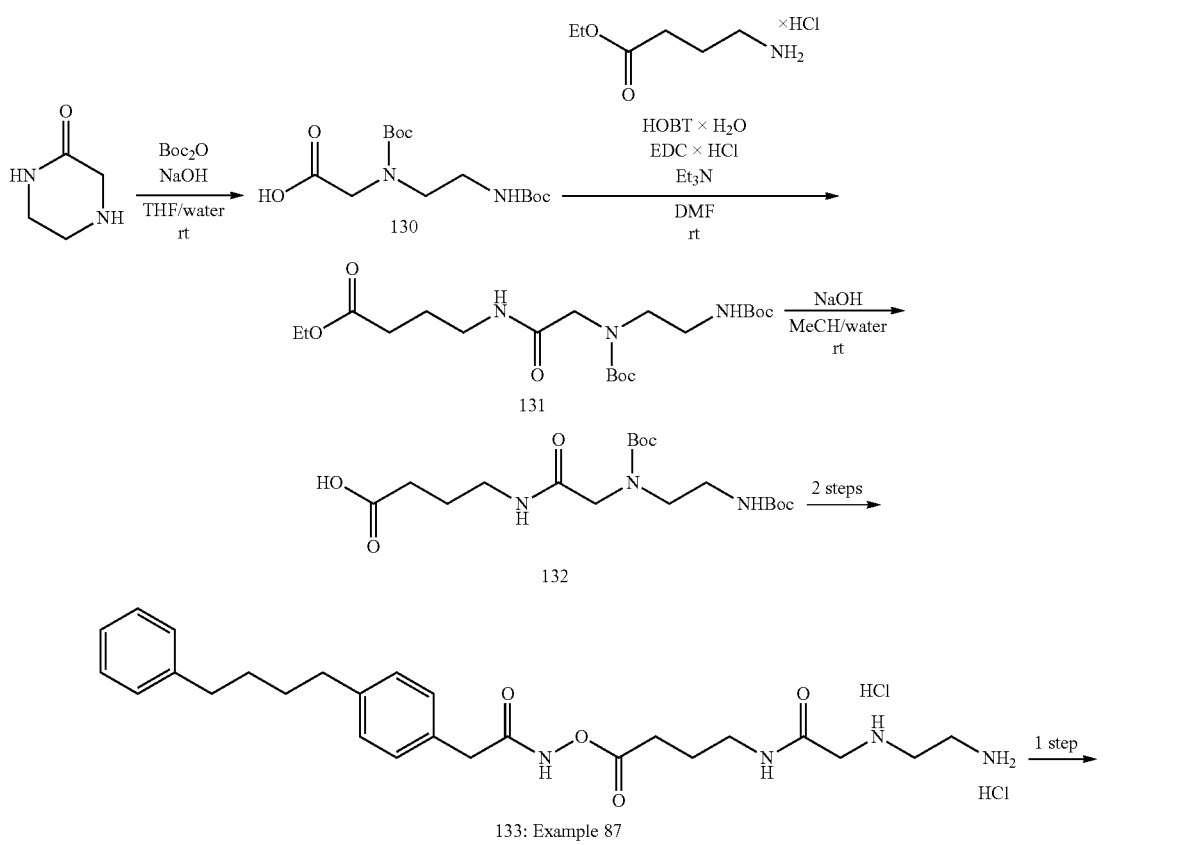

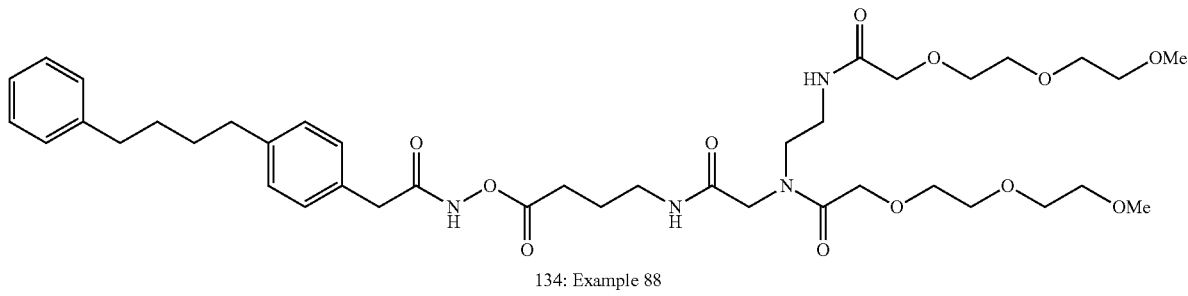

EXAMPLES 87 AND 88

2-(2-(2-Methoxyethoxy)ethoxy)-N-(2-oxo-2-(4-oxo-4-(2-(4-(4-phenylbutyl)phenyl)acetamidooxy)butylamino)ethyl)-N-(10-oxo-2,5,8-trioxa-11-azatridecan-13-yl)acetamide (134)

Step 1. 2-(tert-Butoxycarbonyl(2-(tert-butoxycarbonylamino)ethyl)amino)acetic acid (130)

To a stirred solution of piperazin-2-one (6.15 g, 59.6 mmol) in THF (70 mL) at RT was added 1N NaOH (149 mL) and di-tert-butyl dicarbonate (26 g, 119 mmol). The reaction mixture was stirred at RT overnight, cooled-down to 0° C., acidified with 10% HCl to pH around 3, and extracted with DCM (×2). The combined organic layer was dried over anhydrous magnesium sulfate, filtered, and concentrated. The residue was diluted with a minimum of methanol and triturated in water/brine overnight. The liquid was removed by decantation and the sticky residue was rinsed with water and air-dried. The sticky residue was dissolved in a minimum of ethyl acetate that caused the solidification of the material that diluted with hexanes and triturated overnight. The solid material was collected by filtration, rinsed with hexanes and air-dried. The dry material was triturated once again with a mixture ethyl acetate/hexanes, collected by filtration, rinsed with hexanes, and dried in a vacuum oven at 40° C. overnight to afford the desired product 130 (13 g, 40.8 mmol, 68% yield) as a white fluffy solid. $^1$H NMR (400 MHz, DMSO-$d_6$) δ (ppm): 12.63 (bs, 1H), 6.78-6.64 (m, 1H), 3.81 (d, J=10.6, 2H), 3.20 (t, J=6.4, 2H), 3.02 (hex, J=6.3, 2H), 1.46-1.28 (m, 18H). MS (m/z): 319.3 [M+H]$^+$ and 341.4 [M+Na]$^+$.

Step 2. Ethyl 4-(2-(tert-butoxycarbonyl(2-(tert-butoxycarbonylamino)ethyl)amino)acetamido)butyrate (131)

To a stirred solution of compound 130 (1 g, 3.14 mmol) in DMF (15 mL) at RT under nitrogen were added ethyl 4-aminobutyrate×HCl (632 mg, 3.77 mmol), HOBT×H$_2$O (481 mg, 3.14 mmol), EDC×HCl (1.204 g, 6.28 mmol) and triethylamine (1.31 ml, 9.42 mmol). The reaction mixture was stirred at RT for 2 days, diluted with AcOEt, and successively washed 1N HCl (×3), water (×3), saturated NaHCO$_3$ solution, water and brine, dried over anhydrous magnesium sulfate, filtered, and concentrated to afford the desired product 131 (1.56 g, contaminated with HOBT) as colorless oil.

Step 3. 4-(2-(tert-Butoxycarbonyl(2-(tert-butoxycarbonylamino)ethyl)amino)acetamido)butyric acid (132)

To a stirred solution of compound 131 (1.56 g, from the previous step) in MeOH (20 mL) at RT was added 1N NaOH (9.42 mL). The reaction mixture was stirred at rt overnight, concentrated to a half of its volume, slightly diluted with water, cooled-down to 0° C., acidified with 10% HCl to pH around 1-2, and extracted with DCM (×3). The organic layer was dried over anhydrous magnesium sulfate, filtered, concentrated, and dried under high vacuum to afford the desired product 132 (1.49 g, quant. yield) as colorless sticky oil. MS (m/z): 404.3 [M+H]$^+$ and 426.3 [M+Na]$^+$.

Steps 4 and 5. 2-(2-Aminoethylamino)-N-(4-oxo-4-(2-(4-(4-phenylbutyl)phenyl)acetamidooxy)butyl)acetamide dihydrochloride (133)

Compound 133 (example 87) was prepared in two steps by coupling hydroxamate 1 with compound 132 followed by deprotection of the resultant bis-Boc-intermediate with HCl in dioxane—similarly to compound 110 (scheme 21). $^1$H NMR (400 MHz, DMSO-$d_6$) δ (ppm): 12.03 (bs, 1H), 9.55-9.05 (m, 2H), 8.58 (t, J=5.5, 1H), 8.45-7.95 (m, 3H), 7.30-7.08 (m, 9H), 3.77 (s, 2H), 3.43 (s, 2H), 3.25-3.08 (m, 6H), 2.63-2.52 (m, 4H), 2H are hidden, 1.73 (quint, J=7.1, 2H), 1.63-1.48 (m, 4H). MS (m/z): 469.3 [M+H]$^+$.

Step 6. 2-(2-(2-Methoxyethoxy)ethoxy)-N-(2-oxo-2-(4-oxo-4-(2-(4-(4-phenylbutyl)phenyl)acetamidooxy)butylamino)ethyl)-N-(10-oxo-2,5,8-trioxa-11-azatridecan-13-yl)acetamide (134)

Compound 135 (example 89) was prepared by following the procedures described above for the synthesis of compound 133 (scheme 23) but replacing ethyl 4-aminobutyrate hydrochloride in the step 2 with ethyl 3-aminopropanoate hydrochloride. Compound 136 (example 90) was prepared in one step by coupling compound 135 with 2-(2-(2-methoxyethoxy)ethoxy)acetic acid similarly to compound 134 (scheme 23).

TABLE 18

Characterization of compounds 135-136 (examples 89-90)

| Cpd | Ex. | Structure | Characterization |
|---|---|---|---|
| 135 | 89 | ![structure] 2-(2-aminoethylamino)-N-(3-oxo-3-(2-(4-(4-phenylbutyl)phenyl)acetamidooxy)propyl) acetamide dihydrochloride | $^1$H NMR (400 MHz, DMSO-$d_6$) δ (ppm): 12.10 (bs, 1H), 9.60-9.05 (m, 2H), 8.69 (t, J = 5.5, 1H), 8.50-7.90 (m, 3H), 7.30-7.08 (m, 9H), 3.75 (s, 2H), 3.48-3.33 (m, 4H), 3.26-3.07 (m, 4H), 2.68 (t, J = 6.7, 2H), 2.64-2.52 (m, 4H), 1.64-1.48 (m, 4H). MS (m/z): 455.1-456.9 [M + H]$^+$. |

TABLE 18-continued
Characterization of compounds 135-136 (examples 89-90)
| Cpd | Ex. | Structure | Characterization |
|---|---|---|---|
| 136 | 90 | 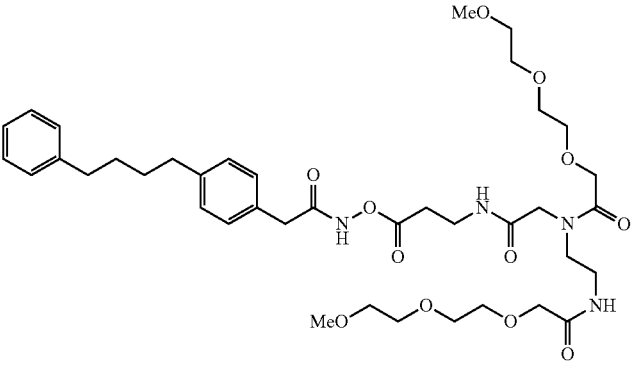<br>2-(2-(2-methoxyethoxy)ethoxy)-N-(2-oxo-2-(3-oxo-3-(2-(4-(4-phenylbutyl)phenyl)acetamidooxy)propylamino)ethyl)-N-(10-oxo-2,5,8-trioxa-11-azatridecan-13-yl)acetamide | $^1$H NMR (400 MHz, DMSO-$d_6$) δ (ppm): mixture of conformers, 12.10-11.86 (bs, 1H), 8.38-7.70 (m, 2H), 7.30-7.04 (m, 9H), 4.20-4.14 (m, 1H), 4.01 (s, 1H), 3.92 (s, 1H), 3.87 (s, 1H), 3.85-3.80 (m, 2H), 3.60-3.14 (m, 30H), 2.70-2.52 (m, 6H), 1.63-1.48 (m, 4H). MS (m/z): 775.5 [M + H]$^+$ and 797.5 [M + Na]$^+$. |
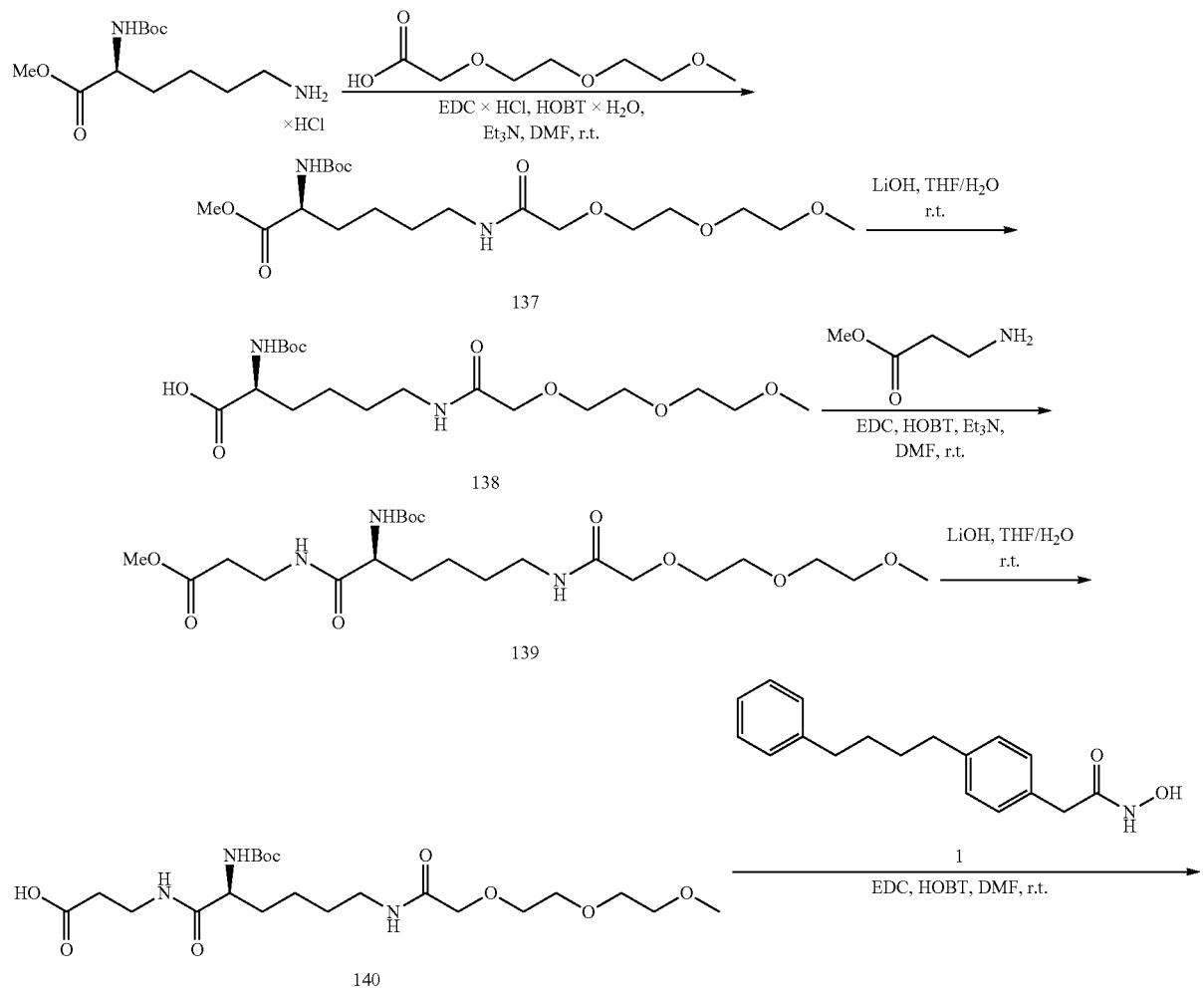
Scheme 24

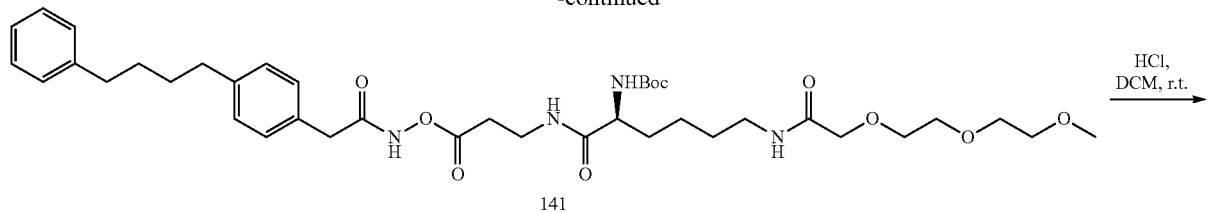

141

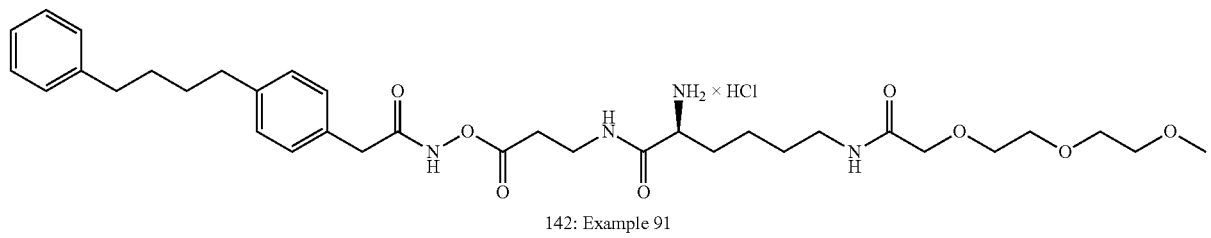

142: Example 91

EXAMPLE 91

(S)-2-Amino-6-(2-(2-(2-methoxyethoxy)ethoxy)acetamido)-N-(3-oxo-3-(2-(4-(4-phenylbutyl)phenyl)acetamidooxy)propyl)hexanamide hydrochloride (142)

Step 1. (S)-Methyl 16-(tert-butoxycarbonylamino)-10-oxo-2,5,8-trioxa-11-azaheptadecan-17-oate (137)

To a stirred solution of N-α-Boc-lys-OMe×HCl (3.0 g, 10.11 mmol) in DMF (30 mL) was added 2-[2-(2-methoxyethoxy)ethoxy]acetic acid (1.98 g, 11.12 mmol), EDC×HCl (2.71 g, 14.15 mmol), HOBT×H$_2$O (2.16 g, 14.15 mmol) and NEt$_3$ (2.82 mL, 20.22 mmol). The reaction mixture was stirred at RT for 2.5 days, diluted with AcOEt, water and a saturated NH$_4$Cl solution, and successively washed water, and brine, dried over anhydrous magnesium sulfate, filtered, and concentrated to afford the desired product 137 (4.6 g, 94.7% yield), contaminated with HOBT) as colorless oil.

Step 2. (S)-16-(tert-Butoxycarbonylamino)-10-oxo-2,5,8-trioxa-11-azaheptadecan-17-oic acid (138)

To a stirred solution of compound 137 (4.6 g, 10.9 mmol) in THF (40 mL)/water (40 mL) was added LiOH (0.48 g, 20.22 mmol). The reaction mixture was stirred at RT for 18 h, concentrated, diluted with AcOEt, water and a saturated NH$_4$Cl solution, and successively washed with water and brine, dried over anhydrous magnesium sulfate, filtered, and concentrated to afford the desired product 138 (4.1 g, 92.3% yield, contaminated with HOBT) as colorless oil.

Step 3. (S)-Methyl 16-(tert-butoxycarbonylamino)-10,17-dioxo-2,5,8-trioxa-11,18-diazahenicosan-21-oate (139)

To a stirred solution of compound 138 (4.1 g, 10.09 mmol)) in DMF (30 mL) was added H-β-Ala-OMe×HCl (1.04 g, 10.09 mmol), EDC×HCl (2.71 g, 14.15 mmol), HOBT×H$_2$O (2.16 g, 14.15 mmol) and NEt$_3$ (2.82 mL, 20.22 mmol). The reaction mixture was stirred at rt for 18 h, diluted with AcOEt, water and a saturated NH$_4$Cl solution, and successively washed water, and brine, dried over anhydrous magnesium sulfate, filtered, and concentrated to afford the desired product 139 (1.75 g, 35.2% yield)) as colorless oil.

Steps 4 (S)-16-(tert-Butoxycarbonylamino)-10,17-dioxo-2,5,8-trioxa-11,18-diazahenicosan-21-oic acid (140)

To a stirred solution of compound 140 (0.69 g, 1.44 mmol) in DMF (10 mL) was added hydroxamate 1 (0.29 g, 1.03 mmol), EDC×HCl (0.27 g, 1.44 mmol) and HOBT×H$_2$O (0.15 g, 0.98 mmol). The reaction mixture was stirred at rt for 20 h, diluted with AcOEt and water, and successively washed water, and brine, dried over anhydrous magnesium sulfate, filtered, and concentrated. The residue was purified by flash column chromatography, eluent 0-10% MeOH in DCM. The purified material was purified yet again by Biotage® by a reverse phase chromatography (cartridge KC18 SH, eluent 20 to 95% MeOH in water), to afford title compound 141 (0.51 g, 67.3% yield) as a colorless honey-like material.

Step 6. (S)-2-Amino-6-(2-(2-(2-methoxyethoxy)ethoxy)acetamido)-N-(3-oxo-3-(2-(4-(4-phenylbutyl)phenyl)acetamidooxy)propyl)hexanamide hydrochloride (142)

To a stirred solution of compound 141 (0.25 g, 0.337 mmol)) in DCM (10 mL) was added HCl 4M in dioxane (0.33 mL, 1.34 mmol). The reaction mixture was stirred at RT for 30 min. More HCl 4M in dioxane (0.33 mL, 1.34 mmol) was added and the reaction mixture was stirred at RT for an additional 30 min then concentrated. The solid was suspended in diethyl ether, and stirred for 45 min. The material was collected by filtration, rinsed with diethyl ether, and dried to afford the desired product 142 (130 mg, 0.19 mmol, 56% yield), presumably as a hydrochloride salt as a white solid. $^1$H NMR (400 MHz, DMSO-d$_6$) δ (ppm): 12.13 (s, 1H), 8.72 and 8.61 (t, J=5.6 Hz, 1H), 8.22 (bs, 3H—HCl), 7.69 (t, J=5.6 Hz, 1H), 7.29-7.22 (m, 2H), 7.20-7.17 (m, 7H), 3.85 (s, 2H), 3.73-3.65 (m, 1H), 3.58-3.49 (m, 6H), 3.46-3.40 (m, 5H), 3.24 and 3.23 (s, 3H), 3.11-3.04 (m, 2H), 2.66 and 2.43 (t, J=5.6 Hz, 2H), 2.63-2.53 (m, 4H), 1.73-1.64 (m, 2H), 1.62-1.52 (m, 4H), 1.46-1.35 (m, 2H), 1.30-1.19 (m, 2H). MS (m/z): 643.7 [M+H]$^+$.

Compounds 143-162 (examples 92-111) were prepared by following the procedures similar to the ones employed in the synthesis of compounds 14 (scheme 2) and 142 (scheme 24). Characterization of compounds 143-162 (examples 92-111) is provided in Table 19.

TABLE 19

Characterization of compounds 143-162 (examples 92-111)

| Cpd | Ex. | Structure |
|---|---|---|
| 143 | 92 | 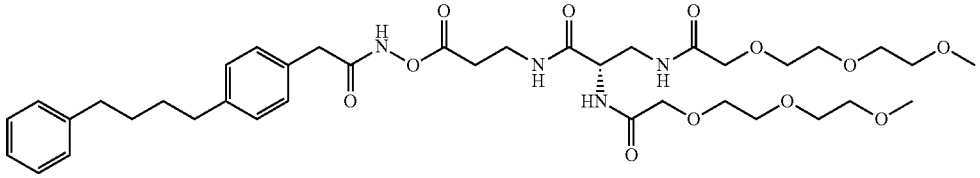 |

(S)-N,N'-(3-oxo-3-(3-oxo-3-(2-(4-(4-phenylbutyl)phenyl)acetamidooxy)propylamino)propane-1,2-diyl)bis(2-(2-(2-methoxyethoxy)ethoxy)acetamide)

| 144 | 93 | 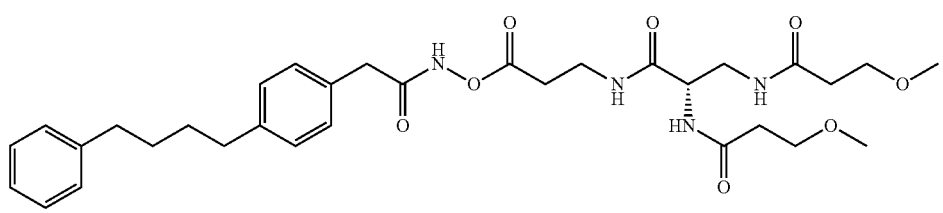 |

(S)-N,N'-(3-oxo-3-(3-oxo-3-(2-(4-(4-phenylbutyl)phenyl)acetamidooxy)propylamino)propane-1,2-diyl)bis(3-methoxypropanamide)

| 145 | 94 | 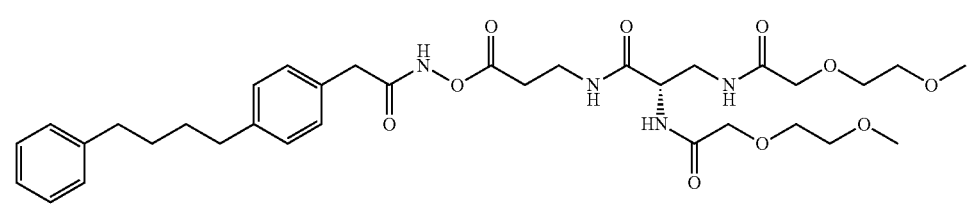 |

(S)-N,N'-(3-oxo-3-(3-oxo-3-(2-(4-(4-phenylbutyl)phenyl)acetamidooxy)propylamino)propane-1,2-diyl)bis(2-(2-methoxyethoxy)acetamide)

| 146 | 95 | 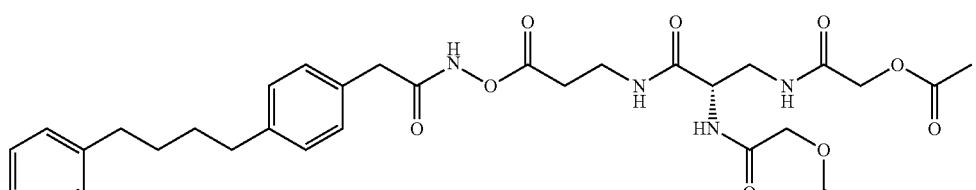 |

(S)-10-(2-acetoxyacetamido)-2,5,9,13-tetraoxo-1-(4-(4-phenylbutyl)phenyl)-4-oxa-3,8,12-triazatetradecan-14-yl acetate

| 147 | 96 | 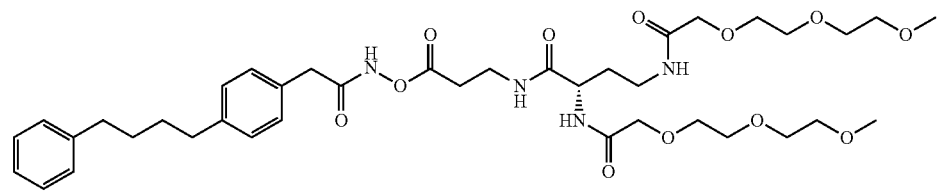 |

(S)-N,N'-(4-oxo-4-(3-oxo-3-(2-(4-(4-phenylbutyl)phenyl)acetamidooxy)propylamino)butane-1,3-diyl)bis(2-(2-(2-methoxyethoxy)ethoxy)acetamide)

TABLE 19-continued

Characterization of compounds 143-162 (examples 92-111)

148  97

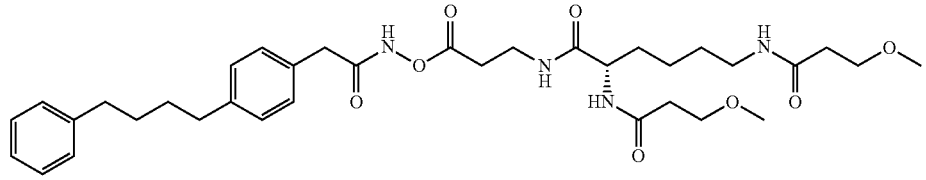

(S)-N,N'-(6-oxo-6-(3-oxo-3-(2-(4-(4-phenylbutyl)phenyl)acetamidooxy)propylamino)
hexane-1,5-diyl)bis(3-methoxypropanamide)

149  98

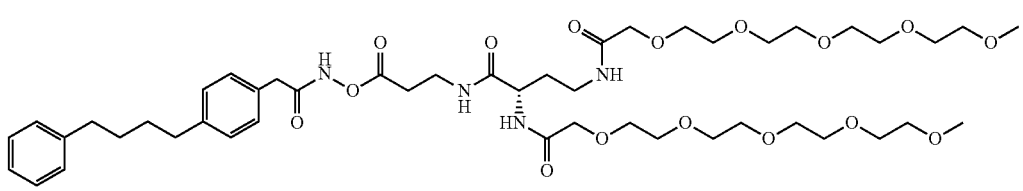

(S)-N,N'-(4-oxo-4-(3-oxo-3-(2-(4-(4-phenylbutyl)phenyl)acetamidooxy)propylamino)
butane-1,3-diyl)bis(2,5,8,11,14-pentaoxahexadecan-16-amide)

150  99

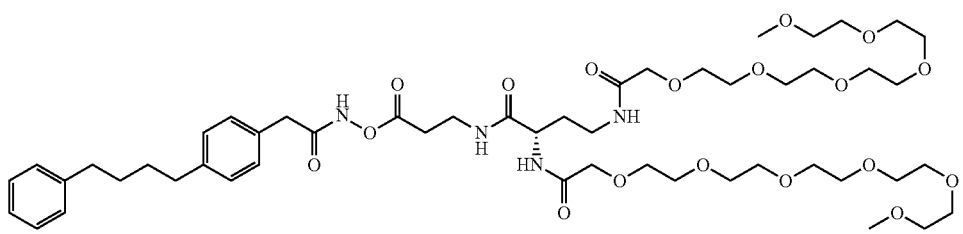

(S)-N,N'-(4-oxo-4-(3-oxo-3-(2-(4-(4-phenylbutyl)phenyl)acetamidooxy)propylamino)butane-1,3-
diyl)bis(2,5,8,11,14,17-hexaoxanonadecan-19-amide)

151  100

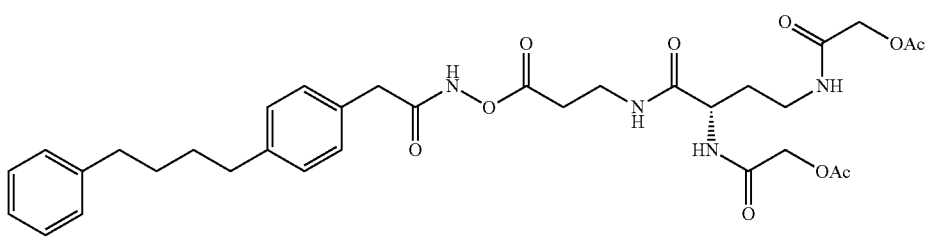

(S)-10-(2-acetoxyacetamido)-2,5,9,14-tetraoxo-1-(4-(4-phenylbutyl)phenyl)-4-oxa-3,8,13-triazapentadecan-
15-yl acetate 152  101

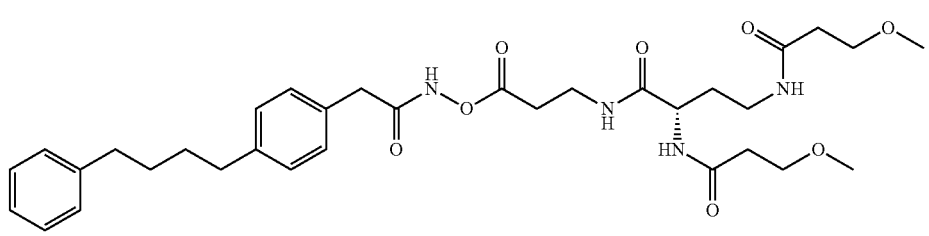

(S)-N,N'-(4-oxo-4-(3-oxo-3-(2-(4-(4-phenylbutyl)phenyl)acetamidooxy)propylamino)butane-1,3-
diyl)bis(3-methoxypropanamide)

TABLE 19-continued

Characterization of compounds 143-162 (examples 92-111)

| 153 | 102 | 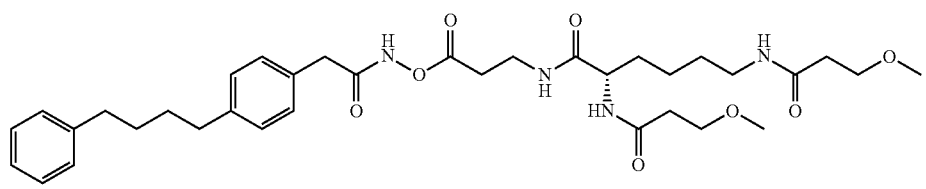 |

(S)-N,N'-(6-oxo-6-(3-oxo-3-(2-(4-(4-phenylbutyl)phenyl)acetamidooxy)propylamino)
hexane-1,5-diyl)bis(3-methoxypropanamide)

| 154 | 103 | 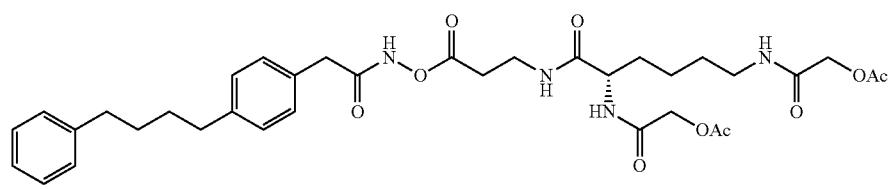 |

(S)-10-(2-acetoxyacetamido)-2,5,9,16-tetraoxo-1-(4-(4-phenylbutyl)phenyl)-4-oxa-3,8,15-
triazaheptadecan-17-yl acetate)

| 155 | 104 | 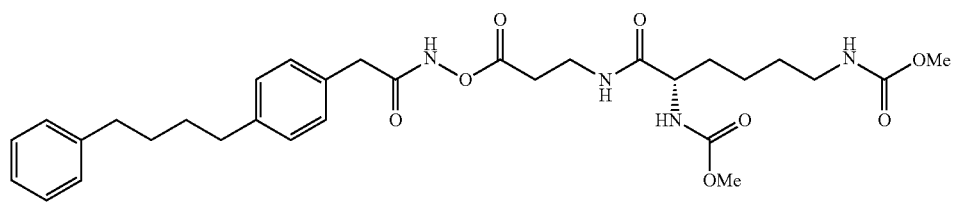 |

(S)-dimethyl 6-oxo-6-(3-oxo-3-(2-(4-(4-phenylbutyl)phenyl)acetamidooxy)propylamino)
hexane-1,5-diyldicarbamate)

| 156 | 105 | 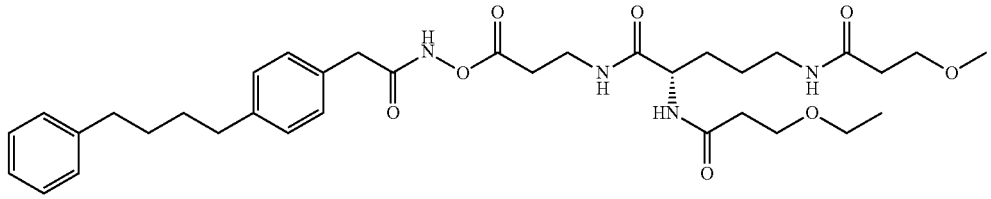 |

(S)-N,N'-(5-oxo-5-(3-oxo-3-(2-(4-(4-phenylbutyl)phenyl)acetamidooxy)propylamino)
pentane-1,4-diyl)bis(3-methoxypropanamide))

| 157 | 106 | 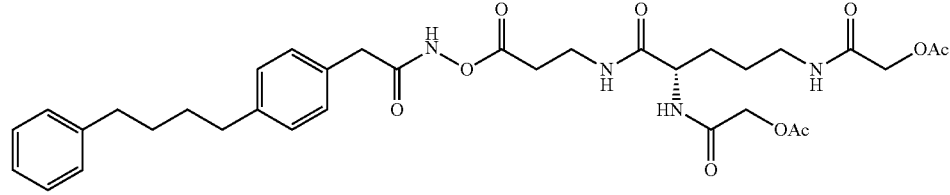 |

(S)-10-(2-acetoxyacetamido)-2,5,9,15-tetraoxo-1-(4-(4-phenylbutyl)phenyl)-4-oxa-3,8,14-
triazahexadecan-16-yl acetate)

| 158 | 107 | 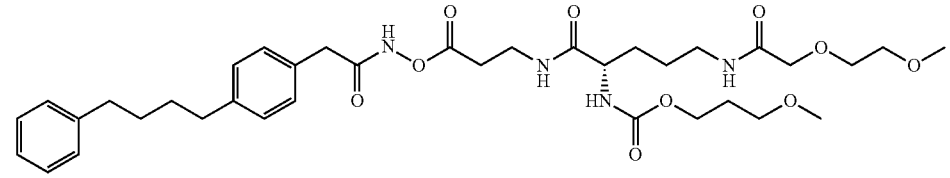 |

(S)-N,N'-(5-oxo-5-(3-oxo-3-(2-(4-(4-phenylbutyl)phenyl)acetamidooxy)propylamino)pentane-1,4-diyl)bis(2-(2-
methoxyethoxy)acetamide)

TABLE 19-continued

Characterization of compounds 143-162 (examples 92-111)

159 108

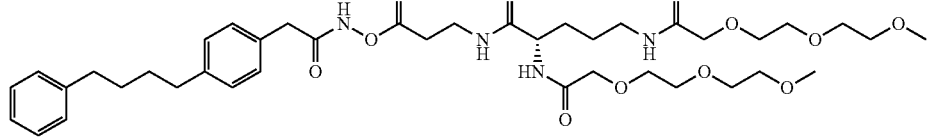

(S)-N,N'-(5-oxo-5-(3-oxo-3-(2-(4-(4-phenylbutyl)phenyl)acetamidooxy)propylamino)pentane-1,4-
diyl)bis(2-(2-(2-methoxyethoxy)ethoxy)acetamide)

160 109

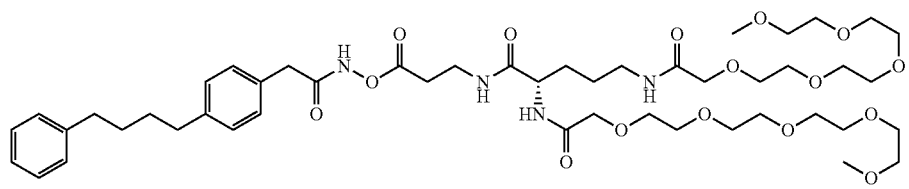

(S)-N,N'-(5-oxo-5-(3-oxo-3-(2-(4-(4-phenylbutyl)phenyl)acetamidooxy)propylamino)pentane-1,4-diyl)bis
(2,5,8,11,14-pentaoxahexadecan-16-amide)

161 110

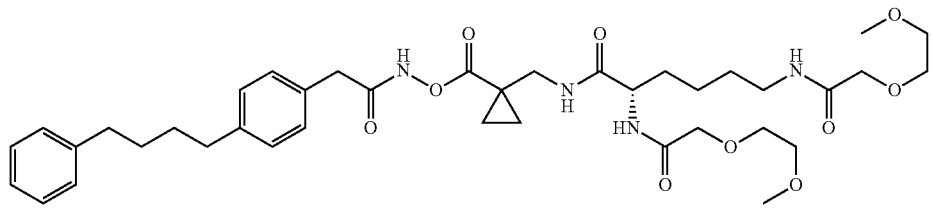

(S)-N,N'-(6-oxo-6-((1-((2-(4-(4-phenylbutyl)phenyl)acetamidooxy)carbonyl)cyclopropyl)
methylamino)hexane-1,5-diyl)bis(2-(2-methoxyethoxy)acetamide)

162 111

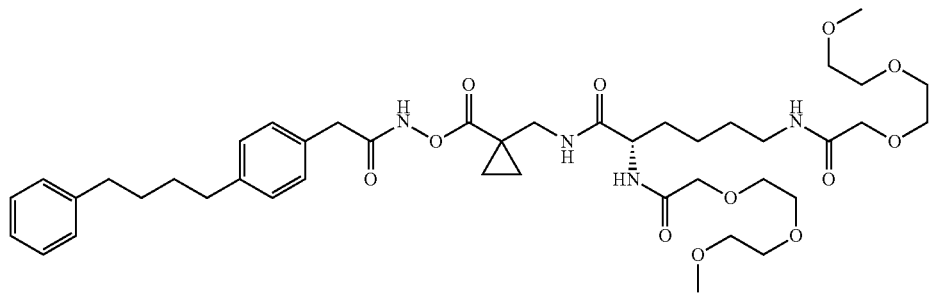

(S)-N,N'-(6-oxo-6-((1-((2-(4-(4-phenylbutyl)phenyl)acetamidooxy)carbonyl)cyclopropyl)
methylamino)hexane-1,5-diyl)bis(2-(2-(2-methoxyethoxy)ethoxy)acetamide)

| Cpd | Ex. | Characterization |
|---|---|---|
| 143 | 92 | $^1$H NMR (400 MHz, DMSO-$d_6$) δ (ppm): 11.92 (bs, 1H), 8.20 (t, J = 1.6 Hz, 1H), 7.78-7.72 (m, 2H), 7.28-7.22 (m, 2H), 7.19-7.08 (m, 7H), 4.34 (td, J = 5.2 and 8.0 Hz, 1H), 3.92 (d, J = 15.2 Hz, 1H), 3.86 (d, J = 15.2 Hz, 1H), 3.85 (s, 2H), 3.60-3.50 (m, 12H), 3.49-3.40 (m, 7H), 3.38-3.26 (m, 1H), 3.23 (s, 6H), 2.64-2.53 (m, 6H), 1.71-1.62 (m, 4H). LRMS (ESI): (calc.) 760.4 (found) 761.6 (MH)+ |
| 144 | 93 | $^1$H NMR (400 MHz, DMSO-$d_6$) δ (ppm): 11.86 (bs, 1H), 8.01 (t, J = 5.2 Hz, 1H), 7.91 (d, J = 8.0 Hz, 1H), 7.77 (t, J = 6.0 Hz, 1H), 7.28-7.22 (m, 2H), 7.19-7.04 (m, 7H), 4.26 (q, J = 6.8 Hz, 1H), 3.54-3.46 (m, 4H), 3.42 (s, 2H), 3.36-3.24 (m, 2H), 3.23-3.16 (m, 6H), 2.64-2.53 (m, 5H), 2.48-2.41 (m, 1H), 2.39-2.33 (m, 2H), 2.32-2.26 (m, 2H), 1.62-1.52 (m, 4H). LRMS (ESI): (calc.) 612.4 (found) 613.6 (MH)+ |
| 145 | 94 | $^1$H NMR (400 MHz, DMSO-$d_6$) δ (ppm): 11.89 (bs, 1H), 8.20 and 8.11 (t, J = 5.6 Hz, 1H), 7.77 (t, J = 7.6 Hz, 1H), 7.72-7.65 (m, 1H), 7.28-7.23 (m, 2H), 7.18-7.06 (m, 7H), 4.34 (td, J = 5.2 and 7.6 Hz, 1H), 3.94-3.84 (m, 2H), 3.85 (d, J = 2.4 Hz, 2H), 3.62-3.53 (m, 6H), 3.50-3.40 (m, 7H), 3.39-3.20 (m, 7H), 2.64-2.54 (m, 5H), 2.46 (t, J = 7.2 Hz, 1H), 1.62-1.52 (m, 4H). LRMS (ESI): (calc.) 672.2 (found) 673.4 (MH)+ |
| 146 | 95 | $^1$H NMR (400 MHz, DMSO-$d_6$) δ (ppm): 11.87 (bs, 1H), 8.12 (t, J = 5.6 Hz, 1H), 8.07 (d, J = 8.0 Hz, 1H), 8.01 (t, J = 6.4 Hz, 1H), 7.28-7.23 (m, 2H), 7.19-7.06 (m, 7H), 4.51-4.40 (m, 2H), 4.41 (s, 2H), 4.32-4.26 (m, 1H), 3.47-3.12 (m, 7H), 2.65-2.52 (m, 5H), 2.11-2.05 (m, 6H), 1.61-1.50 (m, 4H). LRMS (ESI): (calc.) 640.2 (found) 641.7 (MH)+ |

TABLE 19-continued

Characterization of compounds 143-162 (examples 92-111)

| | | |
|---|---|---|
| 147 | 96 | ¹H NMR (400 MHz, DMSO-d$_6$) δ (ppm): 11.91 (bs, 1H), 8.23 (t, J = 5.6 Hz, 1H), 7.68-7.60 (m, 2H), 7.28-7.22 (m, 2H), 7.18-7.06 (m, 7H), 4.32-4.24 (m, 1H), 3.91 (s, 2H), 3.85 (s, 2H), 3.63-3.51 (m, 13H), 3.47-3.40 (m, 5H), 3.39-3.28 (m, 2H), 3.36-3.32 (m, 6H), 3.20-3.00 (m, 2H), 2.65-2.54 (m, 6H), 1.89-1.78 (m, 1H), 1.72-1.62 (m, 1H), 1.61-1.53 (m, 4H). LRMS (ESI): (calc.) 774.4 (found) 775.6 (MH)+ |
| 148 | 97 | ¹H NMR (400 MHz, DMSO-d$_6$) δ (ppm): 11.87 (bs, 1H), 8.01 (t, J = 5.6 Hz, 1H), 7.92 (d, J = 8.0 Hz, 1H), 7.76 (t, J = 5.6 Hz, 1H), 7.28-7.23 (m, 2H), 7.19-7.08 (m, 7H), 4.15 (td, J = 5.2 and 8.8 Hz, 1H), 3.53-3.47 (m, 4H), 3.42 (s, 2H), 3.39-3.24 (m, 2H), 3.22-3.15 (m, 6H), 3.03-2.95 (m, 2H), 2.62-2.52 (m, 5H), 2.48-2.39 (m, 1H), 2.36 (q, J = 6.4 Hz, 2H), 2.27 (t, J = 6.4 Hz, 2H), 1.63-1.50 (m, 5H), 1.50-1.39 (m, 1H), 1.39-1.20 (m, 2H), 1.19-1.12 (m, 1H). LRMS (ESI): (calc.) 654.4 (found) 655.5 (MH)+ |
| 149 | 98 | ¹H NMR (400 MHz, DMSO-d$_6$) δ (ppm): 11.90 (bs, 1H), 8.36-8.26 (m, 1H), 8.16 (t, J = 5.6 Hz, 1H), 7.29-7.21 (m, 2H), 7.20-7.07 (m, 7H), 4.33-4.25 (m, 1H), 3.94-3.90 (m, 1H), 3.87-3.84 (m, 1H), 3.64-3.45 (m, 24H), 3.44-3.39 (m, 4H), 3.39-2.99 (m, 15H), 2.64-2.54 (m, 5H), 1.89-1.78 (m, 1H), 1.71-1.52 (m, 5H). LRMS (ESI): (calc.) 950.4 (found) 951.7 (MH)+ |
| 150 | 99 | ¹H NMR (400 MHz, DMSO-d$_6$) δ (ppm): 11.83 (bs, 1H), 8.38-30 and 8.20-8.13 (m, 1H), 7.70-7.60 (m, 2H), 7.30-7.22 (m, 2H), 7.20-7.08 (m, 7H), 4.33-4.25 (m, 1H), 3.92 and 3.91 (s, 2H), 3.85 and 3.84 (s, 2H), 3.64-3.21 (46H), 3.24 (s, 3H), 3.23 (s, 3H), 3.18-3.10 (m, 1H), 3.09-2.99 (m, 1H), 2.64-2.53 (m, 4H), 1.88-1.78 (m, 1H), 1.71-1.50 (m, 5H). LRMS (ESI): (calc.) 1038.6 (found) 1039.9 (MH)+ |
| 151 | 100 | ¹H NMR (400 MHz, DMSO-d$_6$) δ (ppm): 11.97 (bs, 1H), 8.20 (d, J = 8.0 Hz, 1H), 8.12 (t, J = 5.6 Hz, 1H), 7.91 (t, J = 5.6 Hz, 1H), 7.30-7.22 (m, 2H), 7.21-7.09 (m, 7H), 4.53-4.48 (m, 2H), 4.40 (s, 2H), 4.28-4.21 (m, 1H), 3.59 and 3.42 (s, 2H), 3.40-3.25 (m, 2H), 3.17-3.07 (m, 1H), 3.05-2.96 (m, 1H), 2.56-2.53 (m, 5H), 2.08 (s, 3H), 2.07 (s, 3H), 1.87-1.77 (m, 1H), 1.70-1.52 (m, 5H). LRMS (ESI): (calc.) 654.3 (found) 655.5 (MH)+ |
| 152 | 101 | ¹H NMR (400 MHz, DMSO-d$_6$) δ (ppm): 11.94 (bs, 1H), 8.11-7.90 (m, 2H), 7.76 (t, J = 5.6 Hz, 1H), 7.30-7.22 (m, 2H), 7.21-7.08 (m, 7H), 4.25-4.16 (m, 1H), 3.60-3.40 (m, 6H), 3.38-3.24 (m, 1H), 3.23-3.16 (m, 6H), 3.08-2.93 (m, 2H), 2.64-2.54 (m, 5H), 2.48-2.31 (m, 3H), 2.27 (t, J = 6.4 Hz, 2H), 1.82-1.70 (m, 1H), 1.65-1.53 (m, 5H). LRMS (ESI): (calc.) 626.3 (found) 627.5 (MH)+ |
| 153 | 102 | ¹H NMR (400 MHz, DMSO-d$_6$) δ (ppm): 11.87 (bs, 1H), 8.01 (t, J = 5.6 Hz, 1H), 7.92 (d, J = 8.0 Hz, 1H), 7.76 (t, J = 5.6 Hz, 1H), 7.28-7.23 (m, 2H), 7.19-7.08 (m, 7H), 4.15 (td, J = 5.2 and 8.8 Hz, 1H), 3.53-3.47 (m, 4H), 3.42 (s, 2H), 3.39-3.24 (m, 2H), 3.22-3.15 (m, 6H), 3.03-2.95 (m, 2H), 2.62-2.52 (m, 5H), 2.48-2.39 (m, 1H), 2.36 (q, J = 6.4 Hz, 2H), 2.27 (t, J = 6.4 Hz, 2H), 1.63-1..50 (m, 5H), 1.50-1.39 (m, 1H), 1.39-1.20 (m, 2H), 1.19-1.12 (m, 2H). LRMS (ESI): (calc.) 654.4 (found) 655.5 (MH)+ |
| 154 | 103 | ¹H NMR (400 MHz, DMSO-d$_6$) δ (ppm): 11.89 (bs, 1H), 8.09 (t, J = 5.6 Hz, 1H), 8.06 (d, J = 8.0 Hz, 1H), 7.93 (t, J = 6.0 Hz, 1H), 7.28-7.22 (m, 2H), 7.20-7.07 (m, 7H), 4.47 (d, J = 1.6 Hz, 2H), 4.40 (s, 2H), 4.18 (td, J = 5.2 and 8.8 Hz, 1H), 3.42 (s, 2H), 3.40-3.20 (m, 3H), 3.08-2.98 (m, 2H), 2.07 (s, 3H), 2.06 (s, 3H), 1.69-1.42 (m, 6H), 1.41-1.31 (m, 2H), 1.29-1.12 (m, 2H). LRMS (ESI): (calc.) 682.4 (found) 683.5 (MH)+ |
| 155 | 104 | ¹H NMR (400 MHz, DMSO-d$_6$) δ (ppm): 11.86 (bs, 1H), 8.02 (t, J = 5.6 Hz, 1H), 7.29-7.22 (m, 2H), 7.20-7.08 (m, 7H), 7.03 (t, J = 5.6 Hz, 1H), 6.79 (bs, 1H), 3.89-3.82 (m, 1H), 3.51 (s, 3H), 3.50 (s, 3H), 3.42 (s, 2H), 3.39-3.18 (m, 3H), 2.92 (q, J = 6.4 Hz, 2H), 2.64-2.54 (m, 5H), 1.64-1.34 (m, 10H). LRMS (ESI): (calc.) 598.3 (found) 599.5 (MH)+ |
| 156 | 105 | ¹H NMR (400 MHz, DMSO-d$_6$) δ (ppm): 11.75 (bs, 1H), 8.05 (t, J = 5.6 Hz, 1H), 7.96 (d, J = 8.0 Hz, 1H), 7.79 (t, J = 5.6 Hz, 1H), 7.28-7.22 (m, 2H), 7.20-7.06 (m, 7H), 4.18 (td, J = 4.8 and 8.0 Hz, 1H), 3.55-3.46 (m, 4H), 3.41 (s, 2H), 3.38-3.24 (m, 1H), 3.24-3.17 (m, 1H), 3.19 (s, 3H), 3.18 (s, 3H), 2.99 (q, J = 6.4 Hz, 2H), 2.63-2.54 (m, 5H), 2.47-2.39 (m, 1H), 2.38-2.31 (m, 2H), 2.30-2.24 (m, 2H), 1.65-1.52 (m, 5H), 1.50-1.34 (m, 3H). LRMS (ESI): (calc.) 640.4 (found) 641.6 (MH)+ |
| 157 | 106 | ¹H NMR (400 MHz, DMSO-d$_6$) δ (ppm): 11.93 (bs, 1H), 8.13-8.06 (m, 2H), 7.95 (t, J = 5.6 Hz, 1H), 7.28-7.22 (m, 2H), 7.20-7.06 (m, 7H), 4.47 (s, 2H), 4.40 (s, 2H), 4.22 (td, J = 5.6 and 8.0 Hz, 1H), 3.42 (s, 2H), 3.38-3.25 (m, 2H), 3.03 (q, J = 6.0 Hz, 2H), 2.63-2.53 (m, 6H), 2.07 (s, 3H), 2.06 (s, 3H), 1.66-1.26 (m, 8H). LRMS (ESI): (calc.) 668.4 (found) 669.5 (MH)+ |
| 158 | 107 | ¹H NMR (400 MHz, DMSO-d$_6$) δ (ppm): 11.87 (bs, 1H), 8.20 (t, J = 5.6 Hz, 1H), 7.67 (t, J = 5.6 Hz, 1H), 7.60 (d, J = 8.4 Hz, 1H), 7.28-7.21 (m, 2H), 7.20-7.08 (m, 7H), 4.27 (td, J = 5.6 and 8.0 Hz, 1H), 3.89 (s, 2H), 3.84 (s, 2H), 3.64-3.54 (m, 4H), 3.50-3.45 (m, 3H), 3.44 (bs, 2H), 3.38-3.22 (m, 4H), 3.06 (q, J = 6.4 Hz, 2H), 2.64-2.54 (m, 5H), 1.68-1.31 (m, 8H). LRMS (ESI): (calc.) 700.4 (found) 701.6 (MH)+ |
| 159 | 108 | ¹H NMR (400 MHz, DMSO-d$_6$) δ (ppm): 11.88 (bs, 1H), 8.22 and 8.09 (t, J = 5.6 Hz, 1H), 7.67 (t, J = 5.6 Hz, 1H), 7.57 and 7.55 (d, J = 8.0 Hz, 1H), 7.29-7.21 (m, 2H), 7.20-7.07 (m, 7H), 4.32-4.26 (m, 1H), 3.90 (s, 2H), 3.84 (s, 2H), 3.62-3.50 (m, 11H), 3.48-3.40 (m, 5H), 3.38-3.20 (m, 11H), 3.11-3.03 (m, 2H), 1.68-1.30 (m, 8H). LRMS (ESI): (calc.) 788.4 (found) 789.4 (MH)+ |
| 160 | 109 | ¹H NMR (400 MHz, DMSO-d$_6$) δ (ppm): 11.78 (bs, 1H), 8.30-8.20 and 8.10-8.04 (m, 1H), 7.72-7.63 (m, 1H), 7.59-7.52 (m, 1H), 7.30-7.21 (m, 2H), 7.20-7.07 (m, 7H), 4.32-4.24 (m, 1H), 3.91 and 3.90 (s, 2H), 3.85 and 3.84 (s, 2H), 3.62-3.15 (m, 37H), 3.24 (s, 3H), 3.23 (s, 3H), 3.11-3.04 (m, 2H), 2.62-2.52 (m, 5H), 1.68-1.22 (m, 8H). LRMS (ESI): (calc.) 964.5 (found) 965.8 (MH)+ |
| 161 | 110 | ¹H NMR (400 MHz, DMSO-d$_6$) δ (ppm): 11.96 (bs, 1H), 8.13 (s, 1H), 7.62-7.53 (m, 2H), 7.28-7.22 (m, 2H), 7.19-7.08 (m, 7H), 4.33-4.27 (m, 1H), 3.89 (s, 2H), 3.84 (s, |

TABLE 19-continued

Characterization of compounds 143-162 (examples 92-111)

| | | |
|---|---|---|
| | | 2H), 3.62-3.53 (m, 4H), 3.50-3.24 (m, 16H), 3.10-3.03 (m, 2H), 2.62-2.52 (m, 4H), 1.68-1.46 (m, 6H), 1.45-35 (m, 2H), 1.28-1.10 (m, 4H), 1.09-0.98 (m, 2H). LRMS (ESI): (calc.) 740.4 (found) 741.6 (MH)+ |
| 162 | 111 | $^1$H NMR (400 MHz, DMSO-d$_6$) δ (ppm): 11.91 (bs, 1H), 8.07 (t, J = 6.0 Hz, 1H), 7.60 (t, J = 6.0 Hz, 1H), 7.54 (d, J = 8.4 Hz, 1H), 7.29-7.22 (m, 2H), 7.19-7.09 (m, 7H), 4.29 (td, J = 5.2 and 8.4 Hz, 1H), 3.90 (s, 2H), 3.86 (s, 2H), 3.61-3.50 (m, 16H), 3.48-3.32 (m, 6H), 3.24 (s, 6H), 3.09-3.03 (m, 2H), 2.62-2.53 (m, 4H), 1.68-1.47 (m, 6H), 1.45-1.35 (m, 2H), 1.28-1.12 (m, 4H), 1.06-1.01 (m, 2H). LRMS (ESI): (calc.) 828.3 (found) 829.5 (MH)+ |

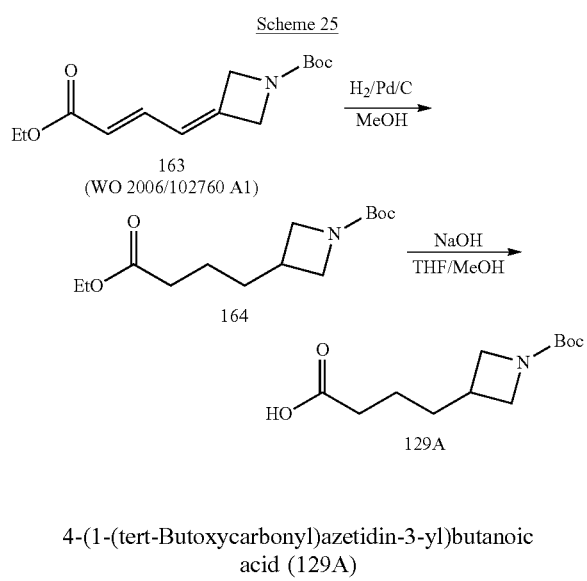

Scheme 25

4-(1-(tert-Butoxycarbonyl)azetidin-3-yl)butanoic acid (129A)

Step 1. Tert-Butyl 3-(4-methoxy-4-oxobutyl)azetidine-1-carboxylate (164)

To a solution of (E)-tert-butyl 3-(4-methoxy-4-oxobut-2-enylidene)azetidine-1-carboxylate (163, WO 2006/102760 A1) (1.47 g, 5.50 mmol) in MeOH (30 mL) was added Pd-C, Degussa type 101 (0.585 g, 0.55 mmol). The mixture was stirred overnight under H$_2$ atmosphere. The suspension was filtered through Celite, washed with MeOH and concentrated to afford the title compound 163 (1.38 g, 5.11 mmol, 93% yield) as a colorless oil. $^1$H NMR (400 MHz, DMSO-d$_6$) δ (ppm): 4.04 (q, J=7.2 Hz, 2H), 3.88 (br s, 2H), 3.41 (br s, 2H), 2.50-2.39 (m, 1H), 2.27 (t, J=7.2 Hz, 2H), 1.53-1.40 (m, 4H), 1.36 (s, 9H), 1.17 (t, J=7.2 Hz, 3H).

Step 2. 4-(1-(tert-Butoxycarbonyl)azetidin-3-yl)butanoic acid (129A)

To a solution of compound 164 (1.38 g, 5.11 mmol) in THF (15 mL) and MeOH (15 mL) was added NaOH 2M (10.22 mL, 20.45 mmol). The mixture was stirred overnight and concentrated. The mixture was diluted with HCl 10% and extracted with EtOAc, dried over Na$_2$SO$_4$, filtered and concentrated to afford the title compound 129A (1.30 g, 5.11 mmol, 99% yield) as a colorless oil. $^1$H NMR (400 MHz, DMSO-d$_6$) δ (ppm): 12.05 (br s, 1H), 3.88 (br s, 2H), 3.41 (br s, 2H), 2.50-2.38 (m, 1H), 2.19 (t, J=7.2 Hz, 2H), 1.563-1.38 (m, 4H), 1.36 (s, 9H).

Pharmaceutical Compositions

In a second aspect, the invention provides pharmaceutical compositions comprising a prodrug of an inhibitor of histone deacetylase represented by formula (2) and a pharmaceutically acceptable carrier, excipient, or diluent.

The prodrugs of the invention or compositions thereof may be formulated by any method well known in the art and may be prepared for administration by any route, including, without limitation, parenteral, oral, sublingual, transdermal, topical, intranasal, intratracheal, or intrarectal. In certain preferred embodiments, the prodrugs of the invention or compositions thereof are administered in an aqueous solution such as by oral administration or intravenously in a hospital setting. In certain other preferred embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

In a third aspect, the invention provides a method of inhibiting histone deacetylase in a cell, comprising contacting a cell in which inhibition of histone deacetylase is desired with a prodrug of an inhibitor of histone deacetylase according to formula (2). In another aspect, the invention provides a method of inhibiting histone deacetylase in a cell within an organism having plasma, comprising administering to the organism a composition comprising a compound of the invention such that said composition will come in contact with said plasma of said organism, whereby said compound will be metabolized in said plasma to form a cleavage product that will come in contact with said cell, whereby said cleavage product will inhibit histone deacetylase in said cell.

Measurement of the enzymatic activity of a histone deacetylase can be achieved using known methodologies. For example, Yoshida et al., J. Biol. Chem., 265: 17174-17179 (1990), describes the assessment of histone deacetylase enzymatic activity by the detection of acetylated histones in trichostatin A treated cells. Taunton et al., Science, 272: 408-411 (1996), similarly describes methods to measure histone deacetylase enzymatic activity using endogenous and recombinant HDAC-1. Both of these references are hereby incorporated by reference in their entirety.

In some preferred embodiments, the histone deacetylase inhibitor interacts with and reduces the activity of all histone deacetylases in the cell. In some other preferred embodiments according to this aspect of the invention, the histone deacetylase inhibitor interacts with and reduces the activity of fewer than all histone deacetylases in the cell. In certain preferred embodiments, the inhibitor interacts with and reduces the activity of one histone deacetylase (e.g., HDAC-1), but does not interact with or reduce the activities of other histone deacetylases (e.g., HDAC-2, HDAC-3, HDAC-4, HDAC-5, HDAC-6, HDAC-7, HDAC-8, HDAC-9, HDAC-10, and HDAC-11). In preferred embodiments, the prodrug of the present invention hydrolyses into a compound that is a weak inhibitor of human HDAC's but an active inhibitor of fungal HDAC's. Certain preferred histone deacetylase inhibitors interact with and reduce the enzymatic activity of a fungal histone deacetylase.

Preferably, the method according to the third aspect of the invention causes an inhibition of cell proliferation of the contacted cells where the cells that are contacted are fungal cells. The phrase "inhibiting cell proliferation" is used to denote an ability of an inhibitor of histone deacetylase to retard the growth of cells contacted with the inhibitor as compared to cells not contacted. An assessment of cell proliferation can be made by counting contacted and non-contacted cells using a Coulter Cell Counter (Coulter, Miami, Fla.) or a hemacytometer, or other appropriate method (which may depend on the cell type being counted) known to those of skill in the art.

Thus, the invention provides a method for treating a fungal infection, comprising administering to an animal in need of such treatment a therapeutically effective amount of a prodrug of a histone deacetylase inhibitor of the invention. Preferably the prodrug is administered as an aqueous solution. Preferably, the animal is a mammal, more preferably a domesticated mammal. Most preferably, the animal is a human.

The present invention further provides a method for treating a fungal disease or infection comprising administering to an animal in need of such treatment a therapeutically effective amount of a prodrug of a histone deacetylase inhibitor of the invention. Preferably the animal is a mammal, more preferably a human. Preferably, the histone deacetylase inhibitor used according to this embodiment of the invention inhibits a fungal histone deacetylase to a greater extent than it inhibits mammalian histone deacetylases, particularly human histone.

The term "therapeutically effective amount" is meant to denote a dosage sufficient to cause inhibition of histone deacetylase activity in the cells of the subject, or a dosage sufficient to inhibit cell proliferation or to induce cell differentiation in the subject. Administration may be by any route, including, without limitation, parenteral, oral, sublingual, transdermal, topical, intranasal, intratracheal, or intrarectal. In certain particularly preferred embodiments, prodrugs of the invention are administered intravenously in a hospital setting. In certain other preferred embodiments, administration may preferably be by the oral route.

When administered systemically, the prodrug of an histone deacetylase inhibitor is preferably administered at a sufficient dosage to attain a blood level of the inhibitor from about 0.01 µM to about 100 µM, more preferably from about 0.05 µM to about 50 µM, still more preferably from about 0.1 µM to about 25 µM, and still yet more preferably from about 0.5 µM to about 25 µM. For localized administration, much lower concentrations than this may be effective, and much higher concentrations may be tolerated. One of skill in the art will appreciate that the dosage of histone deacetylase inhibitor necessary to produce a therapeutic effect may vary considerably depending on the tissue, organ, or the particular animal or patient to be treated.

In one embodiment, the prodrugs of the present invention are administered as combination therapy with an antifungal agent, particularly an azole antifungal agent. In a preferred embodiment the antifungal agents are ergosterol synthesis inhibitors and include, but are not limited to azoles and fenpropimorph. Other antifungal agents include, but are not limited to terbinafine. Preferred azoles include imidazoles and triazoles. Further preferred antifungal agents include, but are not limited to, ketoconazole, itraconazole, fluconazole, voriconazole, posaconazole, ravuconazole and miconazole. Like azoles, fenpropimorph is an ergosterol synthesis inhibitor, but acts on the ergosterol reductase (ERG24) step of the synthesis pathway. Terbinafine, is also an ergosterol inhibitor, but acts on the squalene eposidase (ERG1) step. In preferred embodiments, a cleavage product of a prodrug compound of the present invention shows synergistic activity with an antifungal agent against a fungal species, preferably at concentrations of inhibitor not toxic to mammalian cells. The other antifungal agent may be part of the same composition as the prodrug of the present invention, or it may be co-administered as a separate composition.

EXAMPLE 112

Saline Solubility at 1.00 mg/mL and 0.50 mg/mL, and Stability

Assays were performed to determine the saline solubility at 1.00 and 0.50 mg/ml and the stability of certain of the prodrug compounds of Examples 1-111. The following procedures were used.

Step 1. Sample preparation. An amount of the compound sample was precisely weighed to correspond to around 5 mg of the hydroxamate of compound 1, taking into account the mass of the leaving group and the salt factor if applicable. The sample was placed in a 16×125 mm glass screw cap tube. Saline was added so that the final concentration of hydroxamate 1 was 1.00 mg/mL. The pH was measured with pH indicator paper. The tube was shaken for 1 hour on a Vortex apparatus then centrifuged at 3000 rpm (1800 rcf) for 5 minutes. If the compound example was soluble (no precipitate formed) the procedure continued to step 2. If a precipitate formed then the sample was diluted with saline so that the final concentration of the hydroxamate of compound 1 was 0.50 mg/mL, and the shaking and centrifuging steps were repeated. If the compound example was soluble (no precipitate formed) the procedure continued to step 2. If a precipitate formed the sample was discarded.

Step 2. HPLC analysis. A 500 µL aliquot of a sample solution prepared according to Step 1 was taken up into a 1.5 mL injection vial to which was added 500 µL of saline. The vial was shaken on a Vortex apparatus, injected into the HPLC instrument (UV detection, zero time point) and the retention time and purity of the sample compound were determined. The injection was repeated after 6 hours and 24 hours, and a comparison was made of the retention time, peak areas and level of degradation (if any) using the GDADI50 method.

The results are shown in Table 20 below.

| Cmpd # | Ex # | Structure |
|---|---|---|
| 54 | N/A | 4-phenylbutyl-phenyl-CH₂-C(O)-NH-O-C(O)-C(cyclopropyl)(CH₂NH₂) · HCl |
| 45 | 24 | 4-phenylbutyl-phenyl-CH₂-C(O)-NH-O-C(O)-N(4-methylpiperazine) · HCl |
| 14 | 9 | H₂N-CH(CH₂CH₂CH₂CH₂NH₂)-C(O)-NH-CH₂CH₂-C(O)-O-NH-C(O)-CH₂-(4-(4-phenylbutyl)phenyl) · 2HCl |
| 52 | 31 | 4-phenylbutyl-phenyl-CH₂-C(O)-NH-O-C(O)-CH₂CH₂-cyclohexyl |
| 52B | 31B | 4-phenylbutyl-phenyl-CH₂-C(O)-NH-O-C(O)-CH₂CH₂-OCH₃ |
| 52C | 31C | 4-phenylbutyl-phenyl-CH₂-C(O)-NH-O-C(O)-CH₂-cyclopropyl |
| 52D | 31D | 4-phenylbutyl-phenyl-CH₂-C(O)-NH-O-C(O)-CH₃ |

-continued
| | | |
|---|---|---|
| 52E | 31E | 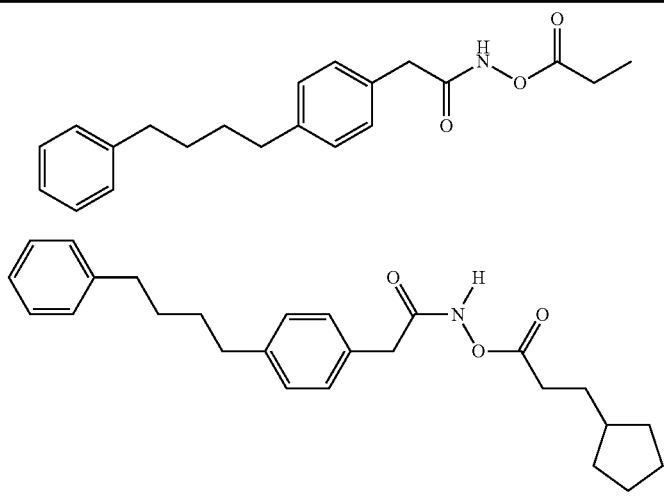 |
| 51 | 30 | |
| 50 | 29 | 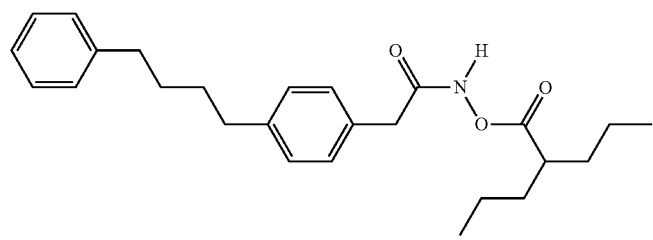 |
| 55 | 33 | 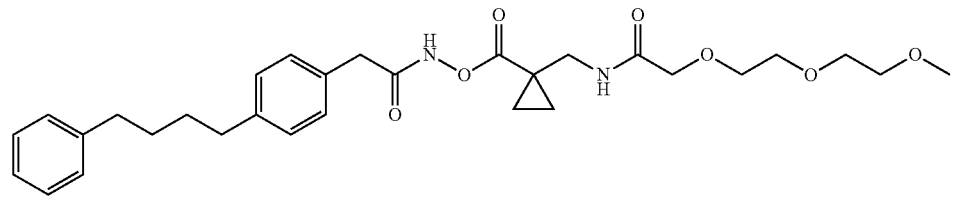 [SMILES: COCCOCCOCC(=O)NCC1(C(=O)ONC(=O)Cc2ccc(CCCCc3ccccc3)cc2)CC1] |
| 63 | 39 | 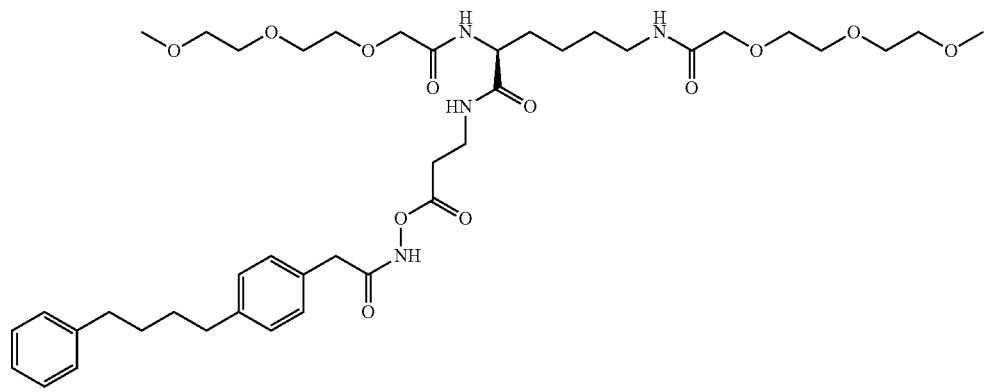 [SMILES: COCCOCCOCC(=O)NCCCC[C@H](NC(=O)COCCOCCOC)C(=O)NCCC(=O)ONC(=O)Cc1ccc(CCCCc2ccccc2)cc1] |
| 7 | 5 | 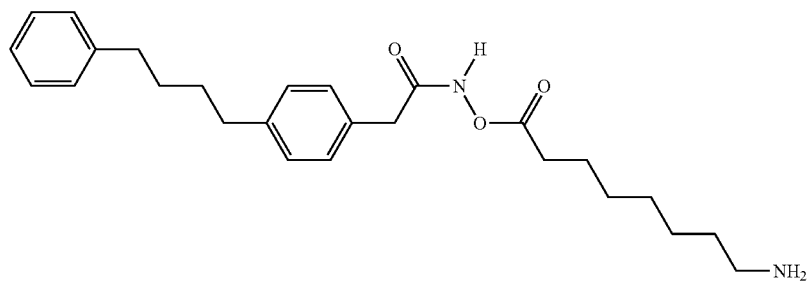 [SMILES: NCCCCCCCC(=O)ONC(=O)Cc1ccc(CCCCc2ccccc2)cc1] |

| | | |
|---|---|---|
| 53 | 32 | 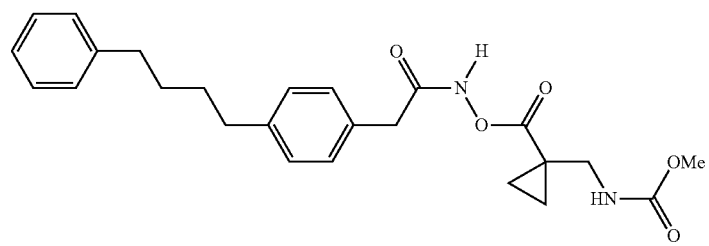 [SMILES: COC(=O)NCC1(C(=O)ONC(=O)Cc2ccc(CCCCc3ccccc3)cc2)CC1] |
| 52A | 31A | 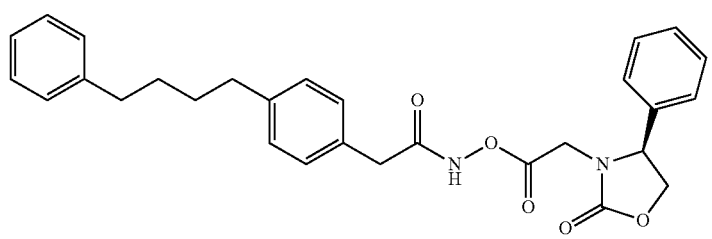 [SMILES: O=C(Cc1ccc(CCCCc2ccccc2)cc1)NOC(=O)CN1C(=O)OC[C@@H]1c1ccccc1] |
| 73 | 47 | 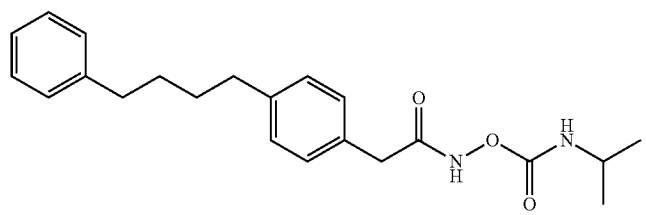 [SMILES: CC(C)NC(=O)ONC(=O)Cc1ccc(CCCCc2ccccc2)cc1] |
| 74 | 48 | 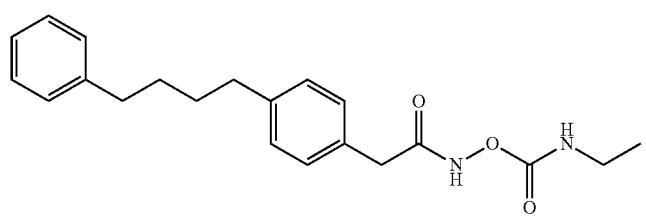 [SMILES: CCNC(=O)ONC(=O)Cc1ccc(CCCCc2ccccc2)cc1] |
| 76 | 50 | 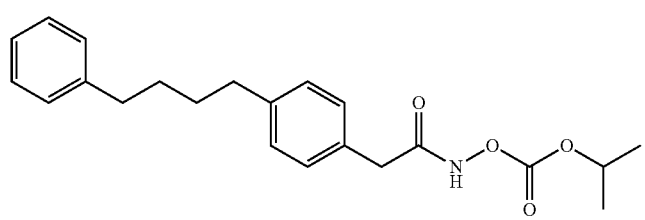 [SMILES: CC(C)OC(=O)ONC(=O)Cc1ccc(CCCCc2ccccc2)cc1] |
| 71 | 46 | 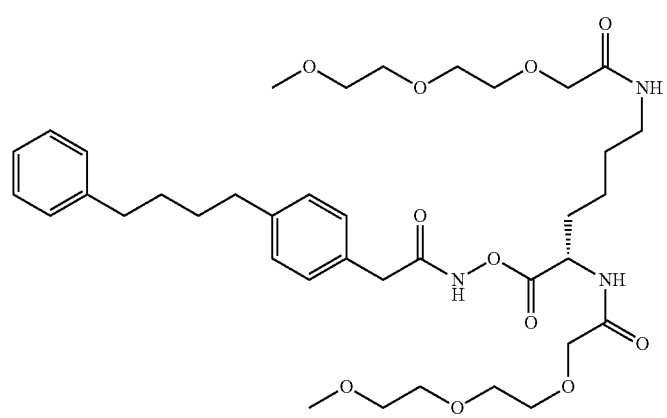 [SMILES: COCCOCCOCC(=O)NCCCC[C@H](NC(=O)COCCOCCOC)C(=O)ONC(=O)Cc1ccc(CCCCc2ccccc2)cc1] |

| | | |
|---|---|---|
| 68 | 43 | 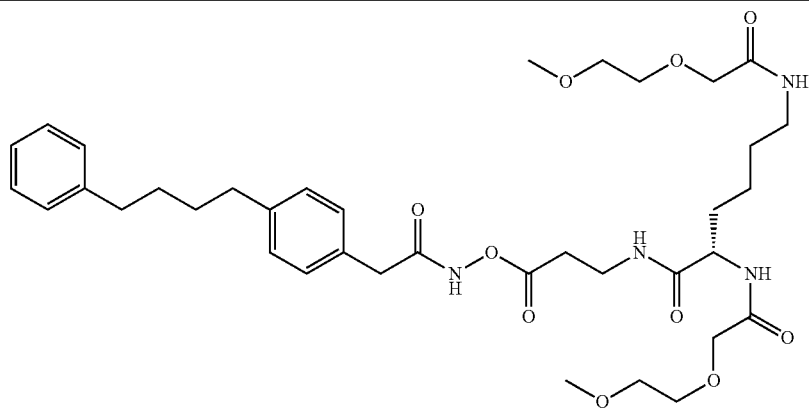 |
| 70 | 45 | 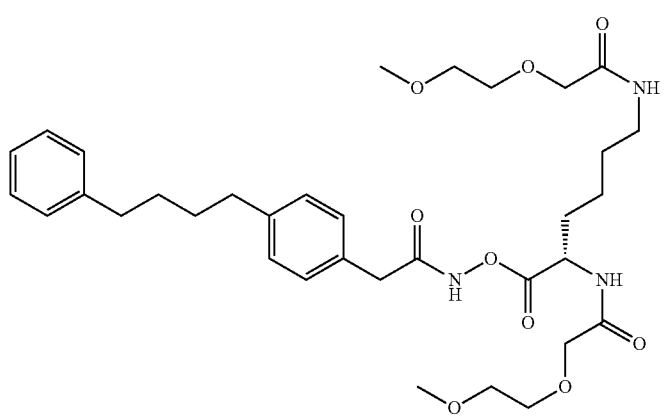 [SMILES: COCCOCC(=O)NCCCC[C@H](NC(=O)COCCOC)C(=O)ONC(=O)Cc1ccc(CCCCc2ccccc2)cc1] |
| 60 | 36 | 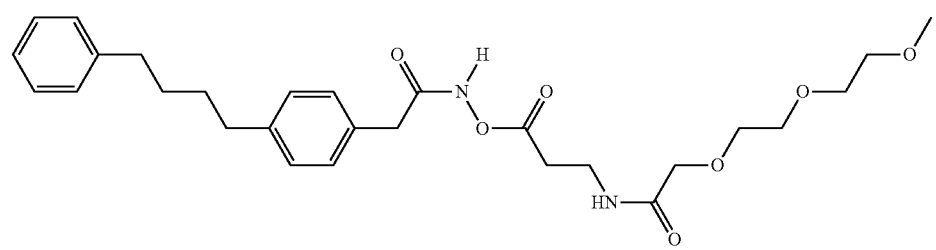 [SMILES: COCCOCCOCC(=O)NCCC(=O)ONC(=O)Cc1ccc(CCCCc2ccccc2)cc1] |
| 75 | 49 | 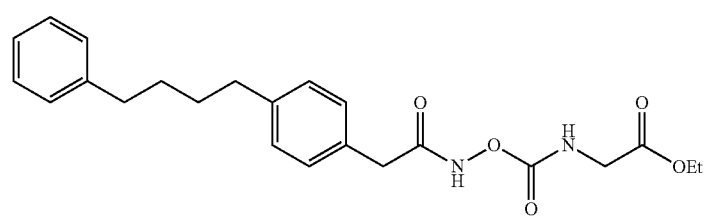 [SMILES: CCOC(=O)CNC(=O)ONC(=O)Cc1ccc(CCCCc2ccccc2)cc1] |
| 56 | 34 | 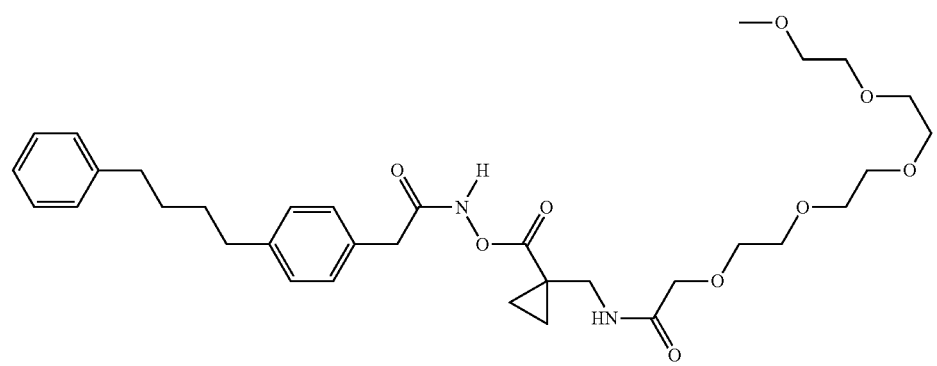 [SMILES: COCCOCCOCCOCCOCC(=O)NCC1(C(=O)ONC(=O)Cc2ccc(CCCCc3ccccc3)cc2)CC1] |

-continued
| 66 | 41 | 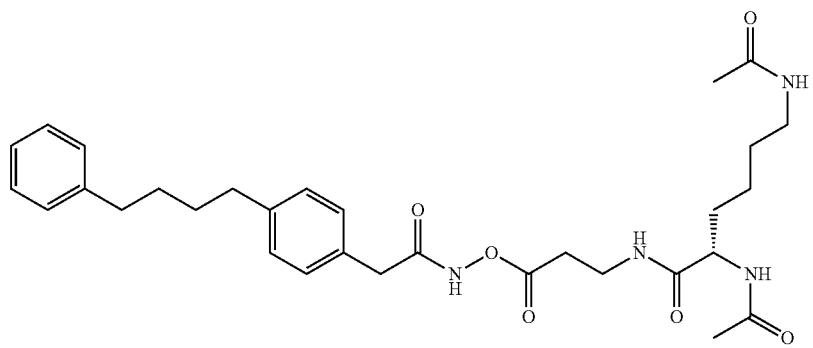 [SMILES: CC(=O)NCCCC[C@H](NC(C)=O)C(=O)NCCC(=O)ONC(=O)Cc1ccc(CCCCc2ccccc2)cc1] |
| 143 | 92 | 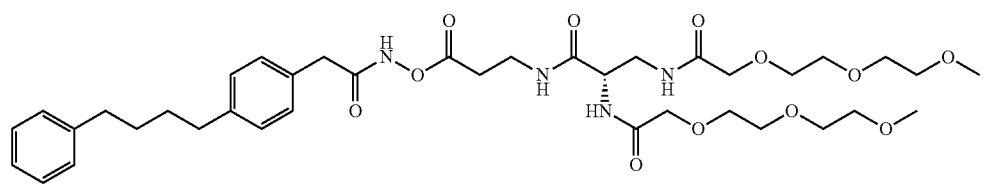 [SMILES: COCCOCCOCC(=O)NC[C@H](NC(=O)COCCOCCOC)C(=O)NCCC(=O)ONC(=O)Cc1ccc(CCCCc2ccccc2)cc1] |
| 144 | 93 | 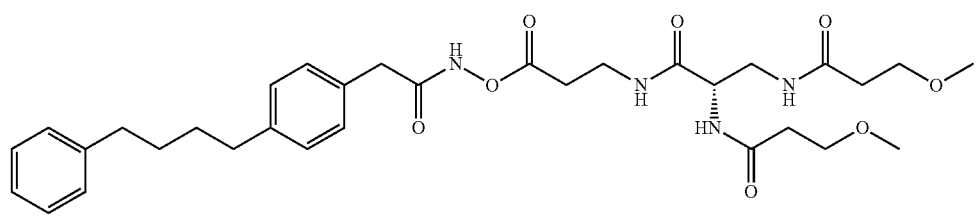 [SMILES: COCCC(=O)NC[C@H](NC(=O)CCOC)C(=O)NCCC(=O)ONC(=O)Cc1ccc(CCCCc2ccccc2)cc1] |
| 145 | 94 | 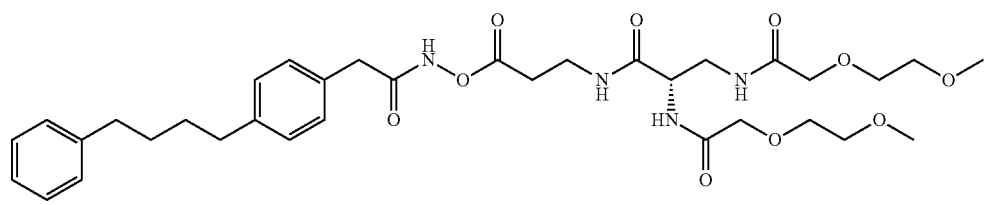 [SMILES: COCCOCC(=O)NC[C@H](NC(=O)COCCOC)C(=O)NCCC(=O)ONC(=O)Cc1ccc(CCCCc2ccccc2)cc1] |
| 146 | 95 | 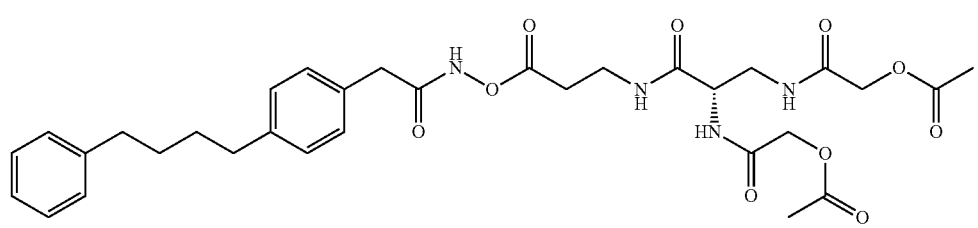 [SMILES: CC(=O)OCC(=O)NC[C@H](NC(=O)COC(C)=O)C(=O)NCCC(=O)ONC(=O)Cc1ccc(CCCCc2ccccc2)cc1] |
| 79 | 51 | 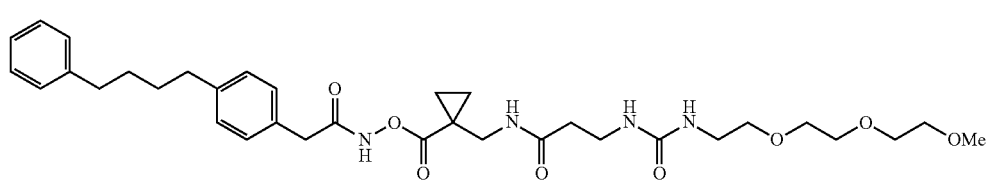 [SMILES: COCCOCCOCCNC(=O)NCCC(=O)NCC1(C(=O)ONC(=O)Cc2ccc(CCCCc3ccccc3)cc2)CC1] |

| | | |
|---|---|---|
| 61 | 37 | 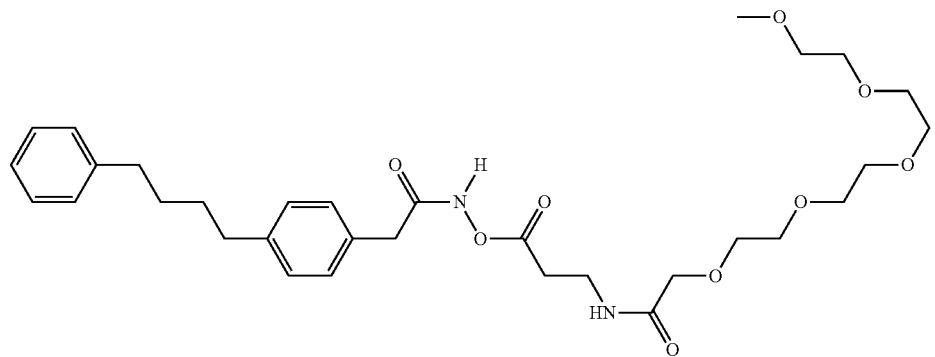 [SMILES: COCCOCCOCCOCCOCC(=O)NCCC(=O)ONC(=O)Cc1ccc(CCCCc2ccccc2)cc1] |
| 83 | 55 | 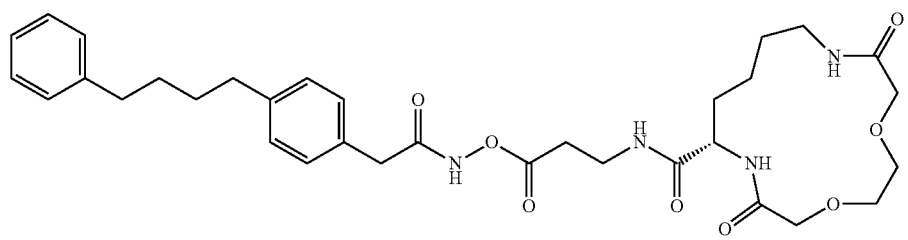 [SMILES: O=C1COCCOCC(=O)N[C@H](C(=O)NCCC(=O)ONC(=O)Cc2ccc(CCCCc3ccccc3)cc2)CCCCN1] |
| 87 | 57 | 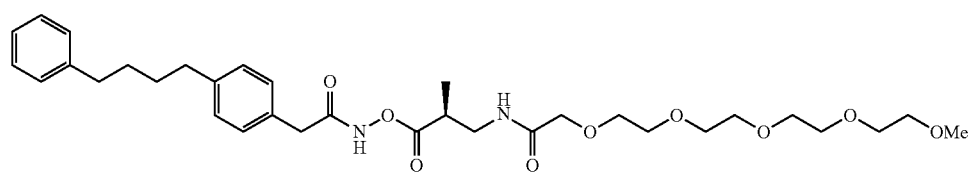 [SMILES: COCCOCCOCCOCCOCC(=O)NC[C@H](C)C(=O)ONC(=O)Cc1ccc(CCCCc2ccccc2)cc1] |
| 147 | 96 | 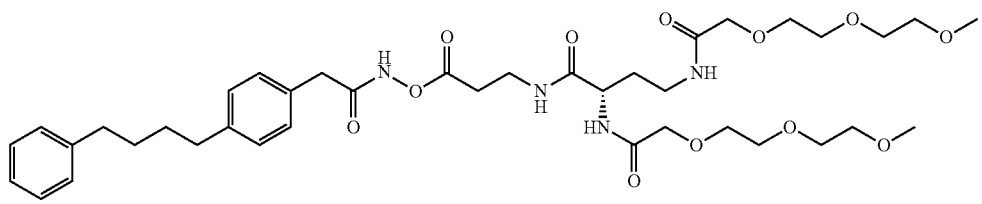 [SMILES: COCCOCCOCC(=O)NCC[C@H](NC(=O)COCCOCCOC)C(=O)NCCC(=O)ONC(=O)Cc1ccc(CCCCc2ccccc2)cc1] |
| 163 | 112 | 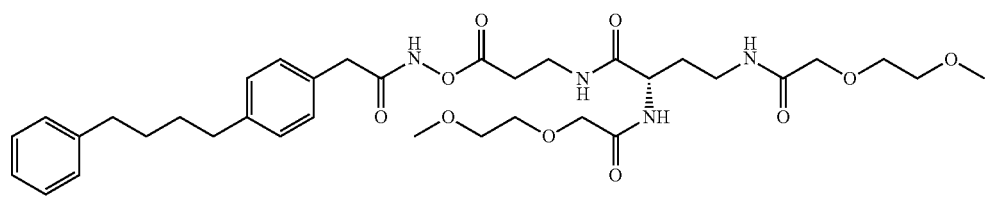 [SMILES: COCCOCC(=O)NCC[C@H](NC(=O)COCCOC)C(=O)NCCC(=O)ONC(=O)Cc1ccc(CCCCc2ccccc2)cc1] |
| 91 | 59 | 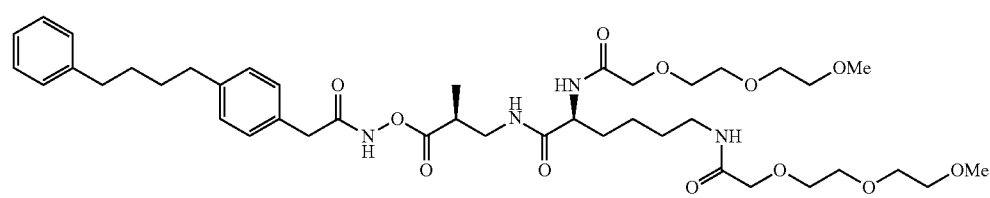 [SMILES: COCCOCCOCC(=O)NCCCC[C@H](NC(=O)COCCOCCOC)C(=O)NC[C@H](C)C(=O)ONC(=O)Cc1ccc(CCCCc2ccccc2)cc1] |
| 148 | 97 | 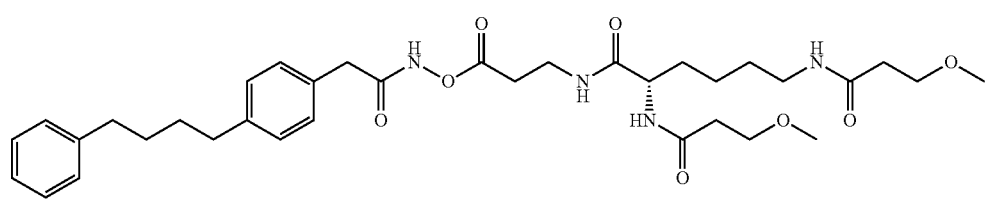 [SMILES: COCCC(=O)NCCCC[C@H](NC(=O)CCOC)C(=O)NCCC(=O)ONC(=O)Cc1ccc(CCCCc2ccccc2)cc1] |

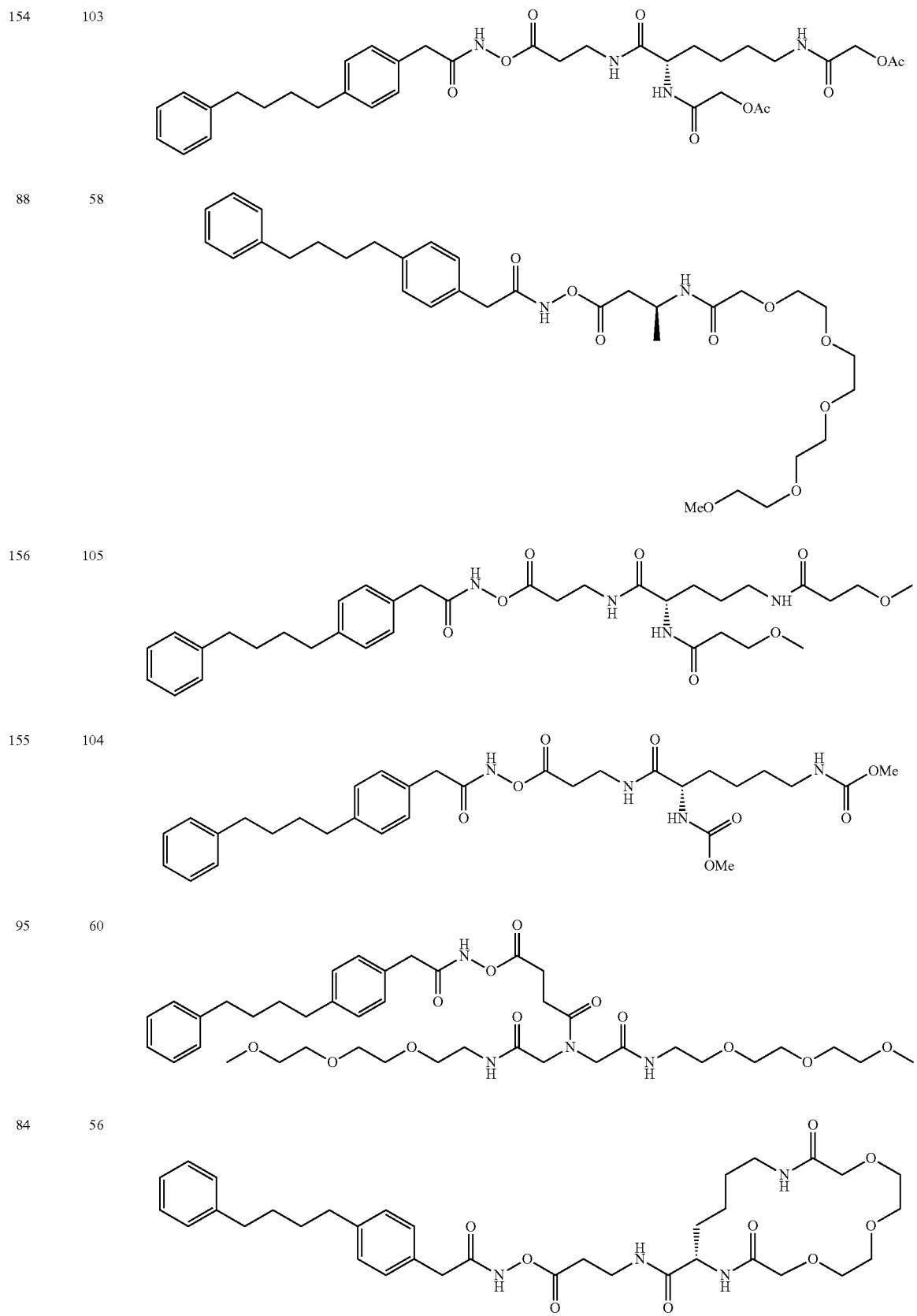

-continued
| | | |
|---|---|---|
| 157 | 106 | 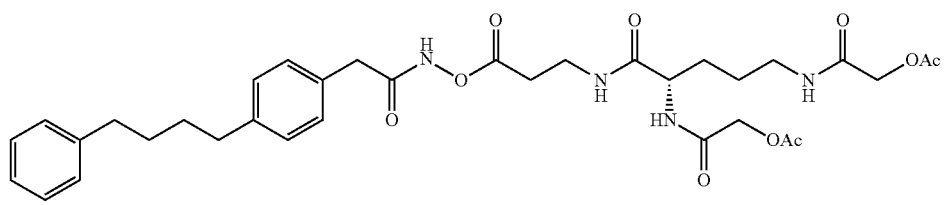 [SMILES: CC(=O)OCC(=O)NCCC[C@H](NC(=O)COC(C)=O)C(=O)NCCC(=O)ONC(=O)Cc1ccc(CCCCc2ccccc2)cc1] |
| 67 | 42 | 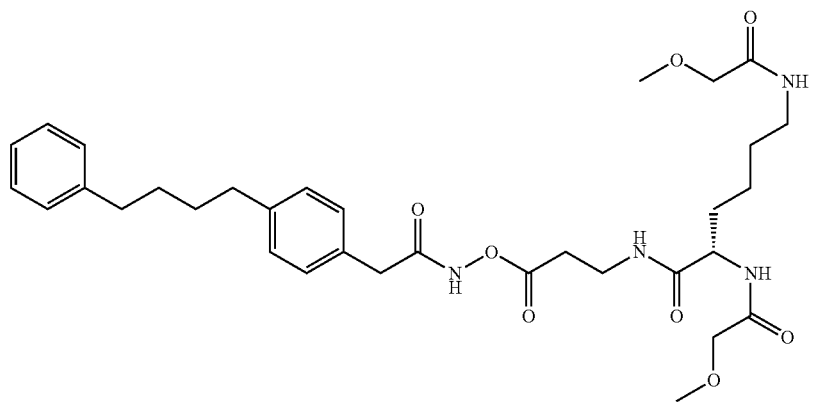 [SMILES: COCC(=O)NCCCC[C@H](NC(=O)COC)C(=O)NCCC(=O)ONC(=O)Cc1ccc(CCCCc2ccccc2)cc1] |
| 158 | 107 | 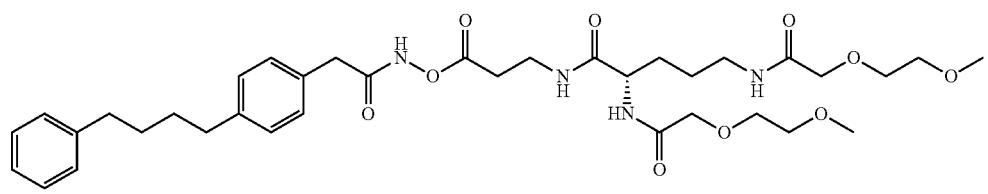 [SMILES: COCCOCC(=O)NCCC[C@H](NC(=O)COCCOC)C(=O)NCCC(=O)ONC(=O)Cc1ccc(CCCCc2ccccc2)cc1] |
| 69 | 44 | 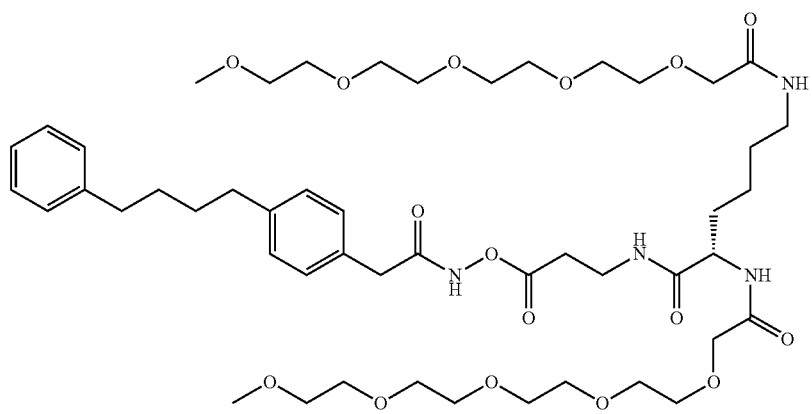 [SMILES: COCCOCCOCCOCCOCC(=O)NCCCC[C@H](NC(=O)COCCOCCOCCOCCOC)C(=O)NCCC(=O)ONC(=O)Cc1ccc(CCCCc2ccccc2)cc1] |
| 159 | 108 | 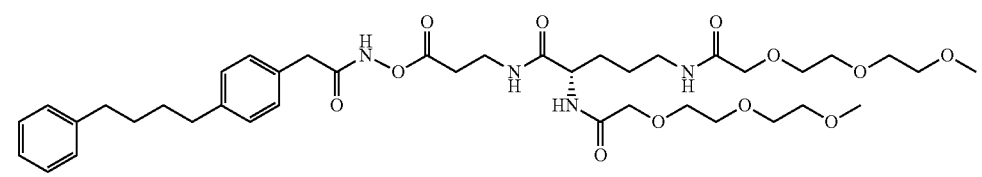 [SMILES: COCCOCCOCC(=O)NCCC[C@H](NC(=O)COCCOCCOC)C(=O)NCCC(=O)ONC(=O)Cc1ccc(CCCCc2ccccc2)cc1] |
| 149 | 98 | 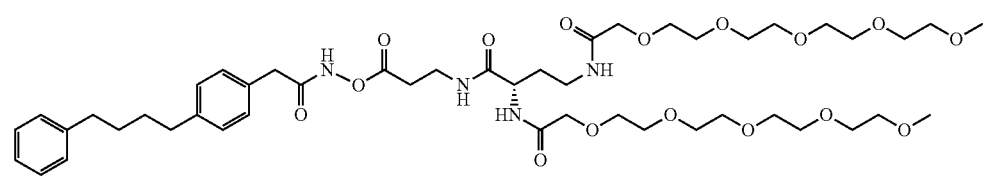 [SMILES: COCCOCCOCCOCCOCC(=O)NCC[C@H](NC(=O)COCCOCCOCCOCCOC)C(=O)NCCC(=O)ONC(=O)Cc1ccc(CCCCc2ccccc2)cc1] |

-continued
| 62 | 38 | 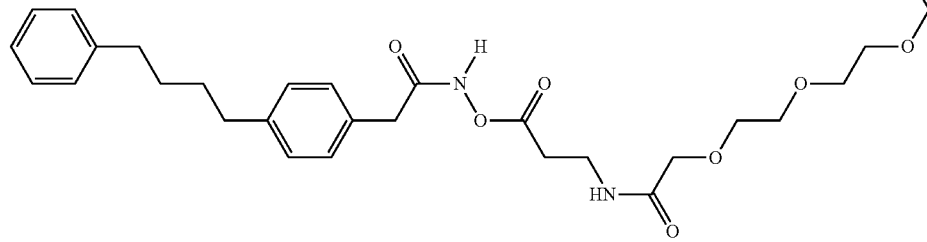 |
| 57 | 35 | 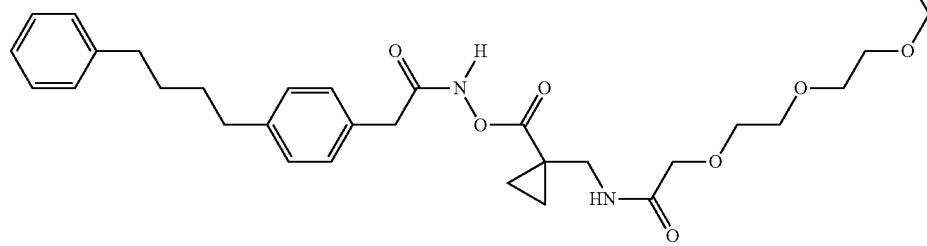 |
| 81 | 53 | 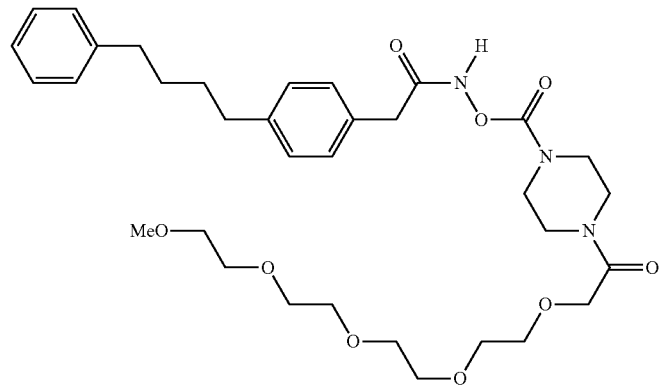 [SMILES: COCCOCCOCCOCCOCC(=O)N1CCN(C(=O)ONC(=O)Cc2ccc(CCCCc3ccccc3)cc2)CC1] |
| 150 | 99 | 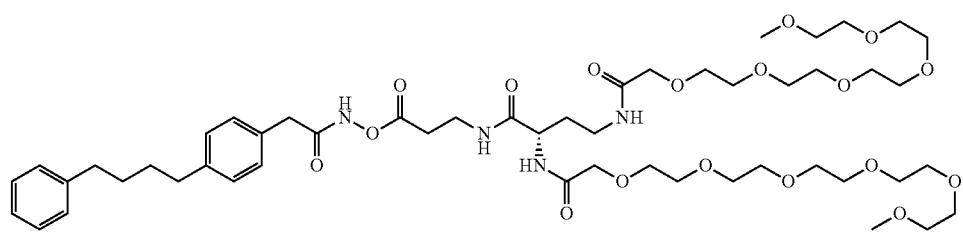 [SMILES: COCCOCCOCCOCCOCCOCC(=O)NCC[C@H](NC(=O)COCCOCCOCCOCCOCCOC)C(=O)NCCC(=O)ONC(=O)Cc1ccc(CCCCc2ccccc2)cc1] |

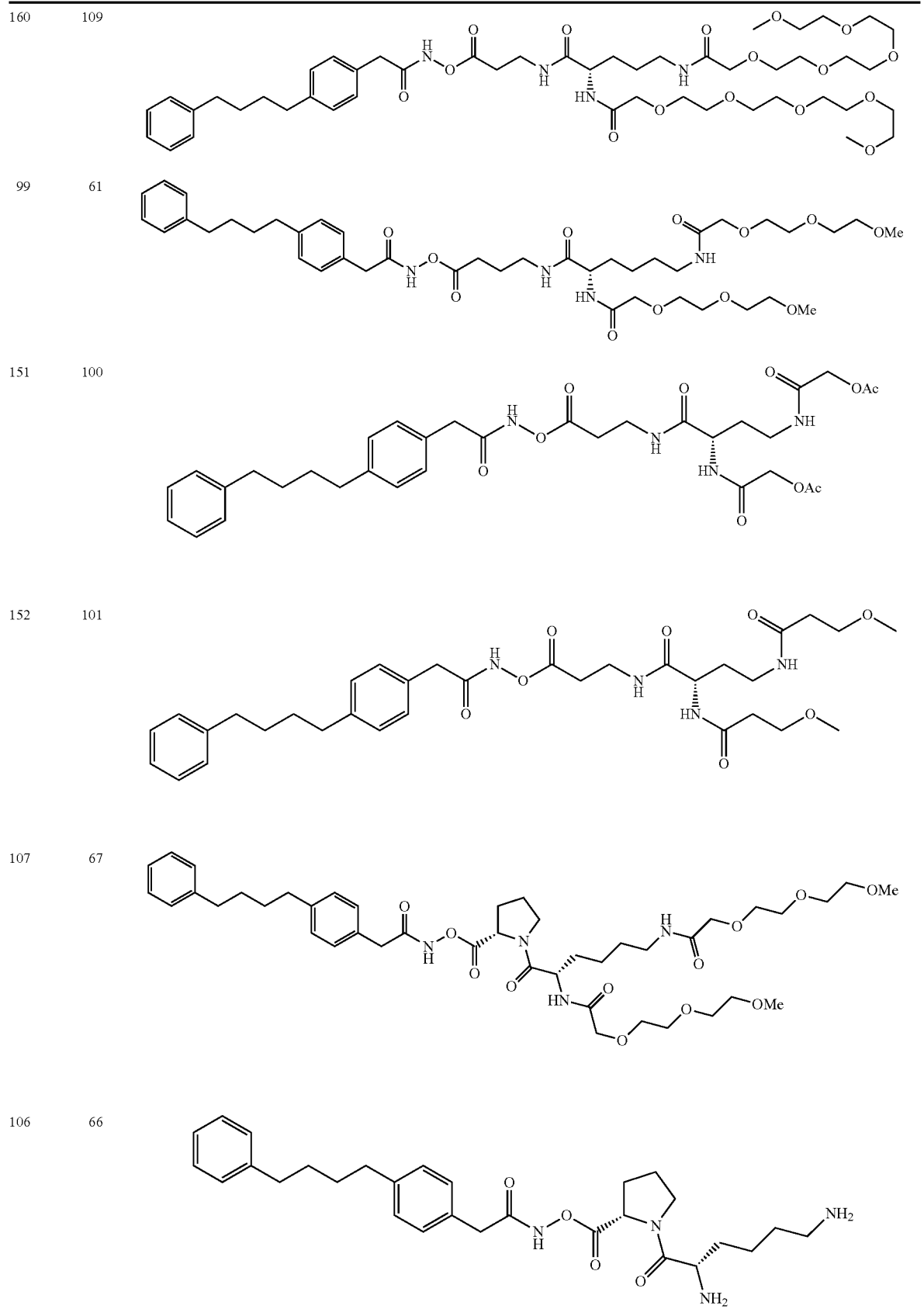

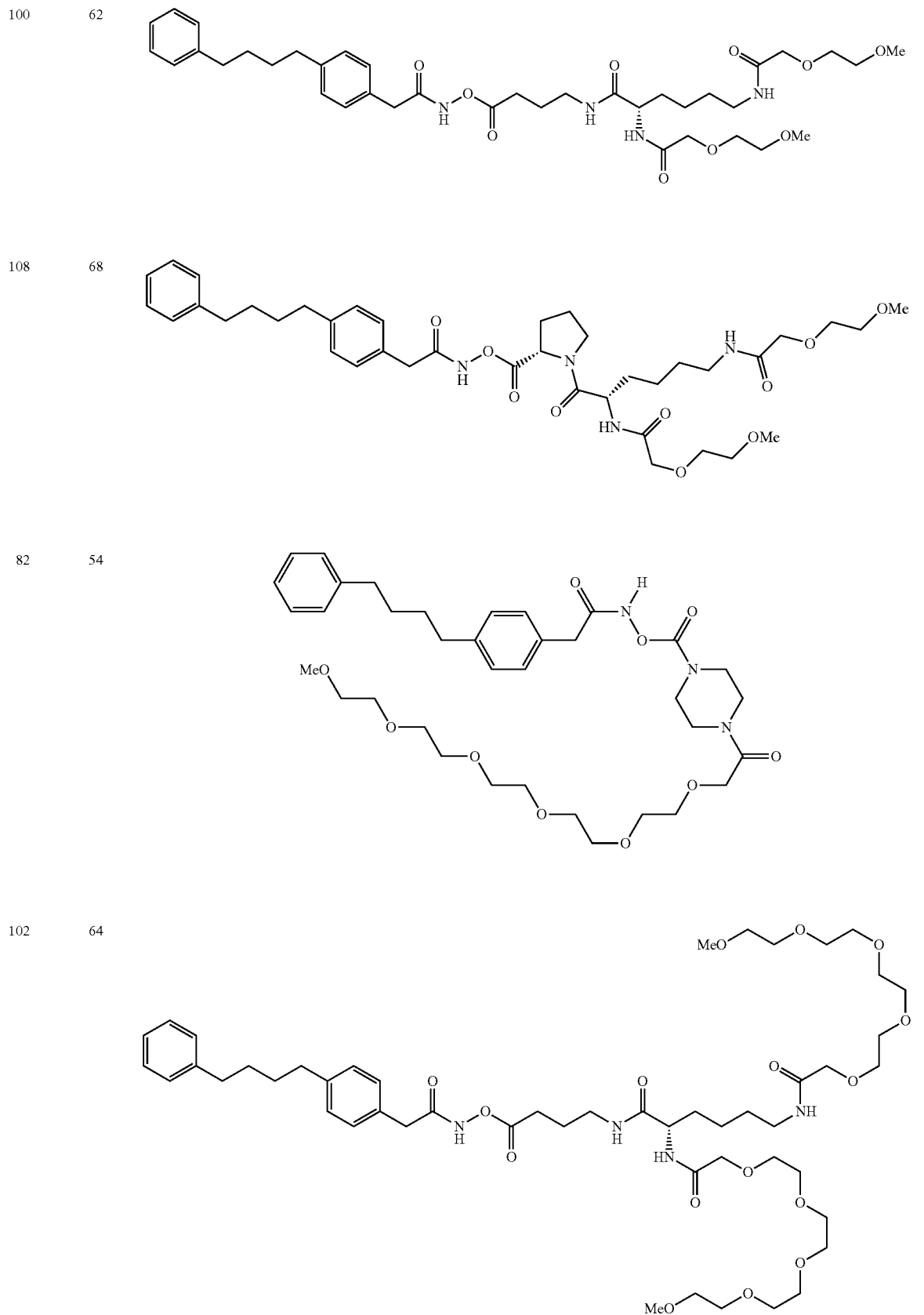

-continued
| 161 | 110 | 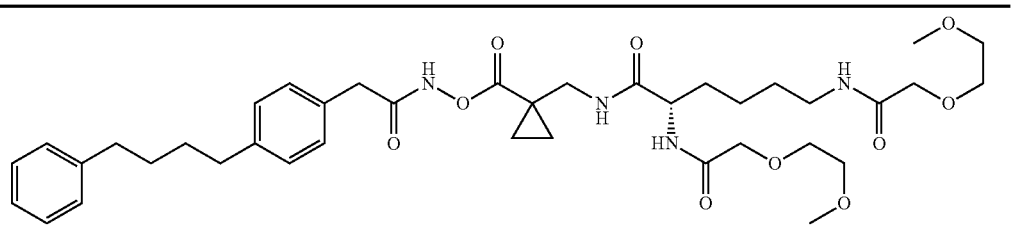 |
| 101 | 63 | 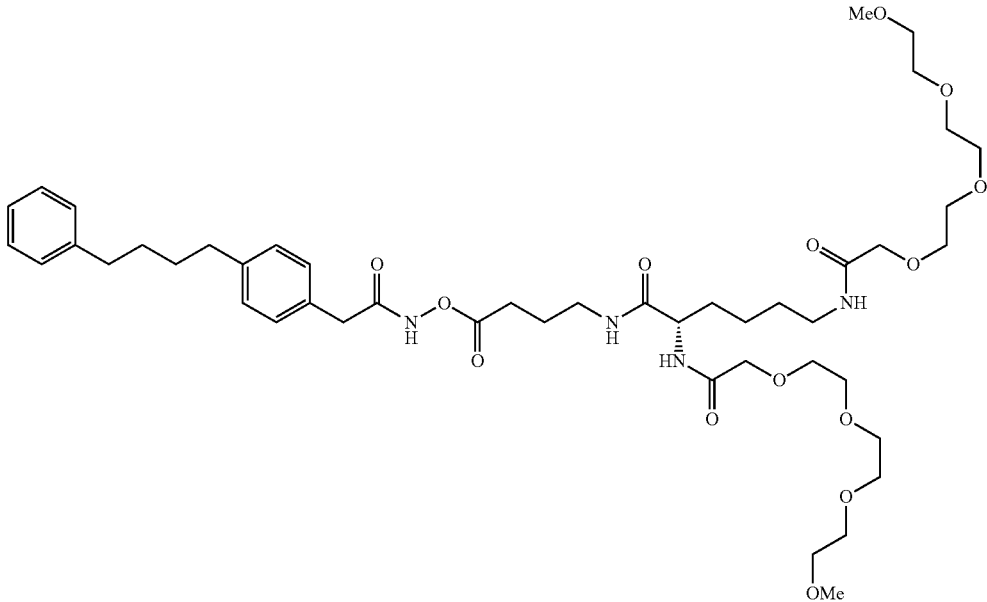 [SMILES: COCCOCCOCCOCC(=O)NCCCC[C@H](NC(=O)COCCOCCOCCOC)C(=O)NCCCC(=O)ONC(=O)Cc1ccc(CCCCc2ccccc2)cc1] |
| 103 | 65 | 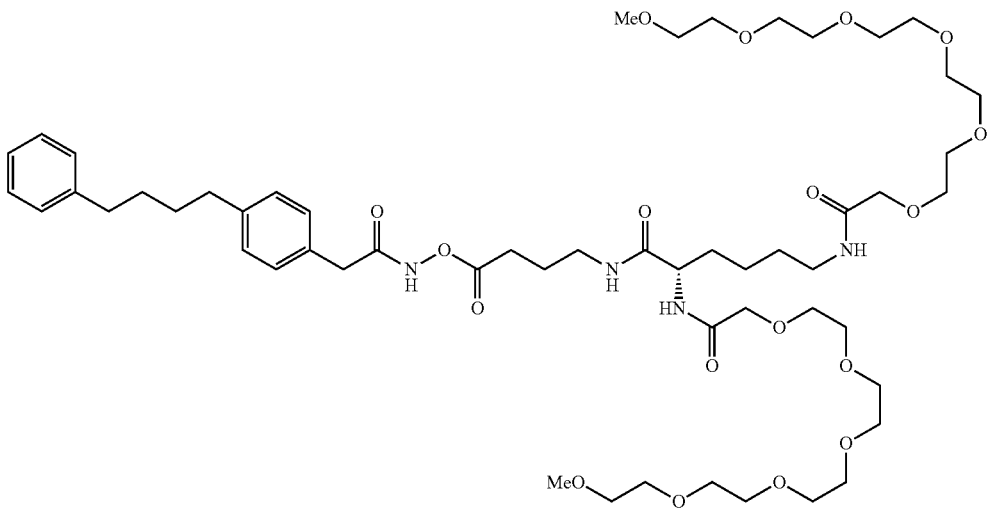 [SMILES: COCCOCCOCCOCCOCCOCC(=O)NCCCC[C@H](NC(=O)COCCOCCOCCOCCOCCOC)C(=O)NCCCC(=O)ONC(=O)Cc1ccc(CCCCc2ccccc2)cc1] |
| 162 | 111 | 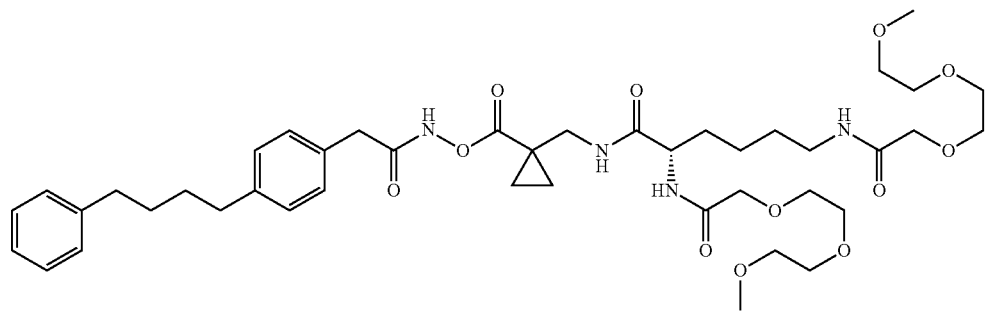 [SMILES: COCCOCCOCC(=O)NCCCC[C@H](NC(=O)COCCOCCOC)C(=O)NCC1(C(=O)ONC(=O)Cc2ccc(CCCCc3ccccc3)cc2)CC1] |

| | | |
|---|---|---|
| 118 | 77 | 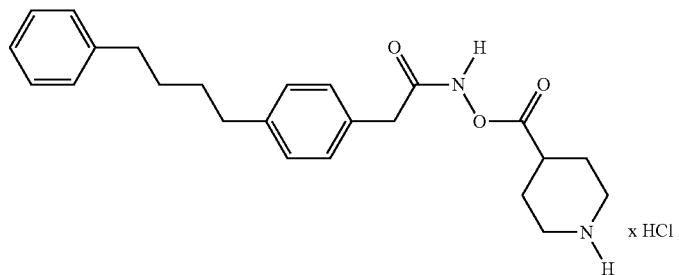 [SMILES: O=C(Cc1ccc(CCCCc2ccccc2)cc1)NOC(=O)C1CCNCC1] |
| 120 | 79 | 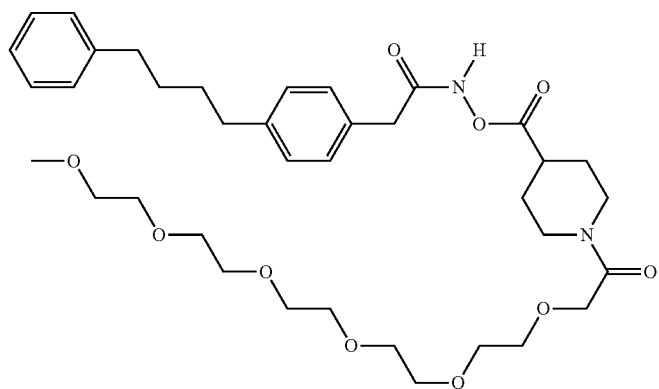 [SMILES: COCCOCCOCCOCCOCCOCC(=O)N1CCC(C(=O)ONC(=O)Cc2ccc(CCCCc3ccccc3)cc2)CC1] |
| 119 | 78 | 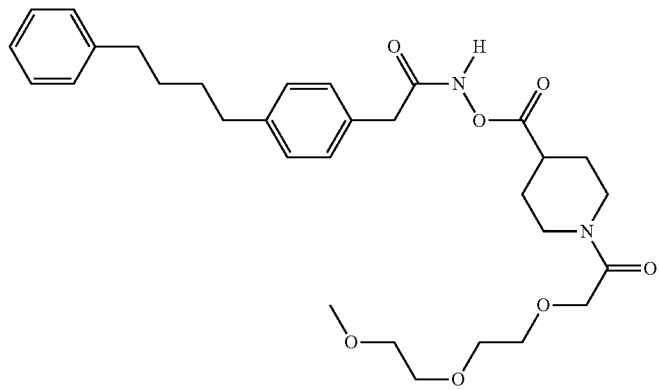 [SMILES: COCCOCCOCC(=O)N1CCC(C(=O)ONC(=O)Cc2ccc(CCCCc3ccccc3)cc2)CC1] |
| 114 | 73 | 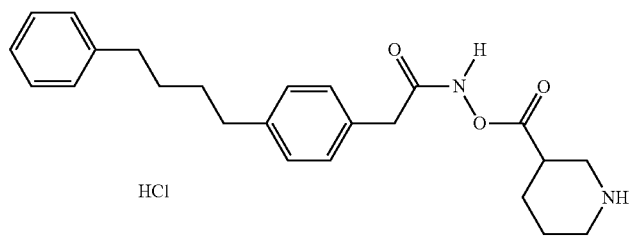 [SMILES: O=C(Cc1ccc(CCCCc2ccccc2)cc1)NOC(=O)C1CCCNC1 ; Cl] |

| 64 | 40 | 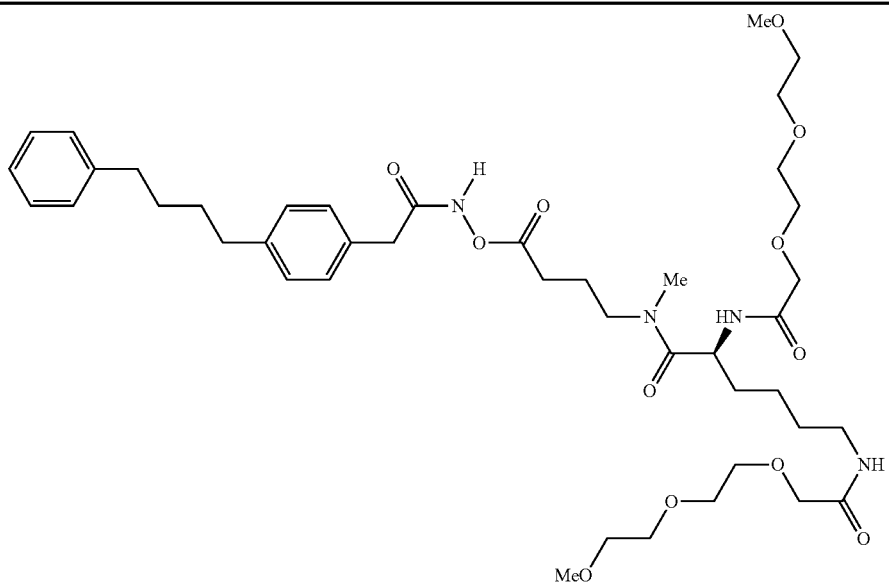 |
| 117 | 76 | 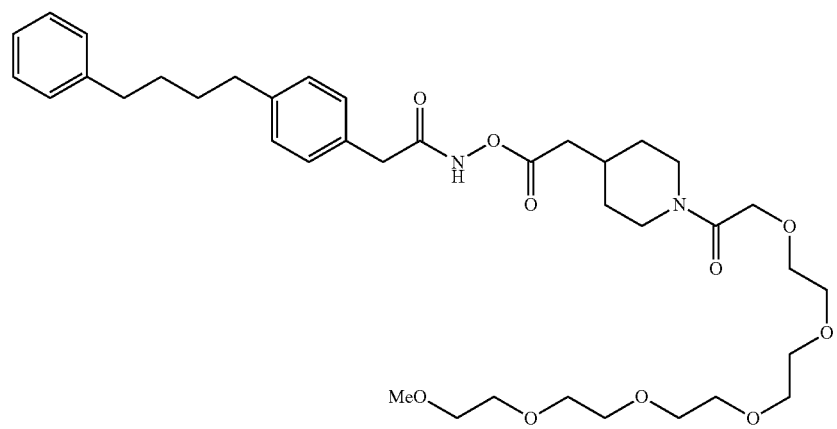 [SMILES: COCCOCCOCCOCCOCCOCC(=O)N1CCC(CC(=O)ONC(=O)Cc2ccc(CCCCc3ccccc3)cc2)CC1] |
| 116 | 75 | 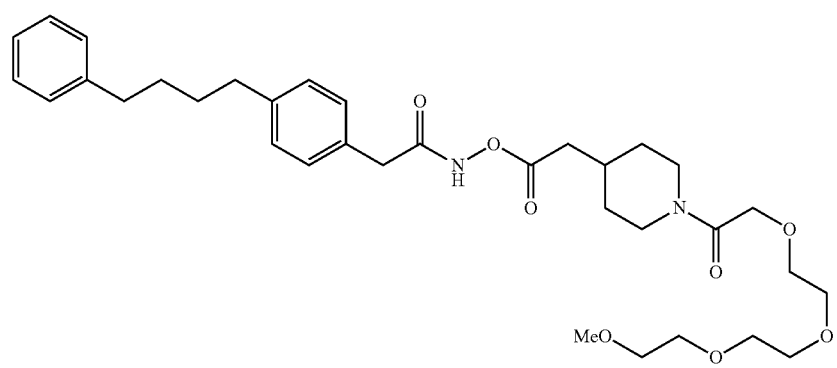 [SMILES: COCCOCCOCCOCC(=O)N1CCC(CC(=O)ONC(=O)Cc2ccc(CCCCc3ccccc3)cc2)CC1] |
| 115 | 74 | 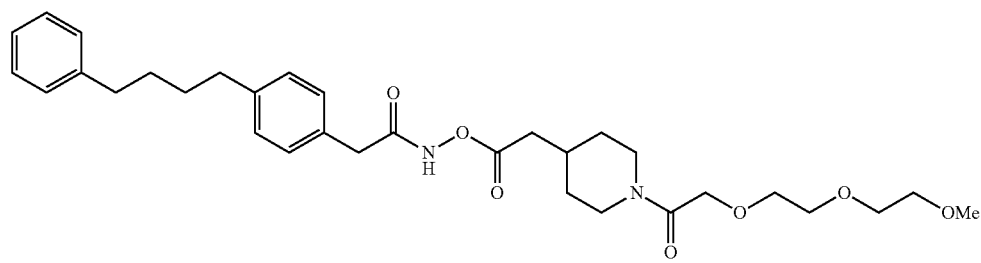 [SMILES: COCCOCCOCC(=O)N1CCC(CC(=O)ONC(=O)Cc2ccc(CCCCc3ccccc3)cc2)CC1] |

-continued
| 110 | 69 | 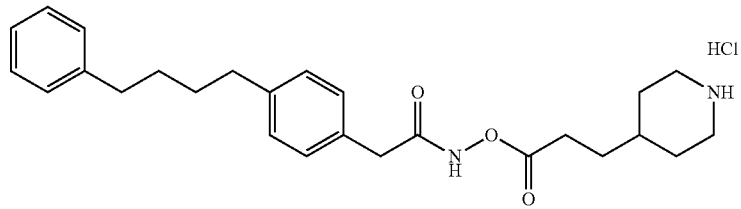 [SMILES: O=C(Cc1ccc(CCCCc2ccccc2)cc1)NOC(=O)CCC1CCNCC1 ; Cl] |
| 111 | 70 | 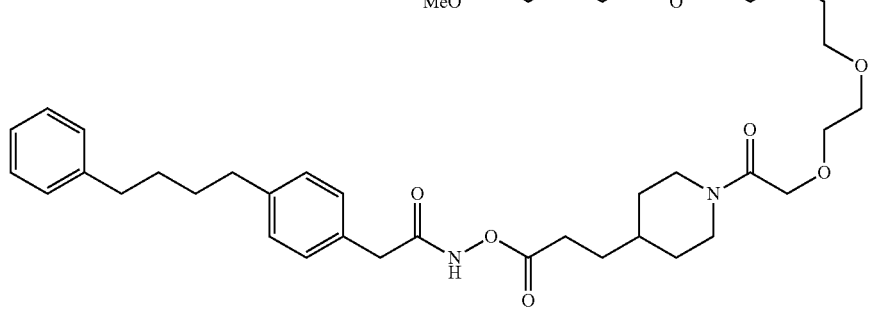 |
| 125 | 84 | 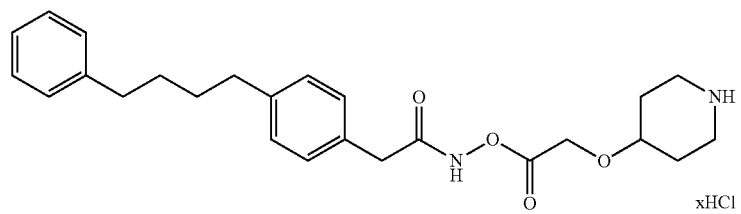 [SMILES: O=C(Cc1ccc(CCCCc2ccccc2)cc1)NOC(=O)COC1CCNCC1] |
| 127 | 85 | 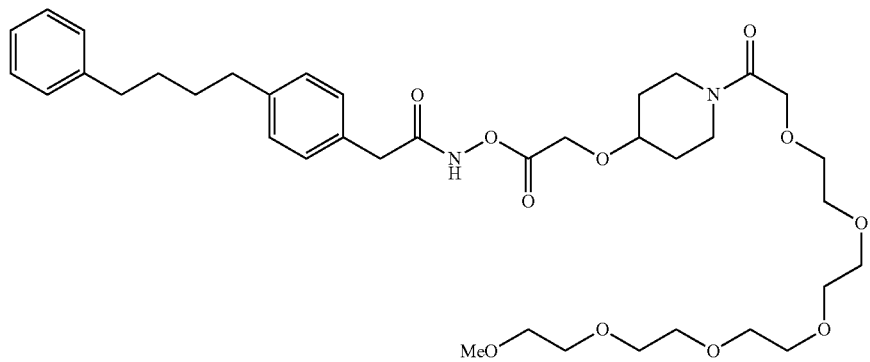 [SMILES: COCCOCCOCCOCCOCCOCC(=O)N1CCC(OCC(=O)ONC(=O)Cc2ccc(CCCCc3ccccc3)cc2)CC1] |
| 142 | 91 | 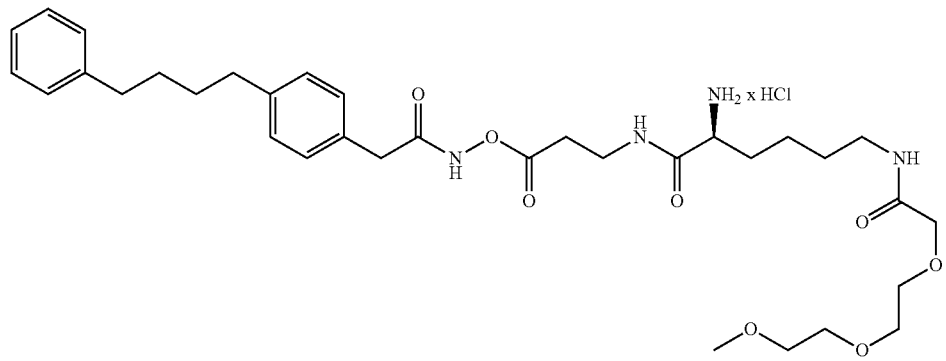 |

| | | |
|---|---|---|
| 121 | 80 | 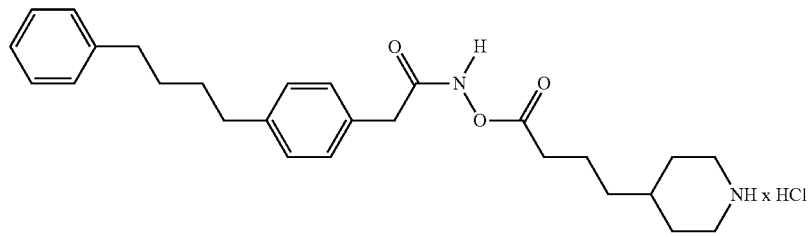 |
| 123 | 82 | 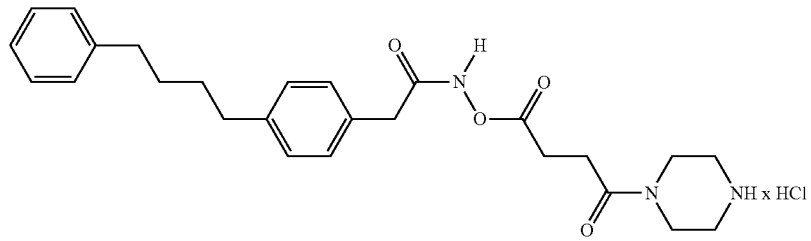 |
| 124 | 83 | 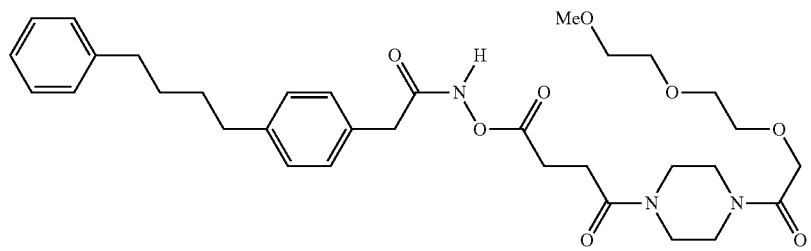 [SMILES: COCCOCCOCC(=O)N1CCN(C(=O)CCC(=O)ONC(=O)Cc2ccc(CCCCc3ccccc3)cc2)CC1] |
| 128 | 86 | 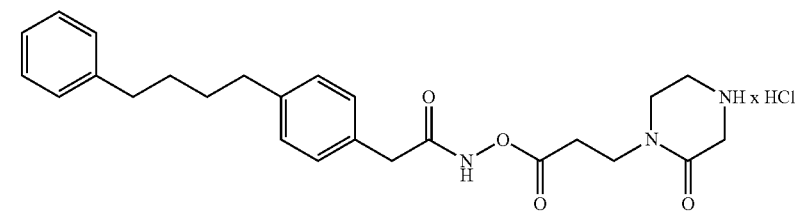 |
| 122 | 81 | 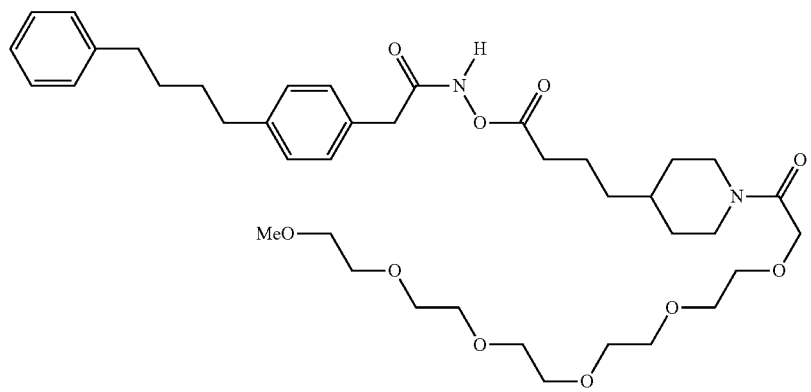 [SMILES: COCCOCCOCCOCCOCCOCC(=O)N1CCC(CCCC(=O)ONC(=O)Cc2ccc(CCCCc3ccccc3)cc2)CC1] |
| 135 | 89 | 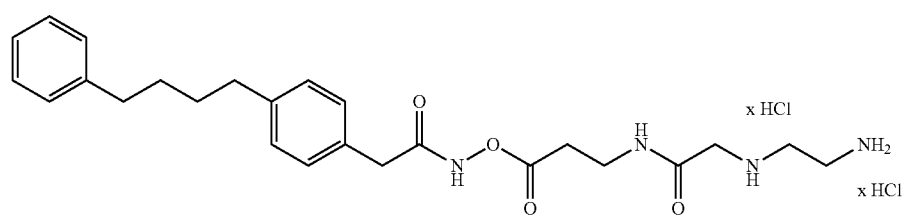 [SMILES: NCCNCC(=O)NCCC(=O)ONC(=O)Cc1ccc(CCCCc2ccccc2)cc1] |

-continued
| 133 | 87 | 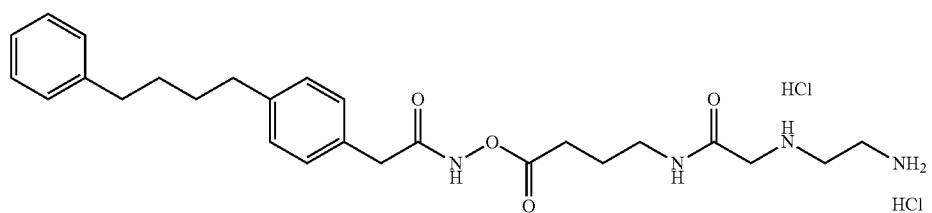 [SMILES: NCCNCC(=O)NCCCC(=O)ONC(=O)Cc1ccc(CCCCc2ccccc2)cc1 ; Cl ; Cl] |
| 128B | 86B | 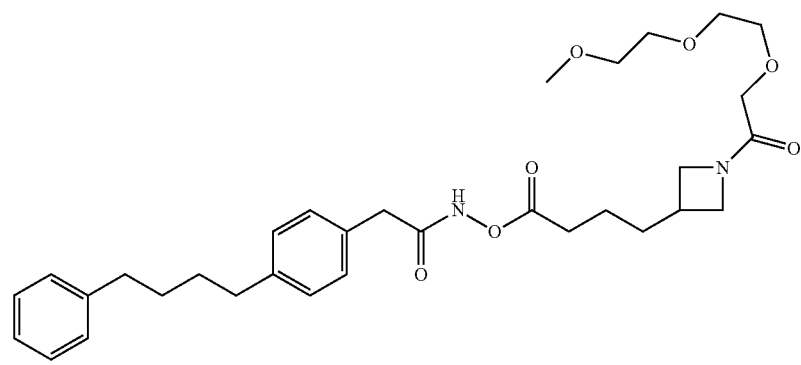 [SMILES: COCCOCCOCC(=O)N1CC(CCCC(=O)ONC(=O)Cc2ccc(CCCCc3ccccc3)cc2)C1] |
| 112 | 71 | 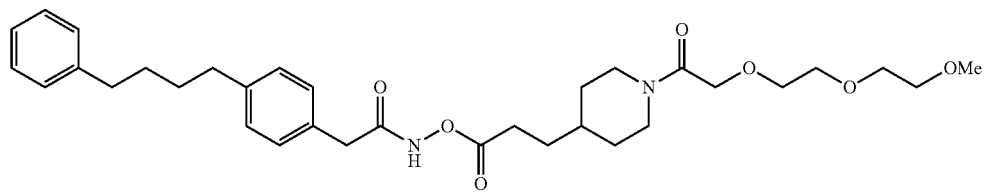 [SMILES: COCCOCCOCC(=O)N1CCC(CCC(=O)ONC(=O)Cc2ccc(CCCCc3ccccc3)cc2)CC1] |
| 113 | 72 | 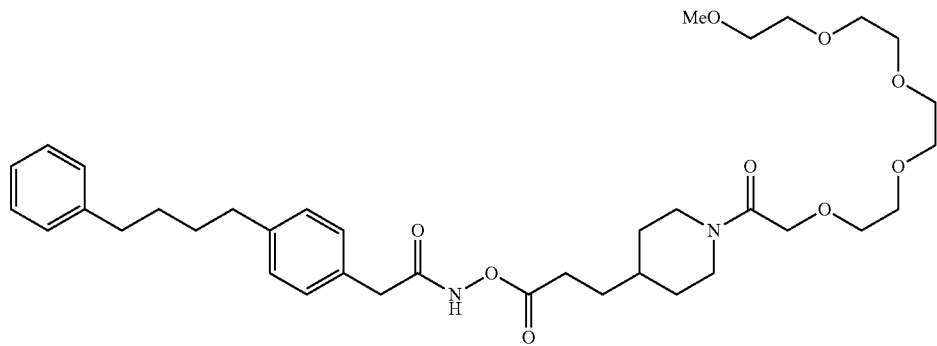 [SMILES: COCCOCCOCCOCCOCC(=O)N1CCC(CCC(=O)ONC(=O)Cc2ccc(CCCCc3ccccc3)cc2)CC1] |
| 134 | 88 | 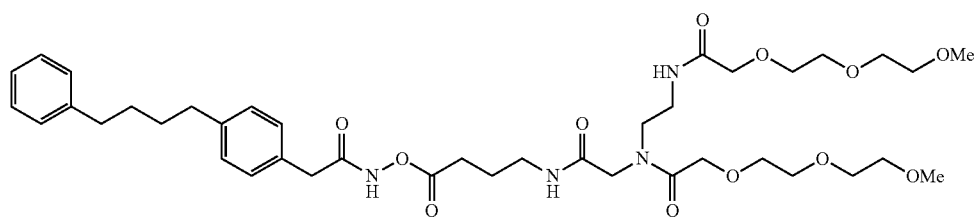 [SMILES: COCCOCCOCC(=O)NCCN(CC(=O)NCCCC(=O)ONC(=O)Cc1ccc(CCCCc2ccccc2)cc1)C(=O)COCCOCCOC] |

| 136 | 90 | 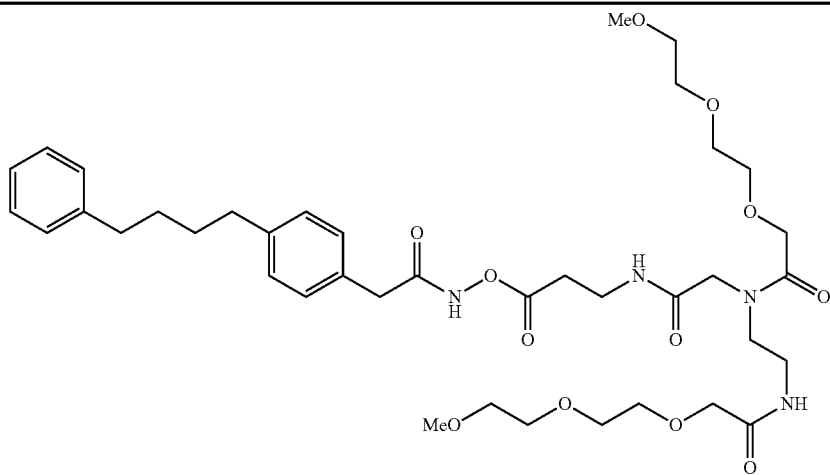 |

| Cmpd # | Ex # | Formula, MW | Appearance | pH at 1.00 mg/mL of MGCD290 in saline | Soluble at 1.00 mg/mL of MGCD290 (Y/N) | Soluble at 0.5 mg/mL of MGCD290 (Y/N) | Recovery after 6 hr in saline with 220 nm | Recovery after 24 hr in saline with 220 nm |
|---|---|---|---|---|---|---|---|---|
| 54 | N/A | $C_{23}H_{28}N_2O_3$, Free Base 380.48 Salt 416.94 | Powder | 4-4.5 | Y | n/ap | 86.4% | 70.8% |
| 45 | 24 | $C_{24}H_{31}N_3O_3$, Free Base 409.52 Salt 445.98 | Powder | 4-4.5 | N | N | | |
| 14 | 9 | $C_{27}H_{37}N_4O_4$, Free Base 481.61 Salt 554.53 | Powder | 4-4.5 | Y | n/ap | 93.2% | 75.7% |
| 52 | 31 | $C_{27}H_{35}NO_3$, 421.57 | Powder | nr | N | N | | |
| 52B | 31B | $C_{22}H_{27}NO_4$, 369.45 | Powder | nr | N | N | | |
| 52C | 31C | $C_{23}H_{27}NO_3$, 365.47 | Powder | nr | N | N | | |
| 52D | 31D | $C_{20}H_{23}NO_3$, 325.40 | Powder | nr | N | N | | |
| 52E | 31E | $C_{21}H_{25}NO_3$, 339.43 | Powder | nr | N | N | | |
| 51 | 30 | $C_{26}H_{33}NO_3$, 407.55 | Powder | nr | N | N | | |
| 50 | 29 | $C_{26}H_{35}NO_3$, 409.56 | Powder | nr | N | N | | |
| 55 | 33 | $C_{30}H_{40}N_2O_7$, 540.65 | Powder | nr | N | N | | |
| 63 | 39 | $C_{41}H_{62}N_4O_{12}$, 802.95 | Gel | nr | Y | n/ap | 95.6% | 84.3% |
| 7 | 5 | $C_{26}H_{36}N_2O_3$, 424.58 Free base 461.08 Salt | Powder | nr | N | N | | |
| 53 | 32 | $C_{25}H_{30}N_2O_5$, 438.52 | Powder | 4.5-5 | N | N | | |
| 52A | 31A | $C_{29}H_{30}N_2O_5$, 486.56 | Wax | 4.5-5 | N | N | | |
| 73 | 47 | $C_{22}H_{28}N_2O_3$, 368.47 | Powder | 4.5-5 | N | N | | |
| 74 | 48 | $C_{21}H_{26}N_2O_3$, 354.44 | Powder | 4.5-5 | N | N | | |
| 76 | 50 | $C_{22}H_{27}NO_4$, 369.45 | Powder | 4.5-5 | N | N | | |
| 71 | 46 | $C_{38}H_{57}N_3O_{11}$, 731.87 | transparent Gel | 4.5-5 | N | N | | |
| 68 | 43 | $C_{37}H_{54}N_4O_{10}$, 714.85 | transparent Gel | 4.5-5 | Y | n/ap | 93.2% | 84.1% |
| 70 | 45 | $C_{34}H_{49}N_3O_9$, 643.77 | Gel | 4.5-5 | N | N | | |
| 60 | 36 | $C_{28}H_{38}N_2O_7$, 514.61 | White powder | 4.5-5 | N | N | | |
| 75 | 49 | $C_{23}H_{28}N_2O_5$, 412.48 | White Powder | 4.5-5 | N | N | | |
| 56 | 34 | $C_{34}H_{48}N_2O_9$, 628.75 | Gel | 4.5-5 | N | N | | |
| 66 | 41 | $C_{31}H_{42}N_4O_6$, 566.69 | Powder | 4.5-5 | N | N | | |
| 143 | 92 | $C_{38}H_{56}N_4O_{12}$, 760.87 | Wax | 4.5-5 | N | N | | |
| 144 | 93 | $C_{32}H_{44}N_4O_8$, 612.71 | Powder | 4.5-5 | N | N | | |
| 145 | 94 | $C_{34}H_{48}N_4O_{10}$, 672.77 | Wax | 4.5-5 | N | N | | |
| 146 | 95 | $C_{32}H_{40}N_4O_{10}$, 640.68 | Powder | 4.5-5 | N | N | | |
| 79 | 51 | $C_{34}H_{48}N_4O_8$, 640.77 | Powder | 4.5-5 | N | N | | |
| 61 | 37 | $C_{32}H_{46}N_2O_9$, 602.72 | Powder | 4.5-5 | N | N | | |
| 83 | 55 | $C_{33}H_{44}N_4O_8$, 624.72 | Powder | 4.5-5 | N | N | | |
| 87 | 57 | $C_{33}H_{48}N_2O_9$, 616.74 | Gel | 4.5-5 | N | N | | |
| 147 | 96 | $C_{39}H_{58}N_4O_{12}$, 774.90 | Wax | 4.5-5 | N | N | | |
| 163 | 112 | $C_{35}H_{50}N_4O_{10}$, 686.79 | Gel | 4.5-5 | N | N | | |
| 91 | 59 | $C_{42}H_{64}N_4O_{12}$, 816.98 | Gel | 4.5-5 | Y | n/ap | 97.3% | 90.2% |
| 148 | 97 | $C_{35}H_{50}N_4O_8$, 654.79 | Powder | 4.5-5 | N | N | | |
| 154 | 103 | $C_{35}H_{46}N_4O_{10}$, 682.76 | Powder | 4.5-5 | N | N | | |
| 88 | 58 | $C_{33}H_{48}N_2O_9$, 616.74 | Gel | 4.5-5 | N | N | | |
| 156 | 105 | $C_{34}H_{48}N_4O_8$, 640.77 | Powder | 4.5-5 | N | N | | |
| 155 | 104 | $C_{31}H_{42}N_4O_8$, 598.69 | Powder | 4.5-5 | N | N | | |
| 95 | 60 | $C_{40}H_{60}N_4O_{12}$, 788.92 | Gel | 4.5-5 | N | Y | 95.2% | 84.3% |
| 84 | 56 | $C_{35}H_{48}N_4O_9$, 668.78 | Gel | 4.5-5 | N | N | | |

| | | | | | | | | |
|---|---|---|---|---|---|---|---|---|
| 157 | 106 | C$_{34}$H$_{44}$N$_4$O$_{10}$, 668.73 | Sticky Powder | 4.5-5 | N | N | | |
| 67 | 42 | C$_{33}$H$_{46}$N$_4$O$_8$, 626.74 | Powder | 4.5-5 | N | N | | |
| 158 | 107 | C$_{36}$H$_{52}$N$_4$O$_{10}$, 700.82 | Gel | 4.5-5 | N | N | | |
| 69 | 44 | C$_{49}$H$_{78}$N$_4$O$_{16}$, 979.16 | Gel | 4.5-5 | Y | n/ap | 97.3% | 92.0% |
| 159 | 108 | C$_{40}$H$_{60}$N$_4$O$_{12}$, 788.92 | Wax | 4.5-5 | N | N | | |
| 149 | 98 | C$_{47}$H$_{74}$N$_4$O$_{16}$, 951.11 | Wax | 4.5-5 | N | N | | |
| 62 | 38 | C$_{34}$H$_{50}$N$_2$O$_{10}$, 646.77 | Powder | 4.5-5 | N | N | | |
| 57 | 35 | C$_{36}$H$_{52}$N$_2$O$_{10}$, 672.81 | Gel | 4.5-5 | N | N | | |
| 81 | 53 | C$_{34}$H$_{49}$N$_3$O$_9$, 643.77 | Wax | 4.5-5 | Y | n/ap | 92.4% | 31.5% |
| 150 | 99 | C$_{51}$H$_{82}$N$_4$O$_{18}$, 1039.21 | Wax | 4.5-5 | N | N | | |
| 160 | 109 | C$_{48}$H$_{76}$N$_4$O$_{16}$, 965.13 | Wax | 4.5-5 | N | N | | |
| 99 | 61 | C$_{42}$H$_{64}$N$_4$O$_{12}$, 816.98 | Gel | 4.5-5 | Y | n/ap | 97.1% | 92.2% |
| 151 | 100 | C$_{33}$H$_{42}$N$_4$O$_{10}$, 654.71 | Wax Solid | 4.5-5 | N | N | | |
| 152 | 101 | C$_{33}$H$_{46}$N$_4$O$_8$, 626.74 | Wax | 4.5-5 | N | N | | |
| 107 | 67 | C$_{43}$H$_{64}$N$_4$O$_{12}$, 828.99 | Gel | 4.5-5 | Y | n/ap | 96.3% | 91.2% |
| 106 | 66 | C$_{29}$H$_{40}$N$_4$O$_4$, 508.65 | Solid | 3.5-4 | N | N | | |
| 100 | 62 | C$_{38}$H$_{56}$N$_4$O$_{10}$, 728.87 | Gel | 4.5-5 | Y | n/ap | 95.2% | 86.7% |
| 108 | 68 | C$_{39}$H$_{56}$N$_4$O$_{10}$, 740.88 | Gel | 4.5-5 | N | N | | |
| 82 | 54 | C$_{36}$H$_{53}$N$_3$O$_{10}$, 687.82 | Wax | 4.5-5 | Y | n/ap | 82.7% | 41.7% |
| 102 | 64 | C$_{50}$H$_{80}$N$_4$O$_{16}$, 993.19 | Gel | 4.5-5 | Y | n/ap | 97.2% | 91.3% |
| 161 | 110 | C$_{39}$H$_{56}$N$_4$O$_{10}$, 740.88 | Yellow Gel | 4.5-5 | N | N | | |
| 101 | 63 | C$_{46}$H$_{72}$N$_4$O$_{14}$, 905.08 | Gel | 4.5-5 | Y | n/ap | 97.0% | 89.9% |
| 103 | 65 | C$_{54}$H$_{88}$N$_4$O$_{18}$, 1081.29 | Gel | 4.5-5 | Y | n/ap | 97.6% | 91.9% |
| 162 | 111 | C$_{43}$H$_{64}$N$_4$O$_{12}$, 828.99 | Gel | 4.5-5 | Y | n/ap | 96.4% | 88.6% |
| 118 | 77 | C$_{24}$H$_{30}$N$_2$O$_3$, Free Base 394.51 Salt 430.97 | Powder | 4-4.5 | N | N | | |
| 120 | 79 | C$_{37}$H$_{54}$N$_2$O$_{10}$, 686.83 | Gel | 4.5-5 | Y | n/ap | 96.9% | 90.7% |
| 119 | 78 | C$_{31}$H$_{42}$N$_2$O$_7$, 554.67 | Gel | 4.5-5 | N | N | | |
| 114 | 73 | C$_{25}$H$_{32}$N$_2$O$_3$, Free Base 408.53 Salt 444.99 | Powder | 4-4.5 | N | N | | |
| 64 | 40 | C$_{43}$H$_{66}$N$_4$O$_{12}$, 831.00 | Gel | 4.5-5 | Y | n/ap | 95.1% | 90.8% |
| 117 | 76 | C$_{38}$H$_{56}$N$_2$O$_{10}$, 700.86 | Gel | 4.5-5 | Y | n/ap | 97.0% | 92.9% |
| 116 | 75 | C$_{34}$H$_{48}$N$_2$O$_8$, 612.75 | Gel | 4.5-5 | N | N | | |
| 115 | 74 | C$_{32}$H$_{44}$N$_2$O$_7$, 568.70 | Gel | 4.5-5 | N | N | | |
| 110 | 69 | C$_{26}$H$_{34}$N$_2$O$_3$, Free Base 422.56 Salt 459.02 | Powder | 4.5-5 | Y | n/ap | 94.4% | 83.1% |
| 111 | 70 | C$_{39}$H$_{58}$N$_2$O$_{10}$, 714.89 | Gel | 4.5-5 | Y | n/ap | 98.3% | 95.6% |
| 125 | 84 | C$_{25}$H$_{32}$N$_2$O$_4$, Free Base 424.53 Salt 460.99 | Powder | 4.5-5 | N | N | | |
| 127 | 85 | C$_{38}$H$_{56}$N$_2$O$_{11}$, 716.86 | Gel | 4.5-5 | N | N | | |
| 142 | 91 | C$_{34}$H$_{50}$N$_4$O$_8$, Free Base 642.78 Salt 679.24 | Powder | 5-5.5 | Y | n/ap | 93.3% | 75.4% |
| 121 | 80 | C$_{27}$H$_{36}$N$_2$O$_3$, Free Base 436.59 Salt 473.05 | Powder | 5.-5.5 | N | N | | |
| 123 | 82 | C$_{26}$H$_{33}$N$_3$O$_4$, Free Base 451.56 Salt 488.02 | Powder | 4.5-5 | Y | n/ap | 95.2% | 72.0% |
| 124 | 83 | C$_{33}$H$_{45}$N$_3$O$_8$, 611.73 | Wax | 5-5.5 | Y | n/ap | 99.7% | 96.6% |
| 128 | 86 | C$_{25}$H$_{31}$N$_3$O$_4$, Free Base 437.53 Salt 473.99 | Powder | 4.5-5 | Y | n/ap | 89.1% | 43.0% |
| 122 | 81 | C$_{40}$H$_{60}$N$_2$O$_{10}$, 728.91 | Gel | 5.-5.5 | Y | n/ap | 96.8% | 93.9% |
| 135 | 89 | C$_{25}$H$_{34}$N$_4$O$_4$, Free Base 454.56 Salt 527.48 | Powder | 4.5-5 | Y | n/ap | 99.6% | 71.8% |
| 133 | 87 | C$_{26}$H$_{36}$N$_4$O$_4$, Free Base 468.59 Salt 527.48 | Powder | 4.5-5 | N | N | | |
| 128B | 86B | C$_{32}$H$_{44}$N$_2$O$_7$, 568.70 | Gel | 5.5-6 | N | N | | |
| 112 | 71 | C$_{33}$H$_{46}$N$_2$O$_7$, 582.73 | Gel | 5.5-6 | N | N | | |
| 113 | 72 | C$_{37}$H$_{54}$N$_2$O$_9$, 670.83 | Gel | 5.5-6 | N | N | | |
| 134 | 88 | C$_{40}$H$_{60}$N$_4$O$_{12}$, 788.92 | Gel | 5.5-6 | Y | n/ap | 99.3% | 95.2% |
| 136 | 90 | C$_{39}$H$_{58}$N$_4$O$_{12}$, 774.90 | Gel | 5.5-6 | N | N | | |

EXAMPLE 113

Saline Solubility at 10.00 mg/mL, 5.00 mg/mL and 2.50 mg/mL, and Conversion of Prodrugs in Human Plasma and Mouse Plasma Assays were performed to determine the saline solubility at 10.00, 5.00 and 2.50 mg/ml of certain of the prodrug compounds of Examples 1-111. The following procedures were used Step 1. Sample preparation. An amount of the compound sample was precisely weighed to correspond to around 10 mg of the hydroxamate of compound 1, taking into account the mass of the leaving group and the salt factor if applicable. The sample was placed in a 16×125 mm glass screw cap tube. Saline was added so that the final concentration of hydroxamate 1 was 10.00 mg/mL. The tube was shaken for 1 hour on a Vortex apparatus then centrifuged at 3000 rpm (1800 rcf) for 5 minutes. If the compound example was soluble (no precipitate formed) then the pH was measured with a pH meter, and the procedure continued to step 2. If a precipitate formed then the sample was diluted with saline so that the final concentration of the hydroxamate of compound 1 became 5.00 mg/mL, and the shaking and centrifuging steps were repeated. If the compound example was soluble (no precipitate formed) then the pH was measured with a pH meter, and the procedure continued to step 2. If a precipitate formed then the sample was diluted with saline so that the final concentration of the hydroxamate of compound 1 became 2.50 mg/mL, and the shaking and centrifuging steps were repeated. If the compound example was soluble (no precipitate formed) then the pH was measured with a pH meter, and the procedure continued to step 2

Step 2. HPLC analysis. A 500 µL aliquot of a sample solution prepared according to Step 1 was taken up into a 1.5 mL injection vial to which was added 500 µL of saline. The vial was shaken on a Vortex apparatus, injected into the HPLC instrument (UV detection, zero time point) and the retention time and purity of the sample compound were determined. The injection was repeated after 6 hours, and a comparison was made of the retention time, peak areas and level of degradation (if any) using the GDADI50 method.

Conversion of Prodrugs in Human Plasma

Step 1. Sample preparation. A quanity of blank human plasma (Na-Heparin treated) was incubated at 37° C. for 30 minutes. An amount of the compound sample was precisely weighed to correspond to around 5.00 mg of the hydroxamate of compound 1, taking into account the mass of the leaving group and the salt factor if applicable. The sample was placed in a 16×125 mm glass screw cap tube. The incubated blank human plasma was added so that the final concentration of hydroxamate 1 was 1.00 mg/mL. The sample was sonicated for 30 seconds, shaken for 30 seconds on a Vortex apparatus, and run through the HPLC procedure of Step 2 to get a time point zero value. The samples were stored in an incubator at 37° C., and the HPLC analysis of Step 2 was repeated in 30 minutes and 1 hour.

Step 2. Protein precipitation and HPLC analysis of plasma. A 50 µL aliquot of plasma was taken in a 1.5 mL Eppendorf vial, to which was added 200 µL of MeCN. The vial was capped and shaken on a Vortex apparatus for 30 seconds, then centrifuged at 13000 rpm (15700 rcf) for five minutes. When centrifuging was complete, 100 µL of the supernatant was placed in an injection vial containing an insert, to which was added 100 µL of 0.1% formic acid in water. The vial was capped and shaken on a Vortex apparatus for 30 seconds, and the contents were injected into the HPLC-UV instrument, and a comparison was made of the retention time, peak areas and level of degradation (if any) using the GDADI50 method.

Step 3. Reference sample preparation. An amount of the compound sample was precisely weighed to correspond to around 5.00 mg of the hydroxamate of compound 1, taking into account the mass of the leaving group and the salt factor if applicable. The sample was placed in a 16×125 mm glass screw cap tube. A quantity of MeCN/H2O 50/50 v/v was added so that the final concentration of hydroxamate 1 was 1.00 mg/mL. An injection vial was filled with 100 µL of this sample stock solution and 900 µL of a solution of 40/60 MeCN/0.1% formic acid in water. The vial was capped and the contents were injected into the HPLC-UV instrument, and a comparison was made of the retention time, peak areas and level of degradation (if any) using the GDADI50 method.

Conversion of Prodrugs in Mouse Plasma

Step 1. Sample preparation. A quanity of blank mouse plasma (Na-Heparin treated) was incubated at 37° C. for 30 minutes. An amount of the compound sample was precisely weighed to correspond to around 5.00 mg of the hydroxamate of compound 1, taking into account the mass of the leaving group and the salt factor if applicable. The sample was placed in a 16×125 mm glass screw cap tube. The incubated blank mouse plasma was added so that the final concentration of hydroxamate 1 was 1.00 mg/mL. The sample was sonicated for 30 seconds, shaken for 30 seconds on a Vortex apparatus, and run through the HPLC procedure of Step 2 to get a time point zero value. The samples were stored in an incubator at 37° C., and the HPLC analysis of Step 2 was repeated at 30 minutes and 1 hour Step 2. Protein precipitation and HPLC analysis of plasma. A 50 µL aliquot of plasma was taken in a 1.5 mL Eppendorf vial, to which was added 200 µL of MeCN. The vial was capped and shaken on a Vortex apparatus for 30 seconds, then centrifuged at 13000 rpm (15700 rcf) for five minutes. When centrifuging was complete, 100 µL of the supernatant was placed in an injection vial containing an insert, to which was added 100 µL of 0.1% formic acid in water. The vial was capped and shaken on a Vortex apparatus for 30 seconds, and the contents were injected into the HPLC-UV instrument, and a comparison was made of the retention time, peak areas and level of degradation (if any) using the GDADI50 method.

The results of the solubility studies, stability studies, and conversion of prodrug studies are shown in Tables 21A and 21B below.

TABLE 21A

Conversion of Prodrug to Compound 1 in Human Plasma (Na-Heparin treated)

| Compound ID | Structure |
|---|---|
| (Cpd 54) | HCl · phenyl-(CH2)3-C6H4-CH2-C(O)-NH-O-C(O)-cyclopropyl-CH2-NH2 |

TABLE 21A-continued
Conversion of Prodrug to Compound 1 in Human Plasma (Na-Heparin treated)
(Cpd 14, ex. 9)
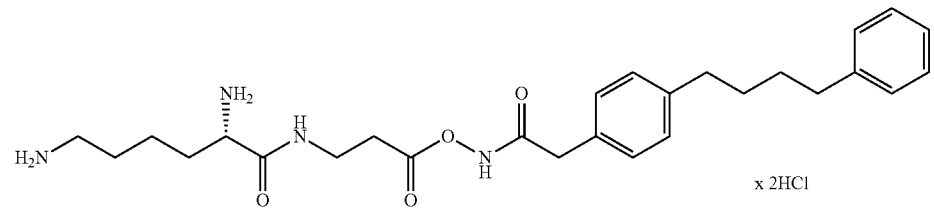 [SMILES: NCCCC[C@H](N)C(=O)NCCC(=O)ONC(=O)Cc1ccc(CCCCc2ccccc2)cc1]
(Cpd 63, ex. 39)
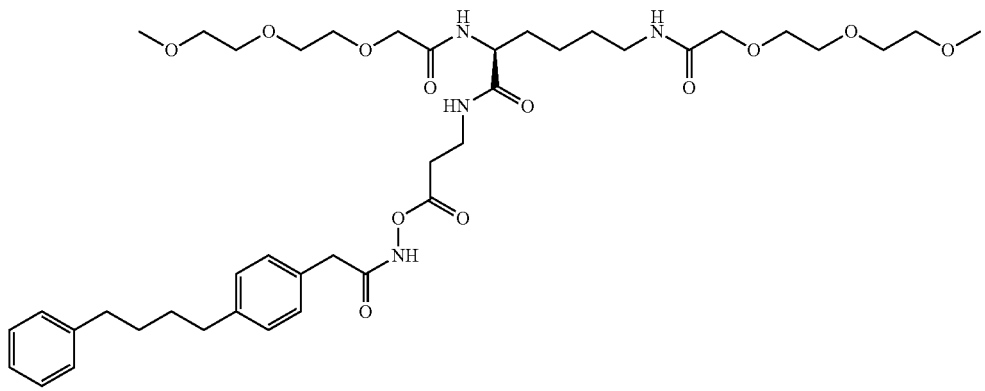 [SMILES: COCCOCCOCC(=O)NCCCC[C@H](NC(=O)COCCOCCOC)C(=O)NCCC(=O)ONC(=O)Cc1ccc(CCCCc2ccccc2)cc1]
(Cpd 68, ex. 43)
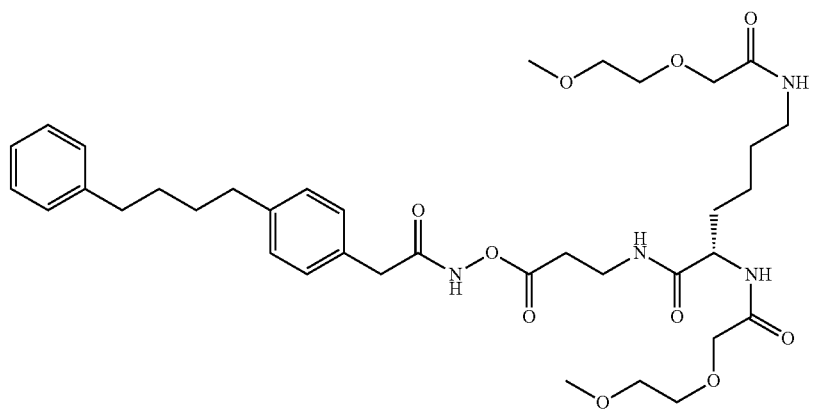 [SMILES: COCCOCC(=O)NCCCC[C@H](NC(=O)COCCOC)C(=O)NCCC(=O)ONC(=O)Cc1ccc(CCCCc2ccccc2)cc1]
(Cpd 99, ex. 61)
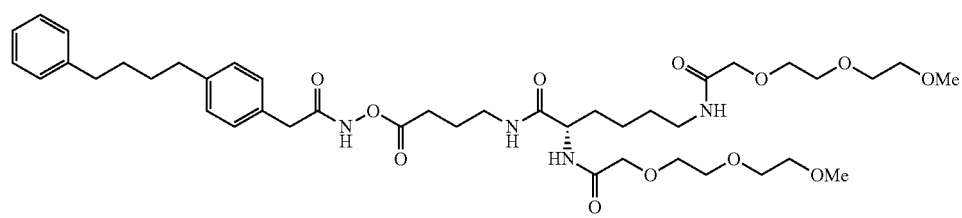 [SMILES: COCCOCCOCC(=O)NCCCC[C@H](NC(=O)COCCOCCOC)C(=O)NCCCC(=O)ONC(=O)Cc1ccc(CCCCc2ccccc2)cc1]
(Cpd 100, ex. 62)
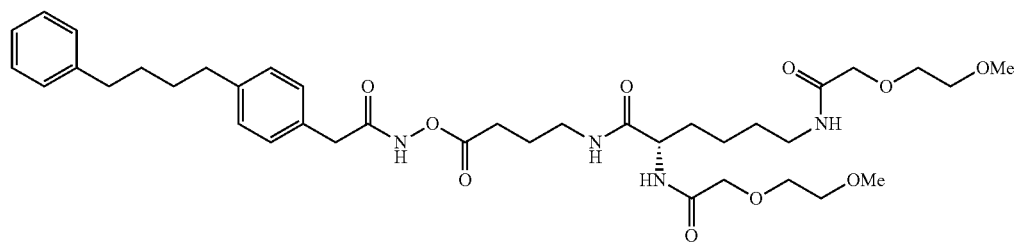 [SMILES: COCCOCC(=O)NCCCC[C@H](NC(=O)COCCOC)C(=O)NCCCC(=O)ONC(=O)Cc1ccc(CCCCc2ccccc2)cc1]

TABLE 21A-continued
Conversion of Prodrug to Compound 1 in Human Plasma (Na-Heparin treated)
(Cpd 64, ex. 40)
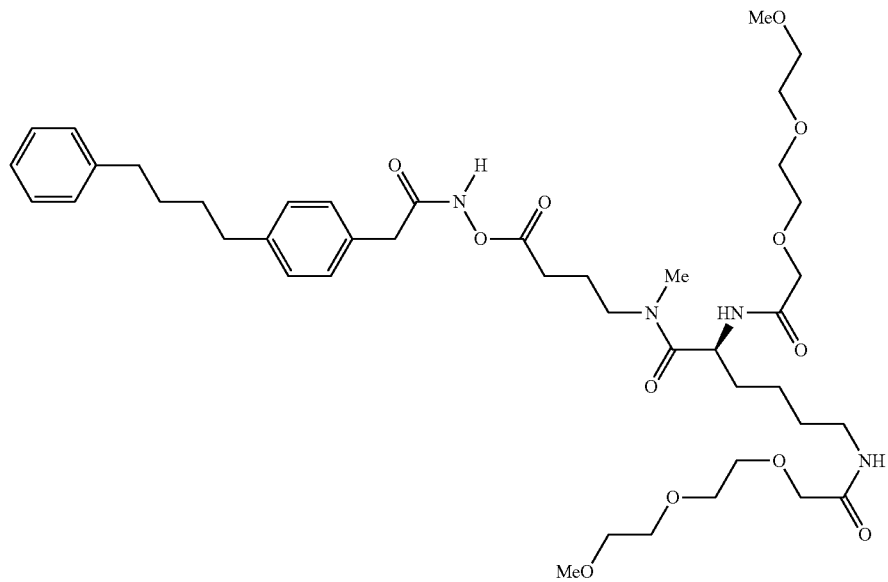 [SMILES: COCCOCCOCC(=O)NCCCC[C@H](NC(=O)COCCOCCOC)C(=O)N(C)CCCC(=O)ONC(=O)Cc1ccc(CCCCc2ccccc2)cc1]
(Cpd 110, ex. 92)
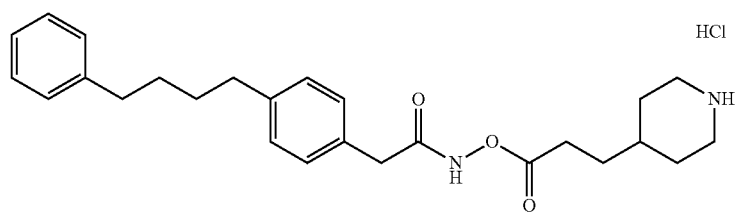 [SMILES: O=C(Cc1ccc(CCCCc2ccccc2)cc1)NOC(=O)CCC1CCNCC1 ; Cl]
(Cpd 111, ex. 70)
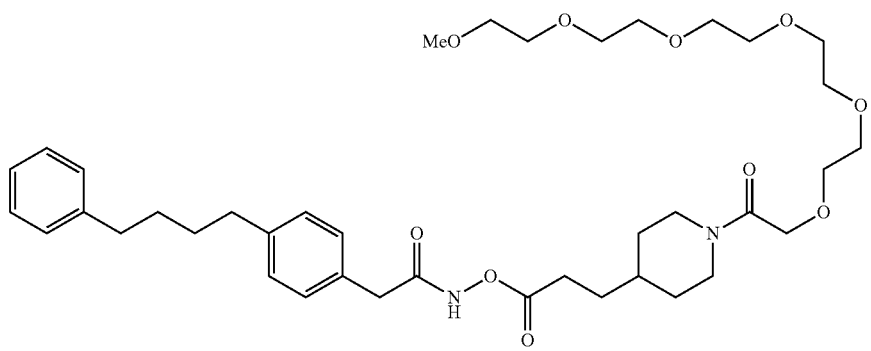 [SMILES: COCCOCCOCCOCCOCCOCC(=O)N1CCC(CCC(=O)ONC(=O)Cc2ccc(CCCCc3ccccc3)cc2)CC1]
(Cpd 122, ex. 81)
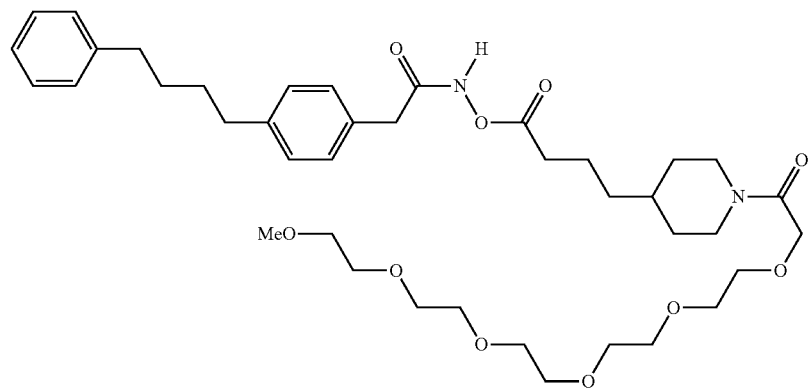 [SMILES: COCCOCCOCCOCCOCCOCC(=O)N1CCC(CCCC(=O)ONC(=O)Cc2ccc(CCCCc3ccccc3)cc2)CC1]

TABLE 21A-continued

Conversion of Prodrug to Compound 1 in Human Plasma (Na-Heparin treated)

(Cpd 135, ex. 89)

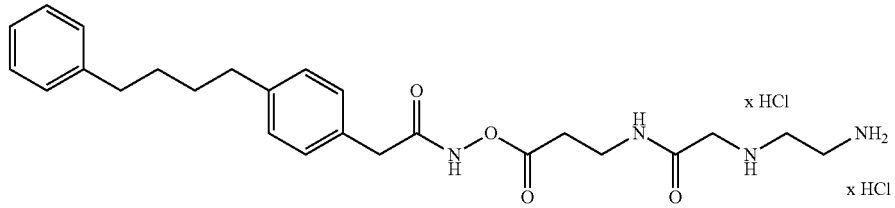 [SMILES: NCCNCC(=O)NCCC(=O)ONC(=O)Cc1ccc(CCCCc2ccccc2)cc1]

| Compound ID | Formula, M.W., Appearance | Cpd 1 at 0 hr (mg/mL) | Prodrug loss at 0.5 hr (%) | Cpd 1 at 0.5 hr (mg/mL) | Prodrug loss at 1 hr (%) | Cpd 1 at 1 hr (mg/mL) | Highest prodrug solubility in saline (equivalent of Cpd 1) |
|---|---|---|---|---|---|---|---|
| (Cpd 54) | $C_{23}H_{28}N_2O_3$ HCl, Free Base 380.48 Salt 416.94, Powder | 0.0153 | 50.9% | 0.0350 | 71.6% | 0.0392 | 2.50 mg/mL |
| (Cpd 14, ex. 9) | $C_{27}H_{37}N_4O_4$ 2HCl, Free Base 481.61 Salt 554.53, Powder | 0.0440 | 100% | 1.38 | 100.0% | 1.34 | 10.0 mg/mL |
| (Cpd 63, ex. 39) | $C_{41}H_{62}N_4O_{12}$ 802.95 Gel | 0.125 | 99.3% | 0.861 | 100.0% | 0.890 | 1.00 mg/mL |
| (Cpd 68, ex. 43) | $C_{37}H_{54}N_4O_{10}$ 714.85 Gel | 0.0583 | 98.6% | 0.873 | 99.4% | 0.948 | 10.0 mg/mL |
| (Cpd 99, ex. 61) | $C_{42}H_{64}N_4O_{12}$ 816.98 Gel | 0.0283 | 22.7% | 0.682 | 89.1% | 1.02 | 2.50 mg/mL |
| (Cpd 100, ex. 62) | $C_{38}H_{56}N_4O_{10}$ 728.87 Gel | 0.0517 | 69.4% | 0.603 | 93.4% | 0.823 | 1.00 mg/mL |
| (Cpd 64, ex. 40) | $C_{43}H_{66}N_4O_{12}$ 831.00 Gel | 0.0227 | 78.7% | 0.572 | 100.0% | 0.703 | 10.0 mg/mL |
| (Cpd 110, ex. 92) | $C_{26}H_{34}N_2O_3$ Free Base 422.56 Salt 459.02 Powder | 0.0408 | 85.5% | 0.876 | 99.6% | 0.977 | 10.0 mg/mL |
| (Cpd 111, ex. 70) | $C_{39}H_{58}N_2O_{10}$ 714.89 Gel | 0.0099 | 65.5% | 0.694 | 90.5% | 0.965 | 10.0 mg/mL |
| (Cpd 122, ex. 81) | $C_{40}H_{60}N_2O_{10}$ 728.91 Gel | 0.0171 | 66.6% | 0.815 | 91.9% | 0.997 | 10.0 mg/mL |
| Cpd 135, ex. 89 | $C_{25}H_{34}N_4O_4$ Free Base 454.56 Salt 527.48 Powder | 0.0610 | 98.7% | 0.977 | 99.8% | 1.002 | 10.0 mg/mL |

TABLE 21B

Conversion of Prodrug to Compound 1 In Mouse Plasma (Na-Heparin treated)

| Compound ID | Structure |
|---|---|
| (Cpd 54) | 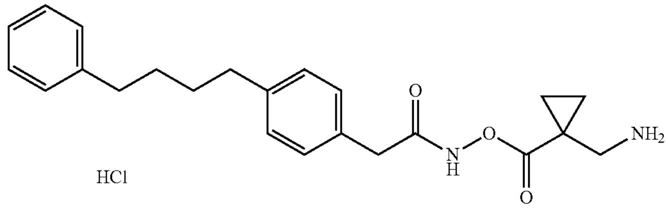 [SMILES: NCC1(C(=O)ONC(=O)Cc2ccc(CCCCc3ccccc3)cc2)CC1 ; Cl] |
| (Cpd 14, ex. 9) | 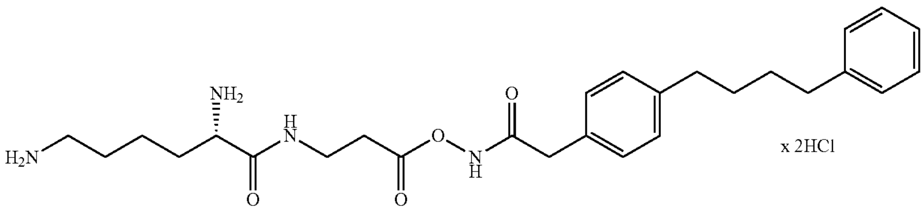 [SMILES: NCCCC[C@H](N)C(=O)NCCC(=O)ONC(=O)Cc1ccc(CCCCc2ccccc2)cc1] |
| (Cpd 63, ex. 39) | 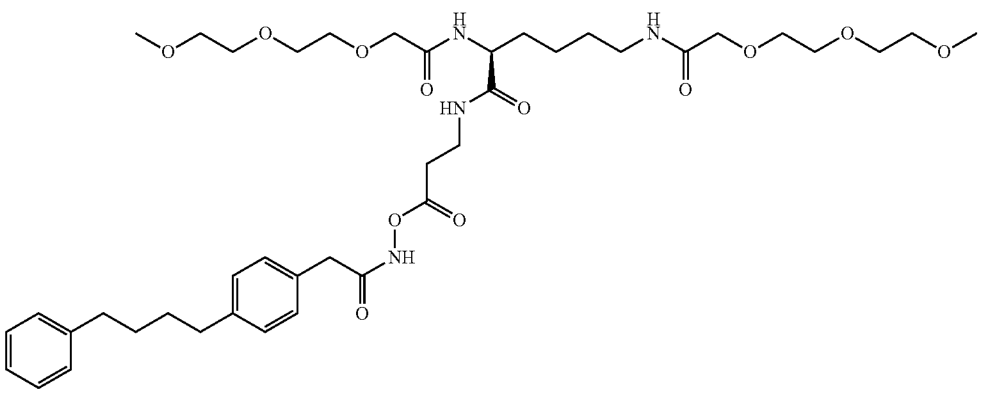 [SMILES: COCCOCCOCC(=O)NCCCC[C@H](NC(=O)COCCOCCOC)C(=O)NCCC(=O)ONC(=O)Cc1ccc(CCCCc2ccccc2)cc1] |
| (Cpd 68, ex. 43) | 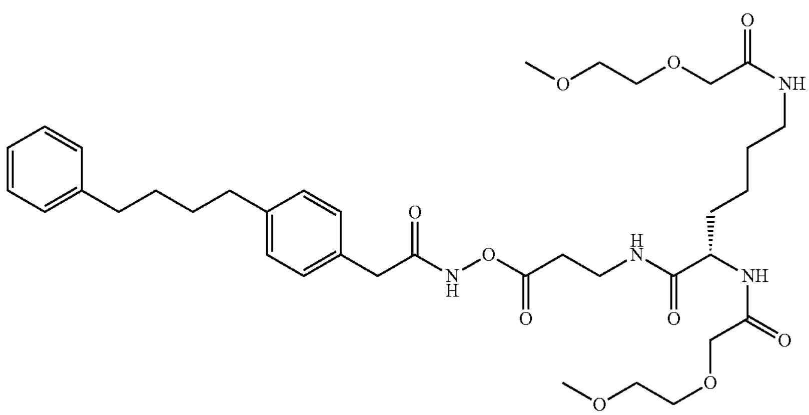 [SMILES: COCCOCC(=O)NCCCC[C@H](NC(=O)COCCOC)C(=O)NCCC(=O)ONC(=O)Cc1ccc(CCCCc2ccccc2)cc1] |
| (Cpd 99, ex. 61) | 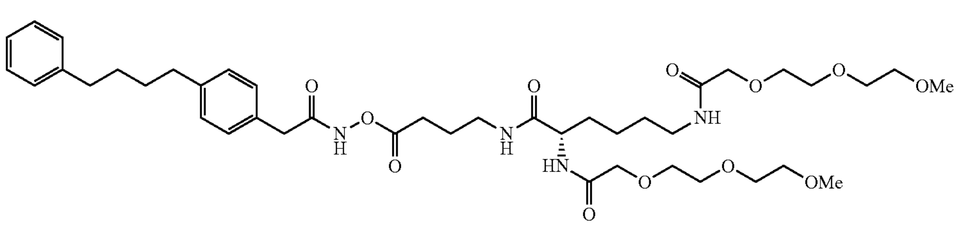 [SMILES: COCCOCCOCC(=O)NCCCC[C@H](NC(=O)COCCOCCOC)C(=O)NCCCC(=O)ONC(=O)Cc1ccc(CCCCc2ccccc2)cc1] |

TABLE 21B-continued
Conversion of Prodrug to Compound 1 In Mouse Plasma (Na-Heparin treated)
(Cpd 100, ex. 62)
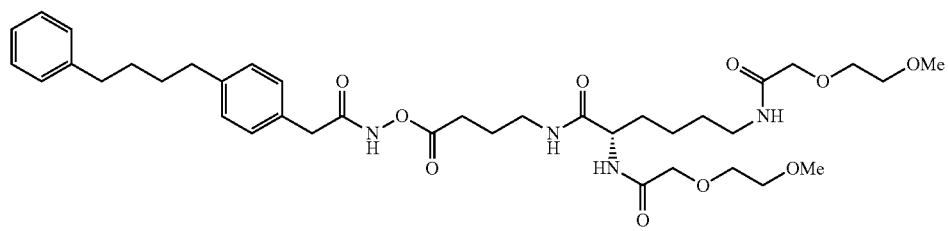 [SMILES: COCCOCC(=O)NCCCC[C@H](NC(=O)COCCOC)C(=O)NCCCC(=O)ONC(=O)Cc1ccc(CCCCc2ccccc2)cc1]
(Cpd 120, ex. 79)
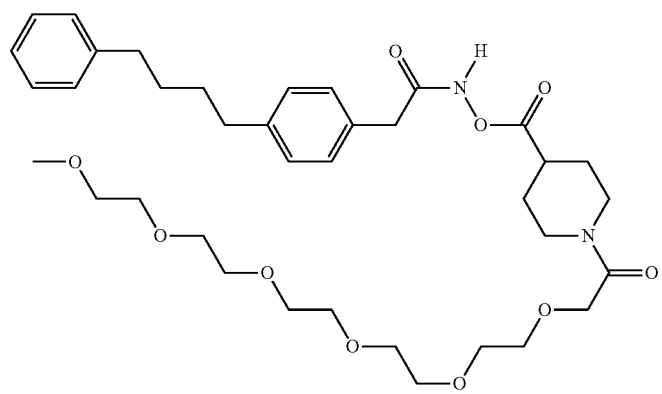 [SMILES: COCCOCCOCCOCCOCCOCC(=O)N1CCC(C(=O)ONC(=O)Cc2ccc(CCCCc3ccccc3)cc2)CC1]
(Cpd 64, ex. 40)
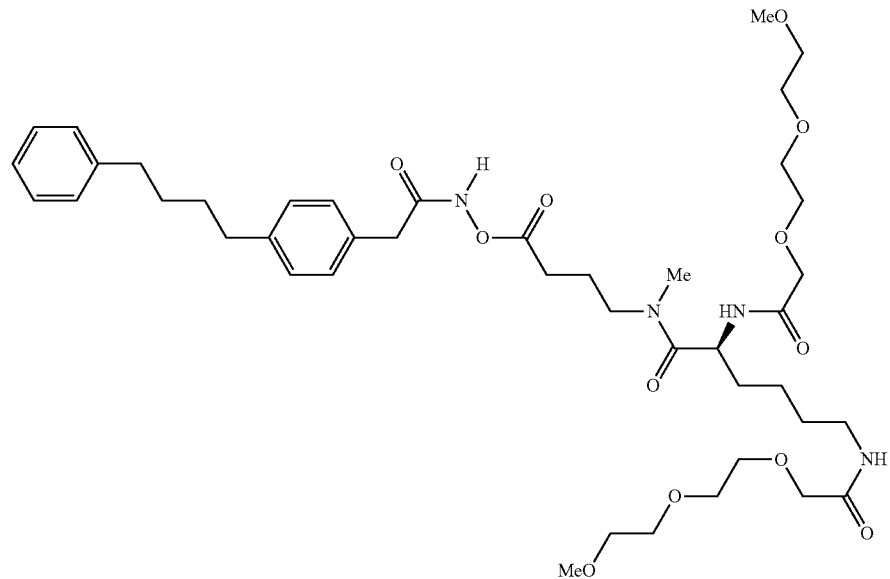 [SMILES: COCCOCCOCC(=O)NCCCC[C@H](NC(=O)COCCOCCOC)C(=O)N(C)CCCC(=O)ONC(=O)Cc1ccc(CCCCc2ccccc2)cc1]
(Cpd 110, ex. 92)
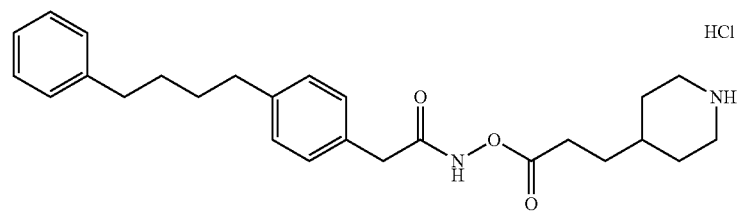 [SMILES: O=C(Cc1ccc(CCCCc2ccccc2)cc1)NOC(=O)CCC1CCNCC1 ; Cl]

TABLE 21B-continued

Conversion of Prodrug to Compound 1 In Mouse Plasma (Na-Heparin treated)

(Cpd 111, ex. 70)

(Cpd 122, ex. 81)

(Cpd 135, ex. 89)

| Compound ID | Formula, M.W., Appearance | Pro-drug solubility in plasma | Compd 1 at 0 hr (mg/mL) | Pro-drug loss at 0.5 hr (%) | Compd 1 at 0.5 hr (mg/mL) | Pro-drug loss at 1 hr (%) |
|---|---|---|---|---|---|---|
| (Cpd 54) | $C_{23}H_{28}N_2O_3$ HCl, Free Base 380.48 Salt 416.94, Powder | Yes | 0.0130 | 62.6% | 0.120 | 100% |
| (Cpd 14, ex. 9) | $C_{27}H_{37}N_4O_4$ 2HCl Free Base 481.61 Salt 554.53, Powder | Yes* | 0.288 | 100% | 0.662 | 100% |
| (Cpd 63, ex. 39) | $C_{41}H_{62}N_4O_{12}$, 802.95 Gel | Yes* | 0.494 | 100% | 0.731 | 100% |
| (Cpd 68, ex. 43) | $C_{37}H_{54}N_4O_{10}$ 714.85 Gel | Yes* | 0.361 | 100% | 0.949 | 100% |
| (Cpd 99, ex. 61) | $C_{42}H_{64}N_4O_{12}$ 816.98 Gel | Yes* | 0.698 | 100% | 0.852 | 100% |
| (Cpd 100, ex. 62) | $C_{38}H_{56}N_4O_{10}$ 728.87 Gel | Yes* | 0.509 | 100% | 0.950 | 100% |
| (Cpd 120, ex. 79) | $C_{37}H_{54}N_2O_{10}$, 686.83 Gel | Yes* | 0.612 | 100% | 0.776 | 100% |
| (Cpd 64, ex. 40) | $C_{43}H_{66}N_4O_{12}$, 831.00 Gel | Yes* | 0.797 | 100% | 0.982 | 100% |
| (Cpd 110, ex. 92) | $C_{26}H_{34}N_2O_3$, Free Base 422.56 Salt 459.02 Powder | Yes* | 0.459 | 100% | 0.867 | 100% |

TABLE 21B-continued

Conversion of Prodrug to Compound 1 In Mouse Plasma (Na-Heparin treated)

| | | | | | | |
|---|---|---|---|---|---|---|
| (Cpd 111, ex. 70) | $C_{39}H_{58}N_2O_{10}$, 714.89 Gel | Yes* | 0.232 | 98% | 1.398 | 99% |
| (Cpd 122, ex. 81) | $C_{40}H_{60}N_2O_{10}$ 728.91 | Yes** | 0.796 | 100% | 0.930 | 100% |
| (Cpd 135, ex. 89) | $C_{25}H_{34}N_4O_4$ Free Base 454.56 Salt 527.48 | Yes* | 0.288 | 100% | 0.948 | 100% |

*Plasma quickly became cloudy

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A compound that is a salt of
   N-(2-aminoacetoxy)-2-(4-(4-phenylbutyl)phenyl)acetamide,
   N-(6-aminohexanoyloxy)-2-(4-(4-phenylbutyl)phenyl)acetamide,
   N-(3-Aminopropanoyloxy)-2-(4-(4-phenylbutyl)phenyl)acetamide,
   N-(4-aminobutanoyloxy)-2-(4-(4-phenylbutyl)phenyl)acetamide, or
   N-(8-aminooctanoyloxy)-2-(4-(4-phenylbutyl)phenyl)acetamide.

2. A compound that is
   N-Hydroxy-N-(morpholinomethyl)-2-(4-(4-phenylbutyl)phenyl)acetamide,
   N-hydroxy-N-((4-methylpiperazin-1-yl)methyl)-2-(4-(4-phenylbutyl)phenyl)acetamide,
   N-hydroxy-N-(hydroxymethyl)-2-(4-(4-phenylbutyl)phenyl)acetamide,
   tert-butyl 8-oxo-8-(2-(4-(4-phenylbutyl)phenyl)acetamidooxy)octylcarbamate,
   Methyl (1-((2-(4-(4-phenylbutyl)phenyl)acetamidooxy)carbonyl)cyclopropyl)methylcarbamate,
   (S)-N,N'-(6-Oxo-6-(2-(4-(4-phenylbutyl)phenyl)acetamidooxy)hexane-1,5-diyl)bis(2-(2-(2-methoxyethoxy)ethoxy)acetamide),
   N-(Isopropylcarbamoyloxy)-2-(4-(4-phenylbutyl)phenyl)acetamide,
   N-(Isopropylcarbamoyloxy)-2-(4-(4-phenylbutyl)phenyl)acetamide,
   N-(ethylcarbamoyloxy)-2-(4-(4-phenylbutyl)phenyl)acetamide,
   (S)-N,N'-(6-Oxo-6-(2-(4-(4-phenylbutyl)phenyl)acetamidooxy)hexane-1,5-diyl)bis(2-(2-methoxyethoxy)acetamide),
   N-([ethoxycarbonylmethyl]carbamoyl)-N-([ethoxycarbonylmethyl]carbamoyloxy)-2-(4-(4-phenylbutyl)phenyl)acetamide,
   (S)-N,N'-(6-Oxo-6-(3-oxo-3-(2-(4-(4-phenylbutyl)phenyl)acetamidooxy)propylamino)hexane-1,5-diyl)diacetamide,
   (S)-N,N'-(3-oxo-3-(3-oxo-3-(2-(4-(4-phenylbutyl)phenyl)acetamidooxy)propylamino)propane-1,2-diyl)bis(3-methoxypropanamide,
   (S)-10-(2-acetoxyacetamido)-2,5,9,13-tetraoxo-1-(4-(4-phenylbutyl)phenyl)-4-oxa-3,8,12-triazatetradecan-14-yl acetate,
   N-1-(2-(2-(2-Methoxyethoxy)ethoxy)ethyl)-N-3-(2-(1-((2-(4-(4-phenylbutyl)phenyl)acetamidooxy)carbonylcyclopropyl)methyl)carbamoylethyl)urea,
   N-1-(2-(2-(2-methoxyethoxy)ethoxy)ethyl)-N-3-(2-(1-(4-(2-(4-(4-phenylbutyl)phenyl)acetamidooxy)carbonylpiperazine)carbamoyl)ethyl)urea,
   (S)-N,N'-(6-oxo-6-(3-oxo-3-(2-(4-(4-phenylbutyl)phenyl)acetamidooxy)propylamino)hexane-1,5-diyl)bis(3-methoxypropanamide),
   (S)-10-(2-acetoxyacetamido)-2,5,9,16-tetraoxo-1-(4-(4-phenylbutyl)phenyl)-4-oxa-3,8,15-triazaheptadecan-17-yl acetate),
   (S)-N,N'-(5-oxo-5-(3-oxo-3-(2-(4-(4-phenylbutyl)phenyl)acetamidooxy)propylamino)pentane-1,4-diyl)bis(3-methoxypropanamide)),
   (S)-dimethyl 6-oxo-6-(3-oxo-3-(2-(4-(4-phenylbutyl)phenyl)acetamidooxy)propylamino)hexane-1,5-diyldicarbamate),
   4-oxo-N,N-bis(12-oxo-2,5,8-trioxa-11-azatridecan-13-yl)-4-(2-(4-(4-phenylbutyl)phenyl)acetamidooxy)butanamide,
   (S)-10-(2-acetoxyacetamido)-2,5,9,15-tetraoxo-1-(4-(4-phenylbutyl)phenyl)-4-oxa-3,8,14-triazahexadecan-16-yl acetate),
   (S)-10-(2-acetoxyacetamido)-2,5,9,14-tetraoxo-1-(4-(4-phenylbutyl)phenyl)-4-oxa-3,8,13-triazapentadecan-15-yl acetate,
   (S)-N,N'-(4-oxo-4-(3-oxo-3-(2-(4-(4-phenylbutyl)phenyl)acetamidooxy)propylamino)butane-1,3-diyl)bis(3-methoxypropanamide),
   N,N'-((S)-6-Oxo-6-((S)-2-((2-(4-(4-phenylbutyl)phenyl)acetamidooxy)carbonyl)pyrrolidin-1-yl)hexane-1,5-diyl)bis(2-(2-(2- methoxyethoxy)ethoxy)acetamide),
   N,N'-((S)-6-oxo-6-((S)-2-((2-(4-(4-phenylbutyl)phenyl)acetamidooxy)carbonyl)pyrrolidin-1-yl)hexane-1,5-diyl)bis(2-(2- methoxyethoxy)acetamide),
   2-(2-(2-Methoxyethoxy)ethoxy)-N-(2-oxo-2-(4-oxo-4-(2-(4-(4-phenylbutyl)phenyl)acetamidooxy)butylamino)ethyl)-N-(10-oxo-2,5,8- trioxa-11-azatridecan-13-yl) acetamide, or
   2-(2-(2-methoxyethoxy)ethoxy)-N-(2-oxo-2-(3-oxo-3-(2-(4-(4-phenylbutyl)phenyl)acetamidooxy)propylamino)ethyl)-N-(10-oxo-2,5,8- trioxa-11-azatridecan-13-yl)acetamide.

3. A compound that is a pharmaceutically acceptable salt of the compound (S)-2,6-diamino-N-(3-oxo-3-(2-(4-(4-phenylbutyl)phenyl)acetamidooxy)propyl)hexanamide.

4. The compound according to claim 3 that is (S)-2,6-diamino-N-(3-oxo-3-(2-(4-(4-phenylbutyl)phenyl)acetamidooxy)propyl)hexanamide dihydrochloride.

5. A composition comprising the compound of claim 3 together with a pharmaceutically acceptable carrier, excipient, and/or diluent.

6. A composition comprising the compound of claim 4 together with a pharmaceutically acceptable carrier, excipient, and/or diluent.

7. A compound that is
N-(3-cyclohexylpropanoyloxy)-2-(4-(4-phenylbutyl)phenyl)acetamide,
N-(3-methoxypropanoyloxy)-2-(4-(4-phenylbutyl)phenyl)acetamide,
N-(2-cyclopropylacetoxy)-2-(4-(4-phenylbutyl)phenyl)acetamide,
N-acetoxy-2-(4-(4-phenylbutyl)phenyl)acetamide,
2-(4-(4-phenylbutyl)phenyl)-N-(propionyloxy)acetamide,
2-(4-(4-Phenylbutyl)phenyl)-N-(2-propylpentanoyloxy)acetamide,
N-(butyryloxy)-2-(4-(4-phenylbutyl)phenyl)acetamide,
N-(pentanoyloxy)-2-(4-(4-phenylbutyl)phenyl)acetamide
(S)-2,6-diamino-N-((S)-1-oxo-1-(2-(4-(4-phenylbutyl)phenyl)acetamidooxy)propan-2-yl)hexanamide,
(S)-6-oxo-6-((S)-1-oxo-3-phenyl-1-(2-(4-(4-phenylbutyl)phenyl)acetamidooxy)propan-2-ylamino)hexane-1,5-diamine,
(S)-2-amino-N-(6-oxo-6-(2-(4-(4-phenylbutyl)phenyl)acetamidooxy)hexyl)-3-phenylpropanamide,
(S)-2-amino-N-(3-oxo-3-(2-(4-(4-phenylbutyl)phenyl)acetamidooxy)propyl)propanamide,
(2S,3S)-2-Amino-3-methyl-N-(3-oxo-3-(2-(4-(4-phenylbutyl)phenyl)acetamidooxy)propyl)pentanamide,
(S)-2-amino-N-(3-oxo-3-(2-(4-(4-phenylbutyl)phenyl)acetamidooxy)propyl)-3-phenylpropanamide,
(S)-2,6-diamino-N-(3-oxo-3-(2-(4-(4-phenylbutyl)phenyl)acetamidooxy)propyl)hexanamide,
(S)-2-amino-N-(4-oxo-4-(2-(4-(4-phenylbutyl)phenyl)acetamidooxy)butyl)-3-phenylpropanamide,
(S)-2-amino-3-(4-hydroxyphenyl)-N-(6-oxo-6-(2-(4-(4-phenylbutyl)phenyl)acetamidooxy)hexyl)propanamide,
(S)-N,N'-(6-Oxo-6-(3-oxo-3-(2-(4-(4-phenylbutyl)phenyl)acetamidooxy)propylamino)hexane-1,5-diyl)bis(2-(2-(2- methoxyethoxy)ethoxy)acetamide),
(S)-N,N'-(3-oxo-3-(3-oxo-3-(2-(4-(4-phenylbutyl)phenyl)acetamidooxy)propylamino)propane-1,2-diyl)bis(2-(2-(2- methoxyethoxy)ethoxy)acetamide),
(S)-N,N'-(3-oxo-3-(3-oxo-3-(2-(4-(4-phenylbutyl)phenyl)acetamidooxy)propylamino)propane-1,2-diyl)bis(2-(2-methoxyethoxy)acetamide),
(S)-N,N'-(4-oxo-4-(3-oxo-3-(2-(4-(4-phenylbutyl)phenyl)acetamidooxy)propylamino)butane-1,3-diyl)bis(2-(2-(2- methoxyethoxy)ethoxy)acetamide),
N,N'-((S)-6-((S)-2-Methyl-3-oxo-3-(2-(4-(4-phenylbutyl)phenyl)acetamidooxy)propylamino)-6-oxohexane-1,5-diyl)bis(2-(2-(2-ethoxyethoxy)ethoxy)acetamide),
(S)-N,N'-(5-oxo-5-(3-oxo-3-(2-(4-(4-phenylbutyl)phenyl)acetamidooxy)propylamino)pentane-1,4-diyl)bis(2-(2-methoxyethoxy)acetamide),
(S)-N,N'-(5-oxo-5-(3-oxo-3-(2-(4-(4-phenylbutyl)phenyl)acetamidooxy)propylamino)pentane-1,4-diyl)bis(2-(2-(2- methoxyethoxy)ethoxy)acetamide),
(S)-N,N'-(4-oxo-4-(3-oxo-3-(2-(4-(4-phenylbutyl)phenyl)acetamidooxy)propylamino)butane-1,3-diyl)bis(2,5,8,11,14-pentaoxahexadecan-16- amide),
(S)-N,N'-(4-oxo-4-(3-oxo-3-(2-(4-(4-phenylbutyl)phenyl)acetamidooxy)propylamino)butane-1,3-diyl)bis(2,5,8,11,14,17-hexaoxanonadecan-19- amide),
(S)-N,N'-(6-oxo-6-((1-((2-(4-(4-phenylbutyl)phenyl)acetamidooxy)carbonyl)cyclopropyl)methylamino)hexane-1,5-diyl)bis(2-(2- methoxyethoxy)acetamide),
(S)-N,N'-(6-Oxo-6-(4-oxo-4-(2-(4-(4-phenylbutyl)phenyl)acetamidooxy)butylamino)hexane-1,5-diyl)bis(2-(2-(2- methoxyethoxy)ethoxy)acetamide),
(S)-N,N'-(6-Oxo-6-(4-oxo-4-(2-(4-(4-phenylbutyl)phenyl)acetamidooxy)butylamino)hexane-1,5-diyl)bis(2-(2-(2- methoxyethoxy)ethoxy)acetamide),
(S)-N,N'-(6-oxo-6-(4-oxo-4-(2-(4-(4-phenylbutyl)phenyl)acetamidooxy)butylamino)hexane-1,5-diyl)bis(2,5,8,11,14-pentaoxahexadecan-16- amide),
(S)-N,N'-(6-oxo-6-((1-((2-(4-(4-phenylbutyl)phenyl)acetamidooxy)carbonyl)cyclopropyl)methylamino)hexane-1,5-diyl)bis(2-(2- methoxyethoxy)acetamide),
(S)-N,N'-(6-oxo-6-(4-oxo-4-(2-(4-(4-phenylbutyl)phenyl)acetamidooxy)butylamino)hexane-1,5-diyl)bis(2,5,8,11-tetraoxatridecan-13-amide),
(S)-N,N'-(6-oxo-6-(4-oxo-4-(2-(4-(4-phenylbutyl)phenyl)acetamidooxy)butylamino)hexane-1,5-diyl)bis(2,5,8,11,14,17-hexaoxanonadecan-19- amide),
(S)-N,N'-(6-oxo-6-((1-((2-(4-(4-phenylbutyl)phenyl)acetamidooxy)carbonyl)cyclopropyl)methylamino)hexane-1,5-diyl)bis(2-(2-(2-methoxyethoxy)ethoxy)acetamide),
(S)-N,N'-(6-(Methyl(4-oxo-4-(2-(4-(4-phenylbutyl)phenyl)acetamidooxy)butyl)amino)-6-oxohexane-1,5-diyl)bis(2-(2-(2- methoxyethoxy)ethoxy)acetamide),
(S)-6,14-Dioxo-N-(3-oxo-3-(2-(4-(4-phenylbutyl)phenyl)acetamidooxy)propyl)-1,4-dioxa-7,13-diazacyclopentadecane-8-carboxamide,
(S)-9,17-dioxo-N-(3-oxo-3-(2-(4-(4-phenylbutyl)phenyl)acetamidooxy)propyl)-1,4,7-trioxa-10,16-diazacyclooctadecane-11-carboxamide,
2-(2-(2-Methoxyethoxy)ethoxy)-N-((1-((2-(4-(4-phenylbutyl)phenyl)acetamidooxy)carbonyl)cyclopropyl)methyl)acetamide,
2-(2-(2-methoxyethoxy)ethoxy)-N-(3-oxo-3-(2-(4-(4-phenylbutyl)phenyl)acetamidooxy)propyl)acetamide,
N-((1-((2-(4-(4-phenylbutyl)phenyl)acetamidooxy)carbonyl)cyclopropyl)methyl)-2,5,8,11,14-pentaoxahexadecan-16-amide,
N-(3-oxo-3-(2-(4-(4-phenylbutyl)phenyl)acetamidooxy)propyl)-2,5,8,11,14-pentaoxahexadecan-16-amide,
(S)-N-(2-Methyl-3-oxo-3-(2-(4-(4-phenylbutyl)phenyl)acetamidooxy)propyl)-2,5,8,11,14-pentaoxahexadecan-16-amide,
(S)-N-(4-oxo-4-(2-(4-(4-phenylbutyl)phenyl)acetamidooxy)butan-2-yl)-2,5,8,11,14-pentaoxahexadecan-16-amide,
N-(3-oxo-3-(2-(4-(4-phenylbutyl)phenyl)acetamidooxy)propyl)-2,5,8,11,14,17-hexaoxanonadecan-19-amide,
N-((1-((2-(4-(4-phenylbutyl)phenyl)acetamidooxy)carbonyl)cyclopropyl)methyl)-2,5,8,11,14,17-hexaoxanonadecan-19-amide,
N-(morpholine-4-carbonyloxy)-2-(4-(4-phenylbutyl)phenyl)acetamide,
N-(2,6-Dioxo-1,2,3,6-tetrahydropyrimidine-4-carbonyloxy)-2-(4-(4-phenylbutyl)phenyl)acetamide,
(S)-N-(2-(2-oxo-4-phenyloxazolidin-3-yl)acetoxy)-2-(4-(4-phenylbutyl)phenyl)acetamide,
N-(4-2,5,8,11,14-pentaoxahexadecanepiperazine-1-carbonyloxy)-2-(4-(4-phenylbutyl)phenyl)acetamide,
N-(4-2,5,8,11,14,17-hexaoxanonadecanepiperazine-1-carbonyloxy)-2-(4-(4-phenylbutyl)phenyl)acetamide,
N-(1-2,5,8,11,14,17-Hexaoxanonadecanepiperidine-4-carbonyloxy)-2-(4-(4-phenylbutyl)phenyl)acetamide, N-(1-(2-(2-(2-Methoxyethoxy)ethoxy)acetyl)piperidine-4-carbonyloxy)-2-(4-(4-phenylbutyl)phenyl)acetamide,
(S)-N,N'-(6-(Methyl(4-oxo-4-(2-(4-(4-phenylbutyl)phenyl)acetamidooxy)butyl)amino)-6-oxohexane-1,5-diyl)bis(2-(2-(2- methoxyethoxy)ethoxy)acetamide),
N-(2-(1-2,5,8,11-tetraoxatridecanepiperidin-4-yl)acetoxy)-2-(4-(4-phenylbutyl)phenyl)acetamide,
N-(2-(1-(2-(2-(2-methoxyethoxy)ethoxy)acetyl)piperidin-4-yl)acetoxy)-2-(4-(4-phenylbutyl)phenyl)acetamide,
N-(3-(1-2,5,8,11,14,17-Hexaoxanonadecanepiperidin-4-yl)propanoyloxy)-2-(4-(4-phenylbutyl)phenyl)acetamide,
N-(2-(1-2,5,8,11,14,17-hexaoxanonadecanepiperidin-4-yloxy)acetoxy)-2-(4-(4-phenylbutyl)phenyl)acetamide,
N-(4-(4-(2-(2-(2-Methoxyethoxy)ethoxy)acetyl)piperazin-1-yl)-4-oxobutanoyloxy)-2-(4-(4-phenylbutyl)phenyl)acetamide,
N-(4-(1-2,5,8,11,14,17-Hexaoxanonadecanepiperidin-4-yl)butanoyloxy)-2-(4-(4-phenylbutyl)phenyl)acetamide,
N-(4-(1-(2-(2-(2-methoxyethoxy)ethoxy)acetyl)azetidin-3-yl)butanoyloxy)-2-(4-(4-phenylbutyl)phenyl)acetamide,
N-(3-(1-(2-(2-(2-methoxyethoxy)ethoxy)acetyl)piperidin-4-yl)propanoyloxy)-2-(4-(4-phenylbutyl)phenyl)acetamide,
N-(3-(1-2,5,8,11,14-pentaoxahexadecanepiperidin-4-yl)propanoyloxy)-2-(4-(4-phenylbutyl)phenyl)acetamide,
4-oxo-4-(2-(4-(4-phenylbutyl)phenyl)acetamidooxy)butyl dihydrogen phosphate,
2-(methyl((2-(4-(4-phenylbutyl)phenyl)acetamidooxy)carbonyl)amino)ethanesulfonic acid,
ethyl 2-((2-(4-(4-phenylbutyl)phenyl)acetamidooxy)carbonylamino)acetate,
2-(2-aminoethylamino)-N-(3-oxo-3-(2-(4-(4-phenylbutyl)phenyl)acetamidooxy)propyl)acetamide,
2-(2-Aminoethylamino)-N-(4-oxo-4-(2-(4-(4-phenylbutyl)phenyl)acetamidooxy)butyl)acetamide,
(S)-2-(4-(4-phenylbutyl)phenyl)-N-(pyrrolidine-2-carbonyloxy)acetamide,
N-(4-Methylpiperazine-1-carbonyloxy)-2-(4-(4-phenylbutyl)phenyl)acetamide,
N-(4-morpholinopiperidine-1-carbonyloxy)-2-(4-(4-phenylbutyl)phenyl)acetamide,
2-(4-(4-Phenylbutyl)phenyl)-N-(piperazine-1-carbonyloxy)acetamide,
2-(4-(4-Phenylbutyl)phenyl)-N-(piperidine-4-carbonyloxy)acetamide,
2-(4-(4-phenylbutyl)phenyl)-N-(2-(piperidin-4-yl)acetoxy)acetamide,
2-(4-(4-Phenylbutyl)phenyl)-N-(3-(piperidin-4-yl)propanoyloxy) acetamide,
2-(4-(4-phenylbutyl)phenyl)-N-(2-(piperidin-4-yloxy)acetoxy)acetamide,
2-(4-(4-Phenylbutyl)phenyl)-N-(4-(piperidin-4-yl)butanoyloxy)acetamide,
N-(4-oxo-4-(piperazin-1-yl)butanoyloxy)-2-(4-(4-phenylbutyl)phenyl)acetamide,
N-(3-(2-oxopiperazin-1-yl)propanoyloxy)-2-(4-(4-phenylbutyl)phenyl)acetamide
(S)-2,6-diamino-N-((S)-1-oxo-1-(2-(4-(4-phenylbutyl)phenyl)acetamidooxy)propan-2-yl)hexanamide,
(S)-6-oxo-6-((S)-1-oxo-3-phenyl-1-(2-(4-(4-phenylbutyl)phenyl)acetamidooxy)propan-2-ylamino)hexane-1,5-diamine,
N-(4-aminobenzoyloxy)-2-(4-(4-phenylbutyl)phenyl)acetamide,
N-(6-aminohexanoyloxy)-2-(4-(4-phenylbutyl)phenyl)acetamide,
2-amino-N-(4-((2-(4-(4-phenylbutyl)phenyl)acetamidooxy)carbonyl)phenyl)acetamide,
(S)-2,6-diamino-N-(4-((2-(4-(4-phenylbutyl)phenyl)acetamidooxy)carbonyl)phenyl)hexanamide,
(S)-2,6-Diamino-N-(3-oxo-3-(2-(4-(4-phenylbutyl)phenyl)acetamidooxy)propyl)hexanamide,
(S)-2-amino-N-(4-oxo-4-(2-(4-(4-phenylbutyl)phenyl)acetamidooxy)butyl)-3-phenylpropanamide,
(S)-2-amino-3-(4-hydroxyphenyl)-N-(6-oxo-6-(2-(4-(4-phenylbutyl)phenyl)acetamidooxy)hexyl)propanamide,
N-((S)-1-((S)-2,6-Diaminohexanoyl)pyrrolidine-2-carbonyloxy)-2-(4-(4-phenylbutyl)phenyl)acetamide, or
(S)-2-Amino-6-(2-(2-(2-methoxyethoxy)ethoxy)acetamido)-N-(3-oxo-3-(2-(4-(4-phenylbutyl)phenyl)acetamidooxy)propyl)hexanamide.

\* \* \* \* \*